United States Patent
Fransson et al.

(10) Patent No.: US 10,544,229 B2
(45) Date of Patent: Jan. 28, 2020

(54) AGONISTIC ANTIBODIES SPECIFICALLY BINDING CD40 AND METHODS OF USE

(71) Applicant: Janssen Biotech, Inc., Horsham, PA (US)

(72) Inventors: Johan Fransson, Toronto (CA); Paul Kim, Spring House, PA (US); Michael Quigley, Ambler, PA (US); Andressa Smith, Spring House, PA (US); Alexey Teplyakov, Spring House, PA (US); Hong Zhou, San Diego, CA (US)

(73) Assignee: Janssen Biotech, Inc., Horsham, PA (US)

(*) Notice: Subject to any disclaimer, the term of this patent is extended or adjusted under 35 U.S.C. 154(b) by 241 days.

(21) Appl. No.: 15/281,670

(22) Filed: Sep. 30, 2016

(65) Prior Publication Data
US 2017/0088624 A1    Mar. 30, 2017

Related U.S. Application Data

(60) Provisional application No. 62/234,812, filed on Sep. 30, 2015.

(51) Int. Cl.
| | |
|---|---|
| C07K 16/28 | (2006.01) |
| A61K 39/395 | (2006.01) |
| A61K 45/06 | (2006.01) |
| C07K 16/42 | (2006.01) |
| A61K 47/68 | (2017.01) |
| C07K 16/46 | (2006.01) |
| A61K 39/00 | (2006.01) |

(52) U.S. Cl.
CPC ...... *C07K 16/2878* (2013.01); *A61K 39/3955* (2013.01); *A61K 39/39558* (2013.01); *A61K 45/06* (2013.01); *A61K 47/6803* (2017.08); *A61K 47/6849* (2017.08); *C07K 16/4208* (2013.01); *C07K 16/468* (2013.01); *A61K 2039/505* (2013.01); *C07K 2317/31* (2013.01); *C07K 2317/565* (2013.01); *C07K 2317/75* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 5,786,456 A | 7/1998 | Ledbetter et al. |
| 6,312,693 B1 | 11/2001 | Aruffo et al. |
| 6,946,129 B1 | 9/2005 | Siegall et al. |
| 7,547,438 B2 | 6/2009 | Thomas et al. |
| 7,820,170 B2 | 10/2010 | Chu et al. |
| 8,303,955 B2 | 11/2012 | Presta et al. |
| 8,551,485 B2 | 10/2013 | Bernett et al. |
| 8,669,352 B2 | 3/2014 | den Hartog et al. |
| 8,778,345 B2 | 7/2014 | Zhang et al. |
| 8,828,396 B2 | 9/2014 | Heusser et al. |
| 8,895,010 B2 | 11/2014 | Nadler et al. |
| 8,957,193 B2 | 2/2015 | Zhang et al. |
| 2004/0110226 A1 | 6/2004 | Lazar et al. |
| 2005/0054019 A1 | 3/2005 | Michaud et al. |
| 2005/0202531 A1 | 9/2005 | Toporik |
| 2006/0166198 A1 | 7/2006 | Furebring et al. |
| 2009/0074711 A1 | 3/2009 | Glennie |
| 2009/0104204 A1 | 4/2009 | Throsby et al. |
| 2009/0311245 A1 | 12/2009 | Devy et al. |
| 2010/0021477 A1 | 1/2010 | Tsui et al. |
| 2010/0234578 A1* | 9/2010 | Mikayama ......... C07K 16/2878 530/388.73 |
| 2011/0027276 A1 | 2/2011 | Bernett et al. |
| 2012/0087927 A1 | 4/2012 | Matsushima et al. |
| 2012/0148578 A1 | 6/2012 | Chu et al. |
| 2012/0225014 A1 | 9/2012 | Bedian et al. |
| 2012/0301488 A1 | 11/2012 | Zhang et al. |
| 2013/0243795 A1 | 9/2013 | Chen et al. |
| 2014/0010812 A1* | 1/2014 | Ravetch ............ A61K 39/3955 424/134.1 |
| 2014/0093497 A1 | 4/2014 | Reimann et al. |
| 2014/0120103 A1 | 5/2014 | Zhang et al. |
| 2014/0178388 A1 | 6/2014 | Chou et al. |

FOREIGN PATENT DOCUMENTS

| | | |
|---|---|---|
| EP | 2 011 802 A2 | 1/2009 |
| EP | 1 682 180 B1 | 11/2009 |
| EP | 1 885 399 B1 | 10/2010 |
| EP | 2 471 813 B1 | 12/2014 |
| WO | WO 94/01547 A2 | 1/1994 |
| WO | WO 95/09653 A1 | 4/1995 |
| WO | WO 99/42075 A2 | 8/1999 |
| WO | WO 01/58953 A2 | 8/2001 |
| WO | WO 01/83755 A2 | 11/2001 |
| WO | WO 03/040170 A2 | 5/2003 |

(Continued)

OTHER PUBLICATIONS

Rudikoff et al, Proc Natl Acad Sci USA 79: 1979-1983 (1982). (Year: 1982).*

(Continued)

*Primary Examiner* — Phillip Gambel
(74) *Attorney, Agent, or Firm* — Kirk Baumeister

(57) ABSTRACT

The present invention relates to agonistic antibodies specifically binding human CD40, polynucleotides encoding the antibodies or antigen-binding fragments, and methods of making and using the foregoing.

45 Claims, 15 Drawing Sheets
Specification includes a Sequence Listing.

(56) References Cited

FOREIGN PATENT DOCUMENTS

| | | |
|---|---|---|
| WO | WO 03/097834 A2 | 11/2003 |
| WO | WO 2006/073443 A2 | 7/2006 |
| WO | WO 2009/085462 A1 | 7/2009 |
| WO | WO 2009/094391 A1 | 7/2009 |
| WO | WO 2010/104747 A2 | 9/2010 |
| WO | WO 2011/123489 A2 | 10/2011 |
| WO | WO 2013/034904 A1 | 3/2013 |
| WO | WO 2014/030728 A1 | 2/2014 |
| WO | WO 2014/093908 A2 | 6/2014 |
| WO | WO 2014/126254 A1 | 8/2014 |
| WO | WO 2015/091853 A2 | 6/2015 |
| WO | WO 2016/028810 A1 | 2/2016 |

OTHER PUBLICATIONS

Colman, Research in Immunology 145: 33-36 (1994). (Year: 1994).*
Kussie et al., J. Immunol.152: 146-152 (1994). (Year: 1994).*
Chen et al., EMBO J., 14: 2784-2794 (1995). (Year: 1995).*
Vonderheide et al., Clin Cancer Res 19: 1035-1043 (2013). (Year: 2013).*
Advani, et al., "Phase I Study of the Humanized Anti-CD40 Monoclonal Antibody Dacetuzumab in Refractory or Recurrent Non-Hodgkin's Lymphoma," Journal of Clinical Oncology, 27(26): 4371-4377 (2009).
Allen, et al, "CD40 Ligand Gene Defects Responsible for X-Linked Hyper-IgM Syndrome," Science, 259(5097): 990-993 (1993).
Armitage, et al., "Molecular and biological characterization of a murine ligand for CD40," Nature, 357: 80-82 (1992).
Bajorath, et al., "Identification of Residues on CD40 and Its Ligan Which Are Critical for the Receptor-Ligand Interaction," Biochemistry, 34: 1833-1844 (1995).
Bajorath, et al, "Analysis of gp39/CD40 Interactions Using Molecular Models and Site-Directed Mutagenesis," Biochemistry, 34: 9884-9892 (1995).
Jürgen Bajorath, "Detailed Comparison of Two Molecular Models of the Human CD40 Ligand with an X-ray Structure and Critical Assessment of Model-based Mutagenesis and Residue Mapping Studies," The Journal of Biological Chemistry, 273(38): 24603-24609 (1998).
Neil L. Berinstein, "Enhancing cancer vaccines with immunomodulators," Vaccine, 25S: B72-B88 (2007).
Diehl, et al., "CD40 activation in vivo overcomes peptide-induced peripheral cytotoxic T-lymphocyte tolerance and augments anti-tumor vaccine efficacy," Nature Medicine: 5(7): 774-779 (1999).
Ellmark, et al., "Modulation of the CD40-CD40 ligand interaction using human anti-CD40 single-chain antibody fragments obtained from the n-CoDeR phage display library," Immunology, 106: 456-463 (2002).
Ellmark, et al., "Pre-assembly of the extracellular domains of CD40 is no necessary for rescue of mouse B cells from anti-immunoglobulin M-induced apoptosis," Immunology, 108: 452-457 (2003).
Ellmark, et al., "Identification of a Strongly Activating Human Anti-CD40 Antibody That Suppresses HIV Type 1 Infection," AIDS Research and Human Retroviruses, 24(3): 367-373. (2008).
Foy, et al., "In Vivo CD40-gp39 Interactions are Essential for Thymus-dependent Humoral Immunity. II. Prolonged Suppression of the Humoral Immune Response by an Antibody to the Ligand of CD40, gp39," Journal of Experimental Medicine, 178: 1567-1575 (1993).
Francisco, et al., "Agonistic Properties and in Vivo Antitumor Activity of the Anti-CD40 Antibody SGN-14," Cancer Research, 60: 3225-3231 (2000).
French, et al., "CD40 antibody evokes a cytotoxic T-cell response that eradicates lymphoma and bypasses T-cell help," Nature Medicine, 5(5): 548-553 (1999).
Gladue, et al., "The CD40 agonist antibody CP-870,893 enhances dendritic cell and B-cell activity and promotes anti-tumor efficacy in SCID-hu mice," Cancer Immunology and Immunotherapy, 60: 1000-1017 (2011).
Houot, et al., "Immunomodulating antibodies and drugs for the treatment of hematological malignancies," Cancer Metastasis Review, 30: 97-109 (2011).
Huang, et al., "Sensitization of SiHa cell to gemcitabine by CD40 activation and its overexpression in cervical carcinoma," Medical Oncology, 28: 781-788 (2011).
Hussein, et al., A phase I multidose study of dacetuzumab (SGN-40.
Kalbasi, et al., "CD40 Expression by Human Melanocytic Lesions and Melanoma Cell Lines and Direct CD40 Targeting With the Therapeutic Anti-CD40 Antibody CP-870,893," Journal of Immunotherapy, 33: 810-816 (2010).
Khalil, et al., "Anti-CD40 agonist antibodies: preclinical and clinical experience," Update Cancer Therapeutics, 2(2): 61-65 (2007).
Law, et al., "Preclinical Antilymphoma Activity of a Humanized Anti-CD40 Monoclonal Antibody, SGN-40," Cancer Research, 65(18): 8331-8338 (2005).
Loskog, et al., "The Janus faces of CD40 in cancer," Seminars in Immunology, 21: 301-307 (2009).
Malmborg Hager, et al., "Affinity and Epitope Profiling of Mouse Anti-CD40 Monoclonal Antibodies," Scandinavian Journal of Immunology, 57: 517-524 (2003).
Melero, et al., "Immunostimulatory monoclonal antibodies for cancer therapy," Nature Reviews, 7: 95-106 (2007).
Cornelis J.M. Melief, "Cancer Immunotherapy by Dendritic Cells," Immunity, 29: 372-383 (2008).
Melief, et al., "Strategies for Immunotherapy of Cancer," Advances in Immunology, 75, 235-282 (2000).
Néron, et al., "CD40-activated B cells from patients with systemic lupus erythematosus can be modulated by therapeutic immunoglobulins in vitro," Arch. Immunol. Ther. Exp., 57: 447-458 (2009).
Néron, et al., "Tuning of CD40-CD154 Interactions in Human B-Lymphocyte Activation: A Broad Array of in Vitro Models for a Complex in Vivo Situation," Arch. Immunol. Ther. Exp., 59: 25-40 (2011).
Osborn, et al., "High-Affinity IgG Antibodies Develop Naturally in If-Knockout Rate Carrying Germline Human IgH/Igκ/Igλ Loci Bearing the Rat $C_H$ Region," The Journal of Immunology, 190: 1481-1490 (2013).
Ottaiano, et al., "CD40 Activation as Potential Toll in Malignant Neoplasms," Tumori, 88: 361-366 (2002).
Pound, et al., "Minimal cross-linking and epitope requirements for CD40-dependent suppression of apoptosis contrast with those for promotion of the cell cycle and homotypic adhesions in human B cells," International Immunology, 11(1): 11-20 (1999).
Quezada, et al., "CD40/CD154 Interactions at the Interface of Tolerance and Immunity," Annual Review of Immunology, 22: 307-328 (2004).
Schönbeck, et al., "The CD40/CD154 receptor/ligand dyad," CMLS Cellular and Molecular Life Sciences, 58: 4-43 (2001).
Shi, et al., "De Novo Selection of High-Affinity Antibodies from Synthetic Fab Libraries Displayed in Phage as pIX Fusion Proteins," Journal of Molecular Biology, 397: 385-396 (2010).
Siepmann, et al., "Rewiring of CD40 is necessary for delivery of rescue signals to B cells in germinal centres and subsequent entry into the memory pool," Immunology, 102: 263-272 (2001).
Sotomayor, et al., "Conversion of tumor-specific CD4+ T-cell tolerance to T-cell priming through in vivo ligation of CD40," Nature Medicine, 5(7): 780-787 (1999).
Stagg, et al., "From cancer immunosurveillance to cancer immunotherapy," Immunological Reviews, 22: 82-101 (2007).
Tong, et al., "Prospects for CD40-directed experimental therapy of human cancer," Cancer Gene Therapy, 10: 1-13 (2003).
Tuft, et al., "T Cell Immunity to Lymphoma Following Treatment with Anti-CD40 Monoclonal Antibody," The Journal of Immunology, 168: 2720-2728 (2002).
Van Mierlo, et al., "CD40 stimulation leads to effective therapy of CD40 tumors through induction of strong systemic cytotoxic T lymphocyte immunity," Proceedings of the National Academy of Science USA, 99(8): 5561-5566 (2002).
Van Mierlo, et al., "Activation of Dendritic Cells that Cross-Present Tumor-Derived Antigen Licenses CD8+ CTL to Cause Tumor Eradication," The Journal of Immunology, 173: 6753-6759 (2004).

(56) References Cited

OTHER PUBLICATIONS

Van Kooten, et al., "CD40-CD40 ligand," Journal of Leukoc. Biology, 67: 2-17 (2000>.
Vanderheide, et al., "Clinical Activity and Immune Modulation in Cancer Patients Treated with CP-870,893, a Novel CD40 Agonist Monoclonal Antibody," Journal of Clinical Oncology, 25(7): 876-883 (2007).
Thomas A. Waldmann, "Effective Cancer Therapy Through Immunomodulation," Annu. Rev. Med., 57: 65-81 (2006).
White, et al., "Interaction with FcγRIIB Is Critical for the Agonistic Activity of Anti-CD40 Monoclonal Antibody," The Journal of Immunology, 187: 1754-1763 (2011).
Wilson, et al., "An Fcγ Receptor-Dependent Mechanism Drives Antibody-Mediated Target-Receptor Signaling in Cancer Cells," Cancer Cell, 19: 101-113 (2011).
Richman, et al., "Role of Crosslinking for Agonistic CD40 monoclonal Antibodies as Immune Therapy of Cancer," Cancer Immunology Research, 2(1): 19-26 (2013).
GeneSeq Accession No. AOF62406 (First entry Feb. 21, 2008).

\* cited by examiner

Figure 3.

```
              1                                          30
C40H43        QLQLQESGPGLVKPSEILSLTCTVSGGSIS
IGHV4-39      QLQLQESGPGLVKPSETLSLTCTVSGGSIS
              *************** **************

31                                         60
C40H43        SSSYYWGWIRQPPGKGLEWIGNIYYRGDTY
IGHV4-39      SSSYYWGWIRQPPGKGLEWIGSIYYSGSTY
              *********************.*** *.**

61                                         90
C40H43        YSPSLKSRVTISVDTSKNQFSLKLNSVTAAD
IGHV4-39      YNPSLKSRVTISVDTSKNQFSLKLSSVTAAD
              *.*********************.******

91      98
C40H43        TAVYYCAK
IGHV4-39      TAVYYCAR
              ******:
```

Figure 4.

```
               1                              30
C40L64         SYELTQPPSVSVSPGQTASITCSGDKLGDK
IGLV3-1        SYELTQPPSVSVSPGQTASITCSGDKLGDK
               ******************************

31                             60
C40L64         YVCWYQQKPGQSPVVVIYQDSKRPSGIPER
IGLV3-1        YACWYQQKPGQSPVLVIYQDSKRPSGIPER
               *.************:**************

61                             90
C40L64         FSGSNSGNTATLTISGTQAMDEAYYYCQAW
IGLV3-1        FSGSNSGNTATLTISGTQAMDEADYYCQAW
               *********************** ******

91  94
C40L64         VSST
IGLV3-1        DSST
                ***
```

AGONISTIC ANTIBODIES SPECIFICALLY BINDING CD40 AND METHODS OF USE

CROSS-REFERENCE TO RELATED APPLICATIONS

This application claims the benefit of U.S. Provisional Application Ser. No. 62/234,812, filed 30 Sep. 2015. The entire content of the aforementioned application is incorporated herein by reference in its entirety.

FIELD OF THE INVENTION

The present invention relates to agonistic antibodies specifically binding human CD40, polynucleotides encoding the antibodies or antigen-binding fragments, and methods of making and using the foregoing.

BACKGROUND OF THE INVENTION

The cell surface CD40 molecule is a member of the tumor necrosis factor receptor superfamily (TNFR) and a key regulator in both innate and adaptive immune responses. CD40 is expressed on human antigen presenting cells, in particular B cells, dendritic cells and macrophages, as well as on fibroblasts, smooth muscle cells, endothelial cells and epithelial cells. CD40 is also expressed on a wide range of tumor cells including all B-lymphomas, 30-70% of solid tumors, melanomas and carcinomas.

The natural ligand of CD40, designated CD154 or CD40L, is mainly expressed on activated T lymphocytes and platelets. The interaction of CD40 with CD40L on T cells induces both humoral and cell-mediated immune responses. CD40 regulates this ligand-receptor pair to activate B cells and other antigen-presenting cells (APC) including dendritic cells (DCs), driving T cell activation. For example, activation of CD40 on B cells induces B cell proliferation, somatic hypermutation, differentiation into antibody secreting cells and isotype switching in germinal centers of secondary lymphoid organs. In vitro studies have shown direct effects of CD40 activation on cytokine production (e.g. IL-6, IL-10, IL-12, TNF-α), expression of adhesion molecules and costimulatory receptors (e.g. ICAM, CD23, CD80 and CD86), and increased expression of MHC class I, MHC class II, and TAP transporter by B lymphocytes.

CD40 antibodies may elicit their antitumor effects by various mechanisms, including activation of antigen-presenting cells resulting in increased activity of tumor specific cytotoxic T lymphocytes and natural killer cells (NK cells), or direct antibody-mediated tumor cell apoptosis or cellular cytotoxicity of CD40 positive tumors. Systemic administration of anti-CD40 antibodies has however also been associated with adverse side effects, such as a cytokine release syndrome.

Thus, there is a need for improved anti-CD40 antibodies for cancer therapy and enhancement of immune response.

SUMMARY OF THE INVENTION

The invention provides for an isolated agonistic antibody specifically binding human CD40 of SEQ ID NO: 75.

The invention also provides for an isolated agonistic antibody specifically binding human CD40, wherein the antibody requires cross-linking for its agonistic activity.

The invention also provides for an isolated agonistic antibody specifically binding human CD40 comprising certain VH, VL, HCDR, LCDR, heavy chain or light chain sequences as described herein.

The invention also provides for a pharmaceutical composition comprising the antibody of the invention and a pharmaceutically acceptable carrier.

The invention also provides for a polynucleotide encoding the antibody VH, the antibody VL, the antibody VH and the antibody VL, the antibody heavy chain, the antibody light chain, or the antibody heavy chain and the antibody light chain of the invention.

The invention also provides for a vector comprising the polynucleotide of the invention.

The invention also provides for a host cell comprising the vector of the invention.

The invention also provides for a method of producing the antibody of the invention, comprising culturing the host cell of the invention in conditions that the antibody is expressed, and recovering the antibody produced by the host cell.

The invention also provides for a method of treating a cancer in a subject, comprising administering a therapeutically effective amount of the isolated antibody of the invention or the pharmaceutical composition of the invention to the subject in need thereof for a time sufficient to treat the cancer.

The invention also provides for a method of enhancing an immune response in a subject, comprising administering a therapeutically effective amount of the isolated antibody of the invention or the pharmaceutical composition of the invention to the subject in need thereof for a time sufficient to enhance the immune response.

The invention also provides for an anti-idiotypic antibody specifically binding the antibody of the invention.

The invention also provides for a kit comprising the antibody of the invention.

BRIEF DESCRIPTION OF THE DRAWINGS

FIG. 3 shows the amino acid alignment of residues 1-98 of VH of C40M9 (C40H43; SEQ ID NO: 60) and the human germline IGHV4-39*01 (SEQ ID NO: 73; shown as IGHV4-39 in the Figure). HCDR1 and HCDR2 amino acids are underlined. C40M9 and IGHV4-39*01 frameworks differed by 3 amino acids.

FIG. 4 shows the amino acid alignment of residues 1-94 VL of C40M18 (C40L64; SEQ ID NO: 66) and the human germline IGLV3-1 (SEQ ID NO: 86). LCDR1 and LCDR2 amino acid sequences are underlined. C40M18 framework differs by 2 amino acids from that of IGLV3-1.

DETAILED DESCRIPTION OF THE INVENTION

Figure 1A:
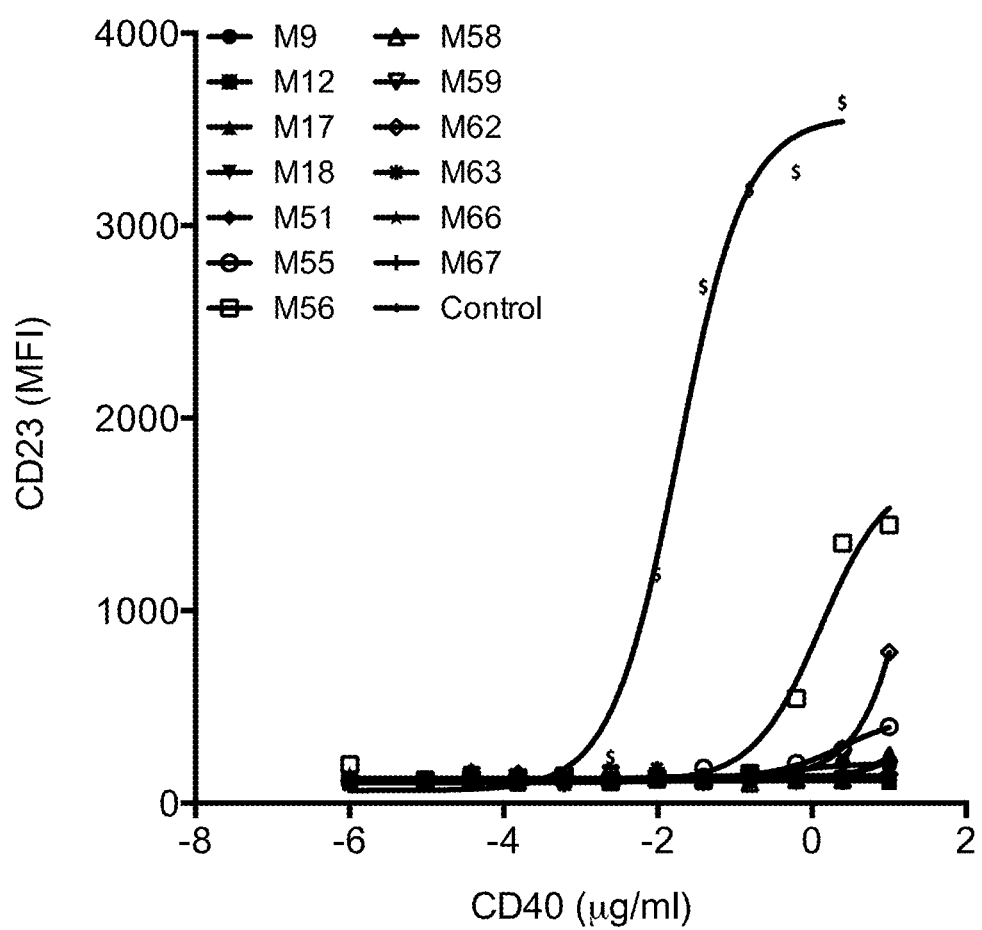
FIG. 1A shows that antibodies specifically binding human CD40 activate B cells in cross-linking dependent manner. B cell activation was measured as increased CD23 surface expression in the absence of a cross-linker. M9 refers to antibody C40M9, etc. Control: CP-870,893.
Figure 1B:
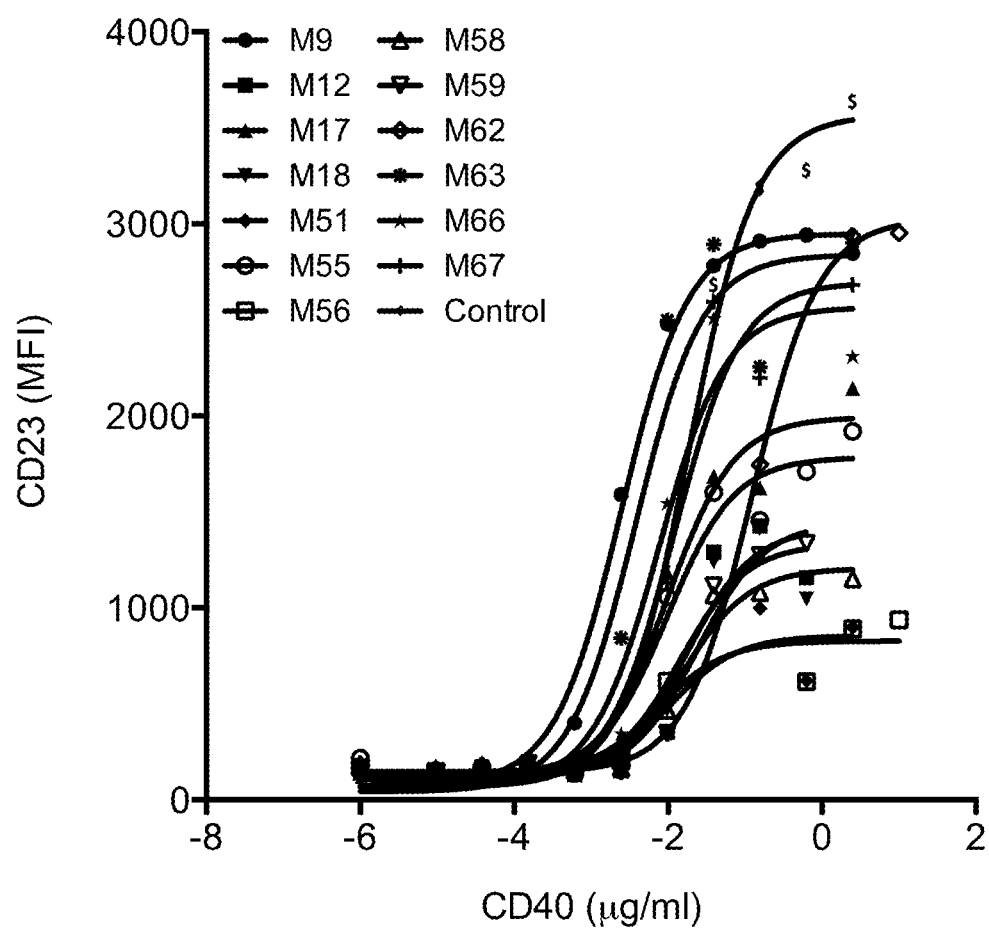
FIG. 1B shows that antibodies specifically binding human CD40 activate B cells in cross-linking dependent manner. B cell activation was measured as increased CD23 surface expression in the presence of a cross-linker. M9 refers to antibody C40M9, etc. Control: CP-870,893.

All publications, including but not limited to patents and patent applications, cited in this specification are herein incorporated by reference as though fully set forth.

It is to be understood that the terminology used herein is for the purpose of describing particular embodiments only and is not intended to be limiting. Unless defined otherwise, all technical and scientific terms used herein have the same meaning as commonly understood by one of ordinary skill in the art to which the invention pertains.

As used herein, the singular forms "a," "and," and "the" include plural reference unless the context clearly dictates otherwise.

Although any methods and materials similar or equivalent to those described herein may be used in the practice for testing of the present invention, exemplary materials and methods are described herein.

"Specific binding" or "specifically binds" or "binds" refer to antibody binding to human CD40 with greater affinity than for non-related antigens. Typically, the antibody binds to human CD40 with a dissociation constant ($K_D$) of $1\times10^{-8}$ M or less, for example $1\times10^{-9}$ M or less, $1\times10^{-10}$ M or less, $1\times10^{-11}$ M or less, or $1\times10^{-12}$ M or less, typically with a $K_D$ that is at least one hundred-fold less than its $K_D$ for binding to a non-related antigen (for example, BSA, casein). The dissociation constant may be measured using standard procedures. Antibodies that specifically bind human CD40 may, however, have cross-reactivity to other related antigens, for example to the same antigen from other species (homologs), such as human or monkey, for example *Macaca fascicularis* (cynomolgus, cyno), Pan troglodytes (chimpanzee, chimp) or *Callithrix jacchus* (common marmoset, marmoset). While a monospecific antibody specifically binds one antigen or one epitope, a bispecific antibody specifically binds two distinct antigens or two distinct epitopes.

"Antibodies" is meant in a broad sense and include immunoglobulin molecules including monoclonal antibodies including murine, human, humanized and chimeric monoclonal antibodies, antigen-binding fragments, bispecific or multispecific antibodies, dimeric, tetrameric or multimeric antibodies, single chain antibodies, domain antibodies and any other modified configuration of the immunoglobulin molecule that comprises an antigen binding site of the required specificity. "Full length antibodies" are comprised of two heavy (H) chains and two light (L) chains inter-connected by disulfide bonds as well as multimers thereof (for example IgM). Each heavy chain is comprised of a heavy chain variable region (VH) and a heavy chain constant region (comprised of domains CH1, hinge CH2 and CH3). Each light chain is comprised of a light chain variable region (VL) and a light chain constant region (CL). The VH and the VL regions may be further subdivided into regions of hypervariability, termed complementarity determining regions (CDR), interspersed with framework regions (FR). Each VH and VL is composed of three CDRs and four FR segments, arranged from amino-terminus to carboxy-terminus in the following order: FR1, CDR1, FR2, CDR2, FR3, CDR3, and FR4.

"Complementarity determining regions (CDR)" are "antigen binding sites" in an antibody. CDRs may be defined using various terms: (i) Complementarity Determining Regions (CDRs), three in the VH (HCDR1, HCDR2, HCDR3) and three in the VL (LCDR1, LCDR2, LCDR3) are based on sequence variability (Wu and Kabat, J Exp Med 132:211-50, 1970; Kabat et al., Sequences of Proteins of Immunological Interest, 5th Ed. Public Health Service, National Institutes of Health, Bethesda, Md., 1991). (ii) "Hypervariable regions", "HVR", or "HV", three in the VH (H1, H2, H3) and three in the VL (L1, L2, L3) refer to the regions of an antibody variable domains which are hypervariable in structure as defined by Chothia and Lesk (Chothia and Lesk, Mol Biol 196:901-17, 1987). The International ImMunoGeneTics (IMGT) database (http_//www_imgt_org) provides a standardized numbering and definition of antigen-binding sites. The correspondence between CDRs, HVs and IMGT delineations is described in Lefranc et al., Dev Comparat Immunol 27:55-77, 2003. The term "CDR", "HCDR1", "HCDR2", "HCDR3", "LCDR1", "LCDR2" and "LCDR3" as used herein includes CDRs defined by any of the methods described supra, Kabat, Chothia or IMGT, unless otherwise explicitly stated in the specification.

Immunoglobulins may be assigned to five major classes, IgA, IgD, IgE, IgG and IgM, depending on the heavy chain constant domain amino acid sequence. IgA and IgG are further sub-classified as the isotypes $IgA_1$, $IgA_2$, $IgG_1$, $IgG_2$, $IgG_3$ and $IgG_4$. Antibody light chains of any vertebrate species can be assigned to one of two clearly distinct types, namely kappa (κ) and lambda (λ), based on the amino acid sequences of their constant domains.

"Antigen-binding fragment" refers to a portion of an immunoglobulin molecule that retains the antigen binding properties of the parental full-length antibody. Exemplary antigen-binding fragments are as heavy chain complementarity determining regions (HCDR) 1, 2 and/or 3, light chain complementarity determining regions (LCDR) 1, 2 and/or 3, a heavy chain variable region (VH), or a light chain variable region (VL), Fab, F(ab')2, Fd and Fv fragments as well as domain antibodies (dAb) consisting of either one VH domain or one VL domain. VH and VL domains may be linked together via a synthetic linker to form various types of single chain antibody designs in which the VH/VL domains pair intramolecularly, or intermolecularly in those cases when the VH and VL domains are expressed by separate chains, to form a monovalent antigen binding site, such as single chain Fv (scFv) or diabody; described for example in Int. Pat. Publ. No. WO1998/44001, Int. Pat. Publ. No. WO1988/01649; Int. Pat. Publ. No. WO1994/13804; Int. Pat. Publ. No. WO1992/01047.

"Monoclonal antibody" refers to an antibody population with single amino acid composition in each heavy and each light chain, except for possible well-known alterations such as removal of C-terminal lysine from the antibody heavy chain. Monoclonal antibodies typically bind one antigenic epitope, except that multispecific monoclonal antibodies bind two or more distinct antigens or epitopes. Bispecific monoclonal antibodies bind two distinct antigenic epitopes. Monoclonal antibodies may have heterogeneous glycosylation within the antibody population. Monoclonal antibodies may be monospecific or multispecific, or monovalent, bivalent or multivalent. A multispecific antibody, such as a bispecific antibody or a trispecific antibody is included in the term monoclonal antibody.

"Isolated antibody" refers to an antibody or an antigen-binding fragment thereof that is substantially free of other antibodies having different antigenic specificities (e.g., an isolated antibody specifically binding human CD40 is substantially free of antibodies that specifically bind antigens other than human CD40). In case of a bispecific antibody, the bispecific antibody specifically binds two antigens of interest, and is substantially free of antibodies that specifically bind antigens other that the two antigens of interest. "Isolated antibody" encompasses antibodies that are isolated to a higher purity, such as antibodies that are 80%, 81%, 82%, 83%, 84%, 85%, 86%, 87%, 88%, 89%, 90%, 91%, 92%, 93%, 94%, 95%, 96%, 97%, 98%, 99% or 100% pure.

"Humanized antibodies" refer to antibodies in which at least one CDR is derived from non-human species and the variable region frameworks are derived from human immunoglobulin sequences. Humanized antibodies may include intentionally introduced mutations in the framework regions so that the framework may not be an exact copy of expressed human immunoglobulin or germline gene sequences.

"Human antibodies" refers to antibodies having heavy and light chain variable regions in which both the framework and all 6 CDRs are derived from sequences of human origin. If the antibody contains a constant region or a portion of the constant region, the constant region also is derived from sequences of human origin.

A human antibody comprises heavy or light chain variable regions that are derived from sequences of human origin if the variable regions of the antibody are obtained from a system that uses human germline immunoglobulin or rearranged immunoglobulin genes. Such exemplary systems are human immunoglobulin gene libraries displayed on phage, and transgenic non-human animals such as mice or rats carrying human immunoglobulin loci as described herein. A human antibody typically contains amino acid differences when compared to the human germline or rearranged immunoglobulin sequences due to, for example naturally occurring somatic mutations, intentional introduction of substitutions into the framework or antigen binding site and amino acid changes introduced during cloning and VDJ recombination in non-human animals. Typically, a human antibody is at least about 80%, 81%, 82%, 83%, 84%, 85%, 86%, 87%, 88%, 89%, 90%, 91%, 92%, 93%, 94%, 95%, 96%, 97%, 98%, 99% or 100% identical in amino acid sequence to an amino acid sequence encoded by a human germline or rearranged immunoglobulin gene. In some cases, a human antibody may contain consensus framework sequences derived from human framework sequence analyses, for example as described in Knappik et al., J Mol Biol 296:57-86, 2000, or synthetic HCDR3 incorporated into human immunoglobulin gene libraries displayed on phage, for example as described in Shi et al., J Mol Biol 397:385-96, 2010 and Int. Pat. Publ. No. WO2009/085462.

"Recombinant" includes antibodies and other proteins that are prepared, expressed, created or isolated by recombinant means.

"Epitope" refers to a portion of an antigen to which an antibody specifically binds. Epitopes typically consist of chemically active (such as polar, non-polar or hydrophobic) surface groupings of moieties such as amino acids or polysaccharide side chains and may have specific three-dimensional structural characteristics, as well as specific charge characteristics. An epitope may be composed of contiguous and/or discontiguous amino acids that form a conformational spatial unit. For a discontiguous epitope, amino acids from differing portions of the linear sequence of the antigen come in close proximity in 3-dimensional space through the folding of the protein molecule.

"Multispecific" refers to an antibody that specifically binds at least two distinct antigens or two distinct epitopes within the antigens, for example three, four or five distinct antigens or epitopes.

"Bispecific" refers to an antibody that specifically binds two distinct antigens or two distinct epitopes within the same antigen. The bispecific antibody may have cross-reactivity to other related antigens or can bind an epitope that is shared between two or more distinct antigens.

"Variant" refers to a polypeptide or a polynucleotide that differs from a reference polypeptide or a reference polynucleotide by one or more modifications for example, substitutions, insertions or deletions.

"Vector" refers to a polynucleotide capable of being duplicated within a biological system or that can be moved between such systems. Vector polynucleotides typically contain elements, such as origins of replication, polyadenylation signal or selection markers, that function to facilitate the duplication or maintenance of these polynucleotides in a biological system. Examples of such biological systems may include a cell, virus, animal, plant, and reconstituted biological systems utilizing biological components capable of duplicating a vector. The polynucleotide comprising a vector may be DNA or RNA molecules or a hybrid of these.

"Expression vector" refers to a vector that can be utilized in a biological system or in a reconstituted biological system to direct the translation of a polypeptide encoded by a polynucleotide sequence present in the expression vector.

"Polynucleotide" refers to a synthetic molecule comprising a chain of nucleotides covalently linked by a sugar-phosphate backbone or other equivalent covalent chemistry. cDNA is a typical example of a polynucleotide.

"Polypeptide" or "protein" refers to a molecule that comprises at least two amino acid residues linked by a peptide bond to form a polypeptide. Small polypeptides of less than 50 amino acids may be referred to as "peptides".

"CD40" or "huCD40" refers to the human CD40 protein. CD40 is also known as tumor necrosis factor receptor superfamily member 5 (TNFRSF5), CD40L receptor or CD154 receptor. The amino acid sequence of the full length human CD40 is shown in SEQ ID NO: 75. Human full length CD40 protein is a type I membrane protein with 277 amino acids. Signal sequence spans residues 1-20, extracellular domain spans residues 21-193, transmembrane domain spans residues 194-215, and cytoplasmic domain spans residues 216-277 of SEQ ID NO: 75. Throughout the specification, the extracellular domain of CD40, "CD40-ECD", refers to the CD40 fragment of residues 21-193 of SEQ ID NO: 75.

"Agonist" or "agonistic" refers to an antibody specifically binding human CD40 that induces B-cell and/or dendritic cell (DC) activation upon binding to CD40. B cell and DC activation may be measured by measuring increased B cell proliferation, or by measuring up-regulation of any of the surface markers CD23, CD80, CD83, CD86 and HLA-DR on B cells or CD80, CD83, CD86 and HLA-DR on DC. The agonist may induce B-cell and/or DC activation in a statistically significant manner when compared to a control sample without the antibody.

"Cross-linking" refers to the higher order multimerization of CD40 on cells induced by an antibody specifically binding human CD40 binding to FcγRIIb cis or trans, resulting in induction of CD40 agonistic activity. Cross-linking may be evaluated in vitro by using anti-human F(ab')2 as a cross-linker as described herein.

"Requires cross-linking for agonistic activity" means that the antibody induces CD23 expression on B cells and CD83 surface expression on dendritic cells in the presence of cross-linker anti-human F(ab')2 at 20 µg/ml in a dose-dependent manner, and that the antibody has no effect on CD23 surface expression on B cells and CD83 surface expression on dendritic cells in the absence of the cross-linker, when surface expression is measured using flow cytometry using methods described in Example 1. No effect means that the signal obtained in flow cytometry indicative of surface expression of CD23 and CD83 is within ±1 SD across antibody titration curve at antibody concentrations ranging from $1 \times 10^{-12}$ M to $1 \times 10^{-6}$ M.

"About" means within an acceptable error range for the particular value as determined by one of ordinary skill in the art, which will depend in part on how the value is measured or determined, i.e., the limitations of the measurement system. Unless explicitly stated otherwise within the Examples or elsewhere in the Specification in the context of a particular assay, result or embodiment, "about" means within one standard deviation per practice in the art, or a range of up to 5%, whichever is larger.

"In combination with" means that two or more therapeutics are be administered to a subject together in a mixture, concurrently as single agents or sequentially as single agents in any order.

Conventional one and three-letter amino acid codes are used herein as shown in Table 1.

TABLE 1

| Amino acid | Three-letter code | One-letter code |
|---|---|---|
| Alanine | Ala | A |
| Arginine | Arg | R |
| Asparagine | Asn | N |
| Aspartate | Asp | D |
| Cysteine | Cys | C |
| Glutamate | Gln | E |
| Glutamine | Glu | Q |
| Glycine | Gly | G |
| Histidine | His | H |
| Isoleucine | Ile | I |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Agonistic Antibodies Specifically Binding Human CD40

The present invention provides agonistic antibodies specifically binding human CD40 that are potent in activating antigen presenting cells (APCs) and B cells. The antibodies may demonstrate minimal or no agonistic activity in the absence of cross-linking, therefore the antibodies may have an improved safety profile while maintaining efficacy when compared to other anti-CD40 antibodies in clinical development for cancer indications.

CD40 agonist CP-870,893, developed as wild-type $IgG_2$, has been previously tested in clinical trials in subjects having pancreatic cancer or melanoma. CP-870,893 is able to activate APCs without the need of cross-linking and is about 20-fold more potent in activating B cells than dendritic cells. This superagonistic activity as a bivalent, soluble mAb coupled with preferential activation of B cells may lead to cytokine release syndrome (CRS) induced by IL-6 secreted by B cells. In patient clinical trials, the most common side effects from this antibody was moderate CRS, characterized by chills, fevers, rigors and other symptoms on the day of antibody intravenous infusion. The effect of CP-870,893 on B cells may thus result in dose-limiting toxicity at a treatment dose which is insufficient to activate APCs.

The agonistic antibodies specifically binding human CD40 of the invention which require cross-linking for their agonistic activity may have decreased CRS-induced potential toxicity. While not wishing to be bound by any particular theory, it is anticipated that the circulating APCs in the periphery are less likely to be activated by the agonistic antibodies specifically binding CD40 of the invention as the antibodies need to reach tissues for significant higher order multimerization to occur via FcγR cross linking, and to result in subsequent APCs activation. The activation of APCs (for example dendritic cells) may be of greater clinical relevance than B cell activation. CD40 agonist therapy of cancer is firmly linked to T cell activation (French et al., 1999, Nature Medicine, 548-553; van Kooten et al., 2000, J Leucoc Biol, 67:2-17; Sotomayor et al., 1999, Nature Medicine, 5:780-787), and this T cell activation depends on activation of professional antigen presenting cells, in particular dendritic cells (Melief et al., 2000, 75: 235-282).

The invention provides for an isolated agonistic antibody specifically binding human CD40 of SEQ ID NO: 75.

The invention also provides for an isolated agonistic antibody specifically binding human CD40 of SEQ ID NO: 75, wherein the antibody requires cross-linking for its agonistic activity.

CD40 is a cell-surface expressed glycoprotein that belongs to the tumor necrosis factor receptor (TNFR) superfamily and plays a central role in the immune system. It is expressed on a variety of immune cells, such as B cells, dendritic cells, monocytes, and macrophages, which cells are activated when signaling via CD40 occurs (reviewed by Tasci et al., 2001, Cell. Mol. Life. Sci., (58), 4-43).

Dendritic cell and B cell activation mediated by CD40 signaling triggers several biological events, including immune cell activation, proliferation, and production of cytokines and chemokines. Methods for determining dendritic cell and B cell activation associated with CD40 are known in the art (Schonbeck et al., 2001, *Cell Mol Life Sci.*, 58:40-43; van Kooten et al., 2000, *J. Leuk., Biol.*, 67: 2-17) and are described herein. An exemplary method is assessment of upregulation of surface markers CD23, CD80, CD83, CD86 and HLA-DR, or a combination thereof, using standard methods such as cytometry.

Dependency on cross-linking for agonistic activity may be assessed in vitro using known methods. For example, B cell or DC activation may be assessed in the absence and in the presence of the cross-linker, such as anti-immunoglobulin antibody. In vivo, cross-linking typically occurs via interaction of antibody Fc with FcγR.

Exemplary agonistic antibodies specifically binding human CD40 requiring cross-linking for their agonistic activity are antibodies C40M67, C40M66, C40M63, C40M62, C40M59, C40M58, C40M56, C40M55, C40M51, C40M18, C40M17, C40M12, C40M102, C40M103, C40M104, C40M105 and C40M121 described herein.

An exemplary agonistic antibody specifically binding human CD40 that agonizes CD40 in cross-linking independent manner is the antibody C40M126. C40M126 has a S267E mutation in an Fc region converting the antibody to cross-linking independent agonist. C40M126 and a cross-linking dependent agonistic mAb C40M121 have identical heavy chain and light chain amino acid sequences except for the S267E mutation.

The invention also provides for an isolated agonistic antibody specifically binding human CD40 that induces CD80, CD83, CD86 and HLA-DR expression measured using flow cytometry on human dendritic cells.

In some embodiment, the isolated agonistic antibody specifically binding human CD40 induces CD23, CD80, CD83, CD86 and HLA-DR expression measured using flow cytometry on human B cells.

In some embodiments, the isolated agonistic antibody specifically binding human CD40 induces CD83 expression measured using flow cytometry on human dendritic cells.

In some embodiments, the isolated agonistic antibody specifically binding human CD40 induces CD23 expression measured using flow cytometry on human B cells.

The invention also provides for an isolated agonistic antibody or an antigen-binding fragment thereof specifically binding human CD40 of SEQ ID NO: 75, comprising a heavy chain variable region (HCDR) 1 of SEQ ID NO: 5, a HCDR2 of SEQ ID NO: 10, a HCDR3 of SEQ ID NO: 18, a light chain variable region (LCDR) 1 of SEQ ID NO: 32, a LCDR2 of SEQ ID NO: 34 and a LCDR3 of SEQ ID NO: 47.

In some embodiments, the antibody binds to human CD40 within residues 46-64 and 75-76 of SEQ ID NO: 75. "Within" means that 80% or more of the epitope residues the antibody binds to reside within the amino acid stretches 46-64 or 75-76, and that up to 20% of the epitope residues the antibody binds to reside outside of the recited amino acid stretches 46-64 or 75-76.

The CD40 epitope the antibody binds to may be resolved for example using hydrogen/deuterium exchange (H/D exchange) or by analyzing a crystal structure of the antibody in complex with CD40. The epitope residues are those which are protected by the antibody by at least 5% difference in deuteration levels through H/D exchange or those surface exposed amino acid residues determined to bind the antibody in a crystal structure of a complex of the antibody and CD40. In the crystal structure of a complex of the antibody and CD40, the epitope residues are those CD40 residues that reside within 4 Å distance or less from any of the antibody CDR residues.

In an H/D exchange assay, CD40 protein is incubated in the presence or absence of the antibody in deuterated water for predetermined times resulting in deuterium incorporation at exchangeable hydrogen atoms which are unprotected by the antibody, followed by protease digestion of the protein and analyses of the peptide fragments using LC-MS. In an exemplary assay, 5 µL of the test antibody (10 µg) or 5 µL of the complex of CD40 and the test antibody (10 & 7.35 µg, respectively) is incubated with 120 µL deuterium oxide labeling buffer (50 mM phosphate, 100 mM sodium chloride at pH 7.4) for 0 sec, 60 sec, 300 sec, 1800 sec, 7200 sec, and 14400 sec. Deuterium exchange is quenched by adding 63 µL of 5 M guanidine hydrochloride and final pH is 2.5. The quenched sample is subjected to on-column pepsin/protease type XIII digestion and LC-MS analysis. For pepsin/protease type XIII digestion, 5 µg of the samples in 125 µL control buffer (50 mM phosphate, 100 mM sodium chloride at pH 7.4) are denatured by adding 63 µL of 5 M guanidine hydrochloride (final pH is 2.5) and incubating the mixture for 3 min. Then, the mixture is subjected to on-column pepsin/protease type XIII digestion and the resultant peptides analyzed using an UPLC-MS system comprised of a Waters Acquity UPLC coupled to a Q Exactive™ Hybrid Quadrupole-Orbitrap Mass Spectrometer (Thermo). Raw MS data is processed using HDX WorkBench, software for the analysis of H/D exchange MS data. The deuterium levels are calculated using the average mass difference between the deuteriated peptide and its native form ($t_0$). Peptide identification is done through searching MS/MS data against the CD40 sequence with Mascot. The mass tolerance for the precursor and product ions is 20 ppm and 0.05 Da, respectively.

For X-ray crystallography, CD40 and the test antibody are expressed and purified using standard protocols. The CD40/test antibody complex is incubated overnight at 4° C., concentrated, and separated from the uncomplexed species using size-exclusion chromatography. The complex is crystallized by the vapor-diffusion method from various known test solutions for example solutions containing PEG3350, ammonium citrate and 2-(N-Morpholino)ethanesulfonic acid (MES).

Antibodies binding within human CD40 residues 46-64 and 75-76 of SEQ ID NO: 75 may be generated by isolating antibodies binding CD40 using phage display libraries, selecting those antibodies that compete with the reference antibody C40M126 (VH of SEQ ID NO: 62 and VL of SEQ ID NO: 69) for binding to CD40 by 100%, and confirming the epitope of the generated antibodies by solving the crystal structure of the antibody/CD40 complex. Alternatively, mice, rats or rabbits may be immunized using peptides encompassing residues 46-64 and 75-76 of SEQ ID NO: 75 and the generated antibodies may be evaluated for their binding within the recited region.

In some embodiments, the antibody has at least one of the following properties: binds to human CD40 of SEQ ID NO: 75 with a dissociation constant ($K_D$) of about $5\times10^{-9}$ M or less, when the $K_D$ is measured using ProteOn XPR36 system at 25° C. in Dulbecco's phosphate buffered saline containing 0.01% polysorbate 20 (PS-20) and 100 µg/ml bovine serum albumin; or requires cross-linking for its agonistic activity on B cells and on dendritic cells (DC), wherein agonistic activity on B cells is measured by B cell CD23 surface expression and agonistic activity on DCs is measured by DC CD83 surface expression in the presence of cross-linker anti-human F(ab')2 at 20 µg/ml in, when CD23 and CD83 surface expression is measured using flow cytometry.

The affinity of an antibody to human CD40 may be determined experimentally using any suitable method. An exemplary method utilizes ProteOn XPR36, Biacore 3000 or KinExA instrumentation, ELISA or competitive binding assays known to those skilled in the art. The measured affinity of a particular antibody to CD40 may vary if measured under different conditions (e.g., osmolarity, pH). Thus, measurements of affinity and other binding parameters (e.g., $K_D$, $K_{on}$, and $K_{off}$) are typically made with standardized conditions and a standardized buffer, such as the buffer described herein. Skilled in the art will appreciate that the internal error for affinity measurements for example using Biacore 3000 or ProteOn (measured as standard deviation, SD) can typically be within 5-33% for measurements within the typical limits of detection. Therefore, the term "about" when referring to a $K_D$ value reflects the typical standard deviation in the assay. For example, the typical SD for a $K_D$ of $1\times10^{-9}$ M is up to $\pm 0.33\times10^{-9}$ M.

For B cell activation assays, human B cells may be isolated from fresh or frozen PBMC using B cells negative isolation kit per manufacturer's protocol (MACS Miltenyi). For DC activation assays, human monocytes may be isolated from either frozen/fresh PBMC using CD14 negative isolation kit per manufacturer's protocol (MACS Miltenyi), cultured for 5 days in complete media RPMI (Invitrogen) in the presence of 100 ng/ml human GM-CSF and human IL-4 (Peprotech) and media replenished every 2 days. Titrations of test CD40 antibodies may be plated on 96-well U bottom plate and either B cells or DCs may be added and the mixture may be incubated for 15 minutes at room temperature. Either media or cross-linker anti-human F(ab')2 at a fixed concentration 20 µg/ml may be added and the complex may be incubated for 24 hours for DC activation assay and 48 hours for B cell activation assay at 37° C. Cells may be harvested at the end of time point, washed twice with flow buffer and incubated with human Fc block (Miltenyi) for 15 minutes at room temperature followed with one wash. Cells may then be stained for activation markers CD23 or CD83 for 30 minutes on ice, followed with two washes. Cells are analyzed using BD Fortessa. Alternatively, surface expression of activation markers CD80, CD86, HLA-DR may also be assessed.

In some embodiments, the antibody heavy chain framework is derived from human IGHV4-39*01 (SEQ ID NO: 73) and the antibody light chain framework derived from human IGLV2-8*01 (SEQ ID NO: 87).

In some embodiments, the antibody comprises a heavy chain variable region (VH) of SEQ ID NOs: 62 or 61 and a light chain variable region (VL) of SEQ ID NO: 69.

In some embodiments, the antibody comprises the VH of SEQ ID NO: 62 and the VL of SEQ ID NO: 69.

In some embodiments, the VH is encoded by a polynucleotide comprising a polynucleotide sequence of SEQ ID NO: 103 and the VL is encoded by a polynucleotide comprising a polynucleotide sequence of SEQ ID NO: 110.

In some embodiments, the antibody comprises the VH of SEQ ID NO: 61 and the VL of SEQ ID NO: 69.

In some embodiments, the VH is encoded by a polynucleotide comprising a polynucleotide sequence of SEQ ID NO: 102 and the VL is encoded by a polynucleotide comprising a polynucleotide sequence of SEQ ID NO: 110.

In some embodiments, the antibody is an IgG1 isotype.

In some embodiments, the antibody is an IgG2 isotype.

In some embodiments, the antibody is an IgG3 isotype.

In some embodiments, the antibody is an IgG4 isotype.

In some embodiments, the antibody comprises the VH of SEQ ID NO: 62 and the VL of SEQ ID NO: 69 and is an IgG1/λ isotype, optionally comprising a S267E mutation when compared to the wild-type IgG1.

In some embodiments, the antibody comprises the VH of SEQ ID NO: 62 and the VL of SEQ ID NO: 69 and is an IgG1/λ isotype, optionally comprising a S267E/I332E mutation when compared to the wild-type IgG1.

In some embodiments, the antibody comprises the VH of SEQ ID NO: 62 and the VL of SEQ ID NO: 69 and is an IgG1/λ isotype, optionally comprising a S267E/L328F mutation when compared to the wild-type IgG1.

In some embodiments, the antibody comprises the VH of SEQ ID NO: 62 and the VL of SEQ ID NO: 69 and is an IgG1/λ isotype, optionally comprising an E233D/G237D/H268D/P271G/A330R/P238D mutation when compared to the wild-type IgG1.

In some embodiments, the antibody comprises the VH of SEQ ID NO: 61 and the VL of SEQ ID NO: 69 and is an IgG1/λ isotype, optionally comprising a S267E mutation when compared to the wild-type IgG1.

In some embodiments, the antibody comprises the VH of SEQ ID NO: 61 and the VL of SEQ ID NO: 69 and is an IgG1/λ isotype, optionally comprising a S267E/I332E mutation when compared to the wild-type IgG1.

In some embodiments, the antibody comprises the VH of SEQ ID NO: 61 and the VL of SEQ ID NO: 69 and is an IgG1/λ isotype, optionally comprising a S267E/L328F mutation when compared to the wild-type IgG1.

In some embodiments, the antibody comprises the VH of SEQ ID NO: 61 and the VL of SEQ ID NO: 69 and is an IgG1/λ isotype, optionally comprising an E233D/G237D/H268D/P271G/A330R/P238D mutation when compared to the wild-type IgG1.

In some embodiments, the antibody comprises a heavy chain (HC) of SEQ ID NO: 129 and a light chain (LC) of SEQ ID NO: 136.

In some embodiments, the HC is encoded by a polynucleotide comprising a polynucleotide sequence of SEQ ID NO: 155 and the LC is encoded by a polynucleotide comprising a polynucleotide sequence of SEQ ID NO: 162.

In some embodiments, the antibody comprises a heavy chain (HC) of SEQ ID NO: 128 and a light chain (LC) of SEQ ID NO: 136.

In some embodiments, the HC is encoded by a polynucleotide comprising a polynucleotide sequence of SEQ ID NO: 154 and the LC is encoded by a polynucleotide comprising a polynucleotide sequence of SEQ ID NO: 162.

In some embodiments, the antibody comprises a heavy chain (HC) of SEQ ID NO: 127 and a light chain (LC) of SEQ ID NO: 136.

In some embodiments, the HC is encoded by a polynucleotide comprising a polynucleotide sequence of SEQ ID NO: 153 and the LC is encoded by a polynucleotide comprising a polynucleotide sequence of SEQ ID NO: 162.

In some embodiments, the antibody is a multispecific antibody.

In some embodiments, the antibody is a bispecific antibody.

The antibody is suitable for use in therapy, for example in treating a cancer.

The antibody is suitable for use in therapy, for example in treating a solid tumor.

The antibody is suitable for use in therapy, for example in treating a melanoma.

The antibody is suitable for use in therapy, for example in treating a lung cancer.

The antibody is suitable for use in therapy, for example in treating a squamous non-small cell lung cancer (NSCLC).

The antibody is suitable for use in therapy, for example in treating a non-squamous NSCLC.

The antibody is suitable for use in therapy, for example in treating a lung adenocarcinoma.

The antibody is suitable for use in therapy, for example in treating a renal cell carcinoma (RCC) (e.g., a kidney clear cell carcinoma or a kidney papillary cell carcinoma), or a metastatic lesion thereof.

The antibody is suitable for use in therapy, for example in treating a mesothelioma.

The antibody is suitable for use in therapy, for example in treating a nasopharyngeal carcinoma (NPC).

The antibody is suitable for use in therapy, for example in treating a colorectal cancer.

The antibody is suitable for use in therapy, for example in treating a prostate cancer or a castration-resistant prostate cancer.

The antibody is suitable for use in therapy, for example in treating a stomach cancer.

The antibody is suitable for use in therapy, for example in treating an ovarian cancer.

The antibody is suitable for use in therapy, for example in treating a gastric cancer.

The antibody is suitable for use in therapy, for example in treating a liver cancer.

The antibody is suitable for use in therapy, for example in treating pancreatic cancer.

The antibody is suitable for use in therapy, for example in treating a thyroid cancer.

The antibody is suitable for use in therapy, for example in treating a squamous cell carcinoma of the head and neck.

The antibody is suitable for use in therapy, for example in treating carcinomas of the esophagus or gastrointestinal tract.

The antibody is suitable for use in therapy, for example in treating a breast cancer.

The antibody is suitable for use in therapy, for example in treating a fallopian tube cancer.

The antibody is suitable for use in therapy, for example in treating a brain cancer.

The antibody is suitable for use in therapy, for example in treating an urethral cancer.

The antibody is suitable for use in therapy, for example in treating an endometriosis.

The antibody is suitable for use in therapy, for example in treating a cervical cancer.

The antibody is suitable for use in therapy, for example in treating a metastatic lesion of the cancer.

The antibody is suitable for use in therapy, for example in treating a multiple myeloma.

The antibody is suitable for use in therapy, for example in treating a lymphoma.

The antibody is suitable for use in therapy, for example in treating a leukemia.

The invention also provides for an isolated agonistic antibody or antigen-binding fragment thereof specifically binding human CD40 of SEQ ID NO: 75, wherein the antibody has at least one of the following properties:

binds to human CD40 of SEQ ID NO: 75 with a dissociation constant ($K_D$) of about $5 \times 10^{-9}$ M or less, when the $K_D$ is measured using ProteOn XPR36 system at 25° C. in Dulbecco's phosphate buffered saline containing 0.01% polysorbate 20 (PS-20) and 100 µg/ml bovine serum albumin; or requires cross-linking for its agonistic activity on B cells and on dendritic cells (DC), wherein agonistic activity on B cells is measured by B cell CD23 surface expression and agonistic activity on DCs is measured by DC CD83 surface expression in the presence of cross-linker anti-human F(ab')2 at 20 µg/ml in, when CD23 and CD83 surface expression is measured using flow cytometry.

In some embodiments, the antibody comprises the HCDR1, the HCDR2, the HCDR3, the LCDR1, the LCDR2 and the LCDR3 of SEQ ID NOs: 1, 8, 22, 28, 38 and 42, respectively, the VH and the VL of SEQ ID NOs: 48 and 63, respectively, and/or the heavy chain (HC) and the light chain (LC) of SEQ ID NOs: 114 and 130, respectively.

In some embodiments, the VH and the VL are encoded by a polynucleotide comprising the polynucleotide sequence of SEQ ID NOs: 89 and 104, respectively.

In some embodiments, the HC and the LC are encoded by a polynucleotide comprising the polynucleotide sequence of SEQ ID NOs: 140 and 156, respectively.

In some embodiments, the antibody comprises the HCDR1, the HCDR2, the HCDR3, the LCDR1, the LCDR2 and the LCDR3 of SEQ ID NOs: 2, 7, 25, 26, 39 and 44, respectively, the VH and the VL of SEQ ID NOs: 49 and 64, respectively, and/or the heavy chain (HC) and the light chain (LC) of SEQ ID NOs: 115 and 131, respectively.

In some embodiments, the VH and the VL are encoded by a polynucleotide comprising the polynucleotide sequence of SEQ ID NOs: 90 and 105, respectively.

In some embodiments, the HC and the LC are encoded by a polynucleotide comprising the polynucleotide sequence of SEQ ID NOs: 141 and 157, respectively.

In some embodiments, the antibody comprises the HCDR1, the HCDR2, the HCDR3, the LCDR1, the LCDR2 and the LCDR3 of SEQ ID NOs: 2, 7, 24, 26, 39 and 44, respectively, the VH and the VL of SEQ ID NOs: 50 and 64, respectively, and/or the heavy chain (HC) and the light chain (LC) of SEQ ID NOs: 116 and 131, respectively.

In some embodiments, the VH and the VL are encoded by a polynucleotide comprising the polynucleotide sequence of SEQ ID NOs: 91 and 105, respectively.

In some embodiments, the HC and the LC are encoded by a polynucleotide comprising the polynucleotide sequence of SEQ ID NOs: 142 and 157, respectively.

In some embodiments, the antibody comprises the HCDR1, the HCDR2, the HCDR3, the LCDR1, the LCDR2 and the LCDR3 of SEQ ID NOs: 2, 7, 23, 26, 39 and 44, respectively, the VH and the VL of SEQ ID NOs: 51 and 64, respectively; and/or the heavy chain (HC) and the light chain (LC) of SEQ ID NOs: 117 and 131, respectively.

In some embodiments, the VH and the VL are encoded by a polynucleotide comprising the polynucleotide sequence of SEQ ID NOs: 92 and 105, respectively.

In some embodiments, the HC and the LC are encoded by a polynucleotide comprising the polynucleotide sequence of SEQ ID NOs: 143 and 157, respectively.

In some embodiments, the antibody comprises the HCDR1, the HCDR2, the HCDR3, the LCDR1, the LCDR2 and the LCDR3 of SEQ ID NOs: 3, 13, 17, 27, 33 and 43, respectively; the VH and the VL of SEQ ID NOs: 52 and 65, respectively; and/or the heavy chain (HC) and the light chain (LC) of SEQ ID NOs: 118 and 132, respectively.

In some embodiments, the VH and the VL are encoded by a polynucleotide comprising the polynucleotide sequence of SEQ ID NOs: 93 and 106, respectively.

In some embodiments, the HC and the LC are encoded by a polynucleotide comprising the polynucleotide sequence of SEQ ID NOs: 144 and 158, respectively.

In some embodiments, the antibody comprises the HCDR1, the HCDR2, the HCDR3, the LCDR1, the LCDR2 and the LCDR3 of SEQ ID NOs: 4, 6, 19, 27, 33 and 43, respectively; the VH and the VL of SEQ ID NOs: 53 and 65, respectively; and/or the heavy chain (HC) and the light chain (LC) of SEQ ID NOs: 119 and 132, respectively.

In some embodiments, the VH and the VL are encoded by a polynucleotide comprising the polynucleotide sequence of SEQ ID NOs: 94 and 106, respectively.

In some embodiments, the HC and the LC are encoded by a polynucleotide comprising the polynucleotide sequence of SEQ ID NOs: 145 and 158, respectively.

In some embodiments, the antibody comprises the HCDR1, the HCDR2, the HCDR3, the LCDR1, the LCDR2 and the LCDR3 of SEQ ID NOs: 4, 6, 20, 27, 33 and 43, respectively; the VH and the VL of SEQ ID NOs: 54 and 65, respectively; and/or the heavy chain (HC) and the light chain (LC) of SEQ ID NOs: 120 and 132, respectively.

In some embodiments, the VH and the VL are encoded by a polynucleotide comprising the polynucleotide sequence of SEQ ID NOs: 95 and 106, respectively.

In some embodiments, the HC and the LC are encoded by a polynucleotide comprising the polynucleotide sequence of SEQ ID NOs: 146 and 158, respectively.

In some embodiments, the antibody comprises the HCDR1, the HCDR2, the HCDR3, the LCDR1, the LCDR2 and the LCDR3 of SEQ ID NOs: 2, 7, 14, 27, 33 and 43, respectively; the VH and the VL of SEQ ID NOs: 55 and 65, respectively; and/or the heavy chain (HC) and the light chain (LC) of SEQ ID NOs: 121 and 132, respectively.

In some embodiments, the VH and the VL are encoded by a polynucleotide comprising the polynucleotide sequence of SEQ ID NOs: 96 and 106, respectively.

In some embodiments, the HC and the LC are encoded by a polynucleotide comprising the polynucleotide sequence of SEQ ID NOs: 147 and 158, respectively.

In some embodiments, the antibody comprises the HCDR1, the HCDR2, the HCDR3, the LCDR1, the LCDR2 and the LCDR3 of SEQ ID NOs: 4, 6, 21, 27, 33 and 43, respectively; the VH and the VL of SEQ ID NOs: 56 and 65, respectively; and/or the heavy chain (HC) and the light chain (LC) of SEQ ID NOs: 122 and 132, respectively.

In some embodiments, the VH and the VL are encoded by a polynucleotide comprising the polynucleotide sequence of SEQ ID NOs: 97 and 106, respectively.

In some embodiments, the HC and the LC are encoded by a polynucleotide comprising the polynucleotide sequence of SEQ ID NOs: 148 and 158, respectively.

In some embodiments, the antibody comprises the HCDR1, the HCDR2, the HCDR3, the LCDR1, the LCDR2 and the LCDR3 of SEQ ID NOs: 4, 9, 15, 30, 36 and 41, respectively, the VH and the VL of SEQ ID NOs: 57 and 66, respectively; and/or the heavy chain (HC) and the light chain (LC) of SEQ ID NOs: 123 and 133, respectively.

In some embodiments, the VH and the VL are encoded by a polynucleotide comprising the polynucleotide sequence of SEQ ID NOs: 98 and 107, respectively.

In some embodiments, the HC and the LC are encoded by a polynucleotide comprising the polynucleotide sequence of SEQ ID NOs: 149 and 159, respectively.

In some embodiments, the antibody comprises the HCDR1, the HCDR2, the HCDR3, the LCDR1, the LCDR2 and the LCDR3 of SEQ ID NOs: 4, 11, 16, 29, 37 and 40, respectively, the VH and the VL of SEQ ID NOs: 58 and 67, respectively; and/or the heavy chain (HC) and the light chain (LC) of SEQ ID NOs: 124 and 134, respectively.

In some embodiments, the VH and the VL are encoded by a polynucleotide comprising the polynucleotide sequence of SEQ ID NOs: 99 and 108, respectively.

In some embodiments, the HC and the LC are encoded by a polynucleotide comprising the polynucleotide sequence of SEQ ID NOs: 150 and 160, respectively.

In some embodiments, the antibody comprises the HCDR1, the HCDR2, the HCDR3, the LCDR1, the LCDR2 and the LCDR3 of SEQ ID NOs: 4, 12, 15, 30, 35 and 46, respectively, the VH and the VL of SEQ ID NOs: 59 and 68, respectively, and/or the heavy chain (HC) and the light chain (LC) of SEQ ID NOs: 125 and 135, respectively.

In some embodiments, the VH and the VL are encoded by a polynucleotide comprising the polynucleotide sequence of SEQ ID NOs: 100 and 109, respectively.

In some embodiments, the HC and the LC are encoded by a polynucleotide comprising the polynucleotide sequence of SEQ ID NOs: 151 and 161, respectively.

In some embodiments, the antibody comprises the HCDR1, the HCDR2, the HCDR3, the LCDR1, the LCDR2 and the LCDR3 of SEQ ID NOs: 4, 9, 15, 30, 36 and 41, respectively, the VH and the VL of SEQ ID NOs: 57 and 70, respectively, and/or the heavy chain (HC) and the light chain (LC) of SEQ ID NOs: 123 and 137, respectively.

In some embodiments, the VH and the VL are encoded by a polynucleotide comprising the polynucleotide sequence of SEQ ID NOs: 98 and 111, respectively.

In some embodiments, the HC and the LC are encoded by a polynucleotide comprising the polynucleotide sequence of SEQ ID NOs: 149 and 163, respectively.

In some embodiments, the antibody comprises the HCDR1, the HCDR2, the HCDR3, the LCDR1, the LCDR2 and the LCDR3 of SEQ ID NOs: 4, 9, 15, 31, 36 and 41, respectively, the VH and the VL of SEQ ID NOs: 57 and 71, respectively, and/or the heavy chain (HC) and the light chain (LC) of SEQ ID NOs: 123 and 138, respectively.

In some embodiments, the VH and the VL are encoded by a polynucleotide comprising the polynucleotide sequence of SEQ ID NOs: 98 and 112, respectively.

In some embodiments, the HC and the LC are encoded by a polynucleotide comprising the polynucleotide sequence of SEQ ID NOs: 149 and 164, respectively.

In some embodiments, the antibody comprises the HCDR1, the HCDR2, the HCDR3, the LCDR1, the LCDR2 and the LCDR3 of SEQ ID NOs: 4, 9, 15, 31, 36 and 41, respectively, the VH and the VL of SEQ ID NOs: 57 and 72, respectively, and/or the heavy chain (HC) and the light chain (LC) of SEQ ID NOs: 123 and 139, respectively.

In some embodiments, the VH and the VL are encoded by a polynucleotide comprising the polynucleotide sequence of SEQ ID NOs: 98 and 113, respectively.

In some embodiments, the HC and the LC are encoded by a polynucleotide comprising the polynucleotide sequence of SEQ ID NOs: 149 and 165, respectively.

In some embodiments, the antibody of the invention comprises heavy chain complementarity determining regions (HCDR) 1 (HCDR1), 2 (HCDR2) and 3 (HCDR3) amino acid sequences of the heavy chain variable region (VH) of SEQ ID NOs: 48, 49, 50, 51, 52, 53, 54, 55, 56, 57, 58, 59, 61 or 62, wherein the HCDRs are defined by Kabat, Chothia or IMGT.

In some embodiments, the antibody of the invention comprises light chain complementarity determining regions (LCDR) 1 (LCDR1), 2 (LCDR2) and 3 (LCDR3) amino acid sequences of the light chain variable region (VL) of SEQ ID NOs: 63, 64, 65, 66, 67, 68, 70, 71 or 72, wherein the LCDRs are defined by Kabat, Chothia or IMGT.

In some embodiments, the antibody of the invention comprises the VH of SEQ ID NOs: 48, 49, 50, 51, 52, 53, 54, 55, 56, 57, 58, 59, 61 or 62.

In some embodiments, the antibody of the invention comprises the VL of SEQ ID NOs: 63, 64, 65, 66, 67, 68, 70, 71 or 72.

The HCDR and LCDR sequence of exemplary anti-CD40 antibodies of the invention are shown in Table 2. The VH, VL, HC and LC protein and amino acid sequences of exemplary anti-CD40 antibodies of the invention are shown in Table 3.

TABLE 2

| mAb | SEQ ID NO: | | | | | | | |
|---|---|---|---|---|---|---|---|---|
| | VH | VL | HCDR1 | HCDR2 | HCDR3 | LCDR1 | LCDR2 | LCDR3 |
| C40M67 | 48 | 63 | 1 | 8 | 22 | 28 | 38 | 42 |
| C40M66 | 49 | 64 | 2 | 7 | 25 | 26 | 39 | 44 |
| C40M63 | 50 | 64 | 2 | 7 | 24 | 26 | 39 | 44 |
| C40M62 | 51 | 64 | 2 | 7 | 23 | 26 | 39 | 44 |
| C40M59 | 52 | 65 | 3 | 13 | 17 | 27 | 33 | 43 |
| C40M58 | 53 | 65 | 4 | 6 | 19 | 27 | 33 | 43 |
| C40M56 | 54 | 65 | 4 | 6 | 20 | 27 | 33 | 43 |
| C40M55 | 55 | 65 | 2 | 7 | 14 | 27 | 33 | 43 |
| C40M51 | 56 | 65 | 4 | 6 | 21 | 27 | 33 | 43 |
| C40M18 | 57 | 66 | 4 | 9 | 15 | 30 | 36 | 41 |
| C40M17 | 58 | 67 | 4 | 11 | 16 | 29 | 37 | 40 |
| C40M12 | 59 | 68 | 4 | 12 | 15 | 30 | 35 | 46 |
| C40M9 | 60 | 69 | 5 | 10 | 18 | 32 | 34 | 47 |
| C40M102 | 57 | 70 | 4 | 9 | 15 | 30 | 36 | 41 |
| C40M103 | 57 | 71 | 4 | 9 | 15 | 31 | 36 | 41 |
| C40M104 | 57 | 72 | 4 | 9 | 15 | 31 | 36 | 41 |
| C40M105 | 61 | 69 | 5 | 10 | 18 | 32 | 34 | 47 |
| C40M121 | 62 | 69 | 5 | 10 | 18 | 32 | 34 | 47 |
| C40M126 | 62 | 69 | 5 | 10 | 18 | 32 | 34 | 47 |

TABLE 3

| mAb | Amino acid sequences | | | | DNA sequences | | | |
|---|---|---|---|---|---|---|---|---|
| | VH SEQ ID NO: | VL SEQ ID NO: | HC SEQ ID NO: | LC SEQ ID NO: | VH DNA SEQ ID NO: | VL DNA SEQ ID NO: | HC DNA SEQ ID NO: | LC DNA SEQ ID NO: |
| C40M67 | 48 | 63 | 114 | 130 | 89 | 104 | 140 | 156 |
| C40M66 | 49 | 64 | 115 | 131 | 90 | 105 | 141 | 157 |
| C40M63 | 50 | 64 | 116 | 131 | 91 | 105 | 142 | 157 |
| C40M62 | 51 | 64 | 117 | 131 | 92 | 105 | 143 | 157 |
| C40M59 | 52 | 65 | 118 | 132 | 93 | 106 | 144 | 158 |
| C40M58 | 53 | 65 | 119 | 132 | 94 | 106 | 145 | 158 |
| C40M56 | 54 | 65 | 120 | 132 | 95 | 106 | 146 | 158 |
| C40M55 | 55 | 65 | 121 | 132 | 96 | 106 | 147 | 158 |
| C40M51 | 56 | 65 | 122 | 132 | 97 | 106 | 148 | 158 |
| C40M18 | 57 | 66 | 123 | 133 | 98 | 107 | 149 | 159 |
| C40M17 | 58 | 67 | 124 | 134 | 99 | 108 | 150 | 160 |
| C40M12 | 59 | 68 | 125 | 135 | 100 | 109 | 151 | 161 |
| C40M9 | 60 | 69 | 126 | 136 | 101 | 110 | 152 | 162 |
| C40M102 | 57 | 70 | 123 | 137 | 98 | 111 | 149 | 163 |
| C40M103 | 57 | 71 | 123 | 138 | 98 | 112 | 149 | 164 |
| C40M104 | 57 | 72 | 123 | 139 | 98 | 113 | 149 | 165 |
| C40M105 | 61 | 69 | 127 | 136 | 102 | 110 | 153 | 162 |
| C40M121 | 62 | 69 | 128 | 136 | 103 | 110 | 154 | 162 |
| C40M126 | 62 | 69 | 129 | 136 | 103 | 110 | 155 | 162 |

Variants of the agonistic antibodies specifically binding CD40 of the invention are within the scope of the invention. For example, variants may comprise one, two, three, four, five, six, seven, eight, nine, ten, eleven, twelve, thirteen, fourteen or fifteen amino acid substitutions in the VH and/or the VL that do not adversely affect the antibody properties. In some embodiments, the sequence identity may be about 90%, 91%, 92%, 93%, 94%, 95%, 96%, 97%, 98% or 99% to a VH or the VL amino acid sequence of the invention.

The percent identity between the two sequences is a function of the number of identical positions shared by the sequences (i.e., % identity=# of identical positions/total # of positions ×100), taking into account the number of gaps, and the length of each gap, which need to be introduced for optimal alignment of the two sequences.

The percent identity between two amino acid sequences may be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percent identity between two amino acid sequences may be determined using the Needleman and Wunsch (J. Mol. Biol. 48:444-453 (1970)) algorithm which has been incorporated into the GAP program in the GCG software package (available at http_//_wwwgcg_com), using either a Blossum 62 matrix or a PAM250 matrix, and a gap weight of 16, 14, 12, 10, 8, 6, or 4 and a length weight of 1, 2, 3, 4, 5, or 6.

In some embodiments, the agonistic antibody specifically binding human CD40 comprises the VH that is at least 90%, 91%, 92%, 93%, 94%, 95%, 96%, 97%, 98%, 99% or 100% identical to the VH of SEQ ID NOs: 48, 49, 50, 51, 52, 53, 54, 55, 56, 57, 58, 59, 61 or 62.

In some embodiments, the agonistic antibody specifically binding human CD40 comprises the VL that is at least 90%, 91%, 92%, 93%, 94%, 95%, 96%, 97%, 98%, 99% or 100% identical to the VL of SEQ ID NOs: 63, 64, 65, 66, 67, 68, 70, 71 or 72.

In some embodiments, the agonistic antibody specifically binding human CD40 of the invention comprises the VH that is at least 90%, 91%, 92%, 93%, 94%, 95%, 96%, 97%, 98%, 99% or 100% identical to the VH of SEQ ID NOs: 48, 49, 50, 51, 52, 53, 54, 55, 56, 57, 58, 59, 61 or 62, and the VL that is at least 90%, 91%, 92%, 93%, 94%, 95%, 96%, 97%, 98%, 99% or 100% identical to the VL of SEQ ID NOs: 63, 64, 65, 66, 67, 68, 70, 71 or 72.

In some embodiments, the agonistic antibody specifically binding human CD40 of the invention comprises the VH of SEQ ID NO: 48 and the VL or SEQ ID NO: 63, wherein the VH, the VL or both the VH and the VL optionally comprise one, two, three, four, five, six, seven, eight, nine, ten, eleven, twelve, thirteen, fourteen or fifteen amino acid substitutions.

In some embodiments, the agonistic antibody specifically binding human CD40 of the invention comprises the VH of SEQ ID NO: 49 and the VL or SEQ ID NO: 64, wherein the VH, the VL or both the VH and the VL optionally comprise one, two, three, four, five, six, seven, eight, nine, ten, eleven, twelve, thirteen, fourteen or fifteen amino acid substitutions.

In some embodiments, the agonistic antibody specifically binding human CD40 comprises the VH of SEQ ID NO: 50 and the VL or SEQ ID NO: 64, wherein the VH, the VL or both the VH and the VL optionally comprise one, two, three, four, five, six, seven, eight, nine, ten, eleven, twelve, thirteen, fourteen or fifteen amino acid substitutions.

In some embodiments, the agonistic antibody specifically binding human CD40 comprises the VH of SEQ ID NO: 51 and the VL or SEQ ID NO: 64, wherein the VH, the VL or both the VH and the VL optionally comprise one, two, three, four, five, six, seven, eight, nine, ten, eleven, twelve, thirteen, fourteen or fifteen amino acid substitutions.

In some embodiments, the agonistic antibody specifically binding human CD40 comprises the VH of SEQ ID NO: 52 and the VL or SEQ ID NO: 65, wherein the VH, the VL or both the VH and the VL optionally comprise one, two, three, four, five, six, seven, eight, nine, ten, eleven, twelve, thirteen, fourteen or fifteen amino acid substitutions.

In some embodiments, the agonistic antibody specifically binding human CD40 comprises the VH of SEQ ID NO: 53 and the VL or SEQ ID NO: 65, wherein the VH, the VL or both the VH and the VL optionally comprise one, two, three, four, five, six, seven, eight, nine, ten, eleven, twelve, thirteen, fourteen or fifteen amino acid substitutions.

In some embodiments, the agonistic antibody specifically binding human CD40 comprises the VH of SEQ ID NO: 54 and the VL or SEQ ID NO: 65, wherein the VH, the VL or both the VH and the VL optionally comprise one, two, three, four, five, six, seven, eight, nine, ten, eleven, twelve, thirteen, fourteen or fifteen amino acid substitutions.

In some embodiments, the agonistic antibody specifically binding human CD40 comprises the VH of SEQ ID NO: 55 and the VL or SEQ ID NO: 65, wherein the VH, the VL or both the VH and the VL optionally comprise one, two, three, four, five, six, seven, eight, nine, ten, eleven, twelve, thirteen, fourteen or fifteen amino acid substitutions.

In some embodiments, the agonistic antibody specifically binding human CD40 comprises the VH of SEQ ID NO: 56 and the VL or SEQ ID NO: 65, wherein the VH, the VL or both the VH and the VL optionally comprise one, two, three, four, five, six, seven, eight, nine, ten, eleven, twelve, thirteen, fourteen or fifteen amino acid substitutions.

In some embodiments, the agonistic antibody specifically binding human CD40 comprises the VH of SEQ ID NO: 57 and the VL or SEQ ID NO: 66, wherein the VH, the VL or both the VH and the VL optionally comprise one, two, three, four, five, six, seven, eight, nine, ten, eleven, twelve, thirteen, fourteen or fifteen amino acid substitutions.

In some embodiments, the agonistic antibody specifically binding human CD40 comprises the VH of SEQ ID NO: 58 and the VL or SEQ ID NO: 67, wherein the VH, the VL or both the VH and the VL optionally comprise one, two, three, four, five, six, seven, eight, nine, ten, eleven, twelve, thirteen, fourteen or fifteen amino acid substitutions.

In some embodiments, the agonistic antibody specifically binding human CD40 comprises the VH of SEQ ID NO: 59 and the VL or SEQ ID NO: 68, wherein the VH, the VL or both the VH and the VL optionally comprise one, two, three, four, five, six, seven, eight, nine, ten, eleven, twelve, thirteen, fourteen or fifteen amino acid substitutions.

In some embodiments, the agonistic antibody specifically binding human CD40 comprises the VH of SEQ ID NO: 57 and the VL or SEQ ID NO: 70, wherein the VH, the VL or both the VH and the VL optionally comprise one, two, three, four, five, six, seven, eight, nine, ten, eleven, twelve, thirteen, fourteen or fifteen amino acid substitutions.

In some embodiments, the agonistic antibody specifically binding human CD40 comprises the VH of SEQ ID NO: 57 and the VL or SEQ ID NO: 71, wherein the VH, the VL or both the VH and the VL optionally comprise one, two, three, four, five, six, seven, eight, nine, ten, eleven, twelve, thirteen, fourteen or fifteen amino acid substitutions.

In some embodiments, the agonistic antibody specifically binding human CD40 comprises the VH of SEQ ID NO: 57 and the VL or SEQ ID NO: 72, wherein the VH, the VL or both the VH and the VL optionally comprise one, two, three, four, five, six, seven, eight, nine, ten, eleven, twelve, thirteen, fourteen or fifteen amino acid substitutions.

In some embodiments, the agonistic antibody specifically binding human CD40 comprises the VH of SEQ ID NO: 61 and the VL or SEQ ID NO: 69, wherein the VH, the VL or both the VH and the VL optionally comprise one, two, three, four, five, six, seven, eight, nine, ten, eleven, twelve, thirteen, fourteen or fifteen amino acid substitutions.

In some embodiments, the agonistic antibody specifically binding human CD40 comprises the VH of SEQ ID NO: 62 and the VL or SEQ ID NO: 69, wherein the VH, the VL or both the VH and the VL optionally comprise one, two, three, four, five, six, seven, eight, nine, ten, eleven, twelve, thirteen, fourteen or fifteen amino acid substitutions.

In some embodiments, the agonistic antibody specifically binding human CD40 comprises a heavy chain variable region comprising HCDR1, HCDR2 and HCDR3 sequences and a light chain variable region comprising LCDR1, LCDR2 and LCDR3 sequences, wherein one or more of the CDR sequences comprise specified amino acid sequences based on the antibodies described herein (for example, antibodies shown in Table 2) or conservative modifications thereof, and wherein the antibodies retain the desired functional properties of the agonistic antibodies specifically binding CD40 of the invention.

The agonistic antibody specifically binding human CD40 comprising certain HCDR1, HCDR2, HCDR3, LCDR1, LCDR2 and LCDR3 sequences and conservative modifications thereof has at least one of the following properties:

binds to human CD40 of SEQ ID NO: 75 with a dissociation constant ($K_D$) of about $5 \times 10^{-9}$ M or less, when the $K_D$ is measured using ProteOn XPR36 system at 25° C. in Dulbecco's phosphate buffered saline containing 0.01% polysorbate 20 (PS-20) and 100 µg/ml bovine serum albumin; or requires cross-linking for its agonistic activity on B cells and on dendritic cells (DC), wherein agonistic activity on B cells is measured by B cell CD23 surface expression and agonistic activity on DCs is measured by DC CD83 surface expression in the presence of cross-linker anti-human F(ab')2 at 20 µg/ml in, when CD23 and CD83 surface expression is measured using flow cytometry.

"Conservative modification" refers to amino acid modifications that do not significantly affect or alter the binding characteristics of the antibody containing the amino acid sequences. Conservative modifications include amino acid substitutions, additions and deletions. Conservative substitutions are those in which the amino acid is replaced with an amino acid residue having a similar side chain. The families of amino acid residues having similar side chains are well defined and include amino acids with acidic side chains (for example, aspartic acid, glutamic acid), basic side chains (for example, lysine, arginine, histidine), nonpolar side chains (for example, alanine, valine, leucine, isoleucine, proline, phenylalanine, methionine), uncharged polar side chains (for example, glycine, asparagine, glutamine, cysteine, serine, threonine, tyrosine, tryptophan), aromatic side chains (for example, phenylalanine, tryptophan, histidine, tyrosine), aliphatic side chains (for example, glycine, alanine, valine, leucine, isoleucine, serine, threonine), amide (for example, asparagine, glutamine), beta-branched side chains (for example, threonine, valine, isoleucine) and sulfur-containing side chains (cysteine, methionine). Furthermore, any native residue in the polypeptide may also be substituted with alanine, as has been previously described for alanine scanning mutagenesis (MacLennan et al., Acta Physiol. Scand. Suppl. 643:55-67, 1998; Sasaki et al., Adv. Biophys. 35:1-24, 1998). Amino acid substitutions to the antibodies of the invention may be made by well-known methods for example by PCR mutagenesis (U.S. Pat. No. 4,683,195). Alternatively, libraries of variants may be generated using known methods, for example using random (NNK) or non-random codons, for example DVK codons, which encode 11 amino acids (Ala, Cys, Asp, Glu, Gly, Lys, Asn, Arg, Ser, Tyr, Trp). The resulting antibody variants may be tested for their characteristics using assays described herein.

Although the embodiments illustrated in the Examples comprise pairs of variable regions, one from a heavy chain and one from a light chain, a skilled artisan will recognize that alternative embodiments may comprise single heavy or light chain variable regions. The single variable region may be used to screen for variable domains capable of forming a two-domain specific antigen-binding fragment capable of for example specifically binding to CD40. The screening may be accomplished by phage display screening methods using for example hierarchical dual combinatorial approach disclosed in Int. Pat. Publ. No. WO1992/01047. In this approach, an individual colony containing either a H or L chain clone, is used to infect a complete library of clones encoding the other chain (L or H), and the resulting two-chain specific antigen-binding domain is selected in accordance with phage display techniques as described herein and tested for its binding to CD40 and agonistic activity.

Antibodies of the invention may be generated using various technologies. For example, the hybridoma method of Kohler and Milstein, Nature 256:495, 1975 may be used to generate monoclonal antibodies. In the hybridoma method, a mouse or other host animal, such as a hamster, rat or monkey, is immunized with human or cyno CD40 fragments of CD40, such as extracellular domain of CD40, followed by fusion of spleen cells from immunized animals with myeloma cells using standard methods to form hybridoma cells (Goding, Monoclonal Antibodies: Principles and Practice, pp. 59-103 (Academic Press, 1986)). Colonies arising from single immortalized hybridoma cells are screened for production of antibodies with desired properties, such as specificity of binding, cross-reactivity or lack thereof, and affinity for the antigen.

Various host animals may be used to produce the CD40 antibodies of the invention. For example, Balb/c mice may be used to generate mouse anti-human CD40 antibodies. The antibodies made in Balb/c mice and other non-human animals may be humanized using various technologies to generate more human-like sequences. Exemplary humanization techniques including selection of human acceptor frameworks are known and include CDR grafting (U.S. Pat. No. 5,225,539), SDR grafting (U.S. Pat. No. 6,818,749), resurfacing (Padlan, Mol Immunol 28:489-499, 1991), specificity determining residues resurfacing (U.S. Pat. Publ. No. 20100261620), human-adaptation (or human framework adaptation) (U.S. Pat. Publ. No. 2009/0118127), Superhumanization (U.S. Pat. No. 7,709,226) and guided selection (Osbourn et al., Methods 36:61-68, 2005; U.S. Pat. No. 5,565,332). In these methods, CDRs of parental antibodies are transferred onto human frameworks that may be selected based on their overall homology to the parental frameworks, based on framework CDR length, homology or canonical structure information, or a combination thereof.

Humanized antibodies may be further optimized to improve their selectivity or affinity to a desired antigen by incorporating altered framework support residues to preserve binding affinity (backmutations) by techniques such as those disclosed as described in Int. Pat. Publ. No. WO90/007861 and in Int. Pat. Publ. No. WO92/22653, or by introducing variation to any of the CDRs to improve for example affinity of the antibody.

Transgenic mice carrying human immunoglobulin (Ig) loci in their genome may be used to generate human antibodies against a target protein, as described in for example Int. Pat. Publ. No. WO90/04036, U.S. Pat. No. 6,150,584, Int. Pat. Publ. No. WO99/45962, Int. Pat. Publ. No. WO02/066630, Int. Pat. Publ. No. WO02/43478, Lonberg et al (1994) Nature 368:856-9; Green et al (1994) Nature Genet. 7:13-21; Green & Jakobovits (1998) Exp. Med. 188:483-95; Lonberg and Huszar (1995) Int. Rev. Immunol. 13:65-93; Bruggemann et al (1991) Eur. J. Immunol. 21:1323-1326; Fishwild et al (1996) Nat. Biotechnol. 14:845-851; Mendez et al (1997) Nat. Genet. 15:146-156; Green (1999) Immunol. Methods 231:11-23; Yang et al (1999) Cancer Res. 59:1236-1243; Brüggemann and Taussig (1997) Curr. Opin. Biotechnol. 8:455-458; Int. Pat. Publ. No. WO02/043478). The endogenous immunoglobulin loci in such mice may be disrupted or deleted, and at least one complete or partial human immunoglobulin locus may be inserted into the mouse genome using homologous or non-homologous recombination, using transchromosomes, or using minigenes. Companies such as Regeneron (http_//_www_regeneron_com), Harbour Antibodies (http_//_www_harbourantibodiescom), Open Monoclonal Technology, Inc. (OMT) (http_//_www_omtincnet), KyMab (http_//_www_kymab_com), Trianni (http//_www.trianni_com) and Ablexis (http_//_www_ablexis_com) may be engaged to provide human antibodies directed against a selected antigen using technology as described above.

Human antibodies may be selected from a phage display library, where the phage is engineered to express human immunoglobulins or portions thereof such as Fabs, single chain antibodies (scFv), or unpaired or paired antibody variable regions (Knappik et al., J. Mol Biol 296:57-86, 2000; Krebs et al., J Immunol Meth 254:67-84, 2001; Vaughan et al., Nature Biotechnology 14:309-314, 1996; Sheets et al., PITAS (USA) 95:6157-6162, 1998; Hoogenboom and Winter, J Mol Biol 227:381, 1991; Marks et al., J Mol Biol 222:581, 1991). The antibodies of the invention may be isolated for example from phage display library expressing antibody heavy and light chain variable regions as fusion proteins with bacteriophage pIX coat protein as described in Shi et al., *J Mol Biol* 397:385-96, 2010 and Int. Pat. Publ. No. WO09/085462). The libraries may be screened for phage binding to human and/or cyno CD40 and the obtained positive clones may further be characterized, the Fabs isolated from the clone lysates, and expressed as full length IgGs. Such phage display methods for isolating human antibodies are described in for example: U.S. Pat. Nos. 5,223,409; 5,403,484; and U.S. Pat. No. 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Preparation of immunogenic antigens and monoclonal antibody production may be performed using any suitable technique, such as recombinant protein production. The immunogenic antigens may be administered to an animal in the form of purified protein, or protein mixtures including whole cells or cell or tissue extracts, or the antigen may be formed de novo in the animal's body from nucleic acids encoding said antigen or a portion thereof.

The antibodies of the invention may be human or humanized.

In some embodiments, the agonistic antibodies specifically binding human CD40 of the invention comprise a VH framework derived from human IGHV3-23*03 (SEQ ID NO: 79), IGHV1-69*01 (SEQ ID NO: 80), IGHV3-23*01 (SEQ ID NO: 81), IGHV3-23*04 (SEQ ID NO: 82) or IGHV4-39*01 (SEQ ID NO: 73).

In some embodiments, the agonistic antibodies specifically binding human CD40 of the invention comprise a VL framework derived from human IGKV3-20*1 (SEQ ID NO: 74), IGKV4-1*01 (SEQ ID NO: 84), IGKV1-39*01 (SEQ ID NO: 85), IGLV3-1*01 (SEQ ID NO: 86) or IGLV2-8*01 (SEQ ID NO: 87).

In some embodiments, the agonistic antibodies specifically binding human CD40 of the invention comprise a heavy chain framework derived from human IGHV3-23*03 (SEQ ID NO: 79) and a light chain framework derived from human IGKV3-20*01 (SEQ ID NO: 74).

In some embodiments, the agonistic antibodies specifically binding human CD40 of the invention comprise a heavy chain framework derived from human IGHV1-69*01 (SEQ ID NO: 80) and a light chain framework derived from human IGKV4-1*01 (SEQ ID NO: 84).

In some embodiments, the agonistic antibodies specifically binding human CD40 of the invention comprise a heavy chain framework derived from human IGHV1-69*01 (SEQ ID NO: 80) and a light chain framework derived from human IGKV1-39*01 (SEQ ID NO: 85).

In some embodiments, the agonistic antibodies specifically binding human CD40 of the invention comprise a heavy chain framework derived from human IGHV3-23*01 (SEQ ID NO: 81) and a light chain framework derived from human IGKV1-39*01 (SEQ ID NO: 85).

In some embodiments, the agonistic antibodies specifically binding human CD40 of the invention comprise a heavy chain framework derived from human IGHV3-23*04 (SEQ ID NO: 82) and a light chain framework derived from human IGLV3-1*01 (SEQ ID NO: 86).

In some embodiments, the agonistic antibodies specifically binding human CD40 of the invention comprise a heavy chain framework derived from human IGHV4-39*01 (SEQ ID NO: 73) and a light chain framework derived from human IGLV2-8*01 (SEQ ID NO: 87).

Antibodies comprising heavy or light chain variable regions "derived from" a particular framework or germline sequence refer to antibodies obtained from a system that uses human germline immunoglobulin genes, such as from transgenic mice or from phage display libraries as discussed infra. An antibody that is "derived from" a particular framework or germline sequence may contain amino acid differences when compared to the sequence it was derived from, due to, for example, naturally-occurring somatic mutations or intentional substitutions.

The antibodies of the invention may be an IgA, IgD, IgE, IgG or IgM isotype. The antibodies of the invention may be an IgG1, an IgG2, an IgG3 or an IgG4 isotype.

The antibodies of the invention may further be engineered to generate modified antibody with similar or altered properties when compared to the parental antibody. The VH, the VL, the VH and the VL, the constant regions, VH framework, VL framework, or any or all of the six CDRs may be engineered in the antibodies of the invention.

The antibodies of the invention may be engineered by CDR grafting. One or more CDR sequences of the antibodies of the invention may be grafted to a different framework sequence. CDR grafting may be done using methods described herein. In some embodiments described herein, and in some embodiments of each and every one of the numbered embodiments listed below, the antibodies of the invention comprise a VH that comprises the HDCR1 of SEQ ID NOs: 1, 2, 3, 4 or 5, the HCDR2 of SEQ ID NOs: 6, 7, 8, 9, 10, 11, 12 or 13, the HCDR3 of SEQ ID NOs: 14, 15, 16, 17, 18, 19, 20, 21, 22, 23, 24 or 25, and a VL that comprises the LCDR1 of SEQ ID NOs: 26, 27, 28, 29, 30, 31 or 32, the LCDR2 of SEQ ID NOs: 33, 34, 35, 36, 37, 38 or 39 and/or the LCDR3 of SEQ ID NOs: 40, 41, 42, 43, 44, 45, 46 or 47, wherein the VH framework is not derived from IGHV3-23*03 (SEQ ID NO: 79), IGHV1-69*01 (SEQ ID NO: 80), IGHV3-23*01 (SEQ ID NO: 81), IGHV3-23*04 (SEQ ID NO: 82) or IGHV4-39*01 (SEQ ID NO: 73), and the VL framework is not derived from IGLV4-1*01 (SEQ ID NO: 84), IGKV1-39*01 (SEQ ID NO: 85), IGLV3-1*01 (SEQ ID NO: 86) or IGLV2-8*01 (SEQ ID NO: 87).

The framework sequences to be used may be obtained from public DNA databases or published references that include germline antibody gene sequences. For example, germline DNA and the encoded protein sequences for human heavy and light chain variable region genes can be found at IMGT®, the international ImMunoGeneTics information System® http_//_www-imgt_org. Framework sequences that may be used to replace the existing framework sequences in the antibodies of the invention are those that show the highest percent identity to the parental frameworks.

The framework sequences of the parental and engineered antibodies may further be modified, for example by back-mutations to restore and/or improve binding of the resulting antibody to the antigen as described for example in U.S. Pat. No. 6,180,370. The framework sequences of the parental and engineered antibodies may further be modified by mutating one or more residues within the framework region, or even within one or more CDR regions, to remove T-cell epitopes to thereby reduce the potential immunogenicity of the antibody. This approach is also referred to as "deimmunization" and described in further detail in U.S. Pat. Publ. No. 2003/0153043.

The CDR residues of the antibodies of the invention may be mutated to improve one or more binding properties of the antibody of interest. Site-directed mutagenesis or PCR-mediated mutagenesis may be performed to introduce the mutation(s) and the effect on antibody binding, or other functional property of interest, may be evaluated in in vitro or in vivo assays as described herein and provided in the Examples. Exemplary substitutions that may be introduced are conservative modifications as discussed supra. Moreover, typically no more than one, two, three, four or five residues within a CDR region are altered.

Mutations in an Fc region may be made to the antibody of the invention to modulate antibody effector functions and pharmacokinetic properties.

In some embodiments, the agonistic antibodies specifically binding human CD40 of the invention comprise at least one substitution in an antibody Fc.

Fc mutations may be made to the antibody of the invention to modulate antibody half-life. For example, a M252Y/S254T/T256E mutation may be introduced to increase the half-life of the resulting antibody (Dall'Acqua et al., J Biol Chem 281:23514-240, 2006).

In some embodiments, the agonistic antibody specifically binding human CD40 of the invention comprises at least one mutation in the Fc region that enhances binding of the antibody to FcγRIIb.

"Enhanced binding to FcγRIIb" refers to a statistically significant increase in binding (e.g. decrease in $EC_{50}$ value) to FcγRIIb by the antibody of the invention comprising at least one mutation in the Fc region when compared to the same antibody without the mutation.

Binding of the antibody to FcγRIIb may be assessed on cells engineered to express FcγRIIb using flow cytometry. In an exemplary binding assay, $2 \times 10^5$ cells per well are seeded in 96-well plate and blocked in BSA Stain Buffer (BD Biosciences, San Jose, USA) for 30 min at 4° C. Cells are incubated with a test antibody on ice for 1.5 hour at 4° C. After being washed twice with BSA stain buffer, the cells are incubated with R-PE labeled anti-human IgG secondary antibody (Jackson Immunoresearch Laboratories) for 45 min at 4° C. The cells are washed twice in stain buffer and then resuspended in 150 μL of Stain Buffer containing 1:200 diluted DRAQ7 live/dead stain (Cell Signaling Technology, Danvers, USA). PE and DRAQ7 signals of the stained cells are detected by Miltenyi MACSQuant flow cytometer (Miltenyi Biotec, Auburn, USA) using B2 and B4 channels, respectively. Live cells are gated on DRAQ7 exclusion and the geometric mean fluorescence signals are determined for at least 10,000 live events collected. FlowJo software (Tree Star) is used for analysis. Data is plotted as the logarithm of antibody concentration versus mean fluorescence signals. Nonlinear regression analysis is performed by GraphPad Prism 6 (GraphPad Software, Inc.) and $EC_{50}$ values are calculated.

Enhanced binding of the agonistic antibody specifically binding human CD40 of the invention to FcγRIIb may enhance crosslinking of CD40 molecules leading to stronger CD40 activation by the agonistic antibodies of the invention. Exemplary Fc mutations that result in antibodies having increased FcγRIIb binding are a S267E mutation, a S267D mutation, a S267E/L328F mutation, a G236D/S267E mutation and an E233D/G237D/H268D/P271G/A330R/P238D mutation, residue numbering according to the EU Index.

In some embodiments, the agonistic antibody specifically binding human CD40 of the invention comprises the S267E mutation in the Fc region, wherein residue numbering is according to the EU Index.

In some embodiments, the agonistic antibody specifically binding human CD40 of the invention comprises the S267E/I332E mutation in the Fc region, wherein residue numbering is according to the EU Index.

In some embodiments, the agonistic antibody specifically binding human CD40 of the invention comprises the S267E/L328F mutation in the F region, wherein residue numbering is according to the EU Index.

In some embodiments, the agonistic antibody specifically binding human CD40 of the invention comprises the E233D/G237D/H268D/P271G/A330R/P238D mutation in the Fc region, wherein residue numbering is according to the EU Index.

In some embodiments, the agonistic antibody specifically binding human CD40 of the invention comprises at least one mutation in the Fc region that enhances binding of the antibody to an Fcγ receptor (FcγR) and/or enhances Fc effector functions such as C1q binding, complement dependent cytotoxicity (GDC), antibody-dependent cell-mediated cytotoxicity (ADCC) or phagocytosis (ADCP).

Fc region positions that may be mutated to increase binding of the antibody to the activating FcγR and/or enhance antibody effector functions are those described for example in U.S. Pat. No. 6,737,056, U.S. Patent Publ. No. 2015/0259434, Shields et al, (2001) J Biol Chem 276:6591-6604, Lazar et al, (2006) Proc Natal Acad Sci, 103:4005-4010, Stavenhagen et al., (2007) Cancer Res 67:8882-8890, Richards et al, (2008) Mol Cancer Ther 7:2517-2527, Diebolder et al. Science; published online Mar. 13, 2014; doi:10.1126/science.1248943, and include positions 236, 239, 243, 256, 290, 292, 298, 300, 305, 312, 326, 330, 332, 333, 334, 345, 360, 339, 378, 396 or 430 (residue numbering according to the EU index). Exemplary mutations that may be made singularly or in combination are a G236A mutation, a S239D mutation, a F243L mutation, a T256A mutation, a K290A mutation, a R292P mutation, a S298A mutation, an Y300L mutation, a V305L mutation, a K326A mutation, an A330K mutation, an I332E mutation, an E333A mutation, a K334A mutation, an A339T mutation and a P396L mutation. Exemplary combination substitutions that result in antibodies with increased ADCC or ADCP are a S239D/I332E mutation, a S298A/E333A/K334A mutation, a F243L/R292P/Y300L mutation, a F243L/R292P/Y300L/P396L mutation, a F243L/R292P/Y300L/V305I/P396L mutation and a G236A/S239D/I332E mutation on IgG1.

Fc region positions that may be mutated to enhance CDC of the antibody are those described for example in Int. Patent Appl. WO2014/108198, Idusogie et al, (2001) J Immunol 166:2571-2575 and Moore et al, (2010) Mabs, 2:181-189, and include positions 267, 268, 324, 326, 333, 345 and 430.

Exemplary mutations that may be made singularly or in combination are a S267E mutation, a F1268F mutation, a S324T mutation, a K326A mutation, a K326W mutation, an E333A mutation, an E345K mutation, an E345Q mutation, an E345R mutation, an E345Y mutation, an E430S mutation, an E430F mutation and an E430T mutation. Exemplary combination mutations that result in antibodies with increased CDC are a K326A/E333A mutation, a K326W/E333A mutation, a H268F/S324T mutation, a S267E/H268F mutation, a S267E/S324T mutation and a S267E/H268F/S324T mutation on IgG1.

The ability of monoclonal antibodies to induce ADCC may also be enhanced by engineering their oligosaccharide component. Human IgG1 or IgG3 are N-glycosylated at Asn297 with the majority of the glycans in the well-known biantennary G0, G0F, G1, G1F, G2 or G2F forms. Antibodies produced by non-engineered CHO cells typically have a glycan fucose content of about at least 85%. The removal of the core fucose from the biantennary complex-type oligosaccharides attached to the Fc regions enhances the ADCC of antibodies via improved FcγRIIIa binding without altering antigen binding or CDC activity. Such mAbs may be achieved using different methods reported to lead to the successful expression of relatively high defucosylated antibodies bearing the biantennary complex-type of Fc oligosaccharides such as control of culture osmolality (Konno et al., Cytotechnology 64:249-65, 2012), application of a variant CHO line Lec13 as the host cell line (Shields et al., J Biol Chem 277:26733-26740, 2002), application of a variant CHO line EB66 as the host cell line (Olivier et al., MAbs; 2(4), 2010; Epub ahead of print; PMID:20562582), application of a rat hybridoma cell line YB2/0 as the host cell line (Shinkawa et al., J Biol Chem 278:3466-3473, 2003), introduction of small interfering RNA specifically against the α 1,6-fucosyltrasferase (FUT8) gene (Mori et al., Biotechnol Bioeng 88:901-908, 2004), or coexpression of β-1,4-N-acetylglucosaminyltransferase III and Golgi α-mannosidase II or a potent alpha-mannosidase I inhibitor, kifunensine (Ferrara et al., J Biol Chem 281:5032-5036, 2006, Ferrara et al., Biotechnol Bioeng 93:851-861, 2006; Xhou et al., Biotechnol Bioeng 99:652-65, 2008).

In some embodiments, the agonistic antibodies specifically binding human CD40 of the invention have a biantennary glycan structure with fucose content of about between 0% to about 15%, for example 15%, 14%, 13%, 12%, 11% 10%, 9%, 8%, 7%, 6%, 5%, 4%, 3%, 2%, 1% or 0%.

In some embodiments, the agonistic antibodies specifically binding human CD40 of the invention have a biantennary glycan structure with fucose content of about 50%, 40%, 45%, 40%, 35%, 30%, 25%, 20%, 15%, 14%, 13%, 12%, 11% 10%, 9%, 8%, 7%, 6%, 5%, 4%, 3%, 2%, 1% or 0%

"Fucose content" means the amount of the fucose monosaccharide within the sugar chain at Asn297. The relative amount of fucose is the percentage of fucose-containing structures related to all glycostructures. These may be characterized and quantified by multiple methods, for example: 1) using MALDI-TOF of N-glycosidase F treated sample (for example complex, hybrid and oligo- and high-mannose structures) as described in Intl. Pat. Publ. No. WO2008/077546; 2) by enzymatic release of the Asn297 glycans with subsequent derivatization and detection/quantitation by HPLC (UPLC) with fluorescence detection and/or HPLC-MS (UPLC-MS); 3) intact protein analysis of the native or reduced mAb, with or without treatment of the Asn297 glycans with Endo S or other enzyme that cleaves between the first and the second GlcNAc monosaccharides, leaving the fucose attached to the first GlcNAc; 4) digestion of the mAb to constituent peptides by enzymatic digestion (for example, trypsin or endopeptidase Lys-C), and subsequent separation, detection and quantitation by HPLC-MS (UPLC-MS) or 5) separation of the mAb oligosaccharides from the mAb protein by specific enzymatic deglycosylation with PNGase F at Asn 297. The oligosaccharides released can be labeled with a fluorophore, separated and identified by various complementary techniques which allow: fine characterization of the glycan structures by matrix-assisted laser desorption ionization (MALDI) mass spectrometry by comparison of the experimental masses with the theoretical masses, determination of the degree of sialylation by ion exchange HPLC (GlycoSep C), separation and quantification of the oligosaccharide forms according to hydrophilicity criteria by normal-phase HPLC (GlycoSep N), and separation and quantification of the oligosaccharides by high performance capillary electrophoresis-laser induced fluorescence (HPCE-LIF).

"Low fucose" or "low fucose content" as used in the application refers to antibodies with fucose content of about 0%-15%.

"Normal fucose" or 'normal fucose content" as used herein refers to antibodies with fucose content of about over 50%, typically about over 60%, 70%, 80% or over 85%.

The agonistic antibodies specifically binding CD40 of the invention having enhanced ADCC, ADCP and/or CDC may be useful in treating CD40-expressing hematological malignancies.

"Antibody-dependent cellular cytotoxicity", "antibody-dependent cell-mediated cytotoxicity" or "ADCC" is a mechanism for inducing cell death that depends upon the interaction of antibody-coated target cells with effector cells possessing lytic activity, such as natural killer cells, monocytes, macrophages and neutrophils via Fc gamma receptors (FcγR) expressed on effector cells. For example, NK cells express FcγRIIIa, whereas monocytes express FcγR1, FcγRII and FcγRIIIa. To assess ADCC activity of the antibodies of the invention, the antibody may be added to target cells in combination with immune effector cells, which may be activated by the antigen antibody complexes resulting in cytolysis of the target cell. Cytolysis is generally detected by the release of label (e.g. radioactive substrates, fluorescent dyes or natural intracellular proteins) from the lysed cells. Exemplary effector cells for such assays include peripheral blood mononuclear cells (PBMC) and NK cells. Exemplary target cells include cells expressing CD40.

"Antibody-dependent cellular phagocytosis" ("ADCP") refers to a mechanism of elimination of antibody-coated target cells by internalization by phagocytic cells, such as macrophages or dendritic cells. ADCP may be evaluated using monocyte-derived macrophages as effector cells and cells expressing CD40 engineered to express GPP or other labeled molecule as target cells. Effector:target cell ratio may be for example 4:1. Effector cells may be incubated with target cells for 4 hours with or without the test CD40 antibody. After incubation, cells may be detached using accutase. Macrophages may be identified with anti-CD11 and anti-CD14 antibodies coupled to a fluorescent label, and percent phagocytosis may be determined based on % GFP fluorescent in the $CD11^+CD14^+$ macrophages using standard methods.

"Complement-dependent cytotoxicity" or "CDC" refers to a mechanism for inducing cell death in which an Fc effector domain of a target-bound antibody binds and activates complement component C1q which in turn activates the complement cascade leading to target cell death. Activation of complement may also result in deposition of complement components on the target cell surface that facilitate ADCC by binding complement receptors (e.g., CR3) on leukocytes. CDC of CD40-expressing cells may be measured for example by plating cells expressing CD40 in an appropriate medium, adding anti-CD4 antibodies into the mixture, followed by addition of pooled human serum. After incubation period, percentage (%) lysed cells may be detected as % propidium iodide stained cells in FACS assay using standard methods.

"Enhanced ADCC", "enhanced CDC" and "enhanced ADCP" refers to a statistically significant increase in ADCC, CDC and/or ADCP mediated by the antibody of the invention comprising at least one mutation in the Fc region when compared to the same antibody without the mutation. ADCC, CDC and/or ADCP, such as assays described herein and in assays described in U.S. Pat. No. 8,871,204.

Additionally, the agonistic antibodies specifically binding human CD40 of the invention may be post-translationally modified by processes such as glycosylation, isomerization, deglycosylation or non-naturally occurring covalent modification such as the addition of polyethylene glycol moieties (pegylation) and lipidation. Such modifications may occur in vivo or in vitro. For example, the antibodies of the invention may be conjugated to polyethylene glycol (PEGylated) to improve their pharmacokinetic profiles. Conjugation may be carried out by techniques known to those skilled in the art. Conjugation of therapeutic antibodies with PEG has been shown to enhance pharmacodynamics while not interfering with function (Knigh et al., Platelets 15:409-18, 2004; Leong et al., Cytokine 16:106-19, 2001; Yang et al., Protein Eng. 16:761-70, 2003).

Antibodies or antigen-binding fragments thereof of the invention modified to improve stability, selectivity, cross-reactivity, affinity, immunogenicity or other desirable biological or biophysical property are within the scope of the invention. Stability of an antibody is influenced by a number of factors, including (1) core packing of individual domains that affects their intrinsic stability, (2) protein/protein interface interactions that have impact upon the HC and LC pairing, (3) burial of polar and charged residues, (4) H-bonding network for polar and charged residues; and (5) surface charge and polar residue distribution among other intra- and inter-molecular forces (Worn et al., *J Mol Biol* 305:989-1010, 2001). Potential structure destabilizing residues may be identified based upon the crystal structure of the antibody or by molecular modeling in certain cases, and the effect of the residues on antibody stability may be tested by generating and evaluating variants harboring mutations in the identified residues. One of the ways to increase antibody stability is to raise the thermal transition midpoint ($T_m$) as measured by differential scanning calorimetry (DSC). In general, the protein $T_m$ is correlated with its stability and inversely correlated with its susceptibility to unfolding and denaturation in solution and the degradation processes that depend on the tendency of the protein to unfold (Remmele et al., Biopharm 13:36-46, 2000). A number of studies have found correlation between the ranking of the physical stability of formulations measured as thermal stability by DSC and physical stability measured by other methods (Gupta et al., AAPS PharmSci 5E8, 2003; Zhang et al., J Pharm Sci 93:3076-89, 2004; Maa et al., Int J Pharm 140:155-68, 1996; Bedu-Addo et al., *Pharm Res* 21:1353-61, 2004; Remmele et al., Pharm Res 15:200-8, 1997). Formulation studies suggest that a Fab $T_m$ has implication for long-term physical stability of a corresponding mAb.

In some embodiments, the antibody of the invention is a multispecific antibody.

In some embodiments, the antibody of the invention is a bispecific antibody.

The agonistic antibodies specifically binding human CD40 of the invention may be engineered into bispecific antibodies which are also encompassed within the scope of the invention.

Full length bispecific antibodies may be generated for example using Fab arm exchange (e.g., half molecule exchange, exchanging on heavy chain-light chain pair) between two monospecific bivalent antibodies by introducing mutations at the heavy chain CH3 interface in each half-molecule to favor heterodimer formation of two antibody half-molecules having distinct specificity either in vitro in cell-free environment or using co-expression. The Fab arm exchange reaction is the result of a disulfide-bond isomerization reaction and dissociation-association of CH3 domains. The heavy chain disulfide bonds in the hinge regions of the parental monospecific antibodies are reduced. The resulting free cysteines of one of the parental monospecific antibody form an inter heavy-chain disulfide bond with cysteine residues of a second parental monospecific antibody molecule and simultaneously CH3 domains of the parental antibodies release and reform by dissociation-association. The CH3 domains of the Fab arms may be engineered to favor heterodimerization over homodimerization. The resulting product is a bispecific antibody having two Fab arms which each bind a distinct epitope. CH3 interface mutations F405L in one heavy chain and K409R in the other heavy chain may be used. To generate bispecific antibodies the first monospecific bivalent antibody and the second monospecific bivalent antibody are engineered to have a F405L or a K409R mutation in the Fc region, the antibodies are incubated together under reducing conditions sufficient to allow the cysteines in the hinge region to undergo disulfide bond isomerization; thereby generating the bispecific antibody by Fab arm exchange. The incubation conditions may optimally be restored to non-reducing. Exemplary reducing agents that may be used are 2-mercaptoethylamine (2-MEA), dithiothreitol (DTT), dithioerythritol (DTE), glutathione, tris(2 carboxyethyl)phosphine (TCEP), L-cysteine and beta-mercaptoethanol. For example, incubation for at least 90 min at a temperature of at least 20° C. in the presence of at least 25 mM 2-MEA or in the presence of at least 0.5 mM dithiothreitol at a pH of from 5-8, for example at pH of 7.0 or at pH of 7.4 may be used.

Bispecific antibodies may also be generated using designs such as the Knob-in-Hole (Genentech), CrossMAbs (Roche) and the electrostatically-matched (Chugai, Amgen, NovoNordisk, Oncomed), the LUZ-Y (Genentech), the Strand Exchange Engineered Domain body (SEEDbody) (EMD Serono), and the Biclonic (Merus).

The "knob-in-hole" strategy (see, e.g., Intl. Publ. No. WO 2006/028936) may be used to generate full length bispecific antibodies of the invention. Briefly, selected amino acids forming the interface of the CH3 domains in human IgG can be mutated at positions affecting CH3 domain interactions to promote heterodimer formation. An amino acid with a small side chain (hole) is introduced into a heavy chain of an antibody specifically binding a first antigen and an amino acid with a large side chain (knob) is introduced into a heavy chain of an antibody specifically binding a second antigen. After co-expression of the two antibodies, a heterodimer is formed as a result of the preferential interaction of the heavy chain with a "hole" with the heavy chain with a "knob". Exemplary CH3 substitution pairs forming a knob and a hole are (expressed as modified position in the first CH3 domain of the first heavy chain/modified position in the second CH3 domain of the second heavy chain): T366Y/F405A, T366W/F405W, F405W/Y407A, T394W/Y407T, T394S/Y407A, T366W/T394S, F405W/T394S and T366W/T366S_L368A_Y407V.

The CrossMAb technology may be used to generate full length bispecific antibodies of the invention. CrossMAbs, in addition to utilizing the "knob-in-hole" strategy to promoter Fab arm exchange, have in one of the half arms the CH1 and the CL domains exchanged to ensure correct light chain pairing of the resulting bispecific antibody (see e.g. U.S. Pat. No. 8,242,247).

Other cross-over strategies may be used to generate full length bispecific antibodies of the invention by exchanging variable or constant, or both domains between the heavy chain and the light chain or within the heavy chain in the bispecific antibodies, either in one or both arms. These exchanges include for example VH-CH1 with VL-CL, VH with VL, CH3 with CL and CH3 with CH1 as described in Int. Patent Publ. Nos. WO2009/080254, WO2009/080251, WO2009/018386 and WO2009/080252.

Other strategies such as promoting heavy chain heterodimerization using electrostatic interactions by substituting positively charged residues at one CH3 surface and negatively charged residues at a second CH3 surface may be used, as described in US Patent Publ. No. 2010/0015133; US Patent Publ. No. 2009/0182127; US Patent P2010/028637 or US Patent Publ. No. 2011/0123532. In other strategies, heterodimerization may be promoted by following substitutions (expressed as modified positions in the first CH3 domain of the first heavy chain/modified position in the second CH3 domain of the second heavy chain): L351Y_F405AY407V/T394W, T366I_K392M_T394W/F405A_Y407V, T366L_K392M_T394W/F405A_Y407V, L351Y_Y407A/T366A_K409F, L351Y_Y407A/T366V_K409F, Y407A/T366A K409F, or T350V_L351Y_F405A_Y407V/T350V_T366L_K392L_T394W as described in U.S. Patent Publ. No. 2012/0149876 or U.S. Patent Publ. No. 2013/0195849.

LUZ-Y technology may be utilized to generate bispecific antibodies of the invention. In this technology, a leucine zipper is added into the C terminus of the CH3 domains to drive the heterodimer assembly from parental mAbs that is removed post-purification as described in Wranik et al., (2012) *J Biol Chem* 287(52): 42221-9.

SEEDbody technology may be utilized to generate bispecific antibodies of the invention. SEEDbodies have, in their constant domains, select IgG residues substituted with IgA residues to promote heterodimerization as described in U.S. Patent Publ. No. 2007/0287170.

Mutations are typically made at the DNA level to a molecule such as the constant domain of the antibody using standard methods.

The antibodies of the invention may be engineered into various well-known antibody formats.

In some embodiments, the bispecific antibodies include recombinant IgG-like dual targeting molecules, wherein the two sides of the molecule each contain the Fab fragment or part of the Fab fragment of at least two different antibodies; IgG fusion molecules, wherein full length IgG antibodies are fused to an extra Fab fragment or parts of Fab fragment; Fc fusion molecules, wherein single chain Fv molecules or stabilized diabodies are fused to heavy chain constant domains, Fc-regions or parts thereof; Fab fusion molecules, wherein different Fab-fragments are fused together; ScFv- and diabody-based and heavy chain antibodies (e.g., domain antibodies, nanobodies) wherein different single chain Fv molecules or different diabodies or different heavy-chain antibodies (e.g. domain antibodies, nanobodies) are fused to each other or to another protein or carrier molecule.

The invention also provides for an agonistic antibody specifically binding human CD40 having certain VH and VL sequences, wherein the VH is encoded by a first polynucleotide and the VL is encoded by a second polynucleotide. The polynucleotide may be a complementary deoxynucleic acid (cDNA) and may be codon optimized for expression in suitable host. Codon optimization is a well-known technology.

Polynucleotide, Vectors, Host Cells

The invention also provides for an isolated polynucleotide encoding the VH of the antibody of the invention, the VL of the antibody of the invention, the heavy chain of the antibody of the invention or the light chain of the antibody of the invention.

The invention also provides for an isolated polynucleotide encoding the VH of SEQ ID NOs: 48, 49, 50, 51, 52, 53, 54, 55, 56, 57, 58, 59, 61 or 62.

The invention also provides for an isolated polynucleotide encoding the VL of SEQ ID NOs: 63, 64, 65, 66, 67, 68, 69, 70, 71 or 72.

The invention also provides for an isolated polynucleotide encoding the VH of SEQ ID NOs: 48, 49, 50, 51, 52, 53, 54, 55, 56, 57, 58, 59, 61 or 62 and the VL of SEQ ID NOs: 63, 64, 65, 66, 67, 68, 69, 70, 71 or 72.

The invention also provides for an isolated polynucleotide comprising the polynucleotide sequence of SEQ ID NOs: 89, 90, 91, 92, 93, 94, 95, 96, 97, 98, 99, 100, 102, 103, 104, 105, 106, 107, 108, 109, 110, 111, 112 or 113.

The invention also provides for an isolated polynucleotide encoding the heavy chain of SEQ ID NOs: 114, 115, 116, 117, 118, 119, 120, 121, 122, 123, 124, 125, 127, 128 or 129.

The invention also provides for an isolated polynucleotide encoding the light chain of SEQ ID NOs: 130, 131, 132, 133, 134, 135, 136, 137, 138 or 139.

The invention also provides for an isolated polynucleotide encoding the heavy chain of SEQ ID NOs: 114, 115, 116, 117, 118, 119, 120, 121, 122, 123, 124, 125, 127, 128 or 129 and a light chain of SEQ ID NOs: 130, 131, 132, 133, 134, 135, 136, 137, 138 or 139.

The invention also provides for an isolated polynucleotide comprising the polynucleotide sequence of SEQ ID NOs: 140, 141, 142, 143, 144, 145, 146, 147, 148, 149, 150, 151, 153, 154, 155, 156, 157, 158, 159, 160, 161, 162, 163, 164 or 165.

The polynucleotide sequences encoding the VH or the VL or an antigen-binding fragment thereof of the antibodies of the invention, or the heavy chain and the light chain of the antibodies of the invention may be operably linked to one or more regulatory elements, such as a promoter or enhancer, that allow expression of the nucleotide sequence in the intended host cell. The polynucleotide may be a cDNA.

The invention also provides for a vector comprising the polynucleotide of the invention. Such vectors may be plasmid vectors, viral vectors, vectors for baculovirus expression, transposon-based vectors or any other vector suitable for introduction of the synthetic polynucleotide of the invention into a given organism or genetic background by any means. For example, polynucleotides encoding light and/or heavy chain variable regions of the antibodies of the invention, optionally linked to constant regions, are inserted into expression vectors. The light and/or heavy chains may be cloned in the same or different expression vectors. The DNA segments encoding immunoglobulin chains may be operably linked to control sequences in the expression vector(s) that ensure the expression of immunoglobulin polypeptides. Such control sequences include signal sequences, promoters (e.g. naturally associated or heterologous promoters), enhancer elements, and transcription termination sequences, and are chosen to be compatible with the host cell chosen to express the antibody. Once the vector has been incorporated into the appropriate host, the host is maintained under conditions suitable for high level expression of the proteins encoded by the incorporated polynucleotides.

In some embodiments, the vector comprises the polynucleotide of SEQ ID NO: 89 and the polynucleotide of SEQ ID NO: 104.

In some embodiments, the vector comprises the polynucleotide of SEQ ID NO: 90 and the polynucleotide of SEQ ID NO: 105.

In some embodiments, the vector comprises the polynucleotide of SEQ ID NO: 91 and the polynucleotide of SEQ ID NO: 105.

In some embodiments, the vector comprises the polynucleotide of SEQ ID NO: 92 and the polynucleotide of SEQ ID NO: 105.

In some embodiments, the vector comprises the polynucleotide of SEQ ID NO: 93 and the polynucleotide of SEQ ID NO: 106.

In some embodiments, the vector comprises the polynucleotide of SEQ ID NO: 94 and the polynucleotide of SEQ ID NO: 106.

In some embodiments, the vector comprises the polynucleotide of SEQ ID NO: 95 and the polynucleotide of SEQ ID NO: 106.

In some embodiments, the vector comprises the polynucleotide of SEQ ID NO: 96 and the polynucleotide of SEQ ID NO: 106.

In some embodiments, the vector comprises the polynucleotide of SEQ ID NO: 97 and the polynucleotide of SEQ ID NO: 106.

In some embodiments, the vector comprises the polynucleotide of SEQ ID NO: 98 and the polynucleotide of SEQ ID NO: 107.

In some embodiments, the vector comprises the polynucleotide of SEQ ID NO: 99 and the polynucleotide of SEQ ID NO: 108.

In some embodiments, the vector comprises the polynucleotide of SEQ ID NO: 100 and the polynucleotide of SEQ ID NO: 109.

In some embodiments, the vector comprises the polynucleotide of SEQ ID NO: 98 and the polynucleotide of SEQ ID NO: 111.

In some embodiments, the vector comprises the polynucleotide of SEQ ID NO: 98 and the polynucleotide of SEQ ID NO: 112.

In some embodiments, the vector comprises the polynucleotide of SEQ ID NO: 98 and the polynucleotide of SEQ ID NO: 113.

In some embodiments, the vector comprises the polynucleotide of SEQ ID NO: 102 and the polynucleotide of SEQ ID NO: 110.

In some embodiments, the vector comprises the polynucleotide of SEQ ID NO: 103 and the polynucleotide of SEQ ID NO: 110.

Suitable expression vectors are typically replicable in the host organisms either as episomes or as an integral part of the host chromosomal DNA. Commonly, expression vectors contain selection markers such as ampicillin-resistance, hygromycin-resistance, tetracycline resistance, kanamycin resistance or neomycin resistance to permit detection of those cells transformed with the desired DNA sequences.

Suitable promoter and enhancer elements are known in the art. For expression in a eukaryotic cell, exemplary promoters include light and/or heavy chain immunoglobulin gene promoter and enhancer elements, cytomegalovirus immediate early promoter, herpes simplex virus thymidine kinase promoter, early and late SV40 promoters, promoter present in long terminal repeats from a retrovirus, mouse metallothionein-I promoter and various known tissue specific promoters. Selection of the appropriate vector and promoter is well within the level of ordinary skill in the art.

Exemplary vectors that may be used are bacterial vectors pBs, phagescript, PsiX174, pBluescript SK, pBs KS, pNH8a, pNH16a, pNH18a, pNH46a (Stratagene, La Jolla, Calif., USA), pTrc99A, pKK223-3, pKK233-3, pDR540, and pRIT5 (Pharmacia, Uppsala, Sweden), eukaryotic vectors pWLneo, pSV2cat, pOG44, PXR1, pSG (Stratagene) pSVK3, pBPV, pMSG, pSVL (Pharmacia), pEE6.4 (Lonza) and pEE12.4 (Lonza).

The invention also provides for a host cell comprising one or more vectors of the invention. "Host cell" refers to a cell into which a vector has been introduced. It is understood that the term host cell is intended to refer not only to the particular subject cell but to the progeny of such a cell, and also to a stable cell line generated from the particular subject cell. Because certain modifications may occur in succeeding generations due to either mutation or environmental influences, such progeny may not be identical to the parent cell, but are still included within the scope of the term "host cell" as used herein. Such host cells may be eukaryotic cells, prokaryotic cells, plant cells or archeal cells.

*Escherichia coli*, bacilli, such as *Bacillus subtilis*, and other enterobacteriaceae, such as *Salmonella, Serratia*, and various *Pseudomonas* species are examples of prokaryotic host cells. Other microbes, such as yeast, are also useful for expression. *Saccharomyces cerevisiae* (for example, *S. cerevisiae*) and *Pichia* are examples of suitable yeast host cells. Exemplary eukaryotic cells may be of mammalian, insect, avian or other animal origins. Mammalian eukaryotic cells include immortalized cell lines such as hybridomas or myeloma cell lines such as SP2/0 (American Type Culture Collection (ATCC), Manassas, Va., CRL-1581), NS0 (European Collection of Cell Cultures (ECACC), Salisbury, Wiltshire, UK, ECACC No. 85110503), FO (ATCC CRL-1646) and Ag653 (ATCC CRL-1580) murine cell lines. An exemplary human myeloma cell line is U266 (ATTC CRL-TIB-196). Other useful cell lines include those derived from Chinese Hamster Ovary (CHO) cells such as CHOK1SV (Lonza Biologics, Walkersville, Md.), Potelligent® CHOK2SV (Lonza), CHO-K1 (ATCC CRL-61) or DG44.

The invention also provides for a method of producing the antibody of the invention comprising culturing the host cell of the invention in conditions that the antibody is expressed, and recovering the antibody produced by the host cell. Methods of making antibodies and purifying them are well known in the art. Once synthesized (either chemically or recombinantly), the whole antibodies, their dimers, individual light and/or heavy chains, or other antibody fragments such as VH and/or VL, may be purified according to standard procedures, including ammonium sulfate precipitation, affinity columns, column chromatography, high performance liquid chromatography (HPLC) purification, gel electrophoresis, and the like (see generally Scopes, Protein Purification (Springer-Verlag, N.Y., (1982)). A subject antibody may be substantially pure, for example, at least about 80% to 85% pure, at least about 85% to 90% pure, at least about 90% to 95% pure, or at least about 98% to 99%, or more, pure, for example, free from contaminants such as cell debris, macromolecules, etc. other than the subject antibody.

Another embodiment of the invention is a method for producing an agonistic antibody specifically binding human CD40 comprising:

incorporating the first polynucleotide encoding the VH of the antibody and the second polynucleotide encoding the VL of the antibody into an expression vector;
transforming a host cell with the expression vector;
culturing the host cell in culture medium under conditions wherein the VL and the VH are expressed and form the antibody; and
recovering the antibody from the host cell or culture medium.

The polynucleotide sequences of the invention may be incorporated into vectors using standard molecular biology methods. Host cell transformation, culture, antibody expression and purification are done using well known methods.

Methods of Treatment

The agonistic antibodies specifically binding human CD40 of the invention have in vitro and in vivo diagnostic, as well as therapeutic and prophylactic utilities. For example, the antibodies of the invention may be administered to cells in culture, in vitro or ex vivo, or to a subject to treat, prevent and/or diagnose a variety of disorders, such as cancers and infectious diseases.

The agonistic antibodies specifically binding human CD40 of the invention, for example antibodies C40M67, C40M66, C40M63, C40M62, C40M59, C40M58, C40M56, C40M55, C40M51, C40M18, C40M17, C40M12, C40M102, C40M103, C40M104, C40M105, C40M121 and C40M126, may be used for the treatment and/or prevention of any condition or disease wherein enhancing CD40 signaling may be therapeutically effective and may reduce the symptoms of the disease.

The methods of the invention may be used to treat a subject belonging to any animal classification. Examples of subjects that may be treated include mammals such as humans, rodents, dogs, cats and farm animals.

The antibodies of the invention may be useful in the preparation of a medicament for such treatment, wherein the medicament is prepared for administration in dosages defined herein.

The invention provides for a method of treating a cancer, comprising administering a therapeutically effective amount of the isolated agonistic antibody specifically binding human CD40 of the invention to a subject in need thereof for a time sufficient to treat the cancer.

Subjects that can be treated with the agonistic antibodies specifically binding human CD40 of the invention are subjects that have been diagnosed as having a brain cancer, a lung cancer, a bone cancer, a pancreatic cancer, a skin cancer, a cancer of the head and neck, a cutaneous or intraocular melanoma, an uterine cancer, an ovarian cancer, a rectal cancer, a cancer of the anal region, a stomach cancer, a gastric cancer, a colorectal cancer, a colon cancer, a gynecologic tumor (for example, uterine sarcomas, carcinoma of the fallopian tubes, a carcinoma of the endometrium, a carcinoma of the cervix, a carcinoma of the vagina or carcinoma of the vulva), a cancer of the esophagus, a cancer of the small intestine, a cancer of the endocrine system (for example, a cancer of the thyroid, parathyroid or adrenal glands), sarcomas of soft tissues, a leukemia, a myeloma, a multiple myeloma, a cancer of the urethra, a cancer of the penis, a prostate cancer, a chronic or an acute leukemia, solid tumors of childhood, lymphocytic lymphomas, non-Hodgkin's lymphoma, a cancer of the bladder, a liver cancer, a renal cancer, a cancer of the kidney or ureter (for example, renal cell carcinoma, carcinoma of the renal pelvis), neoplasms of the central nervous system (for example, primary CNS lymphoma, spinal axis tumors, brain stem gliomas or pituitary adenomas), a glioma or a fibrosarcoma.

The invention also provides for a method of treating a solid tumor, comprising administering a therapeutically effective amount of the isolated agonistic antibody specifically binding human CD40 of the invention to a subject in need thereof for a time sufficient to treat the solid tumor.

The invention also provides for a method of treating a hematological malignancy, comprising administering a therapeutically effective amount of the isolated agonistic antibody specifically binding human CD40 of the invention to a subject in need thereof for a time sufficient to treat the hematological malignancy.

In some embodiments, the solid tumor is a prostate cancer, a breast cancer, a colorectal cancer, a pancreatic cancer, an ovarian cancer, a lung cancer, a cervical cancer, a rhabdomyosarcoma, a neuroblastoma, a melanoma, a bladder cancer, or a head and neck cancer.

In some embodiments, the solid tumor is a melanoma.

In some embodiments, the solid tumor is a lung cancer.

In some embodiments, the solid tumor is a squamous non-small cell lung cancer (NSCLC).

In some embodiments, the solid tumor is a non-squamous NSCLC.

In some embodiments, the solid tumor is a lung adenocarcinoma.

In some embodiments, the solid tumor is a renal cell carcinoma (RCC) (e.g., a kidney clear cell carcinoma or a kidney papillary cell carcinoma), or a metastatic lesion thereof.

In some embodiments, the solid tumor is a mesothelioma.

In some embodiments, the solid tumor is a nasopharyngeal carcinoma (NPC).

In some embodiments, the solid tumor is a colorectal cancer.

In some embodiments, the solid tumor is a prostate cancer or castration-resistant prostate cancer.

In some embodiments, the solid tumor is a stomach cancer.

In some embodiments, the solid tumor is an ovarian cancer.

In some embodiments, the solid tumor is a gastric cancer.

In some embodiments, the solid tumor is a liver cancer.

In some embodiments, the solid tumor is a pancreatic cancer.

In some embodiments, the solid tumor is a thyroid cancer.

In some embodiments, the solid tumor is a squamous cell carcinoma of the head and neck.

In some embodiments, the solid tumor is a carcinoma of the esophagus or gastrointestinal tract.

In some embodiments, the solid tumor is a breast cancer.

In some embodiments, the solid tumor is a fallopian tube cancer.

In some embodiments, the solid tumor is a brain cancer.

In some embodiments, the solid tumor is an urethral cancer.

The invention also provides for a method of enhancing an immune response, comprising administering a therapeutically effective amount of the isolated agonistic antibody specifically binding human CD40 of the invention to a subject in need thereof for a time sufficient to enhance the immune response.

"Treat" or "treatment" refers to therapeutic treatment wherein the object is to slow down (lessen) an undesired physiological change or disease, such as the development or spread of tumor or tumor cells, or to provide a beneficial or desired clinical outcome during treatment. Beneficial or desired clinical outcomes include alleviation of symptoms, diminishment of extent of disease, stabilized (i.e., not worsening) state of disease, delay or slowing of disease progression, lack of metastasis, amelioration or palliation of the disease state, and remission (whether partial or total), whether detectable or undetectable. "Treatment" may also mean prolonging survival as compared to expected survival if a subject was not receiving treatment. Those in need of treatment include those subjects already with the undesired physiological change or diseases as well as those subjects prone to have the physiological change or disease.

"Inhibits growth" (for example referring to tumor cells) refers to a measurable decrease in the tumor cell growth or tumor tissue in vitro or in vivo when contacted with a therapeutic or a combination of therapeutics, when compared to the growth of the same tumor cells or tumor tissue in the absence of the therapeutic(s). Inhibition of growth of a tumor cell or tumor tissue in vitro or in vivo may be at least about 10%, 20%, 30%, 40%, 50%, 60%, 70%, 80%, 90%, 99%, or 100%.

"Therapeutically effective amount" refers to an amount effective, at dosages and for periods of time necessary, to achieve a desired therapeutic result. A therapeutically effective amount may vary according to factors such as the disease state, age, sex, and weight of the individual, and the ability of a therapeutic or a combination of therapeutics to elicit the desired response in the individual. Exemplary indicators of an effective therapeutic or a combination of therapeutics include, for example, improved well-being of the patient, reduction in a tumor burden, arrested or slowed growth of a tumor, and/or absence of metastasis of cancer cells to other locations in the body.

The invention also provides for a method of enhancing an immune response in a subject, comprising administering a therapeutically effective amount of the agonistic antibody specifically binding human CD40 to the subject in need thereof for a time sufficient to enhance the immune response.

In some embodiments, the subject is immunocompromised.

In some embodiments, the subject is at risk of being immunocompromised. Immunocompromised subject may be undergoing or has undergone a chemotherapeutic or radiation therapy.

In some embodiments, the subject is or is at risk of being immunocompromised as a result of an infection.

In some embodiments, the subject has a viral infection.

The invention also provides for a method of treating a viral infection, comprising administering a therapeutically effective amount of the isolated agonistic antibody specifically binding human CD40 of the invention to a subject in need thereof for a time sufficient to treat the viral infection.

Administration/Pharmaceutical Compositions

The agonistic antibodies specifically binding human CD40 of the invention may be provided in suitable pharmaceutical compositions comprising the antibody and a pharmaceutically acceptable carrier. The carrier may be diluent, adjuvant, excipient, or vehicle in which the agonistic antibodies that specifically bind CD40 are administered. Such vehicles may be liquids, such as water and oils, including those of petroleum, animal, vegetable or synthetic origin, such as peanut oil, soybean oil, mineral oil, sesame oil and the like. For example, 0.4% saline and 0.3% glycine can be used. These solutions are sterile and generally free of particulate matter. They may be sterilized by conventional, well-known sterilization techniques (for example, filtration). The compositions may contain pharmaceutically acceptable auxiliary substances as required to approximate physiological conditions such as pH adjusting and buffering agents, stabilizing, thickening, lubricating and coloring agents, etc. The concentration of the molecules or antibodies of the invention in such pharmaceutical formulations may vary widely, i.e., from less than about 0.5%, usually to at least about 1% to as much as 15 or 20%, 25%, 30%, 35%, 40%, 45% or 50% by weight and will be selected primarily based on required dose, fluid volumes, viscosities, etc., according to the particular mode of administration selected. Suitable vehicles and formulations, inclusive of other human proteins, for example, human serum albumin, are described, for example, in for example Remington: The Science and Practice of Pharmacy, $21^{st}$ Edition, Troy, D. B. ed., Lipincott Williams and Wilkins, Philadelphia, Pa. 2006, Part 5, Pharmaceutical Manufacturing pp 691-1092, see especially pp. 958-989.

The mode of administration of the agonistic antibodies specifically binding human CD40 of the invention may be via any suitable route such as parenteral administration, for example, intradermal, intramuscular, intraperitoneal, intravenous or subcutaneous, transmucosal (oral, intranasal, intravaginal, rectal) or other means appreciated by the skilled artisan, as well known in the art. The agonistic antibodies that specifically bind CD40 may be administered intratumorally, to a lymph node draining site for local delivery into the tumor using known methods.

The agonistic antibodies specifically binding human CD40 of the invention may be administered to a patient by any suitable route, for example parentally by intravenous (i.v.) infusion or bolus injection, intramuscularly or subcutaneously or intraperitoneally. i.v. infusion may be given over for example 15, 30, 60, 90, 120, 180, or 240 minutes, or from 1, 2, 3, 4, 5, 6, 7, 8, 9, 10, 11 or 12 hours.

The dose given to a patient is sufficient to alleviate or at least partially arrest the disease being treated ("therapeutically effective amount") and may be sometimes 0.005 mg to about 100 mg/kg, for example about 0.05 mg to about 30 mg/kg or about 5 mg to about 25 mg/kg, or about 4 mg/kg, about 8 mg/kg, about 16 mg/kg or about 24 mg/kg, or for example about 1, 2, 3, 4, 5, 6, 7, 8, 9 or 10 mg/kg, but may even higher, for example about 15, 16, 17, 18, 19, 20, 21, 22, 23, 24, 25, 30, 40, 50, 60, 70, 80, 90 or 100 mg/kg.

A fixed unit dose may also be given, for example, 50, 100, 200, 500 or 1000 mg, or the dose may be based on the patient's surface area, for example, 500, 400, 300, 250, 200, or 100 mg/m². Usually between 1 and 8 doses, (for example, 1, 2, 3, 4, 5, 6, 7 or 8) may be administered, but 9, 10, 11, 12, 13, 14, 15, 16, 17, 18, 19, 20 or more doses may be given.

The administration of the agonistic antibodies specifically binding human CD40 of the invention may be repeated after one day, two days, three days, four days, five days, six days, one week, two weeks, three weeks, one month, five weeks, six weeks, seven weeks, two months, three months, four months, five months, six months or longer. Repeated courses of treatment are also possible, as is chronic administration. The repeated administration may be at the same dose or at a different dose. For example, the agonistic antibodies specifically binding human CD40 of the invention may be administered at 8 mg/kg or at 16 mg/kg at weekly interval for 8 weeks, followed by administration at 8 mg/kg or at 16 mg/kg every two weeks for an additional 16 weeks, followed by administration at 8 mg/kg or at 16 mg/kg every four weeks by intravenous infusion.

The agonistic antibodies specifically binding human CD40 may be administered by maintenance therapy, such as, e.g., once a week for a period of 6 months or more.

For example, the agonistic antibodies specifically binding human CD40 of the invention may be provided as a daily dosage in an amount of about 0.1-100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20 after initiation of treatment, or any combination thereof, using single or divided doses of every 24, 12, 8, 6, 4, or 2 hours, or any combination thereof.

The agonistic antibodies specifically binding human CD40 of the invention may also be administered prophylactically in order to reduce the risk of developing cancer, delay the onset of the occurrence of an event in cancer progression, and/or reduce the risk of recurrence when a cancer is in remission. This may be especially useful in patients wherein it is difficult to locate a tumor that is known to be present due to other biological factors.

The agonistic antibodies specifically binding human CD40 of the invention may be lyophilized for storage and reconstituted in a suitable carrier prior to use. This technique has been shown to be effective with conventional protein preparations and well known lyophilization and reconstitution techniques can be employed.

Combination Therapies

The invention provides for a method of treating a subject having a cancer, comprising administering a therapeutically effective amount of the agonistic antibody specifically binding human CD40 of the invention in combination with a second therapeutic agent.

The second therapeutic agent may be an immune checkpoint modulator, such as an inhibitor, for example an antagonistic antibody specifically binding PD-1, PD-L1, CTLA-4, LAG-3 or TIM-3.

The second therapeutic agent may also be an agonist of a T cell activating molecule, for example an agonistic antibody specifically binding 4-IBB, CD27, ICOS, or OX40.

The second therapeutic agent may also be an inhibitor of the enzyme indolamine 2,3-dioxygenase.

Exemplary anti-PD-1 antibodies that may be used are OPVIDO® (nivolumab) and KEYTRUDA® (pembrolizumab). KEYTRUDA® (pembrolizumab) is described in for example U.S. Pat. No. 8,354,509 and comprises the VH of SEQ ID NO: 166 and the VL of SEQ ID NO: 167. OPVIDO® (nivolumab) is described in for example in U.S. Pat. No. 8,008,449 (antibody 5C4) and comprises the VH of SEQ ID NO: 168 and the VL of SEQ ID NO: 169. The amino acid sequences of OPVIDO® (nivolumab) and KEYTRUDA® (pembrolizumab) are also available through the CAS registry. Additional PD-1 antibodies that may be used are described in U.S. Pat. No. 7,332,582, U.S. Pat. Publ. No. 2014/0044738, Int. Pat. Publ. No. WO2014/17966 and U.S. Pat. Publ. No. 2014/0356363.

SEQ ID NO: 166
QVQLVQSGVEVKKPGASVKVSCKASGYTFTNYYMYWVRQAPGQGLEWMGG
INPSNGGTNFNEKFKNRVTLTTDSSTTTAYMELKSLQFDDTAVYYCARRD
YRFDMGFDYWGQGTTVTVSS

SEQ ID NO: 167
EIVLTQSPATLSLSPGERATLSCRASKGVSTSGYSYLHWYQQKPGQAPRL
LIYLASYLESGVPARFSGSGSGTDFTLTISSLEPEDFAVYYCQHSRDLPL
TFGGGTKVEIK

SEQ ID NO: 168
QVQLVESGGGVWQPGRSLRLDCKASGITFSNSGMHWVRQAPGKGLEWVAV
IWYDGSKRYYADSVKGRFTISRDNSKNTLFLQMNSLRAEDTAVYYCATND
DYWGQGTLVTVSS

SEQ ID NO: 169
EIVLTQSPATLSLSPGERATLSCRASQSVSSYLAWYQQKPGQAPRLLIYD
ASNRATGIPARFSGSGSGTDFTLTISSLEPEDFAVYYCQQSSNWPRTFGQ
GTKVEIK

Exemplary anti-PD-L1 antibodies that may be used are IMFINZI (durvalumab), TECENTRIQ® (atezolizumab) and BAVENCIO® (avelumab), and those described in, for example, U.S. Pat. Publ. No. 2009/0055944, U.S. Pat. Nos. 8,552,154, 8,217,149 and 8,779,108. IMFINZI® (durvalumab) comprises the VH of SEQ ID NO: 170 and the VL of SEQ ID NO: 171. TECENTRIQ® (atezolizumab) comprises the VH of SEQ ID NO: 172 and the VL of SEQ ID NO: 173. BAVENCIO® (avelumab) comprises the VH of SEQ ID NO: 174 and the VL of SEQ ID NO: 175.

SEQ ID NO: 170
EVQLVESGGGLVQPGGSLRLSCAASGFTFSRYWMSWVRQAPGKGLEWVAN
IKQDGSEKYYVDSVKGRFTISRDNAKNSLYLQMNSLRAEDTAVYYCAREG
GWFGELAFDYWGQGTLVTVSS

SEQ ID NO: 171
EIVLTQSPGTLSLSPGERATLSCRASQRVSSSYLAWYQQK PGQAPRLLI
YDASSRATGIPDRFSGSGSGTDFTLTISRLEPEDFAVYYCQQYGSLPWTF
GQGTKVEIK

SEQ ID NO: 172
EVQLVESGGGLVQPGGSLRLSCAASGFTFSDSWIHWVRQAPGKGLEWVAW
ISPYGGSTYYADSVKGRFTISADTSKNTAYLQMNSLRAEDTAVYYCARRH
WPGGFDYWGQGTLVTVSS

SEQ ID NO: 173
DIQMTQSPSSLSASVGDRVTITCRASQDVSTAVAWYQQKPGKAPKLLIYS
ASFLYSGVPSRFSGSGSGTDFTLTISSLQPEDFATYYCQQYLYHPATFGQ
GTKVEIK

SEQ ID NO: 174
EVQLLESGGGLVQPGGSLRLSCAASGFTFSSYIMMWVRQAPGKGLEWVSS
IYPSGGITFYADTVKGRFTISRDNSKNTLYLQMNSLRAEDTAVYYCARIK
LGTVTTVDYWGQGTLVTVSS

SEQ ID NO: 175
QSALTQPASVSGSPGQSITISCTGTSSDVGGYNYVSWYQQHPGKAPKLMI
YDVSNRPSGVSNRFSGSKSGNTASLTISGLQAEDEADYYCSSYTSSSTRV
FGTGTKVTVL

The second therapeutic agent may be any one or more of the chemotherapeutic drugs or other anti-cancer therapeutics known to those of skill in the art. Chemotherapeutic agents include alkylating agents, anti-metabolites, anti-microtubule inhibitors, topoisomerase inhibitors, receptor tyrosine kinase inhibitors, angiogenesis inhibitors and the like. Examples of chemotherapeutic agents include alkylating agents such as thiotepa and CYTOXAN® (cyclosphosphamide)®); alkyl sulfonates such as busulfan, improsulfan and piposulfan; aziridines such as benzodopa, carboquone, meturedopa, and uredopa; ethylenimines and methylamelamines including HEXALEN® (altretamine), triethylenemelamine, trietylenephosphoramide, triethylenethiophosphaoramide and trimethylolomelamine; nitrogen mustards such as LEUKERAN® (chlorambucil), chlornaphazine, cholophosphamide, EMCYT® (estramustine), IFEX® (ifosfamide), MUSTARGEN® (mechlorethamine), ALKERAN® (melphalan), novembichin, phenesterine, MOSTARINA® (prednimustine), trofosfamide, uracil mustard; nitrosureas such as BiCNU® (carmustine), chlorozotocin, MUPHORAN® (fotemustine), GLEOSTINE® (lomustine), nimustine, CYMERIN® (ranimustine); antibiotics such as aclacinomysin, actinomycin, authramycin, azaserine, bleomycin, cactinomycin, calicheamicin, carabicin, carminomycin, carzinophilin, chromomycin, COSMEGEN® (dactinomycin), CERUBIDNE® (daunorubicin), detorubicin, 6-diazo-5-oxo-L-norleucine, ADRIAMYCIN® (doxorubicin), ELLENCE™ (epirubicin), esorubicin, IDAMYCIN® (idarubicin), marcellomycin, MUTAMYCIN® (mitomycin), mycophenolic acid, nogalamycin, olivomycins, peplomycin, potfiromycin, puromycin, quelamycin, rodorubicin, streptonigrin, ZANOSAR® (streptozocin), tubercidin, ubenimex, zinostatin, zorubicin; anti-metabolites such as RASUVO® (methotrexate) and ADRUCIL® (5-FU); folic acid analogues such as denopterin, pteropterin, trimetrexate; purine analogues such as FLUDARA® (fludarabine), PURINETHOL® (6-mercaptopurine), thiamiprine, TABLOID® (thioguanine); pyrimidine analogues such as ancitabine, VIDAZA® (azacitidine), 6-azauridine, carmofur, CYTOSAR-U® (cytarabine), dideoxyuridine, doxifluridine, enocitabine, FUDR® (floxuridine); androgens such as calusterone, dromostanolone propionate, THIOREDON® (epitiostanol), TESLAC® (testolactone); anti-adrenals such as CYTARDEN® (aminoglutethimide), LYSODREN® (mitotane), trilostane; folic acid replenisher such as LEUCOVORIN™ (frolinic acid); aceglatone; aldophosphamide glycoside; aminolevulinic acid; amsacrine; bestrabucil; bisantrene; edatraxate; defofamine; demecolcine; diaziquone; VANIQA® (elfornithine); elliptinium acetate; etoglucid; gallium nitrate; DROXIA® (hydroxyurea); lentinan; lonidamine; mitoguazone; mitoxantrone; mopidamol; nitracrine; NIPENT® (pentostatin); phenamet; pirarubicin; podophyllinic acid; 2-ethylhydrazide; MATULANE® (procarbazine); PSK; razoxane; sizofiran; spirogermanium; tenuazonic acid; triaziquone; 2,2',2"-trichlorotriethylamine; urethan; vindesine; DTIC-DOME® (dacarbazine); mannomustine; mitobronitol; mitolactol; pipobroman; gacytosine; CYTOSAR-U° (arabinoside); CYTOXAN® (cyclophosphamide); THIOPLEX® (thiotepa); members of taxoid or taxane family, such as TAXOL® (paclitaxel) and analogues thereof; LEUKERAN® (chlorambucil); GEMZAR® (gemcitabine); THIOGUANINE TABLOID® (6-thioguanine); PURINETHOL® (mercaptopurine); platinum analogues such as PLATINOL® (cisplatin) and PARAPLATIN® (carboplatin); VELBAN® (vinblastine); TOPOSAR® (platinum; etoposide) (also known as VP-16); MUTAMYCIN® (mitomycin C); NOVANTRONE® (mitoxantrone); ONCOVIN® (vincristine); NAVELBINE® (vinorelbine); novantrone; VUMON® (teniposide); CERUBIDINE® (daunomycin); aminopterin; XELODA® (capecitabine); ibandronate; CAMPTOSAR® (irinotecan) (also known as CPT-11); topoisomerase inhibitor RFS 2000; difluoromethylornithine (DMFO); retinoic acid; esperamicin; inhibitors of receptor tyrosine kinases and/or angiogenesis, including NEXAVAR® (sorafenib), SUTENT® (sunitinib), VOITRIENT® (pazopanib), PALLADIA™ (toceranib), ZACTIMA™ (vandetanib, RECENTIN® (cediranib), STIVARGA® (regorafenib) (also known as BAY 73-4506, INLYTA® (axitinib), lestaurtinib (CEP-701), TARCEVA® (erlotinib), IRESSA® (gefitinib), GILOTRIF® (afatinib) (also known as BIBW 2992), TYKERB® (lapatinib), NERLYNX® (neratinib) (also known as HKI-272), and the like, and pharmaceutically acceptable salts, acids or derivatives of any of the above. Also included in this definition are anti-hormonal agents that act to regulate or inhibit hormone action on tumors such as anti-estrogens including for example NOLVADEX® (tamoxifen), EVISTA® (raloxifene), aromatase inhibiting 4(5)-imidazoles, 4-hydroxytamoxifen, trioxifene, keoxifene, LY 117018, onapristone, and FARESTON® (toremifene); and anti-androgens such as EULEXIN® (flutamide), NILANDRON® (nilutamide), CASODEX® (bicalutamide), leuprolide, and ZOLADEX® (goserelin); and pharmaceutically acceptable salts, acids or derivatives of any of the above. Other conventional cytotoxic chemical compounds as those disclosed in Wiemann et al., 1985, in Medical Oncology (Calabresi et aL, eds.), Chapter 10, McMillan Publishing, are also applicable to the methods of the present invention.

Exemplary agents that may be used in combination with the agonistic antibodies specifically binding human CD40 of the invention include tyrosine kinase inhibitors and targeted anti-cancer therapies such as IRESSA® (gefitinib) and TARCEVA® (erlotinib) and other antagonists of HER2, HER3, HER4 or VEGF. Exemplary HER2 antagonists include CP-724-714, HERCEPTIN® (trastuzumab), OMNITARG® (pertuzumab), mubritinib (also known as TAK-165), TYKERB® (lapatinib) (EGFR and HER2 inhibitor), and GW-282974. Exemplary HER3 antagonists include anti-Her3 antibodies (see e.g., U.S. Pat. Publ. No. 2004/0197332). Exemplary HER4 antagonists include anti-HER4 siRNAs (see e.g., Maatta et al., Mol Biol Cell 17: 67-79, 2006). An exemplary VEGF antagonist is AVASTIN® (bevacizumab).

Exemplary therapeutic agents that may be used in combination with the agonistic antibodies specifically binding CD40 of the invention include standard of care drugs for solid tumors.

The combination of the agonistic antibody specifically binding human CD40 of the invention and the second therapeutic agent may be administered over any convenient timeframe. For example, the agonistic antibody specifically binding human CD40 and the second therapeutic agent may be administered to the subject the same day, and even in the same intravenous infusion. However, the agonistic antibody specifically binding human CD40 of the invention and the second therapeutic agent may also be administered on alternating days or alternating weeks or months, and so on. The agonistic antibody specifically binding human CD40 of the invention and the second therapeutic agent may be administered with sufficient proximity in time that they are simultaneously present (for example, in the serum) at detectable levels in the patient being treated. An entire course of treatment with the agonistic antibody specifically binding human CD40 of the invention consisting of a number of doses over a time period is followed or preceded by a course of treatment with the second therapeutic agent, consisting of a number of doses. A recovery period of 1, 2 or several days or weeks may be used between administration of the agonistic antibody specifically binding human CD40 of the invention and the second therapeutic agent.

The agonistic antibody specifically binding human CD40 of the invention or a combination of the agonistic antibody specifically binding human CD40 of the invention and the second therapeutic agent may be administered together with any form of radiation therapy including external beam radiation, intensity modulated radiation therapy (IMRT), focused radiation, and any form of radiosurgery including Gamma Knife, Cyberlaiife, Linac, and interstitial radiation (for example implanted radioactive seeds, GliaSite balloon), and/or with surgery.

Focused radiation methods that may be used include stereotactic radiosurgery, fractionated stereotactic radiosurgery, and intensity-modulated radiation therapy (IMRT). It is apparent that stereotactic radiosurgery involves the precise delivery of radiation to a tumorous tissue, for example, a brain tumor, while avoiding the surrounding non-tumorous, normal tissue. The dosage of radiation applied using stereotactic radiosurgery may vary typically from 1 Gy to about 30 Gy, and may encompass intermediate ranges including, for example, from 1 to 5, 10, 15, 20, 25, up to 30 Gy in dose. Because of noninvasive fixation devices, stereotactic radiation need not be delivered in a single treatment. The treatment plan may be reliably duplicated day-to-day, thereby allowing multiple fractionated doses of radiation to be delivered. When used to treat a tumor over time, the radiosurgery is referred to as "fractionated stereotactic radiosurgery" or FSR. In contrast, stereotactic radiosurgery refers to a one-session treatment. Fractionated stereotactic radiosurgery may result in a high therapeutic ratio, i.e., a high rate of killing of tumor cells and a low effect on normal tissue. The tumor and the normal tissue respond differently to high single doses of radiation vs. multiple smaller doses of radiation. Single large doses of radiation may kill more normal tissue than several smaller doses of radiation. Accordingly, multiple smaller doses of radiation can kill more tumor cells while sparing normal tissue. The dosage of radiation applied using fractionated stereotactic radiation may vary from range from 1 Gy to about 50 Gy, and may encompass intermediate ranges including, for example, from 1 to 5, 10, 15, 20, 25, 30, 40, or up to 50 Gy in hypofractionated doses. Intensity-modulated radiation therapy (IMRT) may also be used. IMRT is an advanced mode of high-precision three-dimensional conformal radiation therapy (3DCRT), which uses computer-controlled linear accelerators to deliver precise radiation doses to a malignant tumor or specific areas within the tumor, the profile of each radiation beam is shaped to fit the profile of the target from a beam's eye view (BEV) using a multileaf collimator (MLC), thereby producing a number of beams. IMRT allows the radiation dose to conform more precisely to the three-dimensional (3-D) shape of the tumor by modulating the intensity of the radiation beam in multiple small volumes. Accordingly, IMRT allows higher radiation doses to be focused to regions within the tumor while minimizing the dose to surrounding normal critical structures. IMRT improves the ability to conform the treatment volume to concave tumor shapes, for example, when the tumor is wrapped around a vulnerable structure, such as the spinal cord or a major organ or blood vessel.

Anti-Idiotypic Antibodies

The present invention provides for an anti-idiotypic antibody binding to the antibody of the invention.

The invention also provides for an anti-idiotypic antibody specifically binding the antibody comprising the VH of SEQ ID NO: 48 and the VL or SEQ ID NO: 63.

The invention also provides for an anti-idiotypic antibody specifically binding the antibody comprising the VH of SEQ ID NO: 49 and the VL or SEQ ID NO: 64.

The invention also provides for an anti-idiotypic antibody specifically binding the antibody comprising the VH of SEQ ID NO: 50 and the VL or SEQ ID NO: 64.

The invention also provides for an anti-idiotypic antibody specifically binding the antibody comprising the VH of SEQ ID NO: 51 and the VL or SEQ ID NO: 64.

The invention also provides for an anti-idiotypic antibody specifically binding the antibody comprising the VH of SEQ ID NO: 52 and the VL or SEQ ID NO: 65.

The invention also provides for an anti-idiotypic antibody specifically binding the antibody comprising the VH of SEQ ID NO: 53 and the VL or SEQ ID NO: 65.

The invention also provides for an anti-idiotypic antibody specifically binding the antibody comprising the VH of SEQ ID NO: 54 and the VL or SEQ ID NO: 65.

The invention also provides for an anti-idiotypic antibody specifically binding the antibody comprising the VH of SEQ ID NO: 55 and the VL or SEQ ID NO: 65.

The invention also provides for an anti-idiotypic antibody specifically binding the antibody comprising the VH of SEQ ID NO: 55 and the VL or SEQ ID NO: 65.

The invention also provides for an anti-idiotypic antibody specifically binding the antibody comprising the VH of SEQ ID NO: 57 and the VL or SEQ ID NO: 66.

The invention also provides for an anti-idiotypic antibody specifically binding the antibody comprising the VH of SEQ ED NO: 58 and the VL or SEQ ID NO: 67.

The invention also provides for an anti-idiotypic antibody specifically binding the antibody comprising the VH of SEQ ID NO: 59 and the VL or SEQ ID NO: 68.

The invention also provides for an anti-idiotypic antibody specifically binding the antibody comprising the VH of SEQ ID NO: 57 and the VL or SEQ ID NO: 70.

The invention also provides for an anti-idiotypic antibody specifically binding the antibody comprising the VH of SEQ ED NO: 57 and the VL or SEQ ID NO: 71.

The invention also provides for an anti-idiotypic antibody specifically binding the antibody comprising the VH of SEQ ED NO: 57 and the VL or SEQ ID NO: 72.

The invention also provides for an anti-idiotypic antibody specifically binding the antibody comprising the VH of SEQ ID NO: 61 and the VL or SEQ ID NO: 69.

The invention also provides for an anti-idiotypic antibody specifically binding the antibody comprising the VH of SEQ ID NO: 62 and the VL or SEQ ED NO: 69.

An anti-idiotypic (Id) antibody is an antibody which recognizes the antigenic determinants (e.g. the paratope or CDRs) of the antibody. The Id antibody may be antigen blocking or non-blocking. The antigen-blocking Id may be used to detect the free antibody in a sample (e.g. CD40 antibody of the invention described herein). The non-blocking Id may be used to detect the total antibody (free, partially bond to antigen, or fully bound to antigen) in a sample. An Id antibody may be prepared by immunizing an animal with the antibody to which an anti-Id is being prepared.

An anti-Id antibody may also be used as an immunogen to induce an immune response in yet another animal, producing a so-called anti-anti-Id antibody. An anti-anti-Id may be epitopically identical to the original mAb, which induced the anti-Id. Thus, by using antibodies to the idiotypic determinants of a mAb, it is possible to identify other clones expressing antibodies of identical specificity. Anti-Id antibodies may be varied (thereby producing anti-Id antibody variants) and/or derivatized by any suitable technique.
Immunoconjugates An "immunoconjugate" refers to the antibody of the invention conjugated to one or more heterologous molecule(s).

In some embodiments, the antibody of the invention is conjugated to one or more cytotoxic agents or an imaging agent.

Exemplary cytotoxic agents include chemotherapeutic agents or drugs, growth inhibitory agents, toxins (e.g., protein toxins, enzymatically active toxins of bacterial, fungal, plant, or animal origin, or fragments thereof), and radionuclides.

The cytotoxic agent may be one or more drugs, such as to a mayatansinoid (see, e.g., U.S. Pat. No. 5,208,020, U.S. Pat. No. 541,606), an auristatin such as monomethylauristatin drug moieties DE and DF (MMAE and MMAF) (see, e.g., U.S. Pat. Nos. 5,635,483, 5,780,588, and 7,498,298), a dolastatin, a calicheamicin or derivative thereof (see, e.g., U.S. Pat. Nos. 5,712,374, 5,714,586, 5,739,116, 5,767,285, 5,770,701, 5,770,710, 5,773,001, and 5,877,296; Hinman et al., (1993) *Cancer Res* 53:3336-3342; and Lode et al., (1998) *Cancer Res* 58:2925-2928); an anthracycline such as daunomycin or doxorubicin (see, e.g., Kratz et al., (2006) *Current Med. Chem* 13:477-523; Jeffrey et al., (2006) *Bioorganic & Med Chem Letters* 16:358-362; Torgov et al., (2005) *Bioconj Chem* 16:717-721; Nagy et al., (2000) *Proc Natl Acad Sci USA* 97:829-834; Dubowchik et al, *Bioorg. & Med. Chem. Letters* 12: 1529-1532 (2002); King et al., (2002) *J Med Chem* 45:4336-4343; and U.S. Pat. No. 6,630,579), RASUVO® (methotrexate), ELDISINE® (vindesine), a taxane such as TAXOTERE® (docetaxel), TAXOL® (paclitaxel), larotaxel, tesetaxel, and ortataxel.

The cytotoxic agent may also be an enzymatically active toxin or fragment thereof, such as diphtheria A chain, nonbinding active fragments of diphtheria toxin, exotoxin A chain (from *Pseudomonas aeruginosa*), ricin A chain, modeccin A chain, alpha-sarcin, *Aleurites fordii* proteins, dianthins, *Phytolacca americana* proteins (PAPI, PAPII, and PAP-S), *Momordica charantia* inhibitor, curcin, crotin, *Saponaria officinalis* inhibitor, gelonin, mitogellin, restrictocin, phenomycin, enomycin, and the tricothecenes.

The cytotoxic agent or an imaging agent may also be a radionuclide. Exemplary radionuclides include Ac-225, At-211, I-131, I-125, Y-90, Re-186, Re-188, Sm-153, Bi-212, P-32, Pb-212 and radioactive isotopes of Lu. When the radioconjugate is used for detection, it may comprise a radioactive atom for scintigraphic studies, for example Tc-99m or I-123, or a spin label for nuclear magnetic resonance (NMR) imaging (also known as magnetic resonance imaging, mri), such as I-123, I-131, In-111, F-19, C-13, N-15 or O-17.

Conjugates of the antibodies of the invention and the heterologous molecule may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HQ), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin may be prepared as described in Vitetta et al., (1987) *Science* 238: 1098. Carbon-14-labeled 1-isothiocyanatobenzyl-3-methyldiethylene triaminepentaacetic acid (MX-DTPA) is an exemplary chelating agent for conjugation of radionucleotide to the antibody. See, e.g., Int. Patent Publ. No. WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., (1992) *Cancer Res* 52: 127-131; U.S. Pat. No. 5,208,020) may be used.

Conjugates of the antibodies of the invention and the heterologous molecule may be prepared with cross-linker reagents such as BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

The invention also provides for an immunoconjugate comprising the antibody specifically binding CD40 of SEQ ID NO: 75 of the invention linked to a therapeutic agent or an imaging agent.

Diagnostic Uses and Kits

The invention also provides for a kit comprising the agonistic antibody specifically binding human CD40 of the invention.

The kit may be used for therapeutic uses and as diagnostic kits.

The kit may be used to detect the presence of CD40 in a biological sample.

In some embodiments, the kit comprises the agonistic antibody specifically binding human CD40 of the invention and reagents for detecting the antibody. The kit can include one or more other elements including: instructions for use; other reagents, e.g., a label, a therapeutic agent, or an agent useful for chelating, or otherwise coupling, an antibody to a label or therapeutic agent, or a radioprotective composition; devices or other materials for preparing the antibody for administration; pharmaceutically acceptable carriers; and devices or other materials for administration to a subject.

In some embodiments, the kit comprises the antibody of the invention in a container and instructions for use of the kit.

In some embodiments, the antibody in the kit is labeled.

In some embodiments, the kit comprises the antibody C40M67, C40M66, 40M63, C40M62, C40M59, C40M58, C40M56, C40M55, C40M51, C40M18, C40M17, C40M12, C40M102, C40M103, C40M104, C40M105, C40M121 or C40M126.

Methods of Detecting CD40

The invention also provides for a method of detecting CD40 in a sample, comprising obtaining the sample, contacting the sample with the antibody of the invention, and detecting the antibody bound to CD40 in the sample.

In some embodiments, the sample may be derived from urine, blood, serum, plasma, saliva, ascites, circulating cells, circulating tumor cells, cells that are not tissue associated (i.e., free cells), tissues (e.g., surgically resected tumor tissue, biopsies, including fine needle aspiration), histological preparations, and the like.

The antibodies of the invention may be detected using known methods. Exemplary methods include direct labeling of the antibodies using fluorescent or chemiluminescent labels, or radiolabels, or attaching to the antibodies of the invention a moiety which is readily detectable, such as biotin, enzymes or epitope tags. Exemplary labels and moieties are ruthenium, $^{111}$In-DOTA, $^{111}$In-diethylenetri-aminepentaacetic acid (DTPA), horseradish peroxidase, alkaline phosphatase and beta-galactosidase, poly-histidine (HIS tag), acridine dyes, cyanine dyes, fluorene dyes, oxazin dyes, phenanthridine dyes, rhodamine dyes and Alexafluor® dyes.

The antibodies of the invention may be used in a variety of assays to detect CD40 in the sample. Exemplary assays are western blot analysis, radioimmunoassay, surface plasmon resonance, immunoprecipitation, equilibrium dialysis, immunodiffusion, electrochemiluminescence (ECL) immunoassay, and immunohistochemistry, fluorescence-activated cell sorting (FACS) or ELISA assay.

The present invention will now be described with reference to the following specific, non-limiting examples.

Example 1. Materials and Methods

Generation of Antigens Used in the Studies

Cloning, expression and purification of the antigens was done using standard methods. The amino acid sequences of the proteins used are shown below.

```
Full length human CD40 (huCD40);
                                      SEQ ID NO: 75
MVRLPLQCVLWGCLLTAVHPEPPTACREKQYLINSQCCSLCQPGQKLVSD

CTEFTETECLPCGESEFLDTWNRETHCHQHKYCDPNLGLRVQQKGTSETD

TICTCEEGWHCTSEACESCVLHRSCSPGFGVKQIATGVSDTICEPCPVGF

FSNVSSAFEKCHPWTSCETKDLVVQQAGTNKTDVVCGPQDRLRALVVIPI

IFGILFAILLVLVFIKKVAKKPTNKAPHPKQEPQEINFPDDLPGSNTAAP

VQETLHGCQPVTQEDGKESRISVQERQ

Human CD40 extracellular domain (huCD40-ECD);
                                      SEQ ID NO: 76
EPPTACREKQYLINSQCCSLCQPGQKLVSDCTEFTETECLPCGESEFLDT

WNRETHCHQHKYCDPNLGLRVQQKGTSETDTICTCEEGWHCTSEACESCV

LHRSCSPGFGVKQIATGVSDTICEPCPVGFFSNVSSAFEKCHPWTSCETK

DLVVQQAGTNKTDVVCGPQDRLR

Macaca fascicularis (cynomolgous, herein referred
to as cyno) CD40 (cCD40);
                                      SEQ IDNO: 77
MVRLPLQCVLWGCLLTAVYPEPPTACREKQYLINSQCCSLCQPGQKLVSD

CTEFTETECLPCSESEFLDTWNRETRCHQHKYCDPNLGLRVQQKGTSETD

TICTCEEGLHCMSESCESCVPHRSCLPGFGVKQIATGVSDTICEPCPVGF

FSNVSSAFEKCRPWTSCETKDLVVQQAGTNKTDVVCGPQDRQRALVVIPI

CLGILFVILLLVLVFIKKVAKKPNDKAPHPKQEPQEINFLDDLPGSNPAA

PVQETLHGCQPVTQEDGKESRISVQERQ

Cyno CD40 extracellular domain (cCD40-ECD);
                                      SEQ ID NO: 78
EPPTACREKQYLINSQCCSLCQPGQKLVSDCTEFTETECLPCSESEFLDT

WNRETRCHQHKYCDPNLGLRVQQKGTSETDTICTCEEGLHCMSESCESCV

PHRSCLPGFGVKQIATGVSDTICEPCPVGFFSNVSSAFEKCRPWTSCETK

DLVVQQAGTNKTDVVCGPQDRQR

Full length human CD154;
                                      SEQ ID NO: 83
MIETYNQTSPRSAATGLPISMKIFMYLLTVFLITQMIGSALFAVYLHRRL

DKIEDERNLHEDFVFMKTIQRCNTGERSLSLLNCEEIKSQFEGFVKDIML

NKEETKKENSFEMQKGDQNPQIAAHVISEASSKTTSVLQWAEKGYYTMSN

NLVTLENGKQLTVKRQGLYYIYAQVTFCSNREASSQAPFIASLCLKSPGR

FERILLRAANTHSSAKPCGQQSIHLGGVFELQPGASVFVNVTDPSQVSHG

TGFTSFGLL

Soluble human CD154;
                                      SEQ ID NO: 88
MQKGDQNPQIAAHVISEASSKTTSVLQWAEKGYYTMSNNLVTLENGKQLT

VKRQGLYYIYAQVTFCSNREASSQAPFIASLCLKSPGRFERILLRAANTH

SSAKPCGQQSIHLGGVFELQPGASVFVNVTDPSQVSHGTGFTSFGLLKL

Soluble cyno CD154
                                      (SEQ ID NO: 45)
MQKGDQNPQIAAHVISEASSKTTSVLQWAEKGYYTMSNNLVTLENGKQLT

VKRQGLYYIYAQVTFCSNREASSQAPFIASLCLKSPGRFERILLRAANTH

SSAKPCGQQSIHLGGVFELQPGASVFVNVTDPSQVSHGTGFTSFGLLKL
```

Binding Assay in Primary Human and Cyno Dendritic Cells (DCs)

Human monocytes were isolated from either frozen/fresh PBMC using CD14 negative isolation kit per manufacturer's protocol (MACS Miltenyi). Cyno monocytes were isolated from fresh PBMC using CD14 positive isolation kit per manufacturer's protocol (MACS Miltenyi). To generate DCs, monocytes were cultured for 5 days in complete media RPMI (Invitrogen) in the presence of 100 ng/ml human GM-CSF and human IL-4 (Peprotech) and media was replenished every 2 days. On day 5, DCs were stimulated with 100 ng/ml LPS (Sigma) for 24 hours. Cells were then stained with each of the tested CD40 antibody at different concentration in flow cytometry buffer (PBS+1% FBS; BD Bioscience) in 100 μl volume for 30 minutes on ice followed with two washes with flow buffer. Cells were then stained for additional 30 minutes on ice with APC-conjugated anti human IgG (Jackson ImmunoResearch) at the recommended dilution 1:100 and washed twice with flow buffer. Cells were analyzed for percent positive and Mean Fluorescence Intensity (MFI) to determine the antibody binding using Fortessa (BD Bioscience).

Binding Assay in Raji (B Cells Lymphoma Cell Line) and HEKCD40 Cell Line

Raji cells were obtained from ATCC and HEKCD40 cell line was obtained from Invivogen. Cells were cultured in complete RMPI media per company's recommendation. Staining was done as described above for binding assay in primary human and cyno DCs.

Human DCs and B Cells Activation Assay

Human DCs were generated as described above. Human B cells were isolated from fresh or frozen PBMC using B cells negative isolation kit per manufacturer's protocol (MACS Miltenyi). Titrations of each CD40 antibodies were plated on 96-well U bottom plate and cells were added and the mixture was incubated for 15 minutes at room temperature. Either media or cross-linker anti-human F(ab')2 at a fixed concentration 20 μg/ml was added and the complex was incubated for 24 hours for DC assay and 48 hours for B cells assay in 37° C. incubator. Cells were harvested at the end of time point, washed twice with flow buffer and were incubated with human Fc block (Miltenyi) for 15 minutes at room temperature followed with one wash. Cells were then stained for activation markers CD80, CD83, CD86, HLA-DR and CD23 (BD Bioscience and BioLegend) for 30 minutes on ice, followed with two washes. Cells were analyzed using BD Fortessa.

Cyno B Cells Activation Assay

Cyno B cells were isolated from fresh PBMC using B cells positive isolation kit per manufacturer's protocol (MACS Milteny). The activation assays were set up as described above for human DC and B cells.

HEK-Blue™ CD40L NF-κB Activation Assay

HEK-Blue™ CD40L cells over-expressing CD40 (Invivogen) were used to assess ability of the antibodies to either block CD40-CD154 interaction or activate CD40. HEK-Blue™ CD40L cell lines stably express human CD40 and NF-κB-inducible secreted embryonic alkaline phosphatase (SEAP). Activation of CD40 on HEK-Blue™ CD40L cells induces downstream signaling events leading to activation of NF-κB and secretion of SEAP, which can be measured using QUANTI-Blue™ according to manufacturer's instruction. Anti-CD40 antibodies were assessed for their ability to either block or agonize CD40 activation.

Inhibition of CD40 Dependent NF-kB Activation in HEK-Blue CD40L Cell Line

HEK-Blue™ CD40L cell lines (Invivogen), which were handled and maintained according to the vendor's protocol, were seeded into 96 well tissue culture plates at a cell density of $2.5 \times 10^4$ cells per well in 100 µl volume. The assay plates were covered, and the cells recovered overnight (37° C., 5% $CO_2$). On the following day, 4× solutions of rhCD154-ECD-His (40 ng/ml final concentration) and 4× anti-CD40 mAbs, or Fabs, at appropriate concentrations (1-25 µg/ml final concentration), were prepared and 100 µl/well of the resulting 2× solutions added to the 96 well assay plates containing HEK-Blue CD40L™ cells (200 µl/well final volume). After 16-24 h incubation (37° C., 5% $CO_2$) time the supernatants were analyzed for phosphatase activity in a 96 well assay plate by adding 40 µl/well of supernatants to 160 µl/well of pre-warmed QUANTI-Blue™ (Invivogen), which was prepared according to vendor's protocol. The plates were sealed and incubated for 30-60 minutes prior to obtaining absorbance at 650 nm.

CD40 Dependent NF-kB Activation in HEK-Blue CD40L NFkB-SEAP Cell Line

HEK-Blue™ CD40L cells were seeded as described above and recovered overnight. On the following day, CD40 mAbs were added as 2× solutions to the 96 well plate containing HEK-Blue™ CD40L cells (200 µl final volume/well) and the plate incubated overnight (37° C., 5% $CO_2$). For measuring agonist activity of anti-CD40 mAbs alone, a broad range of final assay concentration of 1-25 µg/ml was used. For determining effect of cross-linking on agonist activity of anti-CD40 mAbs, a 4× solution of antibody and 4× solution of F(ab')2 fragment against anti-hIgG Fc fragment (5-10 fold excess relative to mAb) were pre-incubated at RT for 1 hour prior to addition to the cells; a titration starting at 1 µg/ml anti-CD40 mAb was used to obtain dose curves. After 16-24 h incubation (37° C., 5% $CO_2$), the supernatants were analyzed for phosphatase activity in a 96 well assay plate by adding 40 µl/well of supernatants to 160 µl/well of pre-warmed QUANTI-Blue™ (Invivogen), which was prepared according to vendor's protocol. The plates were sealed and incubated for 30-60 minutes prior to obtaining absorbance at 650 nm.

Example 2. Isolation of Anti-CD40 Antibodies from Phage Display Libraries

Isolation of Anti-CD40 Antibodies from Phage Display Libraries

CD40-binding Fabs were selected from de novo pIX phage display libraries as described in Shi et al., J Mol Biol 397:385-96, 2010, Int. Pat. Publ. No. WO2009/085462 and U.S. Pat. Publ. No. 2010/0021477. Briefly, the libraries were generated by diversifying human scaffolds where germline VH genes IGHV1-69*01, IGHV3-23*01, and IGHV5-51*01 were recombined with the human IGHJ-4 minigene via the H3 loop, and human germline VL kappa genes O12 (IGKV1-39*01), L6 (IGKV3-11*01), A27 (IGKV3-20*01), and B3 (IGKV4-1*01) were recombined with the IGKJ-1 minigene to assemble complete VH and VL domains. The positions in the heavy and light chain variable regions around H1, H2, L1, L2 and L3 loops corresponding to positions identified to be frequently in contact with protein and peptide antigens were chosen for diversification. Sequence diversity at selected positions was limited to residues occurring at each position in the IGHV or IGLV germline gene families of the respective IGHV or IGLV genes. Diversity at the H3 loop was generated by utilizing short to mid-sized synthetic loops of lengths 7-14 amino acids. The amino acid distribution at H3 was designed to mimic the observed variation of amino acids in human antibodies. Library design is detailed in Shi et al., J Mol Biol 397:385-96, 2010. The scaffolds utilized to generate libraries were named according to their human VH and VL germline gene origin. The three heavy chain libraries were combined with the four germline light chains or combined with the diversified light chain libraries to generate 12 unique VH:VL combinations. These libraries were later combined further based on library versions to generate additional libraries for panning experiments against CD40.

The libraries were panned against either biotinylated huCD40-ECD or cCD40-ECD fused to Fc. Biotinylated antigen was captured on streptavidin magnetic beads (Dynal) and exposed to the de novo pIX Fab libraries at a final concentration of 100 nM or 10 nM. Non-specific phages were washed away in PBS-Tween and bound phages were recovered by infection of TG1 E. coli cells. Phages were amplified from these cells overnight and panning was repeated for a total of four rounds. Following four rounds of biopanning, monoclonal Fabs were screened for binding to huCD40-ECD and cCD40-ECD fused to Fc or His tag in an ELISA where Fabs were captured on an ELISA plate by Sheep anti-human FD, biotinylated CD40 was added to the captured Fabs, followed by detection of antigens with streptavidin HRP. Clones that demonstrated binding to both human and cyno versions of CD40 were sequenced in the heavy and light chain variable regions.

Select clones were further affinity-matured. Since the de novo panning outputs were pooled by heavy chains, the monoclonal pairing of light chains were not known. Therefore the affinity maturation was done such that the heavy chains from each de novo selection output was cloned into all four possible kappa light chain v5 libraries.

The VH region of each de novo output was PCR amplified and cloned into the light chain libraries via XhoI and NcoI restriction enzyme sites. These libraries were prepared on M13 phage and used for panning and screening as described with the exception of reduced antigen concentrations (10 nM, 1 nM, 0.3 nM). through three rounds of panning. Also, a prolonged one hour wash was done in the third round prior to E. coli cell infections. Monoclonal Fabs obtained from the affinity maturation campaign were screened for binding to both human and cyno CD40 in the same manner as the de novo selection and those showing cross-reactivity were sequenced.

Isolation of Anti-CD40 Antibodies Using Rats Expressing Human Immunoglobulin Loci Anti-CD40 antibodies were generated using transgenic rats expressing human immunoglobulin loci, the OmniRat®; OMT, Inc. The OmniRat® endogenous immunoglobulin loci are replaced by human Igκ and Igλ loci and a chimeric human/rat IgH locus with V, D and J segments of human origin linked to the rat $C_H$ locus. The IgH locus contains 22 human $V_H$s, all human D and $J_H$ segments in natural configuration linked to the rat $C_H$ locus. Generation and characterization of the OmniRat® is described in Osborn, et al. J Immunol 190: 1481-1490, 2013; and Int. Pat. Publ. No. WO14/093908.

Separate cohorts of five OmniRat s were immunized with recombinant human and cyno CD40 ECD-His or human and cyno CD40 ECD-Fc proteins. Following a 31-34 day immunization regimen, lymph nodes were harvested from two rats and used to generate hybridomas. The generated hybridomas were screened for binding to both human and cyno CD40-ECD. Hybridomas exhibiting statistically significant binding to both human and cyno CD40-ECD following one-way ANOVA with a Dunnett's mean comparison post-test were cloned and their V regions sequenced using standard procedures The sequences identified from de novo phage panning and immunization of OMT rats, and subsequent screening of hybridoma supernatants, were expressed as both mAbs and Fabs and screened for potential antagonist activity in the HEK-Blue™ CD40L NF-κB activation assay. Of the 18 de novo phage derived sequences expressed as mAbs, 4 mAbs were identified to exhibit antagonist activity based on the criteria that an antagonist will have a signal that is lower than the 3× standard deviation of the mean signal of HEK-Blue™ CD40L cells treated with rhCD154-ECD-his alone. Of the corresponding 18 Fabs, 15 Fabs were identified as antagonist based on the same criteria. Of the 13 hybridoma derived sequences, 6 mAbs and 8 corresponding Fabs were identified as antagonists. Therefore, from a total of 31 mAbs and corresponding Fabs, 10 mAbs and 23 Fabs were identified as possessing antagonist activity.

The 31 mAbs described above were screened in the HEK-Blue™ CD40L NF-κB activation assay without any CD40 ligand to identify potential agonists. Of the 18 de novo phage derived sequences, 16 mAbs were identified as agonists based on the criteria that an agonist will show a signal that is higher than 3× standard deviation of the mean signal of HEK-Blue™ CD40L cells alone. From the 13 sequences from the hybridoma library, 8 mAbs were identified as agonists. Therefore, out of 31 total mAbs screened 24 mAbs were identified as agonists.

Example 3. Anti-CD40 Antibodies Bind CD40 on Cells

Select antibodies that blocked CD154 binding to CD40 were characterized further for their binding to various cell expressing CD40.

The experiments were conducted using assays described above. 20 antibodies were characterized further based on their binding to human DCs, cyno DCs, Raji cells and HEK-Blue™ CD40L cells. Table 4 shows the $EC_{50}$ values for select antibodies for their binding to these cells, and the source of the antibodies (phage or OmniRat®)

TABLE 4

| Antibody | Antibody source | $EC_{50}$ (µg/ml) | | | |
| --- | --- | --- | --- | --- | --- |
| | | Human mature DCs | Cyno mature DCs | HEK-Blue™ CD40L | Raji |
| C40M9 | OMT | 0.1233 | 0.04507 | 0.09424 | 0.05708 |
| C40M12 | OMT | 0.2984 | 0.04737 | 0.1124 | 0.0299 |
| C40M17 | OMT | 0.1274 | 0.05372 | 0.07505 | 0.07394 |
| C40M18 | OMT | 0.352 | 0.03895 | 0.1262 | 0.07298 |
| C40M51 | Phage | 0.4783 | 0.05439 | 0.128 | 0.04337 |
| C40M55 | Phage | 0.1025 | 0.02182 | 0.06306 | 0.04615 |
| C40M56 | Phage | 0.402 | 0.05652 | 0.1089 | 0.09496 |
| C40M58 | Phage | 0.7238 | 0.07072 | 0.1458 | 0.06109 |
| C40M59 | Phage | 0.8261 | 0.07404 | 0.3536 | 0.1247 |
| C40M62 | Phage | 0.3288 | 0.07157 | 0.2276 | 0.0994 |
| C40M63 | Phage | 0.09962 | 0.03095 | 0.0849 | 0.03957 |
| C40M66 | Phage | 0.2024 | 0.04826 | 0.1688 | 0.07303 |
| C40M67 | Phage | 0.7658 | 0.3269 | 0.5497 | 0.2474 |

Example 4. Characterization of Agonistic Anti-CD40 Antibodies

Figure 1C:
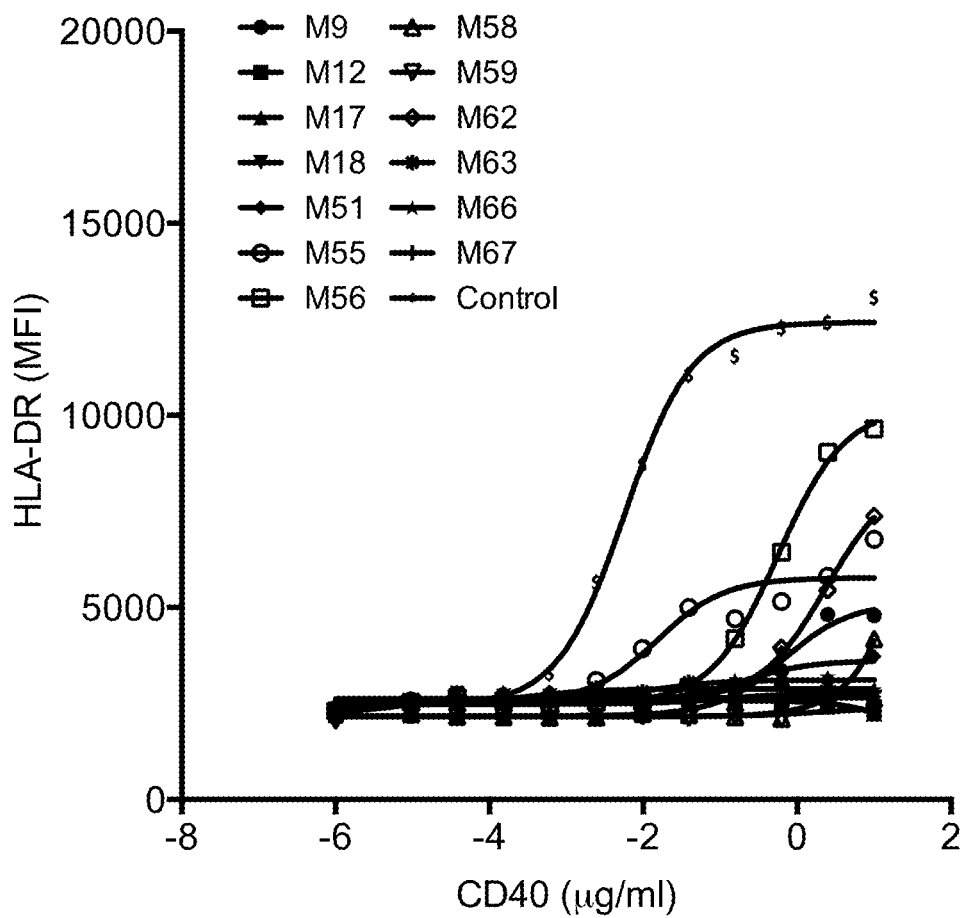
FIG. 1C shows that antibodies specifically binding human CD40 activate B cells in cross-linking dependent manner. B cell activation was measured as increased HLA-DR surface expression in the absence of a cross-linker. M9 refers to antibody C40M9, etc. Control: CP-870,893.
Figure 1D:
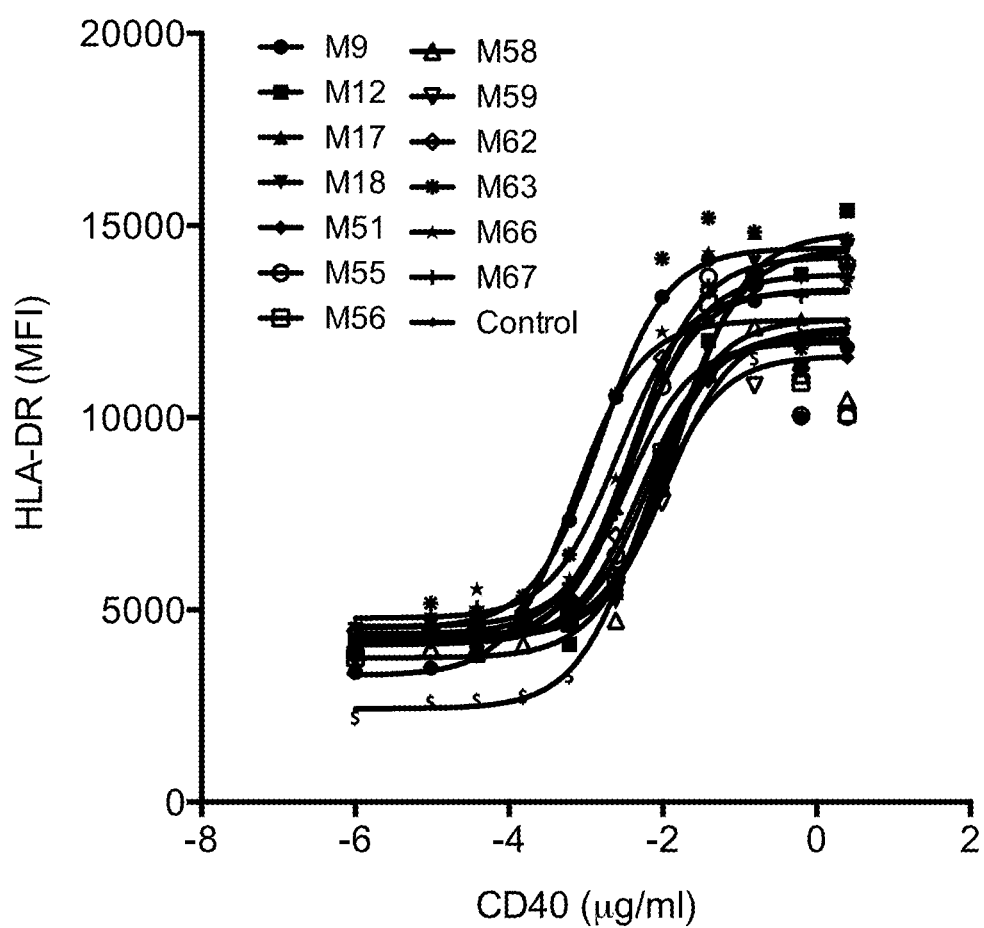
FIG. 1D shows that antibodies specifically binding human CD40 activate B cells in cross-linking dependent manner. B cell activation was measured as increased HLA-DR surface expression in the presence of a cross-linker. M9 refers to antibody C40M9, etc. Control: CP-870,893.
Figure 2A:
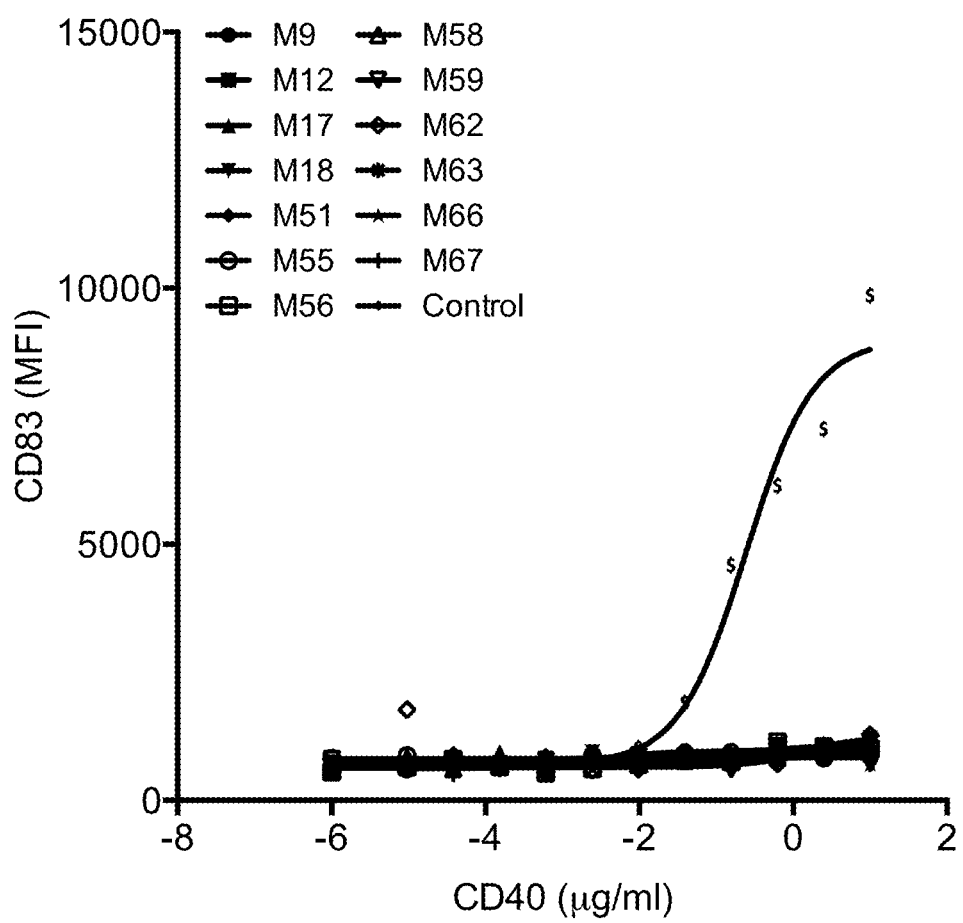
FIG. 2A shows that antibodies specifically binding human CD40 activate dendritic cells (DC) in cross-linking dependent manner. DC activation was measured as increased CD83 surface expression in the absence of a cross-linker. M9 refers to antibody C40M9, etc. Control: CP-870,893.
Figure 2B:
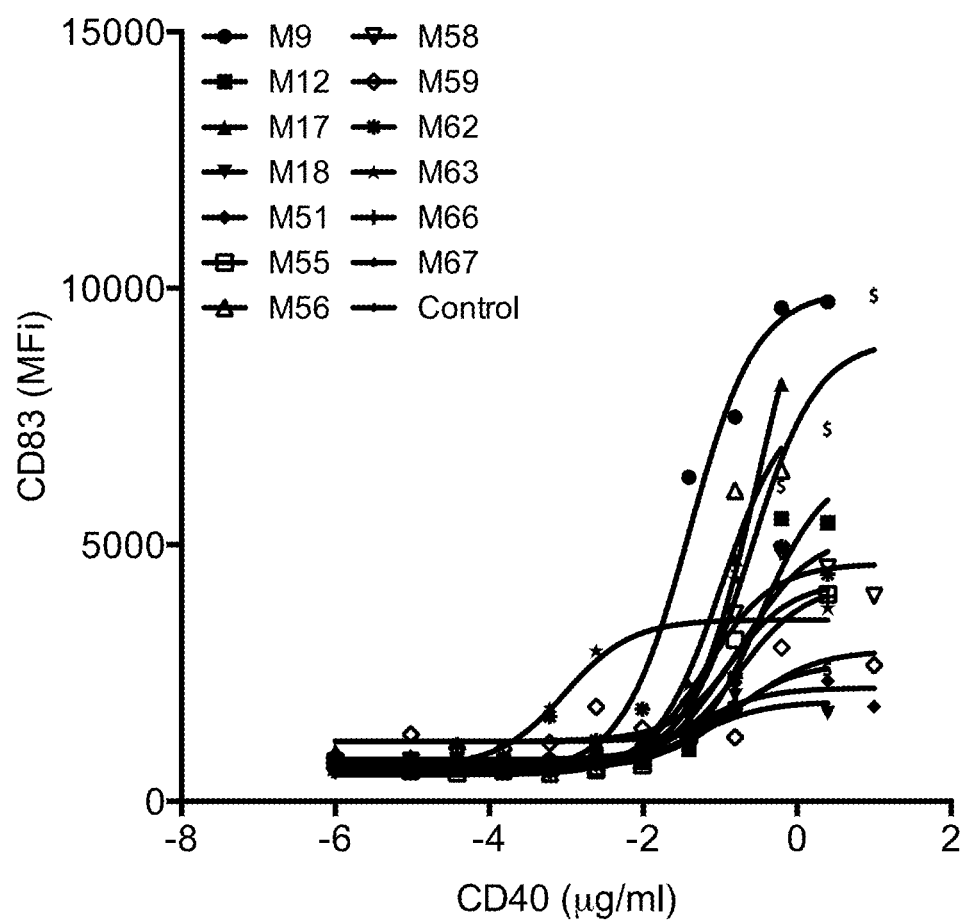
FIG. 2B shows that antibodies specifically binding human CD40 activate dendritic cells (DC) in cross-linking dependent manner. DC activation was measured as increased CD83 surface expression in the presence of a cross-linker. M9 refers to antibody C40M9, etc. Control: CP-870,893.
Figure 2C:
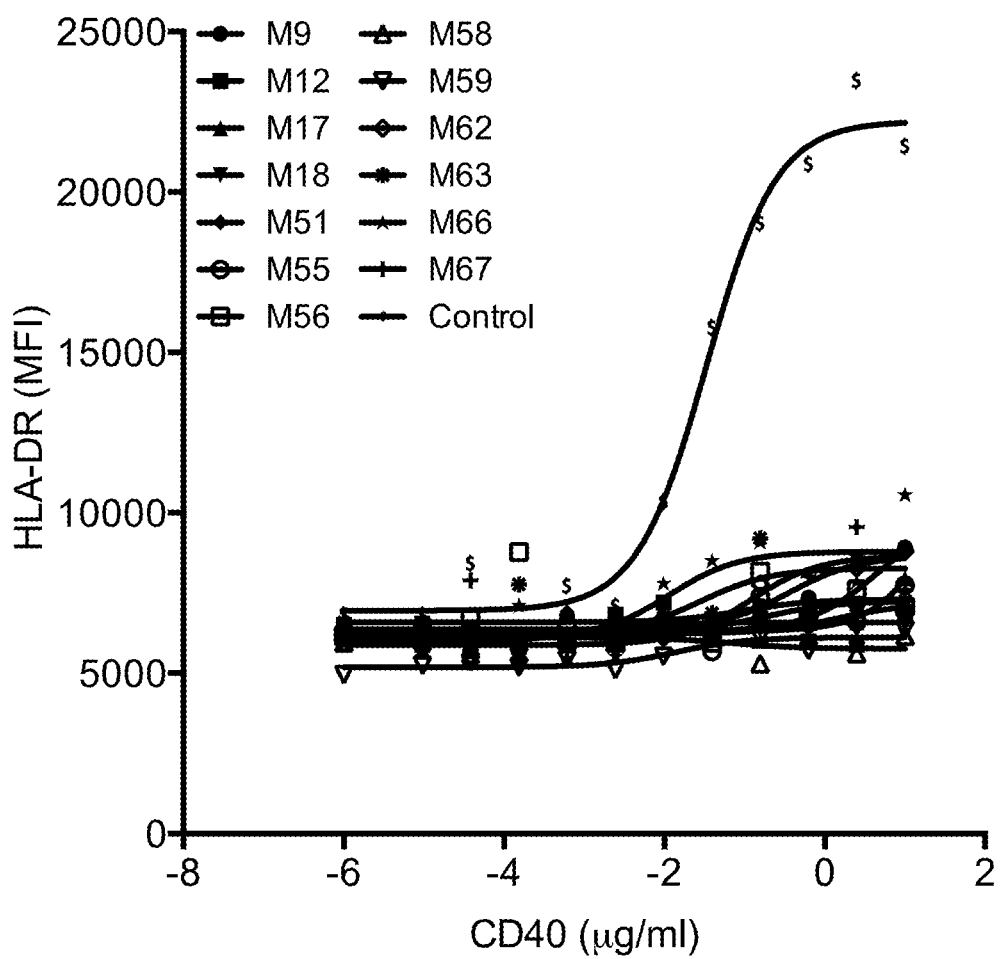
FIG. 2C shows that antibodies specifically binding human CD40 activate dendritic cells (DC) in cross-linking dependent manner. DC activation was measured as increased HLA-DR surface expression in the absence of a cross-linker. M9 refers to antibody C40M9, etc. Control: CP-870,893.
Figure 2D:
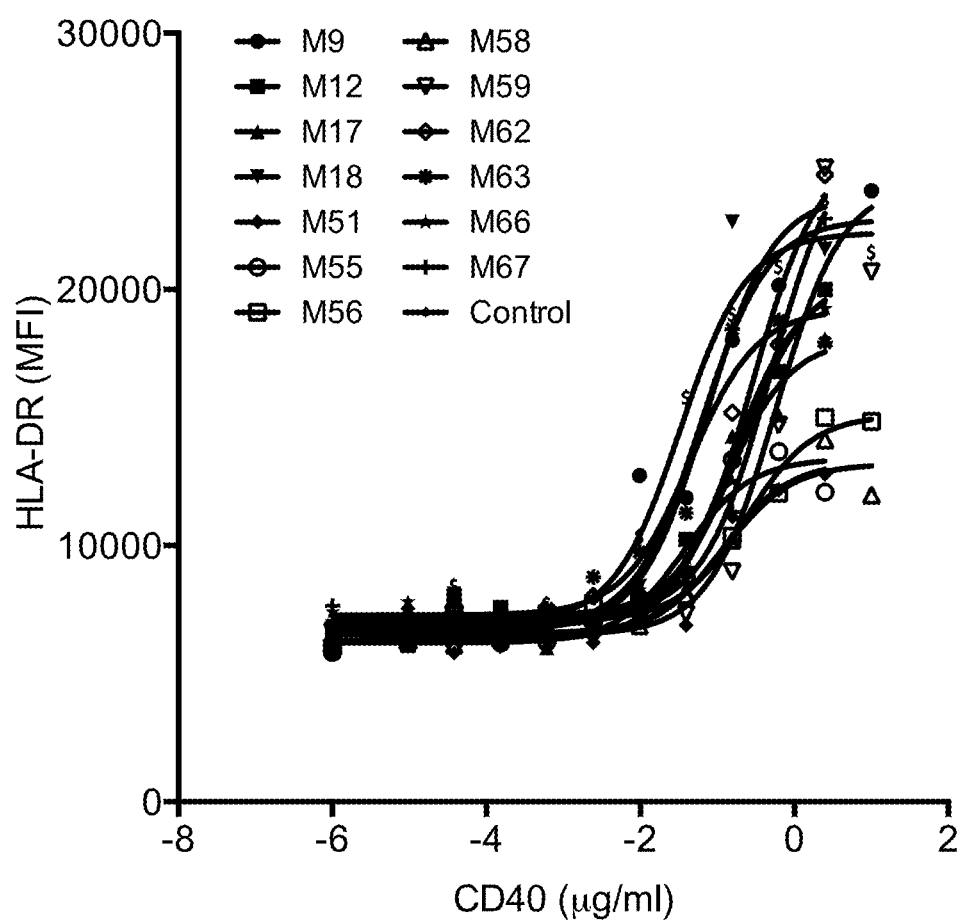
FIG. 2D shows that antibodies specifically binding human CD40 activate dendritic cells (DC) in cross-linking dependent manner. DC activation was measured as increased HLA-DR surface expression in the presence of a cross-linker. M9 refers to antibody C40M9, etc. Control: CP-870,893.

Select antibodies were tested for their ability to activate primary human dendritic cells and B cells in cross-linking dependent manner using assays described above in the presence or absence of cross-linker anti-human (F(ab')2. FIG. 1 shows that select antibodies were able to activate B cells only in the presence of the cross-linker, when B cell activation was assessed by induced CD23 surface expression (FIG. 1A and FIG. 1B) or induced HLA-DR surface expression (FIG. 1C and FIG. 1D). FIG. 2 shows that select antibodies were able to activate DC cells only in the presence of the cross-linker, when DC activation was assessed by induced CD83 surface expression (FIG. 2A and FIG. 2B) or induced HLA-DR surface expression (FIG. 2C and FIG. 2D). A control antibody used in the assays induces B and DC cell activation in cross-linking independent manner (CP-870,893).

$EC_{50}$ values were measured for each tested antibody for induction of surface expression of DC activation markers CD80, CD83, CD86 and HLA-DR and B cell activation markers CD23, CD80, CD83, CD86 and HLA-DR. The antibodies that induced surface expression of all tested DC and B cell markers when cross-linked were classified as agonists. Table 5 shows the $EC_{50}$ values of select antibodies for their induction of surface expression of B cell activation markers. Table 6 shows the $EC_{50}$ values for select antibodies for their induction of surface expression of DC activation markers.

TABLE 5

B cells; EC$_{50}$ (μg/ml)

| Antibody | CD23 | CD80 | CD83 | CD86 | HLA-DR |
|---|---|---|---|---|---|
| C40M9 | 0.002873 | 0.01309 | 0.000006678 | 0.00001087 | 0.00001196 |
| C40M11 | 3.132 | 0.9204 | 0.0208 | 0.01229 | 0.01573 |
| C40M12 | 125.4 | 0.00623 | 0.002844 | 0.002279 | 0.004273 |
| C40M17 | 0.001948 | 0.0008786 | 0.0008382 | 0.004572 | 0.001569 |
| C40M18 | 0.3062 | 0.04806 | 0.06239 | 0.008725 | 0.02386 |
| C40M50 | 1.704 | 2.034 | 1.574 | 1.991 | 1.741 |
| C40M51 | 0.04479 | 0.01831 | 0.02592 | 0.01318 | 0.007773 |
| C40M52 | 1.334 | 0.03019 | 1.481 | 0.007082 | 0.06682 |
| C40M53 | 0.02243 | 0.04693 | 2.247 | 0.006516 | 0.001178 |
| C40M55 | 0.06162 | 0.001433 | 0.001252 | 0.0006455 | 0.0004372 |
| C40M56 | 0.01856 | 0.001414 | 0.001717 | 0.001194 | 0.001054 |
| C40M57 | 0.01587 | 0.001718 | 0.002085 | 0.002345 | 0.001641 |
| C40M58 | 0.06 | 0.02164 | 0.007851 | 0.002352 | 0.004678 |
| C40M59 | 1.236 | 0.01056 | 0.01077 | 0.0154 | 0.004836 |
| C40M60 | 0.02046 | 0.01714 | 0.001706 | 0.001733 | 0.001091 |
| C40M61 | 0.02809 | 0.0224 | 0.004731 | 0.006599 | 0.004719 |
| C40M62 | 0.01253 | 0.001543 | 0.001256 | 0.001135 | 0.0003556 |
| C40M63 | 0.006942 | 0.00001668 | 0.0005813 | 0.00126 | 0.000009663 |
| C40M66 | 0.04141 | 0.005115 | 0.001818 | 0.002464 | 0.001077 |
| C40M67 | 0.004169 | 0.003323 | 0.001463 | 0.002257 | 0.000792 |
| Reference mAb* | 0.003172 | 0.007337 | 0.004283 | 0.004042 | 0.008147 |

*No cross-linker

TABLE 6

DC, EC$_{50}$ (μg/ml)

| Antibody | CD80 | CD83 | CD86 | HLA-DR |
|---|---|---|---|---|
| C40M9 | 0.02769 | 0.03985 | 0.1033 | 0.07974 |
| C40M11 | 0.06097 | 0.312 | 0.1448 | 0.2191 |
| C40M12 | 0.000003935 | 0.3324 | 0.5025 | 0.3006 |
| C40M17 | 0.03602 | 0.3064 | 0.03296 | 1.724E−07 |
| C40M18 | 0.05226 | 0.04784 | 0.03021 | 0.01047 |
| C40M50 | 0.4765 | 0.5989 | 0.0001058 | 0.00004135 |
| C40M51 | 0.9675 | 0.04604 | 0.1281 | 0.05242 |
| C40M52 | 4.207E−11 | 0.1138 | 0.9492 | 0.128 |
| C40M53 | 1.276 | 0.03104 | 0.2996 | 0.04803 |
| C40M55 | 0.0616 | 0.1031 | 0.1981 | 0.08108 |
| C40M56 | 0.05173 | 0.1068 | 0.1321 | 0.06845 |
| C40M57 | 0.1176 | 0.04141 | 0.1284 | 0.05546 |
| C40M58 | 0.05236 | 0.1212 | 0.1149 | 0.000004067 |
| C40M59 | 0.000342 | 0.2755 | 0.009793 | 0.05356 |
| C40M60 | 0.00001139 | 0.01384 | 0.04959 | 0.004906 |
| C40M61 | 0.00001339 | 0.02433 | 0.02089 | 0.001154 |
| C40M62 | 0.6015 | 0.2184 | 0.3811 | 0.06035 |
| C40M63 | 0.07054 | 0.0009615 | 0.2583 | 0.1542 |
| C40M66 | 0.1582 | 0.1746 | 0.4233 | 0.03937 |
| C40M67 | 0.04994 | 0.127 | 0.2015 | 0.05067 |
| Reference mAb | 0.04466 | 0.2454 | 0.133 | 0.2417 |

*No cross-linker

The generated antibodies were compared to the reference antibody CP-870,893 for their ability to induce DC activation using four DC surface markers. Several antibodies induced surface expression of at least one DC activation marker (CD80, CD83, CD86, HLA-DR) with an EC$_{50}$ value comparable or lower than the reference antibody. In the assays, the generated CD40 antibodies were assessed in the presence of the crosslinker, whereas the reference antibody was evaluated in the absence of the crosslinker.

Antibodies C40M9 and C40M48 were more potent in inducing surface expression of all DC activation makers evaluated when compared to the reference antibody.

Antibodies C40M18, C40M55 and C40M63 were more potent in inducing surface expression of three DC activation makers evaluated when compared to the reference antibody.

Antibodies C40M17, C40M51 and C40M56 were more potent in inducing surface expression of two DC activation makers evaluated when compared to the reference antibody.

Antibodies C40M12, C40M62 and C40M66 were more potent in inducing surface expression of one DC activation maker evaluated when compared to the reference antibody.

The experimental data demonstrates that several CD40 agonistic antibodies generated were more potent than the reference antibody in their ability to activate dendritic cells. Importantly, as the generated antibodies were not able to activate DCs or B cells without crosslinking, they are expected to have a beneficial safety profile when compare to the reference antibody.

Example 5. Structural Characterization of CD40 Antibodies

Antibody isolation and sequencing of the polypeptide chains was done using standard methods. The HCDR1 amino acid sequences of select anti-CD40 antibodies are shown in Table 7.
The HCDR2 amino acid sequences of select anti-CD40 antibodies are shown in Table 8.
The HCDR3 amino acid sequences of select anti-CD40 antibodies are shown in Table 9.
The LCDR1 amino acid sequences of select anti-CD40 antibodies are shown in Table 10.
The LCDR2 amino acid sequences of select anti-CD40 antibodies are shown in Table 11.
The LCDR3 amino acid sequences of select anti-CD40 antibodies are shown in Table 12.
The VH amino acid sequences of select anti-CD40 antibodies are shown in Table 13.
The VL amino acid sequences of select anti-CD40 antibodies are shown in Table 14.
The VH DNA sequences of select anti-CD40 antibodies are shown in Table 15.
The VL DNA sequences of select anti-CD40 antibodies are shown in Table 16.
The heavy chain amino acid sequences of select anti-CD40 antibodies are shown in Table 17.
The heavy chain DNA sequences of select anti-CD40 antibodies are shown in Table 18.

The light chain amino acid sequences of select anti-CD40 antibodies are shown in Table 19.

The light chain DNA sequences of select anti-CD40 antibodies are shown in Table 20.

TABLE 7

| | HCDR1 | | | | | | |
|---|---|---|---|---|---|---|---|
| mAb | | | Sequence | | | | SEQ ID NO: |
| C40M67 | D | Y | A | M | N | | 1 |
| C40M66 | S | Y | A | I | S | | 2 |
| C40M63 | S | Y | A | I | S | | 2 |
| C40M62 | S | Y | A | I | S | | 2 |
| C40M59 | S | Y | W | I | S | | 3 |
| C40M58 | S | Y | A | M | S | | 4 |
| C40M56 | S | Y | A | M | S | | 4 |
| C40M55 | S | Y | A | I | S | | 2 |
| C40M51 | S | Y | A | M | S | | 4 |
| C40M18 | S | Y | A | M | S | | 4 |
| C40M17 | S | Y | A | M | S | | 4 |
| C40M12 | S | Y | A | M | S | | 4 |
| C40M9 | S | S | S | Y | Y | W G | 5 |
| C40M102 | S | Y | A | M | S | | 4 |
| C40M103 | S | Y | A | M | S | | 4 |
| C40M104 | S | Y | A | M | S | | 4 |
| C40M105 | S | S | S | Y | Y | W G | 5 |
| C40M121 | S | S | S | Y | Y | W G | 5 |
| C40M126 | S | S | S | Y | Y | W G | 5 |

TABLE 8

| | HCDR2 | | | | | | | | |
|---|---|---|---|---|---|---|---|---|---|
| mAb | | | | Sequence | | | | | SEQ ID NO: |
| C40M67 | GIKSG | GS | SK | YY | AD | SV | KG | | 8 |
| C40M66 | GIIPI | FG | TA | NY | AQ | KF | QG | | 7 |
| C40M63 | GIIPI | FG | TA | NY | AQ | KF | QG | | 7 |
| C40M62 | GIIPI | FG | TA | NY | AQ | KF | QG | | 7 |
| C40M59 | YIIPI | SG | TA | RY | AQ | KF | QG | | 13 |
| C40M58 | AISGS | GG | ST | YY | AD | SV | KG | | 6 |
| C40M56 | AISGS | GG | ST | YY | AD | SV | KG | | 6 |
| C40M55 | GIIPI | FG | TA | NY | AQ | KF | QG | | 7 |
| C40M51 | AISGS | GG | ST | YY | AD | SV | KG | | 6 |
| C40M18 | IINNN | VG | RT | YY | AD | SV | KG | | 9 |
| C40M17 | TINNS | GG | GT | YY | AD | SV | KG | | 11 |
| C40M12 | VISDS | GG | RT | YY | AD | SV | KG | | 12 |
| C40M9 | NIYYR | GD | TY | YS | PS | LK | S | | 10 |
| C40M102 | IINNN | VG | RT | YY | AD | SV | KG | | 9 |
| C40M103 | IINNN | VG | RT | YY | AD | SV | KG | | 9 |
| C40M104 | IINNN | VG | RT | YY | AD | SV | KG | | 9 |
| C40M105 | NIYYR | GD | TY | YS | PS | LK | S | | 10 |
| C40M121 | NIYYR | GD | TY | YS | PS | LK | S | | 10 |
| C40M126 | NIYYR | GD | TY | YS | PS | LK | S | | 10 |

TABLE 9

| | HCDR3 | | | | | | | |
|---|---|---|---|---|---|---|---|---|
| mAb | | | Sequence | | | | | SEQ ID NO: |
| C40M67 | HVD | FY | RA | LD | Y | | | 22 |
| C40M66 | VRY | SA | WY | RD | SL | DY | | 25 |
| C40M63 | VGH | PA | WW | RD | SL | DY | | 24 |
| C40M62 | VAN | AA | YF | RS | GL | DY | | 23 |
| C40M59 | EPG | YS | SG | LS | VD | YF | DY | 17 |
| C40M58 | GPA | YT | IV | FD | Y | | | 19 |
| C40M56 | GPV | YS | LV | FD | Y | | | 20 |
| C40M55 | DGY | RR | YG | IG | RY | GF | DY | 14 |
| C40M51 | GPV | YS | SV | FD | Y | | | 21 |
| C40M18 | EGG | DY | YY | YG | MD | V | | 15 |
| C40M17 | EGG | KY | YY | YA | MD | V | | 16 |
| C40M12 | EGG | DY | YY | YG | MD | V | | 15 |
| C40M9 | GFR | FD | Y | | | | | 18 |
| C40M102 | EGG | DY | YY | YG | MD | V | | 15 |
| C40M103 | EGG | DY | YY | YG | MD | V | | 15 |
| C40M104 | EGG | DY | YY | YG | MD | V | | 15 |
| C40M105 | GFR | FD | Y | | | | | 18 |
| C40M121 | GFR | FD | Y | | | | | 18 |
| C40M126 | GFR | FD | Y | | | | | 18 |

TABLE 10

| mAb | Sequence | SEQ ID NO: |
|---|---|---|
| C40M67 | R A S Q S V K N S S L A | 28 |
| C40M66 | K S S Q S V L Y S S N N K N Y L A | 26 |
| C40M63 | K S S Q S V L Y S S N N K N Y L A | 26 |
| C40M62 | K S S Q S V L Y S S N N K N Y L A | 26 |
| C40M59 | R A S Q S I S S Y L N | 27 |
| C40M58 | R A S Q S I S S Y L N | 27 |
| C40M56 | R A S Q S I S S Y L N | 27 |
| C40M55 | R A S Q S I S S Y L N | 27 |
| C40M51 | R A S Q S I S S Y L N | 27 |
| C40M18 | S G D K L G D K Y V C | 30 |
| C40M17 | S G D K L G D K Y A C | 29 |
| C40M12 | S G D K L G D K Y V C | 30 |
| C40M9 | T G T S S D V G G Y N Y V S | 32 |
| C40M102 | S G D K L G D K Y V C | 30 |
| C40M103 | S G D K L G D K Y V S | 31 |
| C40M104 | S G D K L G D K Y V S | 31 |
| C40M105 | T G T S S D V G G Y N Y V S | 32 |
| C40M121 | T G T S S D V G G Y N Y V S | 32 |
| C40M126 | T G T S S D V G G Y N Y V S | 32 |

TABLE 11

| mAb | Sequence (LCDR2) | SEQ ID NO: |
|---|---|---|
| C40M67 | T A S S R A T | 38 |
| C40M66 | W A S T R E S | 39 |
| C40M63 | W A S T R E S | 39 |
| C40M62 | W A S T R E S | 39 |
| C40M59 | A A S S L Q S | 33 |
| C40M58 | A A S S L Q S | 33 |
| C40M56 | A A S S L Q S | 33 |
| C40M55 | A A S S L Q S | 33 |
| C40M51 | A A S S L Q S | 33 |
| C40M18 | Q D S K R P S | 36 |
| C40M17 | Q D S R R P S | 37 |
| C40M12 | H D N K R P S | 35 |
| C40M9 | E V S K R P S | 34 |
| C40M102 | Q D S K R P S | 36 |
| C40M103 | Q D S K R P S | 36 |
| C40M104 | Q D S K R P S | 36 |
| C40M105 | E V S K R P S | 34 |
| C40M121 | E V S K R P S | 34 |
| C40M126 | E V S K R P S | 34 |

TABLE 12

| mAb | Sequence (LCDR3) | SEQ ID NO: |
|---|---|---|
| C40M67 | Q Q S S A P P W T | 42 |
| C40M66 | Q Q Y Y S T P L T | 44 |
| C40M63 | Q Q Y Y S T P L T | 44 |
| C40M62 | Q Q Y Y S T P L T | 44 |
| C40M59 | Q Q S Y S T P L T | 43 |
| C40M58 | Q Q S Y S T P L T | 43 |
| C40M56 | Q Q S Y S T P L T | 43 |
| C40M55 | Q Q S Y S T P L T | 43 |
| C40M51 | Q Q S Y S T P L T | 43 |
| C40M18 | Q A W V S S T V V | 41 |
| C40M17 | Q A W A S S T V V | 40 |
| C40M12 | Q V W D S S T V V | 46 |
| C40M9 | S S Y A G S N N L V | 47 |
| C40M102 | Q A W V S S T V V | 41 |
| C40M103 | Q A W V S S T V V | 41 |
| C40M104 | Q A W V S S T V V | 41 |
| C40M105 | S S Y A G S N N L V | 47 |
| C40M121 | S S Y A G S N N L V | 47 |
| C40M121 | S S Y A G S N N L V | 47 |

TABLE 13

| mAb | VH | VH Sequence | VH SEQ ID NO: |
|---|---|---|---|
| C40M67 | C40H20 | EVQLLESGGGLVQPGGSLRLSCAASGFTFSDY AMNWVRQAPGKGLEWVSGIKSGGSSKYYADS VKGRFTISRDNSKNTLYLQMNSLRAEDTAVYYC AKHVDFYRALDYWGQGTLVTVSS | 48 |
| C40M66 | C40H21 | QVQLVQSGAEVKKPGSSVKVSCKASGGTFSSY AISWVRQAPGQGLEWMGGIIPIFGTANYAQKFQ GRVTITADESTSTAYMELSSLRSEDTAVYYCAR VRYSAWYRDSLDYWGQGTLVTVSS | 49 |
| C40M63 | C40H25 | QVQLVQSGAEVKKPGSSVKVSCKASGGTFSSY AISWVRQAPGQGLEWMGGIIPIFGTANYAQKFQ GRVTITADESTSTAYMELSSLRSEDTAVYYCAR VGHPAWWRDSLDYWGQGTLVTVSS | 50 |
| C40M62 | C40H26 | QVQLVQSGAEVKKPGSSVKVSCKASGGTFSSY AISWVRQAPGQGLEWMGGIIPIFGTANYAQKFQ GRVTITADESTSTAYMELSSLRSEDTAVYYCAR VANAAYFRSGLDYWGQGTLVTVSS | 51 |
| C40M59 | C40H29 | QVQLVQSGAEVKKPGSSVKVSCKASGGTFSSY WISWVRQAPGQGLEWMGYIIPISGTARYAQKFQ GRVTITADESTSTAYMELSSLRSEDTAVYYCAR EPGYSSGLSVDYFDYWGQGTLVTVSS | 52 |
| C40M58 | C40H30 | EVQLLESGGGLVQPGGSLRLSCAASGFTFSSYA MSWVRQAPGKGLEWVSAISGSGGSTYYADSVK GRFTISRDNSKNTLYLQMNSLRAEDTAVYYCAR GPAYTIVFDYWGQGTLVTVSS | 53 |
| C40M56 | C40H32 | EVQLLESGGGLVQPGGSLRLSCAASGFTFSSYA MSWVRQAPGKGLEWVSAISGSGGSTYYADSVK GRFTISRDNSKNTLYLQMNSLRAEDTAVYYCAR GPVYSLVFDYWGQGTLVTVSS | 54 |
| C40M55 | C40H33 | QVQLVQSGAEVKKPGSSVKVSCKASGGTFSSY AISWVRQAPGQGLEWMGGIIPIFGTANYAQKFQ GRVTITADESTSTAYMELSSLRSEDTAVYYCAR DGYRRYGIGRYGFDYWGQGTLVTVSS | 55 |
| C40M51 | C40H38 | EVQLLESGGGLVQPGGSLRLSCAASGFTFSSYA MSWVRQAPGKGLEWVSAISGSGGSTYYADSVK GRFTISRDNSKNTLYLQMNSLRAEDTAVYYCAR GPVYSSVFDYWGQGTLVTVSS | 56 |
| C40M18 | C40H48 | EVQLVESGGGLVQPGGSLRLSCAASGFTFSSY AMSWVRQAPGKGLEWVSIINNNVGRTYYADSV KGRFTISRDNSKNTLYLQMNSLRAEDTAVYYCA KEGGDYYYYGMDVWGQGTTVTVSS | 57 |
| C40M17 | C40H46 | EVQLVESGGGLVQPGGSLRLSCAASGFTFSSY AMSWVRQAPGRGLEWVSTINNSGGGTYYADS VKGRFTISRDNSKNTLYLHMNSLRAEDTAVYYC AKEGGKYYYYAMDVWGQGTTVTVSS | 58 |
| C40M12 | C40H45 | EVQLVESGGGLVQPGGSLRLSCAASGFTFGSY AMSWVRQAPGKGLEWVSVISDSGGRTYYADSV KGRFTISRDYSKNTLYLQMNSLRAEDTAVYYCA KEGGDYYYYGMDVWGQGTTVTVSS | 59 |
| C40M9 | C40H43 | QLQLQESGPGLVKPSEILSLTCTVSGGSISSSSY YWGWIRQPPGKGLEWIGNIYYRGDTYYSPSLKS RVTISVDTSKNQFSLKLNSVTAADTAVYYCAKGF RFDYWGQGTLVTVSS | 60 |
| C40M102 | C40H48 | EVQLVESGGGLVQPGGSLRLSCAASGFTFSSY AMSWVRQAPGKGLEWVSIINNNVGRTYYADSV KGRFTISRDNSKNTLYLQMNSLRAEDTAVYYCA KEGGDYYYYGMDVWGQGTTVTVSS | 57 |
| C40M103 | C40H48 | EVQLVESGGGLVQPGGSLRLSCAASGFTFSSY AMSWVRQAPGKGLEWVSIINNNVGRTYYADSV KGRFTISRDNSKNTLYLQMNSLRAEDTAVYYCA KEGGDYYYYGMDVWGQGTTVTVSS | 57 |

TABLE 13-continued

| mAb | VH | VH Sequence | VH SEQ ID NO: |
|---|---|---|---|
| C40M104 | C40H48 | EVQLVESGGGLVQPGGSLRLSCAASGFTFSSY AMSWVRQAPGKGLEWVSIINNNVGRTYYADSV KGRFTISRDNSKNTLYLQMNSLRAEDTAVYYCA KEGGDYYYYGMDVWGQGTTVTVSS | 57 |
| C40M105 | C40H52 | QLQLQESGPGLVKPSETLSLTCTVSGGSISSSS YYWGWIRQPPGKGLEWIGNIYYRGDTYYSPSLK SRVTISVDTSKNQFSLKLSSVTAADTAVYYCAR GFRFDYWGQGTLVTVSS | 61 |
| C40M121 | C40H53 | QLQLQESGPGLVKPSETLSLTCTVSGGSISSSS YYWGWIRQPPGKGLEWIGNIYYRGDTYYSPSLK SRVTISVDTSKNQFSLKLSSVTAADTAVYYCAKG FRFDYWGQGTLVTVSS | 62 |
| C40M126 | C40H53 | QLQLQESGPGLVKPSETLSLTCTVSGGSISSSS YYWGWIRQPPGKGLEWIGNIYYRGDTYYSPSLK SRVTISVDTSKNQFSLKLSSVTAADTAVYYCAKG FRFDYWGQGTLVTVSS | 62 |

TABLE 14

| mAb | VL | VL Sequence | VL SEQ ID NO: |
|---|---|---|---|
| C40M67 | C40L10 | EIVLTQSPGTLSLSPGERATLSCRASQSVKNSSL AWYQQKPGQAPRLLIYTASSRATGIPDRFSGSG SGTDFTLTISRLEPEDFAVYYCQQSSAPPWTFG QGTKVEIK | 63 |
| C40M66 | PH9L2 | DIVMTQSPDSLAVSLGERATINCKSSQSVLYSSN NKNYLAWYQQKPGQPPKLLIYWASTRESGVPD RFSGSGSGTDFTLTISSLQAEDVAVYYCQQYYS TPLTFGQGTKVEIK | 64 |
| C40M63 | PH9L2 | DIVMTQSPDSLAVSLGERATINCKSSQSVLYSSN NKNYLAWYQQKPGQPPKLLIYWASTRESGVPD RFSGSGSGTDFTLTISSLQAEDVAVYYCQQYYS TPLTFGQGTKVEIK | 64 |
| C40M62 | PH9L2 | DIVMTQSPDSLAVSLGERATINCKSSQSVLYSSN NKNYLAWYQQKPGQPPKLLIYWASTRESGVPD RFSGSGSGTDFTLTISSLQAEDVAVYYCQQYYS TPLTFGQGTKVEIK | 64 |
| C40M59 | PH9L4 | DIQMTQSPSSLSASVGDRVTITCRASQSISSYLN WYQQKPGKAPKLLIYAASSLQSGVPSRFSGSG SGTDFTLTISSLQPEDFATYYCQQSYSTPLTFGQ GTKVEIK | 65 |
| C40M58 | PH9L4 | DIQMTQSPSSLSASVGDRVTITCRASQSISSYLN WYQQKPGKAPKLLIYAASSLQSGVPSRFSGSG SGTDFTLTISSLQPEDFATYYCQQSYSTPLTFGQ GTKVEIK | 65 |
| C40M56 | PH9L4 | DIQMTQSPSSLSASVGDRVTITCRASQSISSYLN WYQQKPGKAPKLLIYAASSLQSGVPSRFSGSG SGTDFTLTISSLQPEDFATYYCQQSYSTPLTFGQ GTKVEIK | 65 |
| C40M55 | PH9L4 | DIQMTQSPSSLSASVGDRVTITCRASQSISSYLN WYQQKPGKAPKLLIYAASSLQSGVPSRFSGSG SGTDFTLTISSLQPEDFATYYCQQSYSTPLTFGQ GTKVEIK | 65 |
| C40M51 | PH9L4 | DIQMTQSPSSLSASVGDRVTITCRASQSISSYLN WYQQKPGKAPKLLIYAASSLQSGVPSRFSGSG SGTDFTLTISSLQPEDFATYYCQQSYSTPLTFGQ GTKVEIK | 65 |

TABLE 14-continued

| mAb | VL | VL Sequence | VL SEQ ID NO: |
|---|---|---|---|
| C40M18 | C40L64 | SYELTQPPSVSVSPGQTASITCSGDKLGDKYVCWYQQKPGQSPVVIYQDSKRPSGIPERFSGSNSGNTATLTISGTQAMDEAYYYCQAWVSSTVVFGGGTKLTVL | 66 |
| C40M17 | C40L63 | SYELTQPPSVSVSPGQTASITCSGDKLGDKYACWYQQKPGQSPVLVIYQDSRRPSGIPERFSGSNSGNTATLTISGTQAMDEADYYCQAWASSTVVFGGGTKLTVL | 67 |
| C40M12 | C40L62 | SYELTQPPSVSVSPGQTASIICSGDKLGDKYVCWYQQKPGQSPVVIYHDNKRPSGIPERFSGSNSGNTATLTISGTQAMDEADYYCQVWDSSTVVFGGGTKLTVL | 68 |
| C40M9 | BCML12 | QSALTQPPSASGSPGQSVTISCTGTSSDVGGYNYVSWYQQHPGKAPKLMIYEVSKRPSGVPDRFSGSKSGNTASLTVSGLQAEDEADYYCSSYAGSNNLVFGGGTKLTVL | 69 |
| C40M102 | C40L70 | SYELTQPPSVSVSPGQTASITCSGDKLGDKYVCWYQQKPGQSPVLVIYQDSKRPSGIPERFSGSNSGNTATLTISGTQAMDEADYYCQAWVSSTVVFGGGTKLTVL | 70 |
| C40M103 | C40L69 | SYELTQPPSVSVSPGQTASITCSGDKLGDKYVSWYQQKPGQSPVLVIYQDSKRPSGIPERFSGSNSGNTATLTISGTQAMDEADYYCQAWVSSTVVFGGGTKLTVL | 71 |
| C40M104 | C40L68 | SYELTQPPSVSVSPGQTASITCSGDKLGDKYVSWYQQKPGQSPVVIYQDSKRPSGIPERFSGSNSGNTATLTISGTQAMDEAYYYCQAWVSSTVVFGGGTKLTVL | 72 |
| C40M105 | BCML12 | QSALTQPPSASGSPGQSVTISCTGTSSDVGGYNYVSWYQQHPGKAPKLMIYEVSKRPSGVPDRFSGSKSGNTASLTVSGLQAEDEADYYCSSYAGSNNLVFGGGTKLTVL | 69 |
| C40M121 | BCML12 | QSALTQPPSASGSPGQSVTISCTGTSSDVGGYNYVSWYQQHPGKAPKLMIYEVSKRPSGVPDRFSGSKSGNTASLTVSGLQAEDEADYYCSSYAGSNNLVFGGGTKLTVL | 69 |
| C40M126 | BCML12 | QSALTQPPSASGSPGQSVTISCTGTSSDVGGYNYVSWYQQHPGKAPKLMIYEVSKRPSGVPDRFSGSKSGNTASLTVSGLQAEDEADYYCSSYAGSNNLVFGGGTKLTVL | 69 |

TABLE 15

| mAb | VH DNA | VH DNA SEQ ID NO: |
|---|---|---|
| C40M67 | GAAGTGCAGCTGCTGGAAAGCGGCGGCGGCCTGGTGCAGCCGGGCGGCAGCCTGCGCCTGAGCTGCGCGGCGAGCGGCCTTTACCTTTAGCGACTATGCGATGAACTGGGTGCGCCAGGCGCCGGGCAAAGGCCTGGAATGGGTGAGCGGGATCAAGAGCGGCGGTAGCTCCAAATATTATGCGGATAGCGTGAAAGGCCGCTTTACCATTAGCCGCGATAACAGCAAAAACACCCTGTATCTGCAGATGAACAGCCTGCGCGCGGAAGATACCGCGGTGTATTATTGCGCGAAACACGTTGACTTTTATAGGGCCTTGGACTATTGGGGCCAGGGCACCCTGGTGACCGTGAGCAGC | 89 |
| C40M66 | CAGGTGCAGCTGGTGCAGAGCGGCGCGGAAGTGAAAAAACCGGGCAGCAGCGTGAAAGTGAGCTGCAAAGCGAGCGGCGGCACCTTTAGCAGCTATGCGATTAGCTGGGTGCGCCAGGCGCCGGGCCAGGGCCTGGAATGGATGGGCGGCATTATTCGATTTTTGGCACCGCGAACTATGCGCAGAAATTTCAGGGCCGCGTGACCATTACCGCGGATGAAAGCACCAGCACCGCGT | 90 |

TABLE 15-continued

| mAb | VH DNA | VH DNA SEQ ID NO: |
|---|---|---|
| | ATATGGAACTGAGCAGCCTGCGCAGCGAAGATACCGCGGT GTATTATTGCGCGCGCGTTCGGTATTCGGCGTGGTATAGG GACTCTTTGGACTATTGGGGCCAGGGCACCCTGGTGACAG TCTCGAGT | |
| C40M63 | CAGGTGCAGCTGGTGCAGAGCGGCGCGGAAGTGAAAAAA CCGGGCAGCAGCGTGAAAGTGAGCTGCAAAGCGAGCGGC GGCACCTTTAGCAGCTATGCGATTAGCTGGGTGCGCCAGG CGCCGGGCCAGGGCCTGGAATGGATGGGCGGCATTATTC CGATTTTTGGCACCGCGAACTATGCGCAGAAATTTCAGGGC CGCGTGACCATTACCGCGGATGAAAGCACCAGCACCGCGT ATATGGAACTGAGCAGCCTGCGCAGCGAAGATACCGCGGT GTATTATTGCGCGCGCGTAGGCCATCCGGCTTGGTGGCAG GATTCGTTGGACTATTGGGGCCAGGGCACCCTGGTGACCG TGAGCAGC | 91 |
| C40M62 | CAGGTGCAGCTGGTGCAGAGCGGCGCGGAAGTGAAAAAA CCGGGCAGCAGCGTGAAAGTGAGCTGCAAAGCGAGCGGC GGCACCTTTAGCAGCTATGCGATTAGCTGGGTGCGCCAGG CGCCGGGCCAGGGCCTGGAATGGATGGGCGGCATTATTC CGATTTTTGGCACCGCGAACTATGCGCAGAAATTTCAGGGC CGCGTGACCATTACCGCGGATGAAAGCACCAGCACCGCGT ATATGGAACTGAGCAGCCTGCGCAGCGAAGATACCGCGGT GTATTATTGCGCGCGCGTTGCCAACGCTGCGTATTTTAGGT CTGGCTTGGACTATTGGGGCCAGGGCACCCTGGTGACCGT GAGCAGC | 92 |
| C40M59 | CAGGTGCAGCTGGTGCAGAGCGGCGCGGAAGTGAAAAAA CCGGGCAGCAGCGTGAAAGTGAGCTGCAAAGCGAGCGGC GGCACCTTCAGCTCCTACTGGATTAGCTGGGTGCGCCAGG CGCCGGGCCAGGGCCTGGAATGGATGGGCTACATTATTCC GATCAGTGGCACTGCCCGCTACGCGCAGAAATTTCAGGGC CGCGTGACCATTACCGCTGATGAAAGCACCAGCACCGCGT ATATGGAACTGAGCAGCCTGCGCAGCGAAGATACCGCGGT GTATTATTGCGCGCGCGAACCAGGCTACAGTAGTGGCCTG AGCGTTGACTACTTTGATTACTGGGGCCAGGGCACCCTGG TGACAGTCTCGAGT | 93 |
| C40M58 | GAAGTGCAGCTGCTGGAAAGCGGCGGCGGCCTGGTGCAG CCGGGCGGCAGCCTGCGCCTGAGCTGCGCGGCGAGCGG CTTTACCTTTAGCAGCTATGCGATGAGCTGGGTGCGCCAG GCGCCGGGCAAAGGCCTGGAATGGGTGAGCGCGATCAGC GGCTCCGGTGGCTCCACATATTATGCGGATAGCGTGAAAG GCCGCTTTACCATTTCACGAGATAACAGCAAAAACACCCTG TATCTGCAGATGAACAGCCTGCGCGCGGAAGATACCGCGG TGTATTATTGCGCGCGCGGTCCAGCATACACTATCGTTTTT GATTATTGGGGCCAGGGCACCCTGGTGACAGTCTCGAGT | 94 |
| C40M56 | GAAGTGCAGCTGCTGGAAAGCGGCGGCGGCCTGGTGCAG CCGGGCGGCAGCCTGCGCCTGAGCTGCGCGGCGAGCGG CTTTACCTTTAGCAGCTATGCGATGAGCTGGGTGCGCCAG GCGCCGGGCAAAGGCCTGGAATGGGTGAGCGCGATCAGC GGCTCCGGTGGCTCCACATATTATGCGGATAGCGTGAAAG GCCGCTTTACCATTTCACGAGATAACAGCAAAAACACCCTG TATCTGCAGATGAACAGCCTGCGCGCGGAAGATACCGCGG TGTATTATTGCGCGCGCGGTCCTGTTTATTCTCTGGTTTTTG ACTACTGGGGCCAGGGCACCCTGGTGACAGTCTCGAGT | 95 |
| C40M55 | CAGGTGCAGCTGGTGCAGAGCGGCGCGGAAGTGAAAAAA CCGGGCAGCAGCGTGAAAGTGAGCTGCAAAGCGAGCGGC GGCACCTTCAGCAGCTATGCGATTAGCTGGGTGCGCCAGG CGCCGGGCCAGGGCCTGGAATGGATGGGCGGCATTATTC CGATTTTTGGCACCGCTAACTACGCGCAGAAATTTCAGGGC CGCGTGACCATTACCGCTGATGAAAGCACCAGCACCGCGT ATATGGAACTGAGCAGCCTGCGCAGCGAAGATACCGCGGT GTATTATTGCGCGCGCGATGGTTATCGGCGGTATGGCATC GGTCGTTACGGTTTCGATTATTGGGGCCAGGGCACCCTGG TGACAGTCTCGAGT | 96 |
| C40M51 | GAAGTGCAGCTGCTGGAAAGCGGCGGCGGCCTGGTGCAG CCGGGCGGCAGCCTGCGCCTGAGCTGCGCGGCGAGCGG CTTTACCTTTAGCAGCTATGCGATGAGCTGGGTGCGCCAG GCGCCGGGCAAAGGCCTGGAATGGGTGAGCGCGATCAGC GGCTCCGGTGGCTCCACATATTATGCGGATAGCGTGAAAG GCCGCTTTACCATTTCACGAGATAACAGCAAAAACACCCTG TATCTGCAGATGAACAGCCTGCGCGCGGAAGATACCGCGG | 97 |

TABLE 15-continued

| mAb | VH DNA | VH DNA SEQ ID NO: |
|---|---|---|
|  | TGTATTATTGCGCGCGGCCCAGTTTATTCTAGCGTTTTC GACTATTGGGGCCAGGGCACCCTGGTGACAGTCTCGAGT |  |
| C40M18 | GAGGTGCAGCTGGTGGAATCTGGCGGAGGACTGGTGCAG CCTGGCGGCAGCCTGAGACTGTCTTGTGCCGCCAGCGGCT TCACCTTCAGCAGCTACGCTATGAGCTGGGTCCGACAGGC CCCTGGCAAGGGACTGGAATGGGTGTCCATCATCAACAAC AACGTGGGCCGGACCTACTACGCCGACAGCGTGAAGGGC AGATTCACCATCAGCCGGGACAACAGCAAGAACACCCTGT ACCTGCAGATGAACAGCCTGCGGGCCGAGGACACCGCCG TGTACTATTGTGCCAAAGAGGGCGGCGATTACTACTACTAC GGCATGGACGTGTGGGGCCAGGGCACCACCGTGACAGTG TCATCT | 98 |
| C40M17 | GAGGTGCAGCTGGTGGAATCTGGCGGAGGACTGGTGCAG CCTGGCGGCAGCCTGAGACTGTCTTGTGCCGCCAGCGGCT TCACCTTCAGCAGCTACGCTATGAGCTGGGTCCGACAGGC CCCTGGCAGAGGACTCGAGTGGGTGTCCACCATCAACAAC AGCGGCGGAGGCACCTACTACGCCGACAGCGTGAAGGGC AGATTCACCATCAGCCGGGACAACAGCAAGAACACCCTGT ACCTGCACATGAACAGCCTGCGGGCCGAGGACACCGCCGT GTACTATTGTGCCAAAGAGGGCGGCAAGTACTACTACTATG CCATGGACGTGTGGGGCCAGGGCACCACCGTGACAGTGT CATCT | 99 |
| C40M12 | GAGGTGCAGCTGGTGGAATCTGGCGGAGGACTGGTGCAG CCTGGCGGCAGCCTGAGACTGTCTTGTGCCGCCAGCGGCT TCACCTTCGGCAGCTACGCTATGAGCTGGGTCCGACAGGC CCCTGGCAAGGGACTGGAATGGGTGTCCGTGATCAGCGAC AGCGGCGGCAGAACCTACTACGCCGACAGCGTGAAGGGC CGGTTCACCATCAGCCGGGACTACAGCAAGAACACCCTGT ACCTGCAGATGAACAGCCTGCGGGCCGAGGACACCGCCG TGTACTATTGTGCCAAAGAGGGCGGCGATTACTACTACTAC GGCATGGACGTGTGGGGCCAGGGCACCACCGTGACAGTG TCATCT | 100 |
| C40M9 | CAGCTCCAGCTGCAGGAATCTGGCCCTGGCCTGGTCAAGC CCAGCGAGATCCTGAGCCTGACCTGTACCGTGTCCGGCG CAGCATCAGCAGCAGCTCTTACTACTGGGGCTGGATCCGG CAGCCTCCCGGCAAGGGACTGGAATGGATCGGCAACATCT ACTACCGGGGCGACACCTACTACAGCCCCAGCCTGAAGTC CAGAGTGACCATCAGCGTGGACACCAGCAAGAACCAGTTC TCCCTGAAGCTGAACAGCGTGACAGCCGCCGACACCGCCG TGTACTACTGCGCCAAGGGCTTCAGATTCGATTACTGGGGC CAGGGCACCCTGGTCACCGTGTCATCT | 101 |
| C40M102 | GAGGTGCAGCTGGTGGAATCTGGCGGAGGACTGGTGCAG CCTGGCGGCAGCCTGAGACTGTCTTGTGCCGCCAGCGGCT TCACCTTCAGCAGCTACGCTATGAGCTGGGTCCGACAGGC CCCTGGCAAGGGACTGGAATGGGTGTCCATCATCAACAAC AACGTGGGCCGGACCTACTACGCCGACAGCGTGAAGGGC AGATTCACCATCAGCCGGGACAACAGCAAGAACACCCTGT ACCTGCAGATGAACAGCCTGCGGGCCGAGGACACCGCCG TGTACTATTGTGCCAAAGAGGGCGGCGATTACTACTACTAC GGCATGGACGTGTGGGGCCAGGGCACCACCGTGACAGTG TCATCT | 98 |
| C40M103 | GAGGTGCAGCTGGTGGAATCTGGCGGAGGACTGGTGCAG CCTGGCGGCAGCCTGAGACTGTCTTGTGCCGCCAGCGGCT TCACCTTCAGCAGCTACGCTATGAGCTGGGTCCGACAGGC CCCTGGCAAGGGACTGGAATGGGTGTCCATCATCAACAAC AACGTGGGCCGGACCTACTACGCCGACAGCGTGAAGGGC AGATTCACCATCAGCCGGGACAACAGCAAGAACACCCTGT ACCTGCAGATGAACAGCCTGCGGGCCGAGGACACCGCCG TGTACTATTGTGCCAAAGAGGGCGGCGATTACTACTACTAC GGCATGGACGTGTGGGGCCAGGGCACCACCGTGACAGTG TCATCT | 98 |
| C40M104 | GAGGTGCAGCTGGTGGAATCTGGCGGAGGACTGGTGCAG CCTGGCGGCAGCCTGAGACTGTCTTGTGCCGCCAGCGGCT TCACCTTCAGCAGCTACGCTATGAGCTGGGTCCGACAGGC CCCTGGCAAGGGACTGGAATGGGTGTCCATCATCAACAAC AACGTGGGCCGGACCTACTACGCCGACAGCGTGAAGGGC AGATTCACCATCAGCCGGGACAACAGCAAGAACACCCTGT ACCTGCAGATGAACAGCCTGCGGGCCGAGGACACCGCCG TGTACTATTGTGCCAAAGAGGGCGGCGATTACTACTACTAC | 98 |

TABLE 15-continued

| mAb | VH DNA | VH DNA SEQ ID NO: |
|---|---|---|
| | GGCATGGACGTGTGGGGCCAGGGCACCACCGTGACAGTG TCATCT | |
| C40M105 | CAGCTGCAGCTGCAGGAGAGCGGCCCCGGCCTGGTGAAG CCCAGCGAGACCCTGAGCCTGACCTGCACCGTGAGCGGC GGCAGCATCAGCAGCAGCAGCTACTACTGGGGCTGGATCC GGCAGCCCCCCGGCAAGGGCCTGGAGTGGATCGGCAACA TCTACTACCGGGGCGACACCTACTACAGCCCCAGCCTGAA GAGCCGGGTGACCATCAGCGTGGACACCAGCAAGAACCA TTCAGCCTGAAGCTGAGCAGCGTGACCGCCGCCGACACCG CCGTGTACTACTGCGCCCGGGGCTTCCGGTTCGACTACTG GGGCCAGGGCACCCTGGTGACCGTGAGCAGC | 102 |
| C40M121 | CAGCTGCAGCTGCAGGAGAGCGGCCCCGGCCTGGTGAAG CCCAGCGAGACCCTGAGCCTGACCTGCACCGTGAGCGGC GGCAGCATCAGCAGCAGCAGCTACTACTGGGGCTGGATCC GGCAGCCCCCCGGCAAGGGCCTGGAGTGGATCGGCAACA TCTACTACCGGGGCGACACCTACTACAGCCCCAGCCTGAA GAGCCGGGTGACCATCAGCGTGGACACCAGCAAGAACCAG TTCAGCCTGAAGCTGAGCAGCGTGACCGCCGCCGACACCG CCGTGTACTACTGCGCCAAGGGCTTCCGGTTCGACTACTG GGGCCAGGGCACCCTGGTGACCGTGAGCAGC | 103 |
| C40M126 | CAGCTGCAGCTGCAGGAGAGCGGCCCCGGCCTGGTGAAG CCCAGCGAGACCCTGAGCCTGACCTGCACCGTGAGCGGC GGCAGCATCAGCAGCAGCAGCTACTACTGGGGCTGGATCC GGCAGCCCCCCGGCAAGGGCCTGGAGTGGATCGGCAACA TCTACTACCGGGGCGACACCTACTACAGCCCCAGCCTGAA GAGCCGGGTGACCATCAGCGTGGACACCAGCAAGAACCAG TTCAGCCTGAAGCTGAGCAGCGTGACCGCCGCCGACACCG CCGTGTACTACTGCGCCAAGGGCTTCCGGTTCGACTACTG GGGCCAGGGCACCCTGGTGACCGTGAGCAGC | 103 |

TABLE 16

| mAb | VL DNA | VL DNA SEQ ID NO: |
|---|---|---|
| C40M67 | GAAATTGTGCTGACCCAGAGCCCGGGCACCCTGAGCCTGA GCCCGGGCGAACGCGCGACCCTGAGCTGCCGCGCGAGCC AGAGCGTTAAAAATAGCAGTCTGGCGTGGTATCAGCAGAAA CCGGGCCAGGCGCCGCGCCTGCTGATTTATACTGCGAGCA GCCGCGCGACCGGCATTCCGGATCGCTTTAGCGGCAGCG GCAGCGGCACCGATTTTACCCTGACCATTAGCCGCCTGGA ACCGGAAGATTTTGCGGTGTATTATTGCCAGCAGTCCTCCG CACCTCCGTGGACTTTTGGCCAGGGCACCAAAGTGGAAAT TAAA | 104 |
| C40M66 | GACATCGTGATGACCCAGAGCCCCGACAGCCTGGCCGTGA GCCTGGGCGAGCGGGCCACCATCAACTGCAAGAGCAGCC AGAGCGTGCTGTACAGCAGCAACAACAAGAACTACCTGGC CTGGTACCAGCAGAAGCCCGGCCAGCCCCCAAGCTGCTG ATCTACTGGGCCAGCACCCGGGAGAGCGGCGTGCCCGAC CGGTTCAGCGGCAGCGGCAGCGGCACCGACTTCACCCTG ACCATCAGCAGCCTGCAGGCCGAGGACGTGGCCGTGTACT ACTGCCAGCAGTACTACAGCACCCCCCTGACCTTCGGCCA GGGCACCAAGGTGGAGATCAAG | 105 |
| C40M63 | GACATCGTGATGACCCAGAGCCCCGACAGCCTGGCCGTGA GCCTGGGCGAGCGGGCCACCATCAACTGCAAGAGCAGCC AGAGCGTGCTGTACAGCAGCAACAACAAGAACTACCTGGC CTGGTACCAGCAGAAGCCCGGCCAGCCCCCAAGCTGCTG ATCTACTGGGCCAGCACCCGGGAGAGCGGCGTGCCCGAC CGGTTCAGCGGCAGCGGCAGCGGCACCGACTTCACCCTG ACCATCAGCAGCCTGCAGGCCGAGGACGTGGCCGTGTACT ACTGCCAGCAGTACTACAGCACCCCCCTGACCTTCGGCCA GGGCACCAAGGTGGAGATCAAG | 105 |
| C40M62 | GACATCGTGATGACCCAGAGCCCCGACAGCCTGGCCGTGA GCCTGGGCGAGCGGGCCACCATCAACTGCAAGAGCAGCC AGAGCGTGCTGTACAGCAGCAACAACAAGAACTACCTGGC CTGGTACCAGCAGAAGCCCGGCCAGCCCCCAAGCTGCTG | 105 |

TABLE 16-continued

| mAb | VL DNA | VL DNA SEQ ID NO: |
|---|---|---|
| | ATCTACTGGGCCAGCACCCGGGAGAGCGGCGTGCCCGAC CGGTTCAGCGGCAGCGGCAGCGGCACCGACTTCACCCTG ACCATCAGCAGCCTGCAGGCCGAGGACGTGGCCGTGTACT ACTGCCAGCAGTACTACAGCACCCCCCTGACCTTCGGCCA GGGCACCAAGGTGGAGATCAAG | |
| C40M59 | GACATCCAGATGACCCAGAGCCCCAGCAGCCTGAGCGCCA GCGTGGGCGACCGGGTGACCATCACCTGCCGGGCCAGCC AGAGCATCAGCAGCTACCTGAACTGGTACCAGCAGAAGCC CGGCAAGGCCCCCAAGCTGCTGATCTACGCCGCCAGCAGC CTGCAGAGCGGCGTGCCCAGCCGGTTCAGCGGCAGCGGC AGCGGCACCGACTTCACCCTGACCATCAGCAGCCTGCAGC CCGAGGACTTCGCCACCTACTACTGCCAGCAGAGCTACAG CACCCCCCTGACCTTCGGCCAGGGCACCAAGGTGGAGATC AAG | 106 |
| C40M58 | GACATCCAGATGACCCAGAGCCCCAGCAGCCTGAGCGCCA GCGTGGGCGACCGGGTGACCATCACCTGCCGGGCCAGCC AGAGCATCAGCAGCTACCTGAACTGGTACCAGCAGAAGCC CGGCAAGGCCCCCAAGCTGCTGATCTACGCCGCCAGCAGC CTGCAGAGCGGCGTGCCCAGCCGGTTCAGCGGCAGCGGC AGCGGCACCGACTTCACCCTGACCATCAGCAGCCTGCAGC CCGAGGACTTCGCCACCTACTACTGCCAGCAGAGCTACAG CACCCCCCTGACCTTCGGCCAGGGCACCAAGGTGGAGATC AAG | 106 |
| C40M56 | GACATCCAGATGACCCAGAGCCCCAGCAGCCTGAGCGCCA GCGTGGGCGACCGGGTGACCATCACCTGCCGGGCCAGCC AGAGCATCAGCAGCTACCTGAACTGGTACCAGCAGAAGCC CGGCAAGGCCCCCAAGCTGCTGATCTACGCCGCCAGCAGC CTGCAGAGCGGCGTGCCCAGCCGGTTCAGCGGCAGCGGC AGCGGCACCGACTTCACCCTGACCATCAGCAGCCTGCAGC CCGAGGACTTCGCCACCTACTACTGCCAGCAGAGCTACAG CACCCCCCTGACCTTCGGCCAGGGCACCAAGGTGGAGATC AAG | 106 |
| C40M55 | GACATCCAGATGACCCAGAGCCCCAGCAGCCTGAGCGCCA GCGTGGGCGACCGGGTGACCATCACCTGCCGGGCCAGCC AGAGCATCAGCAGCTACCTGAACTGGTACCAGCAGAAGCC CGGCAAGGCCCCCAAGCTGCTGATCTACGCCGCCAGCAGC CTGCAGAGCGGCGTGCCCAGCCGGTTCAGCGGCAGCGGC AGCGGCACCGACTTCACCCTGACCATCAGCAGCCTGCAGC CCGAGGACTTCGCCACCTACTACTGCCAGCAGAGCTACAG CACCCCCCTGACCTTCGGCCAGGGCACCAAGGTGGAGATC AAG | 106 |
| C40M51 | GACATCCAGATGACCCAGAGCCCCAGCAGCCTGAGCGCCA GCGTGGGCGACCGGGTGACCATCACCTGCCGGGCCAGCC AGAGCATCAGCAGCTACCTGAACTGGTACCAGCAGAAGCC CGGCAAGGCCCCCAAGCTGCTGATCTACGCCGCCAGCAGC CTGCAGAGCGGCGTGCCCAGCCGGTTCAGCGGCAGCGGC AGCGGCACCGACTTCACCCTGACCATCAGCAGCCTGCAGC CCGAGGACTTCGCCACCTACTACTGCCAGCAGAGCTACAG CACCCCCCTGACCTTCGGCCAGGGCACCAAGGTGGAGATC AAG | 106 |
| C40M18 | TCCTACGAGCTGACCCAGCCTCCCTCCGTGTCTGTGTCTCC TGGCCAGACCGCCAGCATCACCTGTAGCGGCGACAAGCTG GGCGACAAATACGTGTGCTGGTATCAGCAGAAGCCCGGCC AGAGCCCCGTGGTGGTCATCTACCAGGACAGCAAGAGGCC CAGCGGCATCCCCGAGAGATTCAGCGGCAGCAACAGCGG CAATACCGCCACCCTGACCATCAGCGGCACCCAGGCCATG GACGAGGCCTACTACTACTGCCAGGCTTGGGTGTCCAGCA CCGTGGTGTTTGGCGGAGGCACCAAGCTGACCGTGCTG | 107 |
| C40M17 | TCCTACGAGCTGACCCAGCCTCCCTCCGTGTCTGTGTCTCC TGGCCAGACCGCCAGCATCACCTGTAGCGGCGACAAGCTG GGCGATAAGTACGCCTGCTGGTATCAGCAGAAGCCCGGCC AGAGCCCCGTGCTGGTCATCTACCAGGACAGCAGAAGGCC CAGCGGCATCCCCGAGAGATTCAGCGGCAGCAACAGCGG CAATACCGCCACCCTGACCATCAGCGGCACCCAGGCCATG GACGAGGCCGATTACTATTGTCAGGCCTGGGCCAGCAGCA CCGTGGTGTTTGGCGGCGGAACAAAGCTGACCGTGCTG | 108 |
| C40M12 | TCCTACGAGCTGACCCAGCCTCCCTCCGTGTCTGTGTCTCC TGGCCAGACCGCCAGCATCATCTGCAGCGGCGACAAGCTG | 109 |

TABLE 16-continued

| mAb | VL DNA | VL DNA SEQ ID NO: |
|---|---|---|
| | GGCGACAAATACGTGTGCTGGTATCAGCAGAAGCCCGGCC AGAGCCCCGTGGTGGTCATCTACCACGACAACAAGAGGCC CAGCGGCATCCCCGAGAGATTCAGCGGCAGCAACAGCGG CAATACCGCCACCCTGACCATCAGCGGCACCCAGGCCATG GACGAGGCCGACTACTACTGCCAGGTCTGGGACAGCAGCA CCGTGGTGTTTGGCGGAGGCACCAAGCTGACCGTGCTG | |
| C40M9 | CAGTCTGCCCTGACACAGCCTCCTAGCGCCTCTGGCTCTC CTGGCCAGAGCGTGACCATCAGCTGTACCGGCACCAGCTC CGACGTGGGCGGCTACAACTACGTGTCCTGGTATCAGCAG CACCCCGGCAAGGCCCCTAAGCTGATGATCTACGAGGTGT CCAAGCGGCCCAGCGGCGTGCCAGATAGATTCAGCGGCA GCAAGAGCGGCAACACCGCCAGCCTGACAGTGTCTGGACT GCAGGCCGAGGACGAGGCCGACTACTACTGTAGCAGCTAC GCCAGCAGCAACAACCTGGTGTTCGGCGGAGGCACCAAG CTGACCGTGCTG | 110 |
| C40M102 | AGCTACGAGCTGACCCAGCCCCCCAGCGTGAGCGTGAGC CCCGGCCAGACCGCCAGCATCACCTGCAGCGGCGACAAG CTGGGCGACAAGTACGTGTGCTGGTACCAGCAGAAGCCCG GCCAGAGCCCCGTGCTGGTGATCTACCAGGACAGCAAGCG GCCCAGCGGCATCCCCGAGCGGTTCAGCGGCAGCAACAG CGGCAACACCGCCACCCTGACCATCAGCGGCACCCAGGC CATGGACGAGGCCGACTACTACTGCCAGGCCTGGGTGAGC AGCACCGTGGTGTTCGGCGGCGGCACCAAGCTGACCGTG CTG | 111 |
| C40M103 | AGCTACGAGCTGACCCAGCCCCCCAGCGTGAGCGTGAGC CCCGGCCAGACCGCCAGCATCACCTGCAGCGGCGACAAG CTGGGCGACAAGTACGTGAGCTGGTACCAGCAGAAGCCCG GCCAGAGCCCCGTGCTGGTGATCTACCAGGACAGCAAGCG GCCCAGCGGCATCCCCGAGCGGTTCAGCGGCAGCAACAG CGGCAACACCGCCACCCTGACCATCAGCGGCACCCAGGC CATGGACGAGGCCGACTACTACTGCCAGGCCTGGGTGAGC AGCACCGTGGTGTTCGGCGGCGGCACCAAGCTGACCGTG CTG | 112 |
| C40M104 | AGCTACGAGCTGACCCAGCCCCCCAGCGTGAGCGTGAGC CCCGGCCAGACCGCCAGCATCACCTGCAGCGGCGACAAG CTGGGCGACAAGTACGTGAGCTGGTACCAGCAGAAGCCCG GCCAGAGCCCCGTGGTGGTGATCTACCAGGACAGCAAGCG GCCCAGCGGCATCCCCGAGCGGTTCAGCGGCAGCAACAG CGGCAACACCGCCACCCTGACCATCAGCGGCACCCAGGC CATGGACGAGGCCTACTACTACTGCCAGGCCTGGGTGAGC AGCACCGTGGTGTTCGGCGGCGGCACCAAGCTGACCGTG CTG | 113 |
| C40M105 | CAGTCTGCCCTGACACAGCCTCCTAGCGCCTCTGGCTCTC CTGGCCAGAGCGTGACCATCAGCTGTACCGGCACCAGCTC CGACGTGGGCGGCTACAACTACGTGTCCTGGTATCAGCAG CACCCCGGCAAGGCCCCTAAGCTGATGATCTACGAGGTGT CCAAGCGGCCCAGCGGCGTGCCAGATAGATTCAGCGGCA GCAAGAGCGGCAACACCGCCAGCCTGACAGTGTCTGGACT GCAGGCCGAGGACGAGGCCGACTACTACTGTAGCAGCTAC GCCGGCAGCAACAACCTGGTGTTCGGCGGAGGCACCAAG CTGACCGTGCTG | 110 |
| C40M121 | CAGTCTGCCCTGACACAGCCTCCTAGCGCCTCTGGCTCTC CTGGCCAGAGCGTGACCATCAGCTGTACCGGCACCAGCTC CGACGTGGGCGGCTACAACTACGTGTCCTGGTATCAGCAG CACCCCGGCAAGGCCCCTAAGCTGATGATCTACGAGGTGT CCAAGCGGCCCAGCGGCGTGCCAGATAGATTCAGCGGCA GCAAGAGCGGCAACACCGCCAGCCTGACAGTGTCTGGACT GCAGGCCGAGGACGAGGCCGACTACTACTGTAGCAGCTAC GCCGGCAGCAACAACCTGGTGTTCGGCGGAGGCACCAAG CTGACCGTGCTG | 110 |
| C40M126 | CAGTCTGCCCTGACACAGCCTCCTAGCGCCTCTGGCTCTC CTGGCCAGAGCGTGACCATCAGCTGTACCGGCACCAGCTC CGACGTGGGCGGCTACAACTACGTGTCCTGGTATCAGCAG CACCCCGGCAAGGCCCCTAAGCTGATGATCTACGAGGTGT CCAAGCGGCCCAGCGGCGTGCCAGATAGATTCAGCGGCA | 110 |

TABLE 16-continued

| mAb | VL DNA | VL DNA SEQ ID NO: |
|---|---|---|
| | GCAAGAGCGGCAACACCGCCAGCCTGACAGTGTCTGGACT GCAGGCCGAGGACGAGGCCGACTACTACTGTAGCAGCTAC GCCGGCAGCAACAACCTGGTGTTCGGCGGAGGCACCAAG CTGACCGTGCTG | |

TABLE 17

| mAb | HC amino acid | HC SEQ ID NO: |
|---|---|---|
| C40M67 | EVQLLESGGGLVQPGGSLRLSCAASGFTFSDYAMNWVRQAP GKGLEWVSGIKSGGSSKYYADSVKGRFTISRDNSKNTLYLQM NSLRAEDTAVYYCAKHVDFYRALDYWGQGTLVTVSSASTKGP SVFPLAPSSKSTSGGTAALGCLVKDYFPEPVTVSWNSGALTS GVHTFPAVLQSSGLYSLSSVVTVPSSSLGTQTYICNVNHKPSN TKVDKKVEPKSCDKTHTCPPCPAPELLGGPSVFLFPPKPKDTL MISRTPEVTCVVVDVSHEDPEVKFNWYVDGVEVHNAKTKPRE EQYNSTYRVVSVLTVLHQDWLNGKEYKCKVSNKALPAPIEKTI SKAKGQPREPQVYTLPPSREEMTKNQVSLTCLVKGFYPSDIA VEWESNGQPENNYKTTPPVLDSDGSFFLYSKLTVDKSRWQQ GNVFSCSVMHEALHNHYTQKSLSLSPGK | 114 |
| C40M66 | QVQLVQSGAEVKKPGSSVKVSCKASGGTFSSYAISWVRQAP GQGLEWMGGIIPIFGTANYAQKFQGRVTITADESTSTAYMELS SLRSEDTAVYYCARVRYSAWYRDSLDYWGQGTLVTVSSAST KGPSVFPLAPSSKSTSGGTAALGCLVKDYFPEPVTVSWNSGA LTSGVHTFPAVLQSSGLYSLSSVVTVPSSSLGTQTYICNVNHK PSNTKVDKKVEPKSCDKTHTCPPCPAPELLGGPSVFLFPPKP KDTLMISRTPEVTCVVVDVSHEDPEVKFNWYVDGVEVHNAKT KPREEQYNSTYRVVSVLTVLHQDWLNGKEYKCKVSNKALPAP IEKTISKAKGQPREPQVYTLPPSREEMTKNQVSLTCLVKGFYP SDIAVEWESNGQPENNYKTTPPVLDSDGSFFLYSKLTVDKSR WQQGNVFSCSVMHEALHNHYTQKSLSLSPGK | 115 |
| C40M63 | QVQLVQSGAEVKKPGSSVKVSCKASGGTFSSYAISWVRQAP GQGLEWMGGIIPIFGTANYAQKFQGRVTITADESTSTAYMELS SLRSEDTAVYYCARVGHPAWWRDSLDYWGQGTLVTVSSAST KGPSVFPLAPSSKSTSGGTAALGCLVKDYFPEPVTVSWNSGA LTSGVHTFPAVLQSSGLYSLSSVVTVPSSSLGTQTYICNVNHK PSNTKVDKKVEPKSCDKTHTCPPCPAPELLGGPSVFLFPPKP KDTLMISRTPEVTCVVVDVSHEDPEVKFNWYVDGVEVHNAKT KPREEQYNSTYRVVSVLTVLHQDWLNGKEYKCKVSNKALPAP IEKTISKAKGQPREPQVYTLPPSREEMTKNQVSLTCLVKGFYP SDIAVEWESNGQPENNYKTTPPVLDSDGSFFLYSKLTVDKSR WQQGNVFSCSVMHEALHNHYTQKSLSLSPGK | 116 |
| C40M62 | QVQLVQSGAEVKKPGSSVKVSCKASGGTFSSYAISWVRQAP GQGLEWMGGIIPIFGTANYAQKFQGRVTITADESTSTAYMELS SLRSEDTAVYYCARVANAAYFRSGLDYWGQGTLVTVSSASTK GPSVFPLAPSSKSTSGGTAALGCLVKDYFPEPVTVSWNSGAL TSGVHTFPAVLQSSGLYSLSSVVTVPSSSLGTQTYICNVNHKP SNTKVDKKVEPKSCDKTHTCPPCPAPELLGGPSVFLFPPKPK DTLMISRTPEVTCVVVDVSHEDPEVKFNWYVDGVEVHNAKTK PREEQYNSTYRVVSVLTVLHQDWLNGKEYKCKVSNKALPAPI EKTISKAKGQPREPQVYTLPPSREEMTKNQVSLTCLVKGFYPS DIAVEWESNGQPENNYKTTPPVLDSDGSFFLYSKLTVDKSRW QQGNVFSCSVMHEALHNHYTQKSLSLSPGK | 117 |
| C40M59 | QVQLVQSGAEVKKPGSSVKVSCKASGGTFSSYWISWVRQAP GQGLEWMGYIIPISGTARYAQKFQGRVTITADESTSTAYMELS SLRSEDTAVYYCAREPGYSSGLSVDYFDYWGQGTLVTVSSAS TKGPSVFPLAPSSKSTSGGTAALGCLVKDYFPEPVTVSWNSG ALTSGVHTFPAVLQSSGLYSLSSVVTVPSSSLGTQTYICNVNH KPSNTKVDKKVEPKSCDKTHTCPPCPAPELLGGPSVFLFPPK PKDTLMISRTPEVTCVVVDVSHEDPEVKFNWYVDGVEVHNAK TKPREEQYNSTYRVVSVLTVLHQDWLNGKEYKCKVSNKALPA PIEKTISKAKGQPREPQVYTLPPSREEMTKNQVSLTCLVKGFY PSDIAVEWESNGQPENNYKTTPPVLDSDGSFFLYSKLTVDKS RWQQGNVFSCSVMHEALHNHYTQKSLSLSPGK | 118 |
| C40M58 | EVQLLESGGGLVQPGGSLRLSCAASGFTFSSYAMSWVRQAP GKGLEWVSAISGSGGSTYYADSVKGRFTISRDNSKNTLYLQM | 119 |

TABLE 17-continued

| mAb | HC amino acid | HC SEQ ID NO: |
|---|---|---|
| | NSLRAEDTAVYYCARGPAYTIVFDYWGQGTLVTVSSASTKGP SVFPLAPSSKSTSGGTAALGCLVKDYFPEPVTVSWNSGALTS GVHTFPAVLQSSGLYSLSSVVTVPSSSLGTQTYICNVNHKPSN TKVDKKVEPKSCDKTHTCPPCPAPELLGGPSVFLFPPKPKDTL MISRTPEVTCVVVDVSHEDPEVKFNWYVDGVEVHNAKTKPRE EQYNSTYRVVSVLTVLHQDWLNGKEYKCKVSNKALPAPIEKTI SKAKGQPREPQVYTLPPSREEMTKNQVSLTCLVKGFYPSDIA VEWESNGQPENNYKTTPPVLDSDGSFFLYSKLTVDKSRWQQ GNVFSCSVMHEALHNHYTQKSLSLSPGK | |
| C40M56 | EVQLLESGGGLVQPGGSLRLSCAASGFTFSSYAMSWVRQAP GKGLEWVSAISGSGGSTYYADSVKGRFTISRDNSKNTLYLQM NSLRAEDTAVYYCARGPVYSLVFDYWGQGTLVTVSSASTKGP SVFPLAPSSKSTSGGTAALGCLVKDYFPEPVTVSWNSGALTS GVHTFPAVLQSSGLYSLSSVVTVPSSSLGTQTYICNVNHKPSN TKVDKKVEPKSCDKTHTCPPCPAPELLGGPSVFLFPPKPKDTL MISRTPEVTCVVVDVSHEDPEVKFNWYVDGVEVHNAKTKPRE EQYNSTYRVVSVLTVLHQDWLNGKEYKCKVSNKALPAPIEKTI SKAKGQPREPQVYTLPPSREEMTKNQVSLTCLVKGFYPSDIA VEWESNGQPENNYKTTPPVLDSDGSFFLYSKLTVDKSRWQQ GNVFSCSVMHEALHNHYTQKSLSLSPGK | 120 |
| C40M55 | QVQLVQSGAEVKKPGSSVKVSCKASGGTFSSYAISWVRQAP GQGLEWMGGIIPIFGTANYAQKFQGRVTITADESTSTAYMELS SLRSEDTAVYYCARDGYRRYGIGRYGFDYWGQGTLVTVSSA STKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPP KPKDTLMISRTPEVTCVVVDVSHEDPEVKFNWYVDGVEVHNA KTKPREEQYNSTYRVVSVLTVLHQDWLNGKEYKCKVSNKALP APIEKTISKAKGQPREPQVYTLPPSREEMTKNQVSLTCLVKGF YPSDIAVEWESNGQPENNYKTTPPVLDSDGSFFLYSKLTVDK SRWQQGNVFSCSVMHEALHNHYTQKSLSLSPGK | 121 |
| C40M51 | EVQLLESGGGLVQPGGSLRLSCAASGFTFSSYAMSWVRQAP GKGLEWVSAISGSGGSTYYADSVKGRFTISRDNSKNTLYLQM NSLRAEDTAVYYCARGPVYSSVFDYWGQGTLVTVSSASTKG PSVFPLAPSSKSTSGGTAALGCLVKDYFPEPVTVSWNSGALT SGVHTFPAVLQSSGLYSLSSVVTVPSSSLGTQTYICNVNHKPS NTKVDKKVEPKSCDKTHTCPPCPAPELLGGPSVFLFPPKPKD TLMISRTPEVTCVVVDVSHEDPEVKFNWYVDGVEVHNAKTKP REEQYNSTYRVVSVLTVLHQDWLNGKEYKCKVSNKALPAPIE KTISKAKGQPREPQVYTLPPSREEMTKNQVSLTCLVKGFYPS DIAVEWESNGQPENNYKTTPPVLDSDGSFFLYSKLTVDKSRW QQGNVFSCSVMHEALHNHYTQKSLSLSPGK | 122 |
| C40M18 | EVQLVESGGGLVQPGGSLRLSCAASGFTFSSYAMSWVRQAP GKGLEWVSIINNNVGRTYYADSVKGRFTISRDNSKNTLYLQMN SLRAEDTAVYYCAKEGGDYYYGMDVWGQGTTVTVSSASTK GPSVFPLAPSSKSTSGGTAALGCLVKDYFPEPVTVSWNSGAL TSGVHTFPAVLQSSGLYSLSSVVTVPSSSLGTQTYICNVNHKP SNTKVDKKVEPKSCDKTHTCPPCPAPELLGGPSVFLFPPKPK DTLMISRTPEVTCVVVDVSHEDPEVKFNWYVDGVEVHNAKTK PREEQYNSTYRVVSVLTVLHQDWLNGKEYKCKVSNKALPAPI EKTISKAKGQPREPQVYTLPPSREEMTKNQVSLTCLVKGFYPS DIAVEWESNGQPENNYKTTPPVLDSDGSFFLYSKLTVDKSRW QQGNVFSCSVMHEALHNHYTQKSLSLSPGK | 123 |
| C40M17 | EVQLVESGGGLVQPGGSLRLSCAASGFTFSSYAMSWVRQAP GRGLEWVSTINNSGGGTYYADSVKGRFTISRDNSKNTLYLHM NSLRAEDTAVYYCAKEGGKYYYAMDVWGQGTTVTVSSAST KGPSVFPLAPSSKSTSGGTAALGCLVKDYFPEPVTVSWNSGA LTSGVHTFPAVLQSSGLYSLSSVVTVPSSSLGTQTYICNVNHK PSNTKVDKKVEPKSCDKTHTCPPCPAPELLGGPSVFLFPPKP KDTLMISRTPEVTCVVVDVSHEDPEVKFNWYVDGVEVHNAKT KPREEQYNSTYRVVSVLTVLHQDWLNGKEYKCKVSNKALPAP IEKTISKAKGQPREPQVYTLPPSREEMTKNQVSLTCLVKGFYP SDIAVEWESNGQPENNYKTTPPVLDSDGSFFLYSKLTVDKSR WQQGNVFSCSVMHEALHNHYTQKSLSLSPGK | 124 |
| C40M12 | EVQLVESGGGLVQPGGSLRLSCAASGFTFGSYAMSWVRQAP GKGLEWVSVISDSGGRTYYADSVKGRFTISRDYSKNTLYLQM NSLRAEDTAVYYCAKEGGDYYYGMDVWGQGTTVTVSSAST KGPSVFPLAPSSKSTSGGTAALGCLVKDYFPEPVTVSWNSGA LTSGVHTFPAVLQSSGLYSLSSVVTVPSSSLGTQTYICNVNHK PSNTKVDKKVEPKSCDKTHTCPPCPAPELLGGPSVFLFPPKP | 125 |

TABLE 17-continued

| mAb | HC amino acid | HC SEQ ID NO: |
|---|---|---|
| | KDTLMISRTPEVTCVVVDVSHEDPEVKFNWYVDGVEVHNAKT KPREEQYNSTYRVVSVLTVLHQDWLNGKEYKCKVSNKALPAP IEKTISKAKGQPREPQVYTLPPSREEMTKNQVSLTCLVKGFYP SDIAVEWESNGQPENNYKTTPPVLDSDGSFFLYSKLTVDKSR WQQGNVFSCSVMHEALHNHYTQKSLSLSPGK | |
| C40M9 | QLQLQESGPGLVKPSEILSLTCTVSGGSISSSSYYWGWIRQPP GKGLEWIGNIYYRGDTYYSPSLKSRVTISVDTSKNQFSLKLNS VTAADTAVYYCAKGFRFDYWGQGTLVTVSSASTKGPSVFPLA PSSKSTSGGTAALGCLVKDYFPEPVTVSWNSGALTSGVHTFP AVLQSSGLYSLSSVVTVPSSSLGTQTYICNVNHKPSNTKVDKK VEPKSCDKTHTCPPCPAPELLGGPSVFLFPPKPKDTLMISRTP EVTCVVVDVSHEDPEVKFNWYVDGVEVHNAKTKPREEQYNS TYRVVSVLTVLHQDWLNGKEYKCKVSNKALPAPIEKTISKAKG QPREPQVYTLPPSREEMTKNQVSLTCLVKGFYPSDIAVEWES NGQPENNYKTTPPVLDSDGSFFLYSKLTVDKSRWQQGNVFS CSVMHEALHNHYTQKSLSLSPGK | 126 |
| C40M102 | EVQLVESGGGLVQPGGSLRLSCAASGFTFSSYAMSWVRQAP GKGLEWVSIINNNVGRTYYADSVKGRFTISRDNSKNTLYLQMN SLRAEDTAVYYCAKEGGDYYYYGMDVWGQGTTVTVSSASTK GPSVFPLAPSSKSTSGGTAALGCLVKDYFPEPVTVSWNSGAL TSGVHTFPAVLQSSGLYSLSSVVTVPSSSLGTQTYICNVNHKP SNTKVDKKVEPKSCDKTHTCPPCPAPELLGGPSVFLFPPKPK DTLMISRTPEVTCVVVDVSHEDPEVKFNWYVDGVEVHNAKTK PREEQYNSTYRVVSVLTVLHQDWLNGKEYKCKVSNKALPAPI EKTISKAKGQPREPQVYTLPPSREEMTKNQVSLTCLVKGFYPS DIAVEWESNGQPENNYKTTPPVLDSDGSFFLYSKLTVDKSRW QQGNVFSCSVMHEALHNHYTQKSLSLSPGK | 123 |
| C40M103 | EVQLVESGGGLVQPGGSLRLSCAASGFTFSSYAMSWVRQAP GKGLEWVSIINNNVGRTYYADSVKGRFTISRDNSKNTLYLQMN SLRAEDTAVYYCAKEGGDYYYYGMDVWGQGTTVTVSSASTK GPSVFPLAPSSKSTSGGTAALGCLVKDYFPEPVTVSWNSGAL TSGVHTFPAVLQSSGLYSLSSVVTVPSSSLGTQTYICNVNHKP SNTKVDKKVEPKSCDKTHTCPPCPAPELLGGPSVFLFPPKPK DTLMISRTPEVTCVVVDVSHEDPEVKFNWYVDGVEVHNAKTK PREEQYNSTYRVVSVLTVLHQDWLNGKEYKCKVSNKALPAPI EKTISKAKGQPREPQVYTLPPSREEMTKNQVSLTCLVKGFYPS DIAVEWESNGQPENNYKTTPPVLDSDGSFFLYSKLTVDKSRW QQGNVFSCSVMHEALHNHYTQKSLSLSPGK | 123 |
| C40M104 | EVQLVESGGGLVQPGGSLRLSCAASGFTFSSYAMSWVRQAP GKGLEWVSIINNNVGRTYYADSVKGRFTISRDNSKNTLYLQMN SLRAEDTAVYYCAKEGGDYYYYGMDVWGQGTTVTVSSASTK GPSVFPLAPSSKSTSGGTAALGCLVKDYFPEPVTVSWNSGAL TSGVHTFPAVLQSSGLYSLSSVVTVPSSSLGTQTYICNVNHKP SNTKVDKKVEPKSCDKTHTCPPCPAPELLGGPSVFLFPPKPK DTLMISRTPEVTCVVVDVSHEDPEVKFNWYVDGVEVHNAKTK PREEQYNSTYRVVSVLTVLHQDWLNGKEYKCKVSNKALPAPI EKTISKAKGQPREPQVYTLPPSREEMTKNQVSLTCLVKGFYPS DIAVEWESNGQPENNYKTTPPVLDSDGSFFLYSKLTVDKSRW QQGNVFSCSVMHEALHNHYTQKSLSLSPGK | 123 |
| C40M105 | QLQLQESGPGLVKPSETLSLTCTVSGGSISSSSYYWGWIRQP PGKGLEWIGNIYYRGDTYYSPSLKSRVTISVDTSKNQFSLKLS SVTAADTAVYYCARGFRFDYWGQGTLVTVSSASTKGPSVFPL APSSKSTSGGTAALGCLVKDYFPEPVTVSWNSGALTSGVHTF PAVLQSSGLYSLSSVVTVPSSSLGTQTYICNVNHKPSNTKVDK KVEPKSCDKTHTCPPCPAPELLGGPSVFLFPPKPKDTLMISRT PEVTCVVVDVSHEDPEVKFNWYVDGVEVHNAKTKPREEQYN STYRVVSVLTVLHQDWLNGKEYKCKVSNKALPAPIEKTISKAK GQPREPQVYTLPPSREEMTKNQVSLTCLVKGFYPSDIAVEWE SNGQPENNYKTTPPVLDSDGSFFLYSKLTVDKSRWQQGNVF SCSVMHEALHNHYTQKSLSLSPGK | 127 |
| C40M121 | QLQLQESGPGLVKPSETLSLTCTVSGGSISSSSYYWGWIRQP PGKGLEWIGNIYYRGDTYYSPSLKSRVTISVDTSKNQFSLKLS SVTAADTAVYYCAKGFRFDYWGQGTLVTVSSASTKGPSVFPL APSSKSTSGGTAALGCLVKDYFPEPVTVSWNSGALTSGVHTF PAVLQSSGLYSLSSVVTVPSSSLGTQTYICNVNHKPSNTKVDK KVEPKSCDKTHTCPPCPAPELLGGPSVFLFPPKPKDTLMISRT PEVTCVVVDVSHEDPEVKFNWYVDGVEVHNAKTKPREEQYN STYRVVSVLTVLHQDWLNGKEYKCKVSNKALPAPIEKTISKAK | 128 |

TABLE 17-continued

| mAb | HC amino acid | HC SEQ ID NO: |
|---|---|---|
| | GQPREPQVYTLPPSREEMTKNQVSLTCLVKGFYPSDIAVEWE SNGQPENNYKTTPPVLDSDGSFFLYSKLTVDKSRWQQGNVF SCSVMHEALHNHYTQKSLSLSPGK | |
| C40M126 | QLQLQESGPGLVKPSETLSLTCTVSGGSISSSSYYWGWIRQP PGKGLEWIGNIYYRGDTYYSPSLKSRVTISVDTSKNQFSLKLS SVTAADTAVYYCAKGFRFDYWGQGTLVTVSSASTKGPSVFPL APSSKSTSGGTAALGCLVKDYFPEPVTVSWNSGALTSGVHTF PAVLQSSGLYSLSSVVTVPSSSLGTQTYICNVNHKPSNTKVDK KVEPKSCDKTHTCPPCPAPELLGGPSVFLFPPKPKDTLMISRT PEVTCVVVDVEHEDPEVKFNWYVDGVEVHNAKTKPREEQYN STYRVVSVLTVLHQDWLNGKEYKCKVSNKALPAPIEKTISKAK GQPREPQVYTLPPSREEMTKNQVSLTCLVKGFYPSDIAVEWE SNGQPENNYKTTPPVLDSDGSFFLYSKLTVDKSRWQQGNVF SCSVMHEALHNHYTQKSLSLSPGK | 129 |

TABLE 18

| mAb | HC DNA | HC DNA SEQ ID NO: |
|---|---|---|
| C40M67 | GAAGTGCAGCTGCTGGAAAGCGGCGGCGGCCTGGTGCA GCCGGGCGGCAGCCTGCGCCTGAGCTGCGCGGCGAGC GGCTTTACCTTTAGCGACTATGCGATGAACTGGGTGCGC CAGGCGCCGGGCAAAGGCCTGGAATGGGTGAGCGGGAT CAAGAGCGGCGGTAGCTCCAAATATTATGCGGATAGCGT GAAAGGCCGCTTTACCATTAGCCGCGATAACAGCAAAAA CACCCTGTATCTGCAGATGAACAGCCTGCGCGCGGAAGA TACCGCGGTGTATTATTGCGCGAAACACGTTGACTTTTAT AGGGCCTTGGACTATTGGGGCCAGGGCACCCTGGTGAC CGTGAGCAGCGCCTCCACCAAGGGCCCATCGGTCTTCC CCCTGGCACCCTCCTCCAAGAGCACCTCTGGGGGCACA GCGGCCCTGGGCTGCCTGGTCAAGGACTACTTCCCCGA ACCGGTGACGGTGTCGTGGAACTCAGGCGCCCTGACCA GCGGCGTGCACACCTTCCCGGCTGTCCTACAGTCCTCAG GACTCTACTCCCTCAGCAGCGTGGTGACCGTGCCCTCCA GCAGCTTGGGCACCCAGACCTACATCTGCAACGTGAATC ACAAGCCCAGCAACACCAAGGTGGACAAGAAAGTTGAGC CCAAATCTTGTGACAAAACTCACACATGCCCACCGTGCC CAGCACCTGAACTCCTGGGGGGACCGTCAGTCTTCCTCT TCCCCCCAAAACCCAAGGACACCCTCATGATCTCCCGGA CCCCTGAGGTCACATGCGTGGTGGTGGACGTGAGCCAC GAAGACCCTGAGGTCAAGTTCAACTGGTACGTGGACGGC GTGGAGGTGCATAATGCCAAGACAAAGCCGCGGGAGGA GCAGTACAACAGCACGTACCGTGTGGTCAGCGTCCTCAC CGTCCTGCACCAGGACTGGCTGAATGGCAAGGAGTACAA GTGCAAGGTCTCCAACAAAGCCCTCCCAGCCCCCATCGA GAAAACCATCTCCAAAGCCAAAGGGCAGCCCCGAGAACC ACAGGTGTACACCCTGCCCCCATCCCGGGAGGAGATGA CCAAGAACCAGGTCAGCCTGACCTGCCTGGTCAAAGGCT TCTATCCCAGCGACATCGCCGTGGAGTGGGAGAGCAATG GGCAGCCGGAGAACAACTACAAGACCACGCCTCCCGTG CTGGACTCCGACGGCTCCTTCTTCCTCTACAGCAAGCTC ACCGTGGACAAGAGCAGGTGGCAGCAGGGGAACGTCTT CTCATGCTCCGTGATGCATGAGGCTCTGCACAACCACTA CACGCAGAAGAGCCTCTCCCTGTCTCCGGGTAAA | 140 |
| C40M66 | CAGGTGCAGCTGGTGCAGAGCGGCGCGGAAGTGAAAAA ACCGGGCAGCAGCGTGAAAGTGAGCTGCAAAGCGAGCG GCGGCACCTTTAGCAGCTATGCGATTAGCTGGGTGCGCC AGGCGCCGGGCCAGGGCCTGGAATGGATGGGCGGCATT ATTCCGATTTTTGGCACCGCGAACTATGCGCAGAAATTTC AGGGCCGCGTGACCATTACCGCGGATGAAAGCACCAGC ACCGCGTATATGGAACTGAGCAGCCTGCGCAGCGAAGAT ACCGCGGTGTATTATTGCGCGCGCGTTCGGTATTCGGCG TGGTATAGGGACTCTTTGGACTATTGGGGCCAGGGCACC CTGGTGACAGTCTCGAGTGCCTCCACCAAGGGCCCATCG GTCTTCCCCCTGGCACCCTCCTCCAAGAGCACCTCTGGG GGCACAGCGGCCCTGGGCTGCCTGGTCAAGGACTACTT CCCCGAACCGGTGACGGTGTCGTGGAACTCAGGCGCCC TGACCAGCGGCGTGCACACCTTCCCGGCTGTCCTACAGT CCTCAGGACTCTACTCCCTCAGCAGCGTGGTGACCGTGC | 141 |

TABLE 18-continued

| mAb | HC DNA | HC DNA SEQ ID NO: |
|---|---|---|
| | CCTCCAGCAGCTTGGGCACCCAGACCTACATCTGCAACG TGAATCACAAGCCCAGCAACACCAAGGTGGACAAGAAAG TTGAGCCCAAATCTTGTGACAAAACTCACACATGCCCACC GTGCCCAGCACCTGAACTCCTGGGGGGACCGTCAGTCTT CCTCTTCCCCCCAAAACCCAAGGACACCCTCATGATCTC CCCGGACCCCTGAGGTCACATGCGTGGTGGTGGACGTGA GCCACGAAGACCCTGAGGTCAAGTTCAACTGGTACGTGG ACGGCGTGGAGGTGCATAATGCCAAGACAAAGCCGCGG GAGGAGCAGTACAACAGCACGTACCGTGTGGTCAGCGTC CTCACCGTCCTGCACCAGGACTGGCTGAATGGCAAGGAG TACAAGTGCAAGGTCTCCAACAAAGCCCTCCCAGCCCCC ATCGAGAAAACCATCTCCAAAGCCAAAGGGCAGCCCCGA GAACCACAGGTGTACACCCTGCCCCCATCCCGGGAGGA GATGACCAAGAACCAGGTCAGCCTGACCTGCCTGGTCAA AGGCTTCTATCCCAGCGACATCGCCGTGGAGTGGGAGA GCAATGGGCAGCCGGAGAACAACTACAAGACCACGCCTC CCGTGCTGGACTCCGACGGCTCCTTCTTCCTCTACAGCA AGCTCACCGTGGACAAGAGCAGGTGGCAGCAGGGGAAC GTCTTCTCATGCTCCGTGATGCATGAGGCTCTGCACAAC CACTACACGCAGAAGAGCCTCTCCCTGTCTCCGGGTAAA | |
| C40M63 | CAGGTGCAGCTGGTGCAGAGCGGCGCGGAAGTGAAAAA ACCGGGCAGCAGCGTGAAAGTGAGCTGCAAAGCGAGCG GCGGCACCTTTAGCAGCTATGCGATTAGCTGGGTGCGCC AGGCGCCGGGCCAGGGCCTGGAATGGATGGGCGGCATT ATTCCGATTTTTGGCACCGCGAACTATGCGCAGAAATTTC AGGGCCGCGTGACCATTACCGCGGATGAAAGCACCAGC ACCGCGTATATGGAACTGAGCAGCCTGCGCAGCGAAGAT ACCGCGGTGTATTATTGCGCGCGCGTAGGCCATCCGGCT TGGTGGCGTGATTCGTTGGACTATTGGGGCCAGGGCACC CTGGTGACCGTGAGCAGCGCCTCCACCAAGGGCCCATC GGTCTTCCCCCTGGCACCCTCCTCCAAGAGCACCTCTGG GGGCACAGCGGCCCTGGGCTGCCTGGTCAAGGACTACT TCCCCGAACCGGTGACGGTGTCGTGGAACTCAGGCGCC CTGACCAGCGGCGTGCACACCTTCCCGGCTGTCCTACAG TCCTCAGGACTCTACTCCCTCAGCAGCGTGGTGACCGTG CCCTCCAGCAGCTTGGGCACCCAGACCTACATCTGCAAC GTGAATCACAAGCCCAGCAACACCAAGGTGGACAAGAAA GTTGAGCCCAAATCTTGTGACAAAACTCACACATGCCCAC CGTGCCCAGCACCTGAACTCCTGGGGGGACCGTCAGTC TTCCTCTTCCCCCCAAAACCCAAGGACACCCTCATGATCT CCCCGGACCCCTGAGGTCACATGCGTGGTGGTGGACGTG AGCCACGAAGACCCTGAGGTCAAGTTCAACTGGTACGTG GACGGCGTGGAGGTGCATAATGCCAAGACAAAGCCGCG GGAGGAGCAGTACAACAGCACGTACCGTGTGGTCAGCG TCCTCACCGTCCTGCACCAGGACTGGCTGAATGGCAAGG AGTACAAGTGCAAGGTCTCCAACAAAGCCCTCCCAGCCC CCATCGAGAAAACCATCTCCAAAGCCAAAGGGCAGCCCC GAGAACCACAGGTGTACACCCTGCCCCCATCCCGGGAG GAGATGACCAAGAACCAGGTCAGCCTGACCTGCCTGGTC AAAGGCTTCTATCCCAGCGACATCGCCGTGGAGTGGGAG AGCAATGGGCAGCCGGAGAACAACTACAAGACCACGCCT CCCGTGCTGGACTCCGACGGCTCCTTCTTCCTCTACAGC AAGCTCACCGTGGACAAGAGCAGGTGGCAGCAGGGGAA CGTCTTCTCATGCTCCGTGATGCATGAGGCTCTGCACAA CCACTACACGCAGAAGAGCCTCTCCCTGTCTCCGGGTAAA | 142 |
| C40M62 | CAGGTGCAGCTGGTGCAGAGCGGCGCGGAAGTGAAAAA ACCGGGCAGCAGCGTGAAAGTGAGCTGCAAAGCGAGCG GCGGCACCTTTAGCAGCTATGCGATTAGCTGGGTGCGCC AGGCGCCGGGCCAGGGCCTGGAATGGATGGGCGGCATT ATTCCGATTTTTGGCACCGCGAACTATGCGCAGAAATTTC AGGGCCGCGTGACCATTACCGCGGATGAAAGCACCAGC ACCGCGTATATGGAACTGAGCAGCCTGCGCAGCGAAGAT ACCGCGGTGTATTATTGCGCGCGCGTTGCCAACGCTGCG TATTTTAGGTCTGGCTTGGACTATTGGGGCCAGGGCACC CTGGTGACCGTGAGCAGCGCCTCCACCAAGGGCCCATC GGTCTTCCCCCTGGCACCCTCCTCCAAGAGCACCTCTGG GGGCACAGCGGCCCTGGGCTGCCTGGTCAAGGACTACT TCCCCGAACCGGTGACGGTGTCGTGGAACTCAGGCGCC CTGACCAGCGGCGTGCACACCTTCCCGGCTGTCCTACAG TCCTCAGGACTCTACTCCCTCAGCAGCGTGGTGACCGTG CCCTCCAGCAGCTTGGGCACCCAGACCTACATCTGCAAC GTGAATCACAAGCCCAGCAACACCAAGGTGGACAAGAAA GTTGAGCCCAAATCTTGTGACAAAACTCACACATGCCCAC CGTGCCCAGCACCTGAACTCCTGGGGGGACCGTCAGTC | 143 |

TABLE 18-continued

| mAb | HC DNA | HC DNA SEQ ID NO: |
|---|---|---|
| | TTCCTCTTCCCCCCAAAACCCAAGGACACCCTCATGATCT CCCGGACCCCTGAGGTCACATGCGTGGTGGTGGACGTG AGCCACGAAGACCCTGAGGTCAAGTTCAACTGGTACGTG GACGGCGTGGAGGTGCATAATGCCAAGACAAAGCCGCG GGAGGAGCAGTACAACAGCACGTACCGTGTGGTCAGCG TCCTCACCGTCCTGCACCAGGACTGGCTGAATGGCAAGG AGTACAAGTGCAAGGTCTCCAACAAAGCCCTCCCAGCCC CCATCGAGAAACCATCTCCAAAGCCAAAGGGCAGCCCC GAGAACCACAGGTGTACACCCTGCCCCCATCCCGGGAG GAGATGACCAAGAACCAGGTCAGCCTGACCTGCCTGGTC AAAGGCTTCTATCCCAGCGACATCGCCGTGGAGTGGGAG AGCAATGGGCAGCCGGAGAACAACTACAAGACCACGCCT CCCGTGCTGGACTCCGACGGCTCCTTCTTCCTCTACAGC AAGCTCACCGTGGACAAGAGCAGGTGGCAGCAGGGGAA CGTCTTCTCATGCTCCGTGATGCATGAGGCTCTGCACAA CCACTACACGCAGAAGAGCCTCTCCCTGTCTCCGGGTAAA | |
| C40M59 | CAGGTGCAGCTGGTGCAGAGCGGCGCGGAAGTGAAAAA ACCGGGCAGCAGCGTGAAAGTGAGCTGCAAAGCGAGCG GCGGCACCTTCAGCTCCTACTGGATTAGCTGGGTGCGCC AGGCGCCGGGCCAGGGCCTGGAATGGATGGGCTACATT ATTCCGATCAGTGGCACTGCCCGCTACGCGCAGAAATTT CAGGGCCGCGTGACCATTACCGCTGATGAAAGCACCAGC ACCGCGTATATGGAACTGAGCAGCCTGCGCAGCGAAGAT ACCGCGGTGTATTATTGCGCGCGCGAACCAGGCTACAGT AGTGGCCTGAGCGTTGACTACTTTGATTACTGGGGCCAG GGCACCCTGGTGACAGTCTCGAGTGCCTCCACCAAGGG CCCATCGGTCTTCCCCCTGGCACCCTCCTCCAAGAGCAC CTCTGGGGGCACAGCGGCCCTGGGCTGCCTGGTCAAGG ACTACTTCCCCGAACCGGTGACGGTGTCGTGGAACTCAG GCGCCCTGACCAGCGGCGTGCACACCTTCCCGGCTGTC CTACAGTCCTCAGGACTCTACTCCCTCAGCAGCGTGGTG ACCGTGCCCTCCAGCAGCTTGGGCACCCAGACCTACATC TGCAACGTGAATCACAAGCCCAGCAACACCAAGGTGGAC AAGAAAGTTGAGCCCAAATCTTGTGACAAAACTCACACAT GCCCACCGTGCCCAGCACCTGAACTCCTGGGGGGACCG TCAGTCTTCCTCTTCCCCCCAAAACCCAAGGACACCCTCA TGATCTCCCGGACCCCTGAGGTCACATGCGTGGTGGTGG ACGTGAGCCACGAAGACCCTGAGGTCAAGTTCAACTGGT ACGTGGACGGCGTGGAGGTGCATAATGCCAAGACAAAG CCGCGGGAGGAGCAGTACAACAGCACGTACCGTGTGGT CAGCGTCCTCACCGTCCTGCACCAGGACTGGCTGAATGG CAAGGAGTACAAGTGCAAGGTCTCCAACAAAGCCCTCCC AGCCCCCATCGAGAAACCATCTCCAAAGCCAAAGGGCA GCCCCGAGAACCACAGGTGTACACCCTGCCCCCATCCC GGGAGGAGATGACCAAGAACCAGGTCAGCCTGACCTGC CTGGTCAAAGGCTTCTATCCCAGCGACATCGCCGTGGAG TGGGAGAGCAATGGGCAGCCGGAGAACAACTACAAGAC CACGCCTCCCGTGCTGGACTCCGACGGCTCCTTCTTCCT CTACAGCAAGCTCACCGTGGACAAGAGCAGGTGGCAGC AGGGGAACGTCTTCTCATGCTCCGTGATGCATGAGGCTC TGCACAACCACTACACGCAGAAGAGCCTCTCCCTGTCTC CGGGTAAA | 144 |
| C40M58 | GAAGTGCAGCTGCTGGAAAGCGGCGGCGGCCTGGTGCA GCCGGGCGGCAGCCTGCGCCTGAGCTGCGCGGCGAGC GGCTTTACCTTTAGCAGCTATGCGATGAGCTGGGTGCGC CAGGCGCCGGGCAAAGGCCTGGAATGGGTGAGCGCGAT CAGCGGCTCCGGTGGCTCCACATATTATGCGGATAGCGT GAAAGGCCGCTTTACCATTTCACGAGATAACAGCAAAAAC ACCCTGTATCTGCAGATGAACAGCCTGCGCGCGGAAGAT ACCGCGGTGTATTATTGCGCGCGCGGTCCAGCATACACT ATCGTTTTTGATTATTGGGGCCAGGGCACCCTGGTGACA GTCTCGAGTGCCTCCACCAAGGGCCCATCGGTCTTCCCC CTGGCACCCTCCTCCAAGAGCACCTCTGGGGGCACAGC GGCCCTGGGCTGCCTGGTCAAGGACTACTTCCCCGAACC GGTGACGGTGTCGTGGAACTCAGGCGCCCTGACCAGCG GCGTGCACACCTTCCCGGCTGTCCTACAGTCCTCAGGAC TCTACTCCCTCAGCAGCGTGGTGACCGTGCCCTCCAGCA GCTTGGGCACCCAGACCTACATCTGCAACGTGAATCACA AGCCCAGCAACACCAAGGTGGACAAGAAAGTTGAGCCCA AATCTTGTGACAAAACTCACACATGCCCACCGTGCCCAG CACCTGAACTCCTGGGGGGACCGTCAGTCTTCCTCTTCC CCCCAAAACCCAAGGACACCCTCATGATCTCCCGGACCC CTGAGGTCACATGCGTGGTGGTGGACGTGAGCCACGAA GACCCTGAGGTCAAGTTCAACTGGTACGTGGACGGCGTG | 145 |

TABLE 18-continued

| mAb | HC DNA | HC DNA SEQ ID NO: |
|---|---|---|
| | GAGGTGCATAATGCCAAGACAAAGCCGCGGGAGGAGCA GTACAACAGCACGTACCGTGTGGTCAGCGTCCTCACCGT CCTGCACCAGGACTGGCTGAATGGCAAGGAGTACAAGTG CAAGGTCTCCAACAAAGCCCTCCCAGCCCCCATCGAGAA AACCATCTCCAAAGCCAAAGGGCAGCCCCGAGAACCACA GGTGTACACCCTGCCCCCATCCCGGGAGGAGATGACCA AGAACCAGGTCAGCCTGACCTGCCTGGTCAAAGGCTTCT ATCCCAGCGACATCGCCGTGGAGTGGGAGAGCAATGGG CAGCCGGAGAACAACTACAAGACCACGCCTCCCGTGCTG GACTCCGACGGCTCCTTCTTCCTCTACAGCAAGCTCACC GTGGACAAGAGCAGGTGGCAGCAGGGGAACGTCTTCTC ATGCTCCGTGATGCATGAGGCTCTGCACAACCACTACAC GCAGAAGAGCCTCTCCCTGTCTCCGGGTAAA | |
| C40M56 | GAAGTGCAGCTGCTGGAAAGCGGCGGCGGCCTGGTGCA GCCGGGCGGCAGCCTGCGCCTGAGCTGCGCGGCGAGC GGCTTTACCTTTAGCAGCTATGCGATGAGCTGGGTGCGC CAGGCGCCGGGCAAAGGCCTGGAATGGGTGAGCGCGAT CAGCGGCTCCGGTGGCTCCACATATTATGCGGATAGCGT GAAAGGCCGCTTTACCATTTCACGAGATAACAGCAAAAAC ACCCTGTATCTGCAGATGAACAGCCTGCGCGCGGAAGAT ACCGCGGTGTATTATTGCGCGCGCGGTCCTGTTTATTCTC TGGTTTTTGACTACTGGGGCCAGGGCACCCTGGTGACAG TCTCGAGTGCCTCCACCAAGGGCCCATCGGTCTTCCCCC TGGCACCCTCCTCCAAGAGCACCTCTGGGGGCACAGCG GCCCTGGGCTGCCTGGTCAAGGACTACTTCCCCGAACCG GTGACGGTGTCGTGGAACTCAGGCGCCCTGACCAGCGG CGTGCACACCTTCCCGGCTGTCCTACAGTCCTCAGGACT CTACTCCCTCAGCAGCGTGGTGACCGTGCCCTCCAGCAG CTTGGGCACCCAGACCTACATCTGCAACGTGAATCACAA GCCCAGCAACACCAAGGTGGACAAGAAAGTTGAGCCCAA ATCTTGTGACAAAACTCACACATGCCCACCGTGCCCAGC ACCTGAACTCCTGGGGGGACCGTCAGTCTTCCTCTTCCC CCCAAAACCCAAGGACACCCTCATGATCTCCCGGACCCC TGAGGTCACATGCGTGGTGGTGGACGTGAGCCACAAG ACCCTGAGGTCAAGTTCAACTGGTACGTGGACGGCGTGG AGGTGCATAATGCCAAGACAAAGCCGCGGGAGGAGCAG TACAACAGCACGTACCGTGTGGTCAGCGTCCTCACCGTC CTGCACCAGGACTGGCTGAATGGCAAGGAGTACAAGTGC AAGGTCTCCAACAAAGCCCTCCCAGCCCCATCGAGAAA ACCATCTCCAAAGCCAAAGGGCAGCCCCGAGAACCACAG GTGTACACCCTGCCCCCATCCCGGGAGGAGATGACCAA GAACCAGGTCAGCCTGACCTGCCTGGTCAAAGGCTTCTA TCCCAGCGACATCGCCGTGGAGTGGGAGAGCAATGGGC AGCCGGAGAACAACTACAAGACCACGCCTCCCGTGCTGG ACTCCGACGGCTCCTTCTTCCTCTACAGCAAGCTCACCG TGGACAAGAGCAGGTGGCAGCAGGGGAACGTCTTCTCAT GCTCCGTGATGCATGAGGCTCTGCACAACCACTACACGC AGAAGAGCCTCTCCCTGTCTCCGGGTAAA | 146 |
| C40M55 | CAGGTGCAGCTGGTGCAGAGCGGCGCGGAAGTGAAAAA ACCGGGCAGCAGCGTGAAAGTGAGCTGCAAAGCGAGCG GCGGCACCTTCAGCAGCTATGCGATTAGCTGGGTGCGCC AGGCGCCGGGCCAGGGCCTGGAATGGATGGGCGGCATT ATTCCGATTTTTGGCACCGCTAACTACGCGCAGAAATTTC AGGGCCGCGTGACCATTACCGCTGATGAAAGCACCAGCA CCGCGTATATGGAACTGAGCAGCCTGCGCAGCGAAGATA CCGCGGTGTATTATTGCGCGCGCGATGGTTATCGGCGGT ATGGCATCGGTCGTTACGGTTTCGATTATTGGGGCCAGG GCACCCTGGTGACAGTCTCGAGTGCCTCCACCAAGGGC CCATCGGTCTTCCCCCTGGCACCCTCCTCCAAGAGCACC TCTGGGGGCACAGCGGCCCTGGGCTGCCTGGTCAAGGA CTACTTCCCCGAACCGGTGACGGTGTCGTGGAACTCAGG CGCCCTGACCAGCGGCGTGCACACCTTCCCGGCTGTCC TACAGTCCTCAGGACTCTACTCCCTCAGCAGCGTGGTGA CCGTGCCCTCCAGCAGCTTGGGCACCCAGACCTACATCT GCAACGTGAATCACAAGCCCAGCAACACCAAGGTGGACA AGAAAGTTGAGCCCAAATCTTGTGACAAAACTCACACATG CCCACCGTGCCCAGCACCTGAACTCCTGGGGGGACCGT CAGTCTTCCTCTTCCCCCCAAAACCCAAGGACACCCTCAT GATCTCCCGGACCCCTGAGGTCACATGCGTGGTGGTGG ACGTGAGCCACGAAGACCCTGAGGTCAAGTTCAACTGGT ACGTGGACGGCGTGAGGTGCATAATGCCAAGACAAAG CCGCGGGAGGAGCAGTACAACAGCACGTACCGTGTGGT CAGCGTCCTCACCGTCCTGCACCAGGACTGGCTGAATGG CAAGGAGTACAAGTGCAAGGTCTCCAACAAAGCCCTCCC | 147 |

TABLE 18-continued

| mAb | HC DNA | HC DNA SEQ ID NO: |
|---|---|---|
| | AGCCCCCATCGAGAAAACCATCTCCAAAGCCAAAGGGCA GCCCCGAGAACCACAGGTGTACACCCTGCCCCCATCCC GGGAGGAGATGACCAAGAACCAGGTCAGCCTGACCTGC CTGGTCAAAGGCTTCTATCCCAGCGACATCGCCGTGGAG TGGGAGAGCAATGGGCAGCCGGAGAACAACTACAAGAC CACGCCTCCCGTGCTGGACTCCGACGGCTCCTTCTTCCT CTACAGCAAGCTCACCGTGGACAAGAGCAGGTGGCAGC AGGGGAACGTCTTCTCATGCTCCGTGATGCATGAGGCTC TGCACAACCACTACACGCAGAAGAGCCTCTCCCTGTCTC CGGGTAAA | |
| C40M51 | GAAGTGCAGCTGCTGGAAAGCGGCGGCGGCCTGGTGCA GCCGGGCGGCAGCCTGCGCCTGAGCTGCGCGGCGAGC GGCTTTACCTTTAGCAGCTATGCGATGAGCTGGGTGCGC CAGGCGCCGGGCAAAGGCCTGGAATGGGTGAGCGCGAT CAGCGGCTCCGGTGGCTCCACATATTATGCGGATAGCGT GAAAGGCCGCTTTACCATTTCACGAGATAACAGCAAAAAC ACCCTGTATCTGCAGATGAACAGCCTGCGCGCGGAAGAT ACCGCGGTGTATTATTGCGCGCGCGGCCCAGTTTATTCT AGCGTTTTCGACTATTGGGGCCAGGGCACCCTGGTGACA GTCTCGAGTGCCTCCACCAAGGGCCCATCGGTCTTCCCC CTGGCACCCTCCTCCAAGAGCACCTCTGGGGGCACAGC GGCCCTGGGCTGCCTGGTCAAGGACTACTTCCCCGAACC GGTGACGGTGTCGTGGAACTCAGGCGCCCTGACCAGCG GCGTGCACACCTTCCCGGCTGTCCTACAGTCCTCAGGAC TCTACTCCCTCAGCAGCGTGGTGACCGTGCCCTCCAGCA GCTTGGGCACCCAGACCTACATCTGCAACGTGAATCACA AGCCCAGCAACACCAAGGTGGACAAGAAAGTTGAGCCCA AATCTTGTGACAAAACTCACACATGCCCACCGTGCCCAG CACCTGAACTCCTGGGGGGACCGTCAGTCTTCCTCTTCC CCCCAAAACCCAAGGACACCCTCATGATCTCCCGGACCC CTGAGGTCACATGCGTGGTGGTGGACGTGAGCCACGAA GACCCTGAGGTCAAGTTCAACTGGTACGTGGACGGCGTG GAGGTGCATAATGCCAAGACAAAGCCGCGGGAGGAGCA GTACAACAGCACGTACCGTGTGGTCAGCGTCCTCACCGT CCTGCACCAGGACTGGCTGAATGGCAAGGAGTACAAGTG CAAGGTCTCCAACAAAGCCCTCCCAGCCCCCATCGAGAA AACCATCTCCAAAGCCAAAGGGCAGCCCCGAGAACCACA GGTGTACACCCTGCCCCCATCCCGGGAGGAGATGACCA AGAACCAGGTCAGCCTGACCTGCCTGGTCAAAGGCTTCT ATCCCAGCGACATCGCCGTGGAGTGGGAGAGCAATGGG CAGCCGGAGAACAACTACAAGACCACGCCTCCCGTGCTG GACTCCGACGGCTCCTTCTTCCTCTACAGCAAGCTCACC GTGGACAAGAGCAGGTGGCAGCAGGGGAACGTCTTCTC ATGCTCCGTGATGCATGAGGCTCTGCACAACCACTACAC GCAGAAGAGCCTCTCCCTGTCTCCGGGTAAA | 148 |
| C40M18 | GAGGTGCAGCTGGTGGAATCTGGCGGAGGACTGGTGCA GCCTGGCGGCAGCCTGAGACTGTCTTGTGCCGCCAGCG GCTTCACCTTCAGCAGCTACGCTATGAGCTGGGTCCGAC AGGCCCCTGGCAAGGGACTGGAATGGGTGTCCATCATCA ACAACAACGTGGGCCGGACCTACTACGCCGACAGCGTG AAGGGCAGATTCACCATCAGCCGGGACAACAGCAAGAAC ACCCTGTACCTGCAGATGAACAGCCTGCGGGCCGAGGA CACCGCCGTGTACTATTGTGCCAAAGAGGGCGGCGATTA CTACTACTACGGCATGGACGTGTGGGGCCAGGGCACCA CCGTGACAGTGTCATCTGCCTCCACCAAGGGCCCATCGG TCTTCCCCCTGGCACCCTCCTCCAAGAGCACCTCTGGGG GCACAGCGGCCCTGGGCTGCCTGGTCAAGGACTACTTC CCCGAACCGGTGACGGTGTCGTGGAACTCAGGCGCCCT GACCAGCGGCGTGCACACCTTCCCGGCTGTCCTACAGTC CTCAGGACTCTACTCCCTCAGCAGCGTGGTGACCGTGCC CTCCAGCAGCTTGGGCACCCAGACCTACATCTGCAACGT GAATCACAAGCCCAGCAACACCAAGGTGGACAAGAAAGT TGAGCCCAAATCTTGTGACAAAACTCACACATGCCCACC GTGCCCAGCACCTGAACTCCTGGGGGGACCGTCAGTCTT CCTCTTCCCCCCAAAACCCAAGGACACCCTCATGATCTC CCGGACCCCTGAGGTCACATGCGTGGTGGTGGACGTGA GCCACGAAGACCCTGAGGTCAAGTTCAACTGGTACGTGG ACGGCGTGGAGGTGCATAATGCCAAGACAAAGCCGCGG GAGGAGCAGTACAACAGCACGTACCGTGTGGTCAGCGTC CTCACCGTCCTGCACCAGGACTGGCTGAATGGCAAGGAG TACAAGTGCAAGGTCTCCAACAAAGCCCTCCCAGCCCCC ATCGAGAAACCATCTCCAAAGCCAAAGGGCAGCCCCGA GAACCACAGGTGTACACCCTGCCCCCATCCCGGGAGGA GATGACCAAGAACCAGGTCAGCCTGACCTGCCTGGTCAA | 149 |

TABLE 18-continued

| mAb | HC DNA | HC DNA SEQ ID NO: |
|---|---|---|
| | AGGCTTCTATCCCAGCGACATCGCCGTGGAGTGGGAGA<br>GCAATGGGCAGCCGGAGAACAACTACAAGACCACGCCTC<br>CCGTGCTGGACTCCGACGGCTCCTTCTTCCTCTACAGCA<br>AGCTCACCGTGGACAAGAGCAGGTGGCAGCAGGGGAAC<br>GTCTTCTCATGCTCCGTGATGCATGAGGCTCTGCACAAC<br>CACTACACGCAGAAGAGCCTCTCCCTGTCTCCGGGTAAA | |
| C40M17 | GAGGTGCAGCTGGTGGAATCTGGCGGAGGACTGGTGCA<br>GCCTGGCGGCAGCCTGAGACTGTCTTGTGCCGCCAGCG<br>GCTTCACCTTCAGCAGCTACGCTATGAGCTGGGTCCGAC<br>AGGCCCCTGGCAGAGGACTCGAGTGGGTGTCCACCATC<br>AACAACAGCGGCGGAGGCACCTACTACGCCGACAGCGT<br>GAAGGGCAGATTCACCATCAGCCGGGACAACAGCAAGAA<br>CACCCTGTACCTGCACATGAACAGCCTGCGGGCCGAGG<br>ACACCGCCGTGTACTATTGTGCCAAAGAGGGCGGCAAGT<br>ACTACTACTATGCCATGGACGTGTGGGGCCAGGGCACCA<br>CCGTGACAGTGTCATCTGCCTCCACCAAGGGCCCATCGG<br>TCTTCCCCCTGGCACCCTCCTCCAAGAGCACCTCTGGGG<br>GCACAGCGGCCCTGGGCTGCCTGGTCAAGGACTACTTC<br>CCCGAACCGGTGACGGTGTCGTGGAACTCAGGCGCCCT<br>GACCAGCGGCGTGCACACCTTCCCGGCTGTCCTACAGTC<br>CTCAGGACTCTACTCCCTCAGCAGCGTGGTGACCGTGCC<br>CTCCAGCAGCTTGGGCACCCAGACCTACATCTGCAACGT<br>GAATCACAAGCCCAGCAACACCAAGGTGGACAAGAAAGT<br>TGAGCCCAAATCTTGTGACAAAACTCACACATGCCCACC<br>GTGCCCAGCACCTGAACTCCTGGGGGGACCGTCAGTCTT<br>CCTCTTCCCCCCAAAACCCAAGGACACCCTCATGATCTC<br>CCGGACCCCTGAGGTCACATGCGTGGTGGTGGACGTGA<br>GCCACGAAGACCCTGAGGTCAAGTTCAACTGGTACGTGG<br>ACGGCGTGGAGGTGCATAATGCCAAGACAAAGCCGCGG<br>GAGGAGCAGTACAACAGCACGTACCGTGTGGTCAGCGTC<br>CTCACCGTCCTGCACCAGGACTGGCTGAATGGCAAGGAG<br>TACAAGTGCAAGGTCTCCAACAAAGCCCTCCCAGCCCCC<br>ATCGAGAAAACCATCTCCAAAGCCAAAGGGCAGCCCCGA<br>GAACCACAGGTGTACACCCTGCCCCCATCCCGGGAGGA<br>GATGACCAAGAACCAGGTCAGCCTGACCTGCCTGGTCAA<br>AGGCTTCTATCCCAGCGACATCGCCGTGGAGTGGGAGA<br>GCAATGGGCAGCCGGAGAACAACTACAAGACCACGCCTC<br>CCGTGCTGGACTCCGACGGCTCCTTCTTCCTCTACAGCA<br>AGCTCACCGTGGACAAGAGCAGGTGGCAGCAGGGGAAC<br>GTCTTCTCATGCTCCGTGATGCATGAGGCTCTGCACAAC<br>CACTACACGCAGAAGAGCCTCTCCCTGTCTCCGGGTAAA | 150 |
| C40M12 | GAGGTGCAGCTGGTGGAATCTGGCGGAGGACTGGTGCA<br>GCCTGGCGGCAGCCTGAGACTGTCTTGTGCCGCCAGCG<br>GCTTCACCTTCGGCAGCTACGCTATGAGCTGGGTCCGAC<br>AGGCCCCTGGCAAGGGACTGGAATGGGTGTCCGTGATC<br>AGCGACAGCGGCGGCAGAACCTACTACGCCGACAGCGT<br>GAAGGGCCGGTTCACCATCAGCCGGGACTACAGCAAGA<br>ACACCCTGTACCTGCAGATGAACAGCCTGCGGGCCGAG<br>GACACCGCCGTGTACTATTGTGCCAAAGAGGGCGGCGAT<br>TACTACTACTACGGCATGGACGTGTGGGGCCAGGGCACC<br>ACCGTGACAGTGTCATCTGCCTCCACCAAGGGCCCATCG<br>GTCTTCCCCCTGGCACCCTCCTCCAAGAGCACCTCTGGG<br>GGCACAGCGGCCCTGGGCTGCCTGGTCAAGGACTACTT<br>CCCCGAACCGGTGACGGTGTCGTGGAACTCAGGCGCCC<br>TGACCAGCGGCGTGCACACCTTCCCGGCTGTCCTACAGT<br>CCTCAGGACTCTACTCCCTCAGCAGCGTGGTGACCGTGC<br>CCTCCAGCAGCTTGGGCACCCAGACCTACATCTGCAACG<br>TGAATCACAAGCCCAGCAACACCAAGGTGGACAAGAAAG<br>TTGAGCCCAAATCTTGTGACAAAACTCACACATGCCCACC<br>GTGCCCAGCACCTGAACTCCTGGGGGGACCGTCAGTCTT<br>CCTCTTCCCCCCAAAACCCAAGGACACCCTCATGATCTC<br>CCGGACCCCTGAGGTCACATGCGTGGTGGTGGACGTGA<br>GCCACGAAGACCCTGAGGTCAAGTTCAACTGGTACGTGG<br>ACGGCGTGGAGGTGCATAATGCCAAGACAAAGCCGCGG<br>GAGGAGCAGTACAACAGCACGTACCGTGTGGTCAGCGTC<br>CTCACCGTCCTGCACCAGGACTGGCTGAATGGCAAGGAG<br>TACAAGTGCAAGGTCTCCAACAAAGCCCTCCCAGCCCCC<br>ATCGAGAAAACCATCTCCAAAGCCAAAGGGCAGCCCCGA<br>GAACCACAGGTGTACACCCTGCCCCCATCCCGGGAGGA<br>GATGACCAAGAACCAGGTCAGCCTGACCTGCCTGGTCAA<br>AGGCTTCTATCCCAGCGACATCGCCGTGGAGTGGGAGA<br>GCAATGGGCAGCCGGAGAACAACTACAAGACCACGCCTC<br>CCGTGCTGGACTCCGACGGCTCCTTCTTCCTCTACAGCA<br>AGCTCACCGTGGACAAGAGCAGGTGGCAGCAGGGGAAC | 151 |

TABLE 18-continued

| mAb | HC DNA | HC DNA SEQ ID NO: |
|---|---|---|
|  | GTCTTCTCATGCTCCGTGATGCATGAGGCTCTGCACAAC CACTACACGCAGAAGAGCCTCTCCCTGTCTCCGGGTAAA |  |
| C40M9 | CAGCTCCAGCTGCAGGAATCTGGCCCTGGCCTGGTCAAG CCCAGCGAGATCCTGAGCCTGACCTGTACCGTGTCCGGC GGCAGCATCAGCAGCAGCTCTTACTACTGGGGCTGGATC CGGCAGCCTCCCGGCAAGGGACTGGAATGGATCGGCAA CATCTACTACCGGGGCGACACCTACTACAGCCCCAGCCT GAAGTCCAGAGTGACCATCAGCGTGGACACCAGCAAGAA CCAGTTCTCCCTGAAGCTGAACAGCGTGACAGCCGCCGA CACCGCCGTGTACTACTGCGCCAAGGGCTTCAGATTCGA TTACTGGGGCCAGGGCACCCTGGTCACCGTGTCATCTGC CTCCACCAAGGGCCCATCGGTCTTCCCCCTGGCACCCTC CTCCAAGAGCACCTCTGGGGGCACAGCGGCCCTGGGCT GCCTGGTCAAGGACTACTTCCCCGAACCGGTGACGGTGT CGTGGAACTCAGGCGCCCTGACCAGCGGCGTGCACACC TTCCCGGCTGTCCTACAGTCCTCAGGACTCTACTCCCTCA GCAGCGTGGTGACCGTGCCCTCCAGCAGCTTGGGCACC CAGACCTACATCTGCAACGTGAATCACAAGCCCAGCAAC ACCAAGGTGGACAAGAAAGTTGAGCCCAAATCTTGTGAC AAAACTCACACATGCCCACCGTGCCCAGCACCTGAACTC CTGGGGGGACCGTCAGTCTTCCTCTTCCCCCCAAAACCC AAGGACACCCTCATGATCTCCCGGACCCCTGAGGTCACA TGCGTGGTGGTGGACGTGAGCCACGAAGACCCTGAGGT CAAGTTCAACTGGTACGTGGACGGCGTGGAGGTGCATAA TGCCAAGACAAAGCCGCGGGAGGAGCAGTACAACAGCA CGTACCGTGTGGTCAGCGTCCTCACCGTCCTGCACCAGG ACTGGCTGAATGGCAAGGAGTACAAGTGCAAGGTCTCCA ACAAAGCCCTCCCAGCCCCCATCGAGAAAACCATCTCCA AAGCCAAAGGGCAGCCCCGAGAACCACAGGTGTACACC CTGCCCCCATCCCGGGAGGAGATGACCAAGAACCAGGT CAGCCTGACCTGCCTGGTCAAAGGCTTCTATCCCAGCGA CATCGCCGTGGAGTGGGAGAGCAATGGGCAGCCGGAGA ACAACTACAAGACCACGCCTCCCGTGCTGGACTCCGACG GCTCCTTCTTCCTCTACAGCAAGCTCACCGTGGACAAGA GCAGGTGGCAGCAGGGGAACGTCTTCTCATGCTCCGTGA TGCATGAGGCTCTGCACAACCACTACACGCAGAAGAGCC TCTCCCTGTCTCCGGGTAAA | 152 |
| C40M102 | GAGGTGCAGCTGGTGGAATCTGGCGGAGGACTGGTGCA GCCTGGCGGCAGCCTGAGACTGTCTTGTGCCGCCAGCG GCTTCACCTTCAGCAGCTACGCTATGAGCTGGGTCCGAC AGGCCCCTGGCAAGGGACTGGAATGGGTGTCCATCATCA CAACAACGTGGGCCGACCTACTACGCCGACAGCGTG AAGGGCAGATTCACCATCAGCCGGGACAACAGCAAGAAC ACCCTGTACCTGCAGATGAACAGCCTGCGGGCCGAGGA CACCGCCGTGTACTATTGTGCCAAAGAGGGCGGCGATTA CTACTACTACGGCATGGACGTGTGGGGCCAGGGCACCA CCGTGACAGTGTCATCTGCCTCCACCAAGGGCCCATCGG TCTTCCCCCTGGCACCCTCCTCCAAGAGCACCTCTGGGG GCACAGCGGCCCTGGGCTGCCTGGTCAAGGACTACTTC CCCGAACCGGTGACGGTGTCGTGGAACTCAGGCGCCCT GACCAGCGGCGTGCACACCTTCCCGGCTGTCCTACAGTC CTCAGGACTCTACTCCCTCAGCAGCGTGGTGACCGTGCC CTCCAGCAGCTTGGGCACCCAGACCTACATCTGCAACGT GAATCACAAGCCCAGCAACACCAAGGTGGACAAGAAAGT TGAGCCCAAATCTTGTGACAAAACTCACACATGCCCACC GTGCCCAGCACCTGAACTCCTGGGGGACCGTCAGTCTT CCTCTTCCCCCCAAAACCCAAGGACACCCTCATGATCTC CCGGACCCCTGAGGTCACATGCGTGGTGGTGGACGTGA GCCACGAAGACCCTGAGGTCAAGTTCAACTGGTACGTGG ACGGCGTGGAGGTGCATAATGCCAAGACAAAGCCGCGG GAGGAGCAGTACAACAGCACGTACCGTGTGGTCAGCGTC CTCACCGTCCTGCACCAGGACTGGCTGAATGGCAAGGAG TACAAGTGCAAGGTCTCCAACAAAGCCCTCCCAGCCCCC ATCGAGAAAACCATCTCCAAAGCCAAAGGGCAGCCCCGA GAACCACAGGTGTACACCCTGCCCCCATCCCGGGAGGA GATGACCAAGAACCAGGTCAGCCTGACCTGCCTGGTCAA AGGCTTCTATCCCAGCGACATCGCCGTGGAGTGGGAGA GCAATGGGCAGCCGGAGAACAACTACAAGACCACGCCTC CCGTGCTGGACTCCGACGGCTCCTTCTTCCTCTACAGCA AGCTCACCGTGGACAAGAGCAGGTGGCAGCAGGGGAAC GTCTTCTCATGCTCCGTGATGCATGAGGCTCTGCACAAC CACTACACGCAGAAGAGCCTCTCCCTGTCTCCGGGTAAA | 149 |

TABLE 18-continued

| mAb | HC DNA | HC DNA SEQ ID NO: |
|---|---|---|
| C40M103 | GAGGTGCAGCTGGTGGAATCTGGCGGAGGACTGGTGCA GCCTGGCGGCAGCCTGAGACTGTCTTGTGCCGCCAGCG GCTTCACCTTCAGCAGCTACGCTATGAGCTGGGTCCGAC AGGCCCCTGGCAAGGGACTGGAATGGGTGTCCATCATCA ACAACAACGTGGGCCGGACCTACTACGCCGACAGCGTG AAGGGCAGATTCACCATCAGCCGGGACAACAGCAAGAAC ACCCTGTACCTGCAGATGAACAGCCTGCGGGCCGAGGA CACCGCCGTGTACTATTGTGCCAAAGAGGGCGGCGATTA CTACTACTACGGCATGGACGTGTGGGGCCAGGGCACCA CCGTGACAGTGTCATCTGCCTCCACCAAGGGCCCATCGG TCTTCCCCCTGGCACCCTCCTCCAAGAGCACCTCTGGGG GCACAGCGGCCCTGGGCTGCCTGGTCAAGGACTACTTC CCCGAACCGGTGACGGTGTCGTGGAACTCAGGCGCCCT GACCAGCGGCGTGCACACCTTCCCGGCTGTCCTACAGTC CTCAGGACTCTACTCCCTCAGCAGCGTGGTGACCGTGCC CTCCAGCAGCTTGGGCACCCAGACCTACATCTGCAACGT GAATCACAAGCCCAGCAACACCAAGGTGGACAAGAAAGT TGAGCCCAAATCTTGTGACAAAACTCACACATGCCCACC GTGCCCAGCACCTGAACTCCTGGGGGGACCGTCAGTCTT CCTCTTCCCCCCAAAACCCAAGGACACCCTCATGATCTC CCGGACCCCTGAGGTCACATGCGTGGTGGTGGACGTGA GCCACGAAGACCCTGAGGTCAAGTTCAACTGGTACGTGG ACGGCGTGGAGGTGCATAATGCCAAGACAAAGCCGCGG GAGGAGCAGTACAACAGCACGTACCGTGTGGTCAGCGTC CTCACCGTCCTGCACCAGGACTGGCTGAATGGCAAGGAG TACAAGTGCAAGGTCTCCAACAAAGCCCTCCCAGCCCCC ATCGAGAAAACCATCTCCAAAGCCAAAGGGCAGCCCCGA GAACCACAGGTGTACACCCTGCCCCCATCCCGGGAGGA GATGACCAAGAACCAGGTCAGCCTGACCTGCCTGGTCAA AGGCTTCTATCCCAGCGACATCGCCGTGGAGTGGGAGA GCAATGGGCAGCCGGAGAACAACTACAAGACCACGCCTC CCGTGCTGGACTCCGACGGCTCCTTCTTCCTCTACAGCA AGCTCACCGTGGACAAGAGCAGGTGGCAGCAGGGGAAC GTCTTCTCATGCTCCGTGATGCATGAGGCTCTGCACAAC CACTACACGCAGAAGAGCCTCTCCCTGTCTCCGGGTAAA | 149 |
| C40M104 | GAGGTGCAGCTGGTGGAATCTGGCGGAGGACTGGTGCA GCCTGGCGGCAGCCTGAGACTGTCTTGTGCCGCCAGCG GCTTCACCTTCAGCAGCTACGCTATGAGCTGGGTCCGAC AGGCCCCTGGCAAGGGACTGGAATGGGTGTCCATCATCA ACAACAACGTGGGCCGGACCTACTACGCCGACAGCGTG AAGGGCAGATTCACCATCAGCCGGGACAACAGCAAGAAC ACCCTGTACCTGCAGATGAACAGCCTGCGGGCCGAGGA CACCGCCGTGTACTATTGTGCCAAAGAGGGCGGCGATTA CTACTACTACGGCATGGACGTGTGGGGCCAGGGCACCA CCGTGACAGTGTCATCTGCCTCCACCAAGGGCCCATCGG TCTTCCCCCTGGCACCCTCCTCCAAGAGCACCTCTGGGG GCACAGCGGCCCTGGGCTGCCTGGTCAAGGACTACTTC CCCGAACCGGTGACGGTGTCGTGGAACTCAGGCGCCCT GACCAGCGGCGTGCACACCTTCCCGGCTGTCCTACAGTC CTCAGGACTCTACTCCCTCAGCAGCGTGGTGACCGTGCC CTCCAGCAGCTTGGGCACCCAGACCTACATCTGCAACGT GAATCACAAGCCCAGCAACACCAAGGTGGACAAGAAAGT TGAGCCCAAATCTTGTGACAAAACTCACACATGCCCACC GTGCCCAGCACCTGAACTCCTGGGGGGACCGTCAGTCTT CCTCTTCCCCCCAAAACCCAAGGACACCCTCATGATCTC CCGGACCCCTGAGGTCACATGCGTGGTGGTGGACGTGA GCCACGAAGACCCTGAGGTCAAGTTCAACTGGTACGTGG ACGGCGTGGAGGTGCATAATGCCAAGACAAAGCCGCGG GAGGAGCAGTACAACAGCACGTACCGTGTGGTCAGCGTC CTCACCGTCCTGCACCAGGACTGGCTGAATGGCAAGGAG TACAAGTGCAAGGTCTCCAACAAAGCCCTCCCAGCCCCC ATCGAGAAAACCATCTCCAAAGCCAAAGGGCAGCCCCGA GAACCACAGGTGTACACCCTGCCCCCATCCCGGGAGGA GATGACCAAGAACCAGGTCAGCCTGACCTGCCTGGTCAA AGGCTTCTATCCCAGCGACATCGCCGTGGAGTGGGAGA GCAATGGGCAGCCGGAGAACAACTACAAGACCACGCCTC CCGTGCTGGACTCCGACGGCTCCTTCTTCCTCTACAGCA AGCTCACCGTGGACAAGAGCAGGTGGCAGCAGGGGAAC GTCTTCTCATGCTCCGTGATGCATGAGGCTCTGCACAAC CACTACACGCAGAAGAGCCTCTCCCTGTCTCCGGGTAAA | 149 |
| C40M105 | CAGCTGCAGCTGCAGGAGAGCGGCCCCGGCCTGGTGAA GCCCAGCGAGACCCTGAGCCTGACCTGCACCGTGAGCG GCGGCAGCATCAGCAGCAGCAGCTACTACTGGGGCTGG | 153 |

TABLE 18-continued

| mAb | HC DNA | HC DNA SEQ ID NO: |
|---|---|---|
| | ATCCGGCAGCCCCCGGCAAGGGCCTGGAGTGGATCGG<br>CAACATCTACTACCGGGGCGACACCTACTACAGCCCCAG<br>CCTGAAGAGCCGGGTGACCATCAGCGTGGACACCAGCA<br>AGAACCAGTTCAGCCTGAAGCTGAGCAGCGTGACCGCC<br>GCCGACACCGCCGTGTACTACTGCGCCCCGGGGCTTCCG<br>GTTCGACTACTGGGGCCAGGGCACCCTGGTGACCGTGA<br>GCAGCGCCTCCACCAAGGGCCCATCGGTCTTCCCCCTG<br>GCACCCTCCTCCAAGAGCACCTCTGGGGGCACAGCGGC<br>CCTGGGCTGCCTGGTCAAGGACTACTTCCCCGAACCGGT<br>GACGGTGTCGTGGAACTCAGGCGCCCTGACCAGCGGCG<br>TGCACACCTTCCCGGCTGTCCTACAGTCCTCAGGACTCT<br>ACTCCCTCAGCAGCGTGGTGACCGTGCCCTCCAGCAGCT<br>TGGGCACCCAGACCTACATCTGCAACGTGAATCACAAGC<br>CCAGCAACACCAAGGTGGACAAGAAAGTTGAGCCCAAAT<br>CTTGTGACAAAACTCACACATGCCCACCGTGCCCAGCAC<br>CTGAACTCCTGGGGGACCGTCAGTCTTCCTCTTCCCCC<br>CAAAACCCAAGGACACCCTCATGATCTCCCGGACCCCTG<br>AGGTCACATGCGTGGTGGTGGACGTGAGCCACGAAGAC<br>CCTGAGGTCAAGTTCAACTGGTACGTGGACGGCGTGGAG<br>GTGCATAATGCCAAGACAAAGCCGCGGGAGGAGCAGTA<br>CAACAGCACGTACCGTGTGGTCAGCGTCCTCACCGTCCT<br>GCACCAGGACTGGCTGAATGGCAAGGAGTACAAGTGCAA<br>GGTCTCCAACAAAGCCCTCCCAGCCCCCATCGAGAAAAC<br>CATCTCCAAAGCCAAAGGGCAGCCCCGAGAACCACAGGT<br>GTACACCCTGCCCCCATCCCGGGAGGAGATGACCAAGAA<br>CCAGGTCAGCCTGACCTGCCTGGTCAAAGGCTTCTATCC<br>CAGCGACATCGCCGTGGAGTGGGAGAGCAATGGGCAGC<br>CGGAGAACAACTACAAGACCACGCCTCCCGTGCTGGACT<br>CCGACGGCTCCTTCTTCCTCTACAGCAAGCTCACCGTGG<br>ACAAGAGCAGGTGGCAGCAGGGGAACGTCTTCTCATGCT<br>CCGTGATGCATGAGGCTCTGCACAACCACTACACGCAGA<br>AGAGCCTCTCCCTGTCTCCGGGTAAA | |
| C40M121 | CAGCTGCAGCTGCAGGAGAGCGGCCCCGGCCTGGTGAA<br>GCCCAGCGAGACCCTGAGCCTGACCTGCACCGTGAGCG<br>GCGGCAGCATCAGCAGCAGCAGCTACTACTGGGGCTGG<br>ATCCGGCAGCCCCCGGCAAGGGCCTGGAGTGGATCGG<br>CAACATCTACTACCGGGGCGACACCTACTACAGCCCCAG<br>CCTGAAGAGCCGGGTGACCATCAGCGTGGACACCAGCA<br>AGAACCAGTTCAGCCTGAAGCTGAGCAGCGTGACCGCC<br>GCCGACACCGCCGTGTACTACTGCGCCAAGGGCTTCCG<br>GTTCGACTACTGGGGCCAGGGCACCCTGGTGACCGTGA<br>GCAGCGCCTCCACCAAGGGCCCATCGGTCTTCCCCCTG<br>GCACCCTCCTCCAAGAGCACCTCTGGGGGCACAGCGGC<br>CCTGGGCTGCCTGGTCAAGGACTACTTCCCCGAACCGGT<br>GACGGTGTCGTGGAACTCAGGCGCCCTGACCAGCGGCG<br>TGCACACCTTCCCGGCTGTCCTACAGTCCTCAGGACTCT<br>ACTCCCTCAGCAGCGTGGTGACCGTGCCCTCCAGCAGCT<br>TGGGCACCCAGACCTACATCTGCAACGTGAATCACAAGC<br>CCAGCAACACCAAGGTGGACAAGAAAGTTGAGCCCAAAT<br>CTTGTGACAAAACTCACACATGCCCACCGTGCCCAGCAC<br>CTGAACTCCTGGGGGACCGTCAGTCTTCCTCTTCCCCC<br>CAAAACCCAAGGACACCCTCATGATCTCCCGGACCCCTG<br>AGGTCACATGCGTGGTGGTGGACGTGAGCCACGAAGAC<br>CCTGAGGTCAAGTTCAACTGGTACGTGGACGGCGTGGAG<br>GTGCATAATGCCAAGACAAAGCCGCGGGAGGAGCAGTA<br>CAACAGCACGTACCGTGTGGTCAGCGTCCTCACCGTCCT<br>GCACCAGGACTGGCTGAATGGCAAGGAGTACAAGTGCAA<br>GGTCTCCAACAAAGCCCTCCCAGCCCCCATCGAGAAAAC<br>CATCTCCAAAGCCAAAGGGCAGCCCCGAGAACCACAGGT<br>GTACACCCTGCCCCCATCCCGGGAGGAGATGACCAAGAA<br>CCAGGTCAGCCTGACCTGCCTGGTCAAAGGCTTCTATCC<br>CAGCGACATCGCCGTGGAGTGGGAGAGCAATGGGCAGC<br>CGGAGAACAACTACAAGACCACGCCTCCCGTGCTGGACT<br>CCGACGGCTCCTTCTTCCTCTACAGCAAGCTCACCGTGG<br>ACAAGAGCAGGTGGCAGCAGGGGAACGTCTTCTCATGCT<br>CCGTGATGCATGAGGCTCTGCACAACCACTACACGCAGA<br>AGAGCCTCTCCCTGTCTCCGGGTAAA | 154 |
| C40M126 | CAGCTGCAGCTGCAGGAGAGCGGCCCCGGCCTGGTGAA<br>GCCCAGCGAGACCCTGAGCCTGACCTGCACCGTGAGCG<br>GCGGCAGCATCAGCAGCAGCAGCTACTACTGGGGCTGG<br>ATCCGGCAGCCCCCGGCAAGGGCCTGGAGTGGATCGG<br>CAACATCTACTACCGGGGCGACACCTACTACAGCCCCAG<br>CCTGAAGAGCCGGGTGACCATCAGCGTGGACACCAGCA<br>AGAACCAGTTCAGCCTGAAGCTGAGCAGCGTGACCGCC | 155 |

TABLE 18-continued

| mAb | HC DNA | HC DNA SEQ ID NO: |
|---|---|---|
| | GCCGACACCGCCGTGTACTACTGCGCCAAGGGCTTCCG GTTCGACTACTGGGGCCAGGGCACCCTGGTGACCGTGA GCAGCGCCTCCACCAAGGGCCCATCGGTCTTCCCCCTG GCACCCTCCTCCAAGAGCACCTCTGGGGGCACAGCGGC CCTGGGCTGCCTGGTCAAGGACTACTTCCCCGAACCGGT GACGGTGTCGTGGAACTCAGGCGCCCTGACCAGCGGCG TGCACACCTTCCCGGCTGTCCTACAGTCCTCAGGACTCT ACTCCCTCAGCAGCGTGGTGACCGTGCCCTCCAGCAGCT TGGGCACCCAGACCTACATCTGCAACGTGAATCACAAGC CCAGCAACACCAAGGTGGACAAGAAAGTTGAGCCCAAAT CTTGTGACAAAACTCACACATGCCCACCGTGCCCAGCAC CTGAACTCCTGGGGGGACCGTCAGTCTTCCTCTTCCCCC CAAAACCCAAGGACACCCTCATGATCTCCCGGACCCCTG AGGTCACATGCGTGGTGGTGGACGTGAGCACGAAGAC CCTGAGGTCAAGTTCAACTGGTACGTGGACGGCGTGGAG GTGCATAATGCCAAGACAAAGCCGCGGGAGGAGCAGTA CAACAGCACGTACCGTGTGGTCAGCGTCCTCACCGTCCT GCACCAGGACTGGCTGAATGGCAAGGAGTACAAGTGCAA GGTCTCCAACAAAGCCCTCCCAGCCCCCATCGAGAAAAC CATCTCCAAAGCCAAAGGGCAGCCCCGAGAACCACAGGT GTACACCCTGCCCCCATCCCGGGAGGAGATGACCAAGAA CCAGGTCAGCCTGACCTGCCTGGTCAAAGGCTTCTATCC CAGCGACATCGCCGTGGAGTGGGAGAGCAATGGGCAGC CGGAGAACAACTACAAGACCACGCCTCCCGTGCTGGACT CCGACGGCTCCTTCTTCCTCTACAGCAAGCTCACCGTGG ACAAGAGCAGGTGGCAGCAGGGGAACGTCTTCTCATGCT CCGTGATGCATGAGGCTCTGCACAACCACTACACGCAGA AGAGCCTCTCCCTGTCTCCGGGTAAA | |

TABLE 19

| mAb | LC amino acid | LC SEQ ID NO: |
|---|---|---|
| C40M67 | EIVLTQSPGTLSLSPGERATLSCRASQSVKNSSLAWYQQKP GQAPRLLIYTASSRATGIPDRFSGSGSGTDFTLTISRLEPEDF AVYYCQQSSAPPWTFGQGTKVEIKRTVAAPSVFIFPPSDEQL KSGTASVVCLLNNFYPREAKVQWKVDNALQSGNSQESVTE QDSKDSTYSLSSTLTLSKADYEKHKVYACEVTHQGLSSPVTK SFNRGEC | 130 |
| C40M66 | DIVMTQSPDSLAVSLGERATINCKSSQSVLYSSNNKNYLAWY QQKPGQPPKLLIYWASTRESGVPDRFSGSGSGTDFTLTISSL QAEDVAVYYCQQYYSTPLTFGQGTKVEIKRTVAAPSVFIFPP SDEQLKSGTASVVCLLNNFYPREAKVQWKVDNALQSGNSQ ESVTEQDSKDSTYSLSSTLTLSKADYEKHKVYACEVTHQGLS SPVTKSFNRGEC | 131 |
| C40M63 | DIVMTQSPDSLAVSLGERATINCKSSQSVLYSSNNKNYLAWY QQKPGQPPKLLIYWASTRESGVPDRFSGSGSGTDFTLTISSL QAEDVAVYYCQQYYSTPLTFGQGTKVEIKRTVAAPSVFIFPP SDEQLKSGTASVVCLLNNFYPREAKVQWKVDNALQSGNSQ ESVTEQDSKDSTYSLSSTLTLSKADYEKHKVYACEVTHQGLS SPVTKSFNRGEC | 131 |
| C40M62 | DIVMTQSPDSLAVSLGERATINCKSSQSVLYSSNNKNYLAWY QQKPGQPPKLLIYWASTRESGVPDRFSGSGSGTDFTLTISSL QAEDVAVYYCQQYYSTPLTFGQGTKVEIKRTVAAPSVFIFPP SDEQLKSGTASVVCLLNNFYPREAKVQWKVDNALQSGNSQ ESVTEQDSKDSTYSLSSTLTLSKADYEKHKVYACEVTHQGLS SPVTKSFNRGEC | 131 |
| C40M59 | DIQMTQSPSSLSASVGDRVTITCRASQSISSYLNWYQQKPGK APKLLIYAASSLQSGVPSRFSGSGSGTDFTLTISSLQPEDFAT YYCQQSYSTPLTFGQGTKVEIKRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKSF NRGEC | 132 |
| C40M58 | DIQMTQSPSSLSASVGDRVTITCRASQSISSYLNWYQQKPGK APKLLIYAASSLQSGVPSRFSGSGSGTDFTLTISSLQPEDFAT YYCQQSYSTPLTFGQGTKVEIKRTVAAPSVFIFPPSDEQLKS | 132 |

TABLE 19-continued

| mAb | LC amino acid | LC SEQ ID NO: |
|---|---|---|
| | GTASVVCLLNNFYPREAKVQWKVDNALQSGNSQESVTEQD SKDSTYSLSSTLTLSKADYEKHKVYACEVTHQGLSSPVTKSF NRGEC | |
| C40M56 | DIQMTQSPSSLSASVGDRVTITCRASQSISSYLNWYQQKPGK APKLLIYAASSLQSGVPSRFSGSGSGTDFTLTISSLQPEDFAT YYCQQSYSTPLTFGQGTKVEIKRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKSF NRGEC | 132 |
| C40M55 | DIQMTQSPSSLSASVGDRVTITCRASQSISSYLNWYQQKPGK APKLLIYAASSLQSGVPSRFSGSGSGTDFTLTISSLQPEDFAT YYCQQSYSTPLTFGQGTKVEIKRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKSF NRGEC | 132 |
| C40M51 | DIQMTQSPSSLSASVGDRVTITCRASQSISSYLNWYQQKPGK APKLLIYAASSLQSGVPSRFSGSGSGTDFTLTISSLQPEDFAT YYCQQSYSTPLTFGQGTKVEIKRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKSF NRGEC | 132 |
| C40M18 | SYELTQPPSVSVSPGQTASITCSGDKLGDKYVCWYQQKPGQ SPVVVIYQDSKRPSGIPERFSGSNSGNTATLTISGTQAMDEA YYYCQAWVSSTVVFGGGTKLTVLGQPKAAPSVTLFPPSSEE LQANKATLVCLISDFYPGAVTVAWKADSSPVKAGVETTTPSK QSNNKYAASSYLSLTPEQWKSHRSYSCQVTHEGSTVEKTVA PTECS | 133 |
| C40M17 | SYELTQPPSVSVSPGQTASITCSGDKLGDKYACWYQQKPGQ SPVLVIYQDSRRPSGIPERFSGSNSGNTATLTISGTQAMDEA DYYCQAWASSTVVFGGGTKLTVLGQPKAAPSVTLFPPSSEE LQANKATLVCLISDFYPGAVTVAWKADSSPVKAGVETTTPSK QSNNKYAASSYLSLTPEQWKSHRSYSCQVTHEGSTVEKTVA PTECS | 134 |
| C40M12 | SYELTQPPSVSVSPGQTASIICSGDKLGDKYVCWYQQKPGQ SPVVVIYHDNKRPSGIPERFSGSNSGNTATLTISGTQAMDEA DYYCQVWDSSTVVFGGGTKLTVLGQPKAAPSVTLFPPSSEE LQANKATLVCLISDFYPGAVTVAWKADSSPVKAGVETTTPSK QSNNKYAASSYLSLTPEQWKSHRSYSCQVTHEGSTVEKTVA PTECS | 135 |
| C40M9 | QSALTQPPSASGSPGQSVTISCTGTSSDVGGYNYVSWYQQ HPGKAPKLMIYEVSKRPSGVPDRFSGSKSGNTASLTVSGLQ AEDEADYYCSSYAGSNNLVFGGGTKLTVLGQPKAAPSVTLF PPSSEELQANKATLVCLISDFYPGAVTVAWKADSSPVKAGVE TTTPSKQSNNKYAASSYLSLTPEQWKSHRSYSCQVTHEGST VEKTVAPTECS | 136 |
| C40M102 | SYELTQPPSVSVSPGQTASITCSGDKLGDKYVCWYQQKPGQ SPVLVIYQDSKRPSGIPERFSGSNSGNTATLTISGTQAMDEA DYYCQAWVSSTVVFGGGTKLTVLGQPKAAPSVTLFPPSSEE LQANKATLVCLISDFYPGAVTVAWKADSSPVKAGVETTTPSK QSNNKYAASSYLSLTPEQWKSHRSYSCQVTHEGSTVEKTVA PTECS | 137 |
| C40M103 | SYELTQPPSVSVSPGQTASITCSGDKLGDKYVSWYQQKPGQ SPVLVIYQDSKRPSGIPERFSGSNSGNTATLTISGTQAMDEA DYYCQAWVSSTVVFGGGTKLTVLGQPKAAPSVTLFPPSSEE LQANKATLVCLISDFYPGAVTVAWKADSSPVKAGVETTTPSK QSNNKYAASSYLSLTPEQWKSHRSYSCQVTHEGSTVEKTVA PTECS | 138 |
| C40M104 | SYELTQPPSVSVSPGQTASITCSGDKLGDKYVSWYQQKPGQ SPVVVIYQDSKRPSGIPERFSGSNSGNTATLTISGTQAMDEA YYYCQAWVSSTVVFGGGTKLTVLGQPKAAPSVTLFPPSSEE LQANKATLVCLISDFYPGAVTVAWKADSSPVKAGVETTTPSK QSNNKYAASSYLSLTPEQWKSHRSYSCQVTHEGSTVEKTVA PTECS | 139 |
| C40M105 | QSALTQPPSASGSPGQSVTISCTGTSSDVGGYNYVSWYQQ HPGKAPKLMIYEVSKRPSGVPDRFSGSKSGNTASLTVSGLQ | 136 |

TABLE 19-continued

| mAb | LC amino acid | LC SEQ ID NO: |
|---|---|---|
| | AEDEADYYCSSYAGSNNLVFGGGTKLTVLGQPKAAPSVTLF PPSSEELQANKATLVCLISDFYPGAVTVAWKADSSPVKAGVE TTTPSKQSNNKYAASSYLSLTPEQWKSHRSYSCQVTHEGST VEKTVAPTECS | |
| C40M121 | QSALTQPPSASGSPGQSVTISCTGTSSDVGGYNYVSWYQQ HPGKAPKLMIYEVSKRPSGVPDRFSGSKSGNTASLTVSGLQ AEDEADYYCSSYAGSNNLVFGGGTKLTVLGQPKAAPSVTLF PPSSEELQANKATLVCLISDFYPGAVTVAWKADSSPVKAGVE TTTPSKQSNNKYAASSYLSLTPEQWKSHRSYSCQVTHEGST VEKTVAPTECS | 136 |
| C40M126 | QSALTQPPSASGSPGQSVTISCTGTSSDVGGYNYVSWYQQ HPGKAPKLMIYEVSKRPSGVPDRFSGSKSGNTASLTVSGLQ AEDEADYYCSSYAGSNNLVFGGGTKLTVLGQPKAAPSVTLF PPSSEELQANKATLVCLISDFYPGAVTVAWKADSSPVKAGVE TTTPSKQSNNKYAASSYLSLTPEQWKSHRSYSCQVTHEGST VEKTVAPTECS | 136 |

TABLE 20

| mAb | LC DNA | LC DNA SEQ ID NO: |
|---|---|---|
| C40M67 | GAAATTGTGCTGACCCAGAGCCCGGGCACCCTGAGCCTGA GCCCGGGCGAACGCGCGACCCTGAGCTGCCGCGCGAGCC AGAGCGTTAAAAATAGCAGTCTGGCTGGTATCAGCAGAAA CCGGGCCAGGCGCCGCGCCTGCTGATTTATACTGCGAGCA GCCGCGCGACCGGCATTCCGGATCGCTTTAGCGGCAGCG GCAGCGGCACCGATTTTACCCTGACCATTAGCCGCCTGGA ACCGGAAGATTTTGCGGTGTATTATTGCCAGCAGTCCTCCG CACCTCCGTGGACTTTTGGCCAGGGCACCAAAGTGGAAAT TAAACGTACGGTGGCTGCACCATCTGTCTTCATCTTCCCGC CATCTGATGAGCAGTTGAAATCTGGAACTGCCTCTGTTGTG TGCCTGCTGAATAACTTCTATCCCAGAGAGGCCAAAGTACA GTGGAAGGTGGATAACGCCCTCCAATCGGGTAACTCCCAG GAGAGTGTCACAGAGCAGGACAGCAAGGACAGCACCTACA GCCTCAGCAGCACCCTGACGCTGAGCAAAGCAGACTACGA GAAACACAAAGTCTACGCCTGCGAAGTCACCCATCAGGGC CTGAGCTCGCCCGTCACAAAGAGCTTCAACAGGGGAGAGT GT | 156 |
| C40M66 | GACATCGTGATGACCCAGAGCCCCGACAGCCTGGCCGTGA GCCTGGGCGAGCGGGCCACCATCAACTGCAAGAGCAGCC AGAGCGTGCTGTACAGCAGCAACAACAAGAACTACCTGGC CTGGTACCAGCAGAAGCCCGGCCAGCCCCCCAAGCTGCTG ATCTACTGGGCCAGCACCCGGGAGAGCGGCGTGCCCGAC CGGTTCAGCGGCAGCGGCAGCGGCACCGACTTCACCCTG ACCATCAGCAGCCTGCAGGCCGAGGACGTGGCCGTGTACT ACTGCCAGCAGTACTACAGCACCCCCCTGACCTTCGGCCA GGGCACCAAGGTGGAGATCAAGCGGACCGTGGCCGCCCC CAGCGTGTTCATCTTCCCCCCCAGCGACGAGCAGCTGAAG AGCGGAACCGCAAGCGTGGTGTGCCTGCTGAACAACTTCT ACCCCCGGGAGGCCAAGGTGCAGTGGAAGGTGGACAACG CCCTGCAGAGCGGCAACAGCCAGGAGAGCGTGACCGAGC AGGACAGCAAGGACAGCACCTACAGCCTGAGCAGCACCCT GACCCTGAGCAAGGCCGACTACGAGAAGCACAAGGTGTAC GCTTGCGAGGTGACCCACCAGGGCCTGAGCAGCCCCGTG ACCAAGAGCTTCAACCGGGGCGAGTGC | 157 |
| C40M63 | GACATCGTGATGACCCAGAGCCCCGACAGCCTGGCCGTGA GCCTGGGCGAGCGGGCCACCATCAACTGCAAGAGCAGCC AGAGCGTGCTGTACAGCAGCAACAACAAGAACTACCTGGC CTGGTACCAGCAGAAGCCCGGCCAGCCCCCCAAGCTGCTG ATCTACTGGGCCAGCACCCGGGAGAGCGGCGTGCCCGAC CGGTTCAGCGGCAGCGGCAGCGGCACCGACTTCACCCTG ACCATCAGCAGCCTGCAGGCCGAGGACGTGGCCGTGTACT ACTGCCAGCAGTACTACAGCACCCCCCTGACCTTCGGCCA GGGCACCAAGGTGGAGATCAAGCGGACCGTGGCCGCCCC CAGCGTGTTCATCTTCCCCCCCAGCGACGAGCAGCTGAAG AGCGGAACCGCAAGCGTGGTGTGCCTGCTGAACAACTTCT ACCCCCGGGAGGCCAAGGTGCAGTGGAAGGTGGACAACG CCCTGCAGAGCGGCAACAGCCAGGAGAGCGTGACCGAGC | 157 |

TABLE 20-continued

| mAb | LC DNA | LC DNA SEQ ID NO: |
|---|---|---|
| | AGGACAGCAAGGACAGCACCTACAGCCTGAGCAGCACCCT GACCCTGAGCAAGGCCGACTACGAGAAGCACAAGGTGTAC GCTTGCGAGGTGACCCACCAGGGCCTGAGCAGCCCCGTG ACCAAGAGCTTCAACCGGGGCGAGTGC | |
| C40M62 | GACATCGTGATGACCCAGAGCCCCGACAGCCTGGCCGTGA GCCTGGGCGAGCGGGCCACCATCAACTGCAAGAGCAGCC AGAGCGTGCTGTACAGCAGCAACAACAAGAACTACCTGGC CTGGTACCAGCAGAAGCCCGGCCAGCCCCCCAAGCTGCTG ATCTACTGGGCCAGCACCCGGGAGAGCGGCGTGCCCGAC CGGTTCAGCGGCAGCGGCAGCGGCACCGACTTCACCCTG ACCATCAGCAGCCTGCAGGCCGAGGACGTGGCCGTGTACT ACTGCCAGCAGTACTACAGCACCCCCCTGACCTTCGGCCA GGGCACCAAGGTGGAGATCAAGCGGACCGTGGCCGCCCC CAGCGTGTTCATCTTCCCCCCCAGCGACGAGCAGCTGAAG AGCGGAACCGCAAGCGTGGTGTGCCTGCTGAACAACTTCT ACCCCCGGGAGGCCAAGGTGCAGTGGAAGGTGGACAACG CCCTGCAGAGCGGCAACAGCCAGGAGAGCGTGACCGAGC AGGACAGCAAGGACAGCACCTACAGCCTGAGCAGCACCCT GACCCTGAGCAAGGCCGACTACGAGAAGCACAAGGTGTAC GCTTGCGAGGTGACCCACCAGGGCCTGAGCAGCCCCGTG ACCAAGAGCTTCAACCGGGGCGAGTGC | 157 |
| C40M59 | GACATCCAGATGACCCAGAGCCCCAGCAGCCTGAGCGCCA GCGTGGGCGACCGGGTGACCATCACCTGCCGGGCCAGCC AGAGCATCAGCAGCTACCTGAACTGGTACCAGCAGAAGCC CGGCAAGGCCCCCAAGCTGCTGATCTACGCCGCCAGCAGC CTGCAGAGCGGCGTGCCCAGCCGGTTCAGCGGCAGCGGC AGCGGCACCGACTTCACCCTGACCATCAGCAGCCTGCAGC CGGAGGACTTCGCCACCTACTACTGCCAGCAGAGCTACAG CACCCCCCTGACCTTCGGCCAGGGCACCAAGGTGGAGATC AAGCGGACCGTGGCCGCCCCCAGCGTGTTCATCTTCCCCC CCAGCGACGAGCAGCTGAAGAGCGGAACCGCAAGCGTGG TGTGCCTGCTGAACAACTTCTACCCCCGGGAGGCCAAGGT GCAGTGGAAGGTGGACAACGCCCTGCAGAGCGGCAACAG CCAGGAGAGCGTGACCGAGCAGGACAGCAAGGACAGCAC CTACAGCCTGAGCAGCACCCTGACCCTGAGCAAGGCCGAC TACGAGAAGCACAAGGTGTACGCTTGCGAGGTGACCCACC AGGGCCTGAGCAGCCCCGTGACCAAGAGCTTCAACCGGG GCGAGTGC | 158 |
| C40M58 | GACATCCAGATGACCCAGAGCCCCAGCAGCCTGAGCGCCA GCGTGGGCGACCGGGTGACCATCACCTGCCGGGCCAGCC AGAGCATCAGCAGCTACCTGAACTGGTACCAGCAGAAGCC CGGCAAGGCCCCCAAGCTGCTGATCTACGCCGCCAGCAGC CTGCAGAGCGGCGTGCCCAGCCGGTTCAGCGGCAGCGGC AGCGGCACCGACTTCACCCTGACCATCAGCAGCCTGCAGC CGGAGGACTTCGCCACCTACTACTGCCAGCAGAGCTACAG CACCCCCCTGACCTTCGGCCAGGGCACCAAGGTGGAGATC AAGCGGACCGTGGCCGCCCCCAGCGTGTTCATCTTCCCCC CCAGCGACGAGCAGCTGAAGAGCGGAACCGCAAGCGTGG TGTGCCTGCTGAACAACTTCTACCCCCGGGAGGCCAAGGT GCAGTGGAAGGTGGACAACGCCCTGCAGAGCGGCAACAG CCAGGAGAGCGTGACCGAGCAGGACAGCAAGGACAGCAC CTACAGCCTGAGCAGCACCCTGACCCTGAGCAAGGCCGAC TACGAGAAGCACAAGGTGTACGCTTGCGAGGTGACCCACC AGGGCCTGAGCAGCCCCGTGACCAAGAGCTTCAACCGGG GCGAGTGC | 158 |
| C40M56 | GACATCCAGATGACCCAGAGCCCCAGCAGCCTGAGCGCCA GCGTGGGCGACCGGGTGACCATCACCTGCCGGGCCAGCC AGAGCATCAGCAGCTACCTGAACTGGTACCAGCAGAAGCC CGGCAAGGCCCCCAAGCTGCTGATCTACGCCGCCAGCAGC CTGCAGAGCGGCGTGCCCAGCCGGTTCAGCGGCAGCGGC AGCGGCACCGACTTCACCCTGACCATCAGCAGCCTGCAGC CGGAGGACTTCGCCACCTACTACTGCCAGCAGAGCTACAG CACCCCCCTGACCTTCGGCCAGGGCACCAAGGTGGAGATC AAGCGGACCGTGGCCGCCCCCAGCGTGTTCATCTTCCCCC CCAGCGACGAGCAGCTGAAGAGCGGAACCGCAAGCGTGG TGTGCCTGCTGAACAACTTCTACCCCCGGGAGGCCAAGGT GCAGTGGAAGGTGGACAACGCCCTGCAGAGCGGCAACAG CCAGGAGAGCGTGACCGAGCAGGACAGCAAGGACAGCAC CTACAGCCTGAGCAGCACCCTGACCCTGAGCAAGGCCGAC TACGAGAAGCACAAGGTGTACGCTTGCGAGGTGACCCACC AGGGCCTGAGCAGCCCCGTGACCAAGAGCTTCAACCGGG GCGAGTGC | 158 |

TABLE 20-continued

| mAb | LC DNA | LC DNA SEQ ID NO: |
|---|---|---|
| C40M55 | GACATCCAGATGACCCAGAGCCCCAGCAGCCTGAGCGCCA GCGTGGGCGACCGGGTGACCATCACCTGCCGGGCCAGCC AGAGCATCAGCAGCTACCTGAACTGGTACCAGCAGAAGCC CGGCAAGGCCCCCAAGCTGCTGATCTACGCCGCCAGCAGC CTGCAGAGCGGCGTGCCCAGCCGGTTCAGCGGCAGCGGC AGCGGCACCGACTTCACCCTGACCATCAGCAGCCTGCAGC CCGAGGACTTCGCCACCTACTACTGCCAGCAGAGCTACAG CACCCCCCTGACCTTCGGCCAGGGCACCAAGGTGGAGATC AAGCGGACCGTGGCCGCCCCCAGCGTGTTCATCTTCCCCC CCAGCGACGAGCAGCTGAAGAGCGGAACCGCAAGCGTGG TGTGCCTGCTGAACAACTTCTACCCCGGGAGGCCAAGGT GCAGTGGAAGGTGGACAACGCCCTGCAGAGCGGCAACAG CCAGGAGAGCGTGACCGAGCAGGACAGCAAGGACAGCAC CTACAGCCTGAGCAGCACCCTGACCCTGAGCAAGGCCGAC TACGAGAAGCACAAGGTGTACGCTTGCGAGGTGACCCACC AGGGCCTGAGCAGCCCCGTGACCAAGAGCTTCAACCGGG GCGAGTGC | 158 |
| C40M51 | GACATCCAGATGACCCAGAGCCCCAGCAGCCTGAGCGCCA GCGTGGGCGACCGGGTGACCATCACCTGCCGGGCCAGCC AGAGCATCAGCAGCTACCTGAACTGGTACCAGCAGAAGCC CGGCAAGGCCCCCAAGCTGCTGATCTACGCCGCCAGCAGC CTGCAGAGCGGCGTGCCCAGCCGGTTCAGCGGCAGCGGC AGCGGCACCGACTTCACCCTGACCATCAGCAGCCTGCAGC CCGAGGACTTCGCCACCTACTACTGCCAGCAGAGCTACAG CACCCCCCTGACCTTCGGCCAGGGCACCAAGGTGGAGATC AAGCGGACCGTGGCCGCCCCCAGCGTGTTCATCTTCCCCC CCAGCGACGAGCAGCTGAAGAGCGGAACCGCAAGCGTGG TGTGCCTGCTGAACAACTTCTACCCCGGGAGGCCAAGGT GCAGTGGAAGGTGGACAACGCCCTGCAGAGCGGCAACAG CCAGGAGAGCGTGACCGAGCAGGACAGCAAGGACAGCAC CTACAGCCTGAGCAGCACCCTGACCCTGAGCAAGGCCGAC TACGAGAAGCACAAGGTGTACGCTTGCGAGGTGACCCACC AGGGCCTGAGCAGCCCCGTGACCAAGAGCTTCAACCGGG GCGAGTGC | 158 |
| C40M18 | TCCTACGAGCTGACCCAGCCTCCCTCCGTGTCTGTGTCTCC TGGCCAGACCGCCAGCATCACCTGTAGCGGCGACAAGCTG GGCGACAAATACGTGTGCTGGTATCAGCAGAAGCCCGGCC AGAGCCCCGTGGTGGTCATCTACCAGGACAGCAAGAGGCC CAGCGGCATCCCCGAGAGATTCAGCGGCAGCAACAGCGG CAATACCGCCACCCTGACCATCAGCGGCACCCAGGCCATG GACGAGGCCTACTACTGCCAGGCTTGGGTGTCCAGCA CCGTGGTGTTTGGCGGAGGCACCAAGCTGACCGTGCTGG GTCAGCCCAAGGCTGCACCCAGTGTCACTCTGTTCCCGCC CTCCCTCTGAGGAGCTTCAAGCCAACAAGGCCACACTGGTG TGTCTCATAAGTGACTTCTACCCGGGAGCCGTGACAGTGG CCTGGAAGGCCGATAGCAGCCCCGTCAAGGCGGGAGTGG AGACCACCACACCCTCCAAACAAAGCAACAACAAGTACGC GGCCAGCAGCTATCTGAGCCTGACGCCTGAGCAGTGGAAG TCCCACAGAAGCTACAGCTGCCAGGTCACGCATGAAGGGA GCACCGTGGAGAAGACAGTGGCCCCTACAGAATGTTCA | 159 |
| C40M17 | TCCTACGAGCTGACCCAGCCTCCCTCCGTGTCTGTGTCTCC TGGCCAGACCGCCAGCATCACCTGTAGCGGCGACAAGCTG GGCGATAAGTACGCCTGCTGGTATCAGCAGAAGCCCGGCC AGAGCCCCGTGCTGGTCATCTACCAGGACAGCAGAAGGCC CAGCGGCATCCCCGAGAGATTCAGCGGCAGCAACAGCGG CAATACCGCCACCCTGACCATCAGCGGCACCCAGGCCATG GACGAGGCCGATTACTATTGTCAGGCCTGGGCCAGCAGCA CCGTGGTGTTTGGCGGCGGAACAAAGCTGACCGTGCTGGG TCAGCCCAAGGCTGCACCCAGTGTCACTCTGTTCCCGCCC TCCTCTGAGGAGCTTCAAGCCAACAAGGCCACACTGGTGT GTCTCATAAGTGACTTCTACCCGGGAGCCGTGACAGTGGC CTGGAAGGCCGATAGCAGCCCCGTCAAGGCGGGAGTGGA GACCACCACACCCTCCAAACAAAGCAACAACAAGTACGCG GCCAGCAGCTATCTGAGCCTGACGCCTGAGCAGTGGAAGT CCCACAGAAGCTACAGCTGCCAGGTCACGCATGAAGGGAG CACCGTGGAGAAGACAGTGGCCCCTACAGAATGTTCA | 160 |
| C40M12 | TCCTACGAGCTGACCCAGCCTCCCTCCGTGTCTGTGTCTCC TGGCCAGACCGCCAGCATCATCTGCAGCGGCGACAAGCTG GGCGACAAATACGTGTGCTGGTATCAGCAGAAGCCCGGCC AGAGCCCCGTGGTGGTCATCTACCACGACAACAAGAGGCC CAGCGGCATCCCCGAGAGATTCAGCGGCAGCAACAGCGG CAATACCGCCACCCTGACCATCAGCGGCACCCAGGCCATG GACGAGGCCGACTACTACTGCCAGGTCTGGGACAGCAGCA | 161 |

TABLE 20-continued

| mAb | LC DNA | LC DNA SEQ ID NO: |
|---|---|---|
| | CCGTGGTGTTTGGCGGAGGCACCAAGCTGACCGTGCTGG<br>GTCAGCCCAAGGCTGCACCCAGTGTCACTCTGTTCCCGCC<br>CTCCTCTGAGGAGCTTCAAGCCAACAAGGCCACACTGGTG<br>TGTCTCATAAGTGACTTCTACCCGGGAGCCGTGACAGTGG<br>CCTGGAAGGCCGATAGCAGCCCCGTCAAGGCGGGAGTGG<br>AGACCACCACACCCTCCAAACAAAGCAACAACAAGTACGC<br>GGCCAGCAGCTATCTGAGCCTGACGCCTGAGCAGTGGAAG<br>TCCCACAGAAGCTACAGCTGCCAGGTCACGCATGAAGGGA<br>GCACCGTGGAGAAGACAGTGGCCCCTACAGAATGTTCA | |
| C40M9 | CAGTCTGCCCTGACACAGCCTCCTAGCGCCTCTGGCTCTC<br>CTGGCCAGAGCGTGACCATCAGCTGTACCGGCACCAGCTC<br>CGACGTGGGCGGCTACAACTACGTGTCCTGGTATCAGCAG<br>CACCCCGGCAAGGCCCCTAAGCTGATGATCTACGAGGTGT<br>CCAAGCGGCCCAGCGGCGTGCCAGATAGATTCAGCGGCA<br>GCAAGAGCGGCAACACCGCCAGCCTGACAGTGTCTGGACT<br>GCAGGCCGAGGACGAGGCCGACTACTACTGTAGCAGCTAC<br>GCCGGCAGCAACAACCTGGTGTTCGGCGGAGGCACCAAG<br>CTGACCGTGCTGGGTCAGCCCAAGGCTGCACCCAGTGTCA<br>CTCTGTTCCCGCCCTCCTCTGAGGAGCTTCAAGCCAACAAG<br>GCCACACTGGTGTGTCTCATAAGTGACTTCTACCCGGGAG<br>CCGTGACAGTGGCCTGGAAGGCCGATAGCAGCCCCGTCAA<br>GGCGGGAGTGGAGACCACCACACCCTCCAAACAAAGCAAC<br>AACAAGTACGCGGCCAGCAGCTATCTGAGCCTGACGCCTG<br>AGCAGTGGAAGTCCCACAGAAGCTACAGCTGCCAGGTCAC<br>GCATGAAGGGAGCACCGTGGAGAAGACAGTGGCCCCTACA<br>GAATGTTCA | 162 |
| C40M102 | AGCTACGAGCTGACCCAGCCCCCCAGCGTGAGCGTGAGC<br>CCCGGCCAGACCGCCAGCATCACCTGCAGCGGCGACAAG<br>CTGGGCGACAAGTACGTGTGCTGGTACCAGCAGAAGCCCG<br>GCCAGAGCCCCGTGCTGGTGATCTACCAGGACAGCAAGCG<br>GCCCAGCGGCATCCCCGAGCGGTTCAGCGGCAGCAACAG<br>CGGCAACACCGCCACCCTGACCATCAGCGGCACCCAGGC<br>CATGGACGAGGCCGACTACTACTGCCAGGCCTGGGTGAGC<br>AGCACCGTGGTGTTCGGCGGCGGCACCAAGCTGACCGTG<br>CTGGGTCAGCCCAAGGCTGCACCCAGTGTCACTCTGTTCC<br>CGCCCTCCTCTGAGGAGCTTCAAGCCAACAAGGCCACACT<br>GGTGTGTCTCATAAGTGACTTCTACCCGGGAGCCGTGACA<br>GTGGCCTGGAAGGCCGATAGCAGCCCCGTCAAGGCGGGA<br>GTGGAGACCACCACACCCTCCAAACAAAGCAACAACAAGTA<br>CGCGGCCAGCAGCTATCTGAGCCTGACGCCTGAGCAGTGG<br>AAGTCCCACAGAAGCTACAGCTGCCAGGTCACGCATGAAG<br>GGAGCACCGTGGAGAAGACAGTGGCCCCTACAGAATGTTCA | 163 |
| C40M103 | AGCTACGAGCTGACCCAGCCCCCCAGCGTGAGCGTGAGC<br>CCCGGCCAGACCGCCAGCATCACCTGCAGCGGCGACAAG<br>CTGGGCGACAAGTACGTGAGCTGGTACCAGCAGAAGCCCG<br>GCCAGAGCCCCGTGCTGGTGATCTACCAGGACAGCAAGCG<br>GCCCAGCGGCATCCCCGAGCGGTTCAGCGGCAGCAACAG<br>CGGCAACACCGCCACCCTGACCATCAGCGGCACCCAGGC<br>CATGGACGAGGCCGACTACTACTGCCAGGCCTGGGTGAGC<br>AGCACCGTGGTGTTCGGCGGCGGCACCAAGCTGACCGTG<br>CTGGGTCAGCCCAAGGCTGCACCCAGTGTCACTCTGTTCC<br>CGCCCTCCTCTGAGGAGCTTCAAGCCAACAAGGCCACACT<br>GGTGTGTCTCATAAGTGACTTCTACCCGGGAGCCGTGACA<br>GTGGCCTGGAAGGCCGATAGCAGCCCCGTCAAGGCGGGA<br>GTGGAGACCACCACACCCTCCAAACAAAGCAACAACAAGTA<br>CGCGGCCAGCAGCTATCTGAGCCTGACGCCTGAGCAGTGG<br>AAGTCCCACAGAAGCTACAGCTGCCAGGTCACGCATGAAG<br>GGAGCACCGTGGAGAAGACAGTGGCCCCTACAGAATGTTCA | 164 |
| C40M104 | AGCTACGAGCTGACCCAGCCCCCCAGCGTGAGCGTGAGC<br>CCCGGCCAGACCGCCAGCATCACCTGCAGCGGCGACAAG<br>CTGGGCGACAAGTACGTGAGCTGGTACCAGCAGAAGCCCG<br>GCCAGAGCCCCGTGGTGGTGATCTACCAGGACAGCAAGCG<br>GCCCAGCGGCATCCCCGAGCGGTTCAGCGGCAGCAACAG<br>CGGCAACACCGCCACCCTGACCATCAGCGGCACCCAGGC<br>CATGGACGAGGCCTACTACTGCCAGGCCTGGGTGAGC<br>AGCACCGTGGTGTTCGGCGGCGGCACCAAGCTGACCGTG<br>CTGGGTCAGCCCAAGGCTGCACCCAGTGTCACTCTGTTCC<br>CGCCCTCCTCTGAGGAGCTTCAAGCCAACAAGGCCACACT<br>GGTGTGTCTCATAAGTGACTTCTACCCGGGAGCCGTGACA<br>GTGGCCTGGAAGGCCGATAGCAGCCCCGTCAAGGCGGGA<br>GTGGAGACCACCACACCCTCCAAACAAAGCAACAACAAGTA | 165 |

TABLE 20-continued

| mAb | LC DNA | LC DNA SEQ ID NO: |
|---|---|---|
|  | CGCGGCCAGCAGCTATCTGAGCCTGACGCCTGAGCAGTGG AAGTCCCACAGAAGCTACAGCTGCCAGGTCACGCATGAAG GGAGCACCGTGGAGAAGACAGTGGCCCCTACAGAATGTTCA |  |
| C40M105 | CAGTCTGCCCTGACACAGCCTCCTAGCGCCTCTGGCTCTC CTGGCCAGAGCGTGACCATCAGCTGTACCGGCACCAGCTC CGACGTGGGCGGCTACAACTACGTGTCCTGGTATCAGCAG CACCCCGGCAAGGCCCCTAAGCTGATGATCTACGAGGTGT CCAAGCGGCCCAGCGGCGTGCCAGATAGATTCAGCGGCA GCAAGAGCGGCAACACCGCCAGCCTGACAGTGTCTGGACT GCAGGCCGAGGACGAGGCCGACTACTACTGTAGCAGCTAC GCCGGCAGCAACAACCTGGTGTTCGGCGGAGGCACCAAG CTGACCGTGCTGGGTCAGCCCAAGGCTGCACCCAGTGTCA CTCTGTTCCCGCCCTCCTCTGAGGAGCTTCAAGCCAACAAG GCCACACTGGTGTGTCTCATAAGTGACTTCTACCCGGGAG CCGTGACAGTGGCCTGGAAGGCCGATAGCAGCCCCGTCAA GGCGGGAGTGGAGACCACCACACCCTCCAAACAAAGCAAC AACAAGTACGCGGCCAGCAGCTATCTGAGCCTGACGCCTG AGCAGTGGAAGTCCCACAGAAGCTACAGCTGCCAGGTCAC GCATGAAGGGAGCACCGTGGAGAAGACAGTGGCCCCTACA GAATGTTCA | 162 |
| C40M121 | CAGTCTGCCCTGACACAGCCTCCTAGCGCCTCTGGCTCTC CTGGCCAGAGCGTGACCATCAGCTGTACCGGCACCAGCTC CGACGTGGGCGGCTACAACTACGTGTCCTGGTATCAGCAG CACCCCGGCAAGGCCCCTAAGCTGATGATCTACGAGGTGT CCAAGCGGCCCAGCGGCGTGCCAGATAGATTCAGCGGCA GCAAGAGCGGCAACACCGCCAGCCTGACAGTGTCTGGACT GCAGGCCGAGGACGAGGCCGACTACTACTGTAGCAGCTAC GCCGGCAGCAACAACCTGGTGTTCGGCGGAGGCACCAAG CTGACCGTGCTGGGTCAGCCCAAGGCTGCACCCAGTGTCA CTCTGTTCCCGCCCTCCTCTGAGGAGCTTCAAGCCAACAAG GCCACACTGGTGTGTCTCATAAGTGACTTCTACCCGGGAG CCGTGACAGTGGCCTGGAAGGCCGATAGCAGCCCCGTCAA GGCGGGAGTGGAGACCACCACACCCTCCAAACAAAGCAAC AACAAGTACGCGGCCAGCAGCTATCTGAGCCTGACGCCTG AGCAGTGGAAGTCCCACAGAAGCTACAGCTGCCAGGTCAC GCATGAAGGGAGCACCGTGGAGAAGACAGTGGCCCCTACA GAATGTTCA | 162 |
| C40M126 | CAGTCTGCCCTGACACAGCCTCCTAGCGCCTCTGGCTCTC CTGGCCAGAGCGTGACCATCAGCTGTACCGGCACCAGCTC CGACGTGGGCGGCTACAACTACGTGTCCTGGTATCAGCAG CACCCCGGCAAGGCCCCTAAGCTGATGATCTACGAGGTGT CCAAGCGGCCCAGCGGCGTGCCAGATAGATTCAGCGGCA GCAAGAGCGGCAACACCGCCAGCCTGACAGTGTCTGGACT GCAGGCCGAGGACGAGGCCGACTACTACTGTAGCAGCTAC GCCGGCAGCAACAACCTGGTGTTCGGCGGAGGCACCAAG CTGACCGTGCTGGGTCAGCCCAAGGCTGCACCCAGTGTCA CTCTGTTCCCGCCCTCCTCTGAGGAGCTTCAAGCCAACAAG GCCACACTGGTGTGTCTCATAAGTGACTTCTACCCGGGAG CCGTGACAGTGGCCTGGAAGGCCGATAGCAGCCCCGTCAA GGCGGGAGTGGAGACCACCACACCCTCCAAACAAAGCAAC AACAAGTACGCGGCCAGCAGCTATCTGAGCCTGACGCCTG AGCAGTGGAAGTCCCACAGAAGCTACAGCTGCCAGGTCAC GCATGAAGGGAGCACCGTGGAGAAGACAGTGGCCCCTACA GAATGTTCA | 162 |

The antibody frameworks were compared to the closest germline gene sequences in order to identify potential immunogenicity risks. C40M18, C40M17, C40M12 and C40M9 mAb VH and/or VL had mutations when compared to the closest germline sequences. Table 20 shows the antibody frameworks and number of mutations.

TABLE 21

| mAb | Closest heavy chain Framework | Number of mutations in VH | Closest light chain framework | Number of mutations in VL |
|---|---|---|---|---|
| C40M67 | IGHV3-23*03 | 0 | IGKV3-20*01 | NA |
| C40M66 | IGHV1-69*01 | 0 | IGKV4-1*01 | 0 |
| C40M63 | IGHV1-69*01 | 0 | IGKV4-1*01 | 0 |
| C40M62 | IGHV1-69*01 | 0 | IGKV4-1*01 | 0 |
| C40M59 | IGHV1-69*01 | 0 | IGKV1-39*01 | 0 |
| C40M58 | IGHV3-23*01 | 0 | IGKV1-39*01 | 0 |
| C40M56 | IGHV3-23*01 | 0 | IGKV1-39*01 | 0 |
| C40M55 | IGHV1-69*01 | 0 | IGKV1-39*01 | 0 |
| C40M51 | IGHV3-23*01 | 0 | IGKV1-39*01 | 0 |
| C40M18 | IGHV3-23*04 | 0 | IGLV3-1*01 | 3 |
| C40M17 | IGHV3-23*04 | 2 | IGLV3-1*01 | 0 |
| C40M12 | IGHV3-23*04 | 1 | IGLV3-1*01 | 2 |

TABLE 21-continued

| mAb | Closest heavy chain Framework | Number of mutations in VH | Closest light chain framework | Number of mutations in VL |
|---|---|---|---|---|
| C40M9 | IGHV4-39*01 | 3 | IGLV2-8*01 | 0 |
| C40M102 | IGHV3-23*04 | 0 | IGLV3-1*01 | 1 |
| C40M103 | IGHV3-23*04 | 0 | IGLV3-1*01 | 0 |
| C40M104 | IGHV3-23*04 | 0 | IGLV3-1*01 | 2 |
| C40M105 | IGHV4-39*01 | 0 | IGLV2-8*01 | 0 |
| C40M121 | IGHV4-39*01 | 1 | IGLV2-8*01 | 0 |

```
Framework sequences:
IGHV3-23*03
                                        (SEQ ID NO: 79)
>IGHV3-23*03
EVQLLESGGGLVQPGGSLRLSCAASGFTFSSYAMSWVRQAPGKGLEWVSV

IYSGGSSTYYADSVKGRFTISRDNSKNTLYLQMNSLRAEDTAVYYCAK

IGHV1-69*01
                                        (SEQ ID NO: 80)
>IGHV1-69*01
QVQLVQSGAEVKKPGSSVKVSCKASGGTFSSYAISWVRQAPGQGLEWMGG

IIPIFGTANYAQKFQGRVTITADESTSTAYMELSSLRSEDTAVYYCAR

IGHV3-23*01
                                        (SEQ ID NO: 81)
>IGHV3-23*01
EVQLLESGGGLVQPGGSLRLSCAASGFTFSSYAMSWVRQAPGKGLEWVSA

ISGSGGSTYYADSVKGRFTISRDNSKNTLYLQMNSLRAEDTAVYYCAK

IGHV3-23*04
                                        (SEQ ID NO: 82)
>IGHV3-23*04
EVQLVESGGGLVQPGGSLRLSCAASGFTFSSYAMSWVRQAPGKGLEWVSA

ISGSGGSTYYADSVKGRFTISRDNSKNTLYLQMNSLRAEDTAVYYCAK

IGHV4-39*01
                                        (SEQ ID NO: 73)
>IGHV4-39*01
QLQLQESGPGLVKPSETLSLTCTVSGGSISSSSYYWGWIRQPPGKGLEWI

GSIYYSGSTYYNPSLKSRVTISVDTSKNQFSLKLSSVTAADTAVYYCAR

IGKV3-20*01
                                        (SEQ ID NO: 74)
EIVLTQSPGTLSLSPGERATLSCRASQSVSSSYLAWYQQKPGQAPRLLIY

GASSRATGIPDRFSGSGSGTDFTLTISRLEPEDFAVYYCQQYGSSP

IGKV4-1*01
                                        (SEQ ID NO: 84)
>IGKV4-1*01
DIVMTQSPDSLAVSLGERATINCKSSQSVLYSSNNKNYLAWYQQKPGQPP

KLLIYWASTRESGVPDRFSGSGSGTDFTLTISSLQAEDVAVYYCQQYYST

P

IGKV1-39*01
                                        (SEQ ID NO: 85)
>IGKV1-39*01
DIQMTQSPSSLSASVGDRVTITCRASQSISSYLNWYQQKPGKAPKLLIYA

ASSLQSGVPSRFSGSGSGTDFTLTISSLQPEDFATYYCQQSYSTP

IGLV3-1*01
                                        (SEQ ID NO: 86)
IGLV3-1*01
SYELTQPPSVSVSPGQTASITCSGDKLGDKYACWYQQKPGQSPVLVIYQD

SKRPSGIPERFSGSNSGNTATLTISGTQAMDEADYYCQAWDSST

IGLV2-8*01
                                        (SEQ ID NO: 87)
>IGLV2-8*01
QSALTQPPSASGSPGQSVTISCTGTSSDVGGYNYVSWYQQHPGKAPKLMI

YEVSKRPSGVPDRFSGSKSGNTASLTVSGLQAEDEADYYCSSYAGSNNF
```

Example 6. Optimization of Agonistic CD40 Antibodies

The VH of C40M9 (C40H43; SEQ ID NO: 60) had three amino acids in the framework region that differed from the sequence of the closest human germline sequence of IGHV4-39 (SEQ ID NO: 73). The alignment of C40H43 residues 1-98 in comparison to IGHV4-39 is shown in FIG. 3.

```
IGHV4-39 SEQ ID NO: 73:
QLQLQESGPGLVKPSETLSLTCTVSGGSISSSSYYWGWIRQPPGKGLEWI

GSIYYSGSTYYNPSLKSRVTISVDTSKNQFSLKLSSVTAADTAVYYCAR
```

Variants of C40H43 were made to mutate the positions differing from germline sequences individually or in combination. The resulting VH chains were combined with the parental VL chain BCML12 and the resulting antibodies were tested in binding and functional assays.

The VL of C40M18 (C40L64; SEQ ID NO: 66) had two amino acids in the framework region that differed from the sequence of the closest human germline sequence of IGLV3-1 (SEQ ID NO: 86). The alignment of C40M18 VL in comparison to IGVL3-1 is shown in FIG. 4.

```
IGLV3-1
                                        (SEQ ID NO: 86)
SYELTQPPSVSVSPGQTASITCSGDKLGDKYACWYQQKPGQSPVLVIYQD

SKRPSGIPERFSGSNSGNTATLTISGTQAMDEADYYCQAWDSST
```

Variants of C40L64 were made to mutate the positions differing from germline sequences individually or in combination. In addition, a cysteine resided in CDR1 of C40L64 that was mutated. The resulting variant VL chains were combined with the parental VH chain C40H48 and the resulting antibodies were tested in binding and functional assays.

Table 22 shows the generated variant antibodies. Antibodies C40M103 and C40M104 with C40L64 chain with mutated cysteine at LCDR1 have the LCDR1 sequence of SGDKLGDKYVS (SEQ ID NO: 31) and other CDRs as in the parental VH and VL. All generated antibody variants were cloned as IgG1.

TABLE 22

| mAb | VH | VH SEQ ID NO: | Number of VH substitutions * | VL | VHL SEQ ID NO: | Number of VL substitutions * |
|---|---|---|---|---|---|---|
| C40M102 | C40H48 | 57 | 0 | C40L70 | 70 | 2 |
| C40M103 | C40H48 | 57 | 0 | C40L69 | 71 | 3 |
| C40M104 | C40H48 | 57 | 0 | C40L68 | 72 | 1 |
| C40M105 | C40H52 | 61 | 3 | BCML12 | 69 | 0 |
| C40M121 | C40H53 | 62 | 2 | BCML12 | 69 | 0 |

* in comparison to parental

The resulting antibodies were tested for their binding to CD40 and in functional assays to evaluate effect, if any, of the substitutions that were made. Table 23 shows the $EC_{50}$ values for binding of the mAbs to CD40 on B cells, DC cell or on HEK-Blue™ CD40L cells. mAbs C40M102, C40M103 and C40M104 retained comparable binding to that of the parental C40M18. C40M105 had reduced binding when compared to the parental C40M9.

TABLE 23

| | EC50 (µg/ml) | | |
|---|---|---|---|
| Antibody | HEK-Blue ™ CD40L | Human B cells | Human DCs |
| C40M102 | 0.1621 | 0.15930 | 0.4379 |
| C40M103 | 0.1122 | 0.07502 | 0.1430 |
| C40M104 | 0.1775 | 0.10960 | 0.2526 |
| C40M105 | 2.1610 | 6.64800 | 5.7650 |
| C40M9 | 0.1433 | 0.06091 | 0.1522 |
| C40M18 | 0.1499 | 0.11000 | 0.2674 |
| C40M9* | 0.6146 | 0.01910 | 0.04620 |
| C49M121* | 0.464 | 0.02283 | 0.05720 |

*Results are from a separate experiment

The antibodies were tested for their agonistic activity on HEK-Blue™ CD40L cells and in primary B cells. Table 24 shows the $EC_{50}$ values for the antibodies in the assays. C40M102, C40M103 and C40M104 had similar potency in activating B cells when compared to the parental C40M18 mAb. C40M105 had decreased activity when compared to the parental C40M9.

TABLE 24

| | Assay ($EC_{50}$) (µg/ml) | | |
|---|---|---|---|
| Antibody | HEK-Blue ™ CD40L | Human DC (HLA-DR) | Human B cells (CD83) |
| C40M102 | 0.07515 | 0.3667 | 0.02388 |
| C40M103 | 0.002742 | 0.3875 | 0.004790 |
| C40M104 | 0.03078 | 0.1655 | 0.01671 |
| C40M105 | 0.01733 | 2.972 | 0.002819 |
| C40M9 | 0.01376 | 0.1178 | 0.0007661 |
| C40M18 | 0.06962 | 0.1662 | 0.02262 |
| C40M9* | 0.006210 | 0.01671 | 0.0001452 |
| C40M121* | 0.006332 | 0.01852 | 0.0003343 |

*Result are from a separate experiment

Example 7. Agonistic Anti-CD40 Antibodies Bind with High Affinity to Human CD40

Affinity measurements were performed using Surface Plasmon Resonance (SPR) using a ProteOn XPR36 system (BioRad). A biosensor surface was prepared by coupling anti-Human IgG Fc (Jackson cat#109-005-098) to the modified alginate polymer layer surface of a GLC chip (BioRad, Cat#176-5011) using the manufacturer instructions for amine-coupling chemistry. Approximately 5000 RU (response units) of mAbs were immobilized. The kinetic experiments were performed at 25° C. in running buffer (DPBS+0.01% P20+100 µg/ml BSA). To perform kinetic experiments, 200 RU of mAbs were captured followed by injections of analytes (human or cyno CD40) at 5 concentrations (in a 4-fold serial dilution). The association phase was monitored for 3 minutes at 50 µL/min, then followed by 15 minutes of buffer flow (dissociation phase). The chip surface was regenerated with two 18 second pulses of 100 mM $H_3PO_4$ (Sigma, Cat#7961) at 100 µL/min.

The collected data were processed using ProteOn Manager software. First, the data was corrected for background using inter-spots. Then, double reference subtraction of the data was performed by using the buffer injection for analyte injections. The kinetic analysis of the data was performed using a Langmuir 1:1 binding model. The result for each mAb was reported in the format of Ka (On-rate), Kd (Off-rate) and KD (equilibrium dissociation constant).

Summary of kinetics affinity for select CD40 mAbs for binding to human CD40 is shown in Table 25. The parameters reported in this table were obtained from a 1:1 Langmuir binding model for all samples. Affinity, KD=kd/ka.

TABLE 25

| Antibody | ka (1/Ms) | kd (1/s) | $K_D$ (M) |
|---|---|---|---|
| C40M9 (n = 5) | 7.27(1.83)E+05 | 2.85(0.97)E−03 | 4.09(1.51)E−09 |
| C40M12 | 1.30E+06 | 1.76E−04 | 1.36E−10 |
| C40M17 | 2.74E+06 | 8.06E−05 | 2.94E−11 |
| C40M18 | 1.07E+06 | 1.62E−04 | 1.51E−10 |
| C40M51 | 7.40E+05 | 8.78E−04 | 1.19E−09 |
| C40M55 (n = 2) | 9.44(8.68-10.2)E+05 | 2.03(1.88-2.17)E−03 | 2.15(2.12-2.17)E−09 |
| C40M56 | 7.77E+05 | 1.01E−03 | 1.30E−09 |
| C40M58 | 4.17E+05 | 7.14E−04 | 1.71E−09 |
| C40M59 | 1.18E+05 | 1.06E−03 | 9.00E−09 |
| C40M62 | 1.89E+05 | 2.47E−03 | 1.31E−08 |
| C40M63 | 5.28E+05 | 6.41E−04 | 1.21E−09 |
| C40M66 | 3.78E+05 | 1.16E−03 | 3.05E−09 |
| C40M67 | 1.63E+05 | 3.10E−04 | 1.91E−09 |

C40M9 n = 5 replicates, values listed as average and (standard deviation)
C40M55 n = 2 replicates, values listed as average and
(range 2 samples (C40M9, C40M55) did not fit well to 1:1 binding model.

Summary of kinetics affinity for select CD40 mAbs binding to cyno CD40 is shown in Table 26. The parameters reported in this table were obtained from a 1:1 Langmuir binding model for all samples. Affinity, KD=kd/ka.

TABLE 26

| Antibody | ka (1/Ms) | kd (1/s) | $K_D$ (M) |
|---|---|---|---|
| C40M9 (n = 3) | 9.01(1.02)E+05 | 1.26(0.07)E−03 | 1.42(0.24)E−09 |
| C40M12 | 1.81E+06 | 4.41E−04 | 2.43E−10 |
| C40M17 | 4.27E+06 | 1.57E−04 | 3.68E−11 |

TABLE 26-continued

| Antibody | ka (1/Ms) | kd (1/s) | K$_D$ (M) |
|---|---|---|---|
| C40M18 | 1.32E+06 | 9.41E−05 | 7.12E−11 |
| C40M51 | 4.19E+05 | 9.49E−04 | 2.27E−09 |
| C40M55 | 8.31E+05 | 2.15E−03 | 2.59E−09 |
| C40M56 | 8.06E+05 | 6.47E−04 | 8.03E−10 |
| C40M58 | 4.53E+05 | 7.23E−04 | 1.60E−09 |
| C40M59 | 1.44E+05 | 9.95E−04 | 6.92E−09 |
| C40M62 | 3.43E+05 | 9.08E−04 | 2.64E−09 |
| C40M63 | 7.46E+05 | 3.07E−04 | 4.12E−10 |
| C40M66 | 3.52E+05 | 5.77E−04 | 1.64E−09 |
| C40M67 | 1.84E+05 | 3.41E−04 | 1.85E−09 |

C40M9 n = 3 replicates, values listed as average and (standard deviation)
4 samples (C40M55, C40M56, C40M62, C40M63) did not fit well to 1:1 binding model.

Example 8. Fc Engineering of Agonistic Anti-CD40 Antibodies

Figure 6:
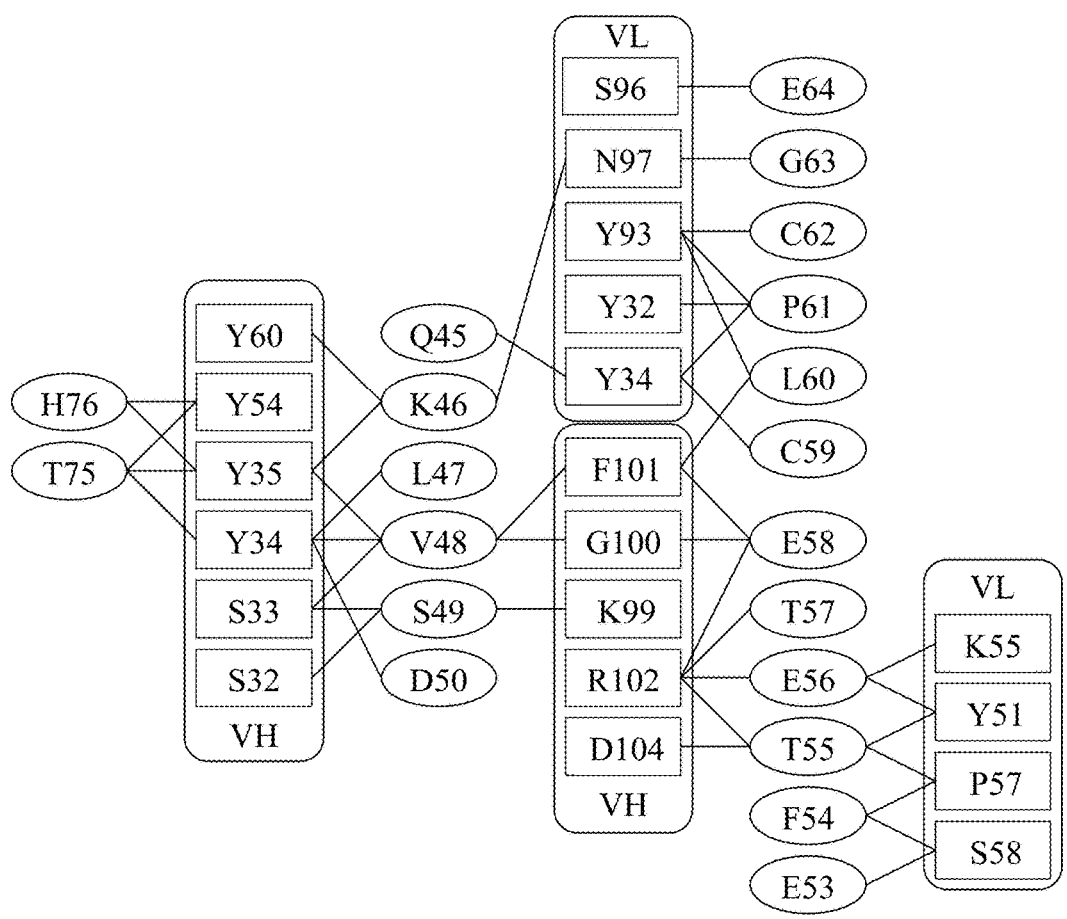
FIG. 6 shows the cartoon of C40B126 epitope and paratope residues. CD40 residue numbering is according to SEQ ID NO: 75. C40M126 VH and VL residue numbering is according to SEQ ID NOs: 62 and 69, respectively.
Figure 7:
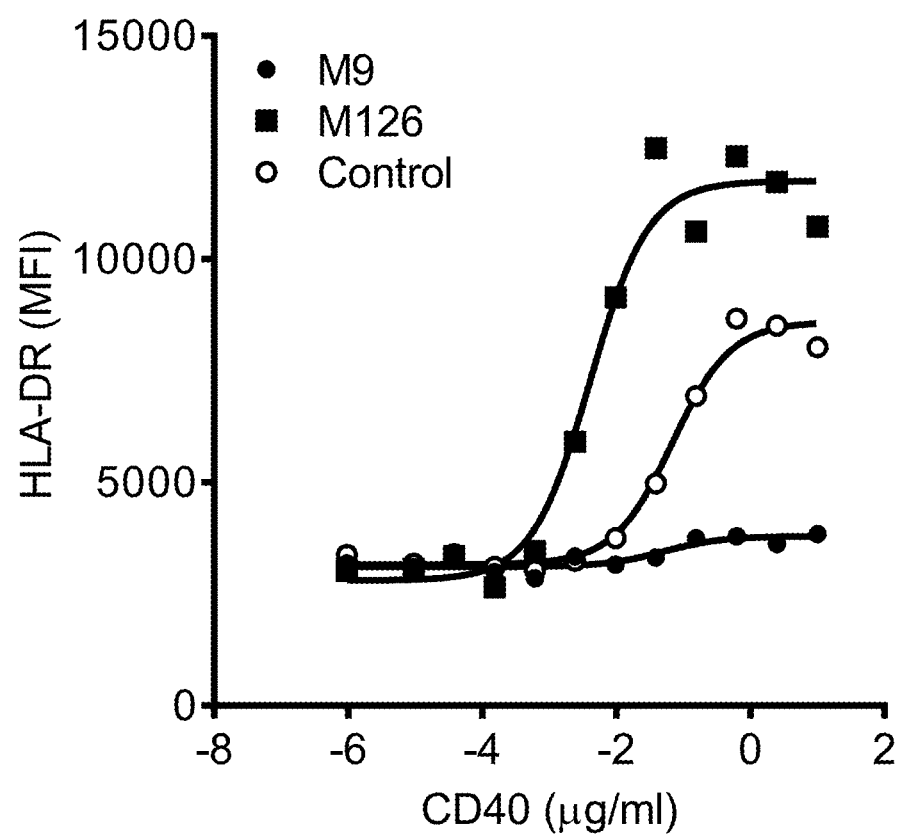
FIG. 7 shows that C40M126 is more potent in activating dendritic cells when compared to the control antibody CP-870,893 and that C40M9 has minimal cross-linking independent agonism. DC activation was measured as increased HLA-DR surface expression in the absence of a cross-linker. M9 refers to antibody C40M9 and M126 refers to antibody C40M126. Control: CP-870,893.

A S267E mutation was introduced to C40M121 to generate mAb C40M126. C40M126 demonstrated enhanced agonism independent of cross-linking as assessed by induced HLA-DR surface expression on dendritic cells (FIG. 6).

Example 9. Crystal Structure of C40M126 in Complex with Human CD40

Methods

The His-tagged extracellular domain (ECD) of human CD40 was expressed in baculovirus-infected Hi5 insect cells and purified by affinity and size-exclusion chromatography at Genscript (Piscataway, N.J.). The His-tagged Fab fragment of mAb C40M126 was expressed in HEK293 Expi cells and purified by affinity and size-exclusion chromatography. The antibody-antigen complex was prepared by mixing the components at a molar ratio of 1:1.2 with the excess of Fab and was incubated overnight at 4° C. The protein was concentrated to 12 mg/mL in 20 mM HEPES pH 7.5, 100 mM NaCl and crystallized by the vapor-diffusion method from solution containing 1.6 M ammonium sulfate, 5% PEG 400, 0.1 M HEPES, pH 7.5. One crystal was transferred to the mother liquor supplemented with 24% glycerol, frozen in liquid nitrogen, and used for X-ray diffraction data collection. The structure was determined at 3.0 A resolution.

Results

Figure 5:
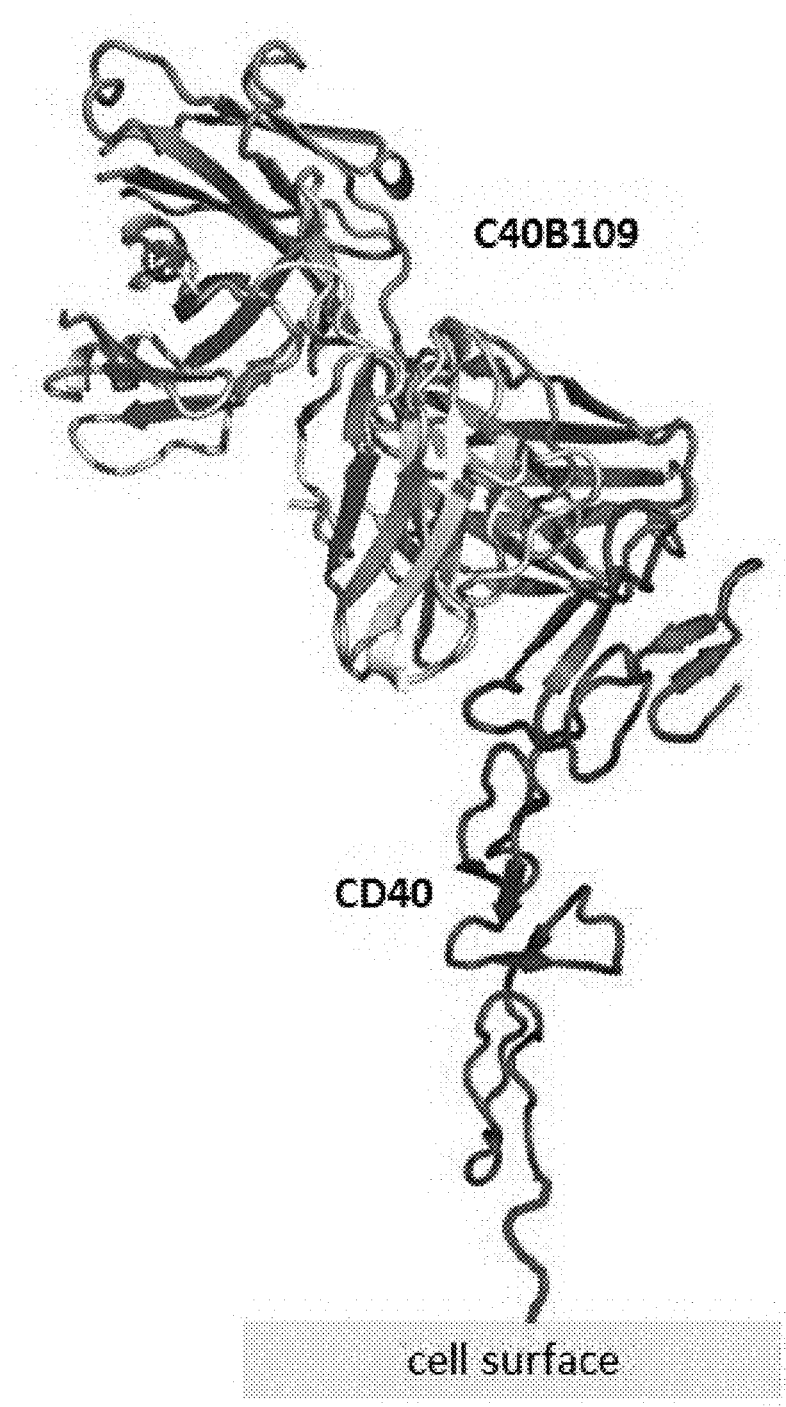
FIG. 5 shows the crystal structure of C40M126 in complex with CD40.

C40M126 binds CD40 at the site distal to the cell surface (FIG. 5). The epitope is conformational and includes a continuous stretch of amino acid residues 46-64 that forms a beta-hairpin and two more residues, 75-76, from the neighboring loop (residue numbering according to SEQ ID NO: 75). The antibody residues involved in binding of CD40 include 9 residues from the light chain and 11 residues from the heavy chain (FIG. 6). All six CDRs are involved in binding. The antibody-antigen interface is extended and covers over 900 Å$^2$ on each molecule.

C40M126 is a variant of C40M9 having two mutations in the framework region of the heavy chain, I17T and N85S, when compared to C40M9. These two residues face away from the mAb binding site and do not impact binding characteristics of the antibody. Therefore, C40M9 is expected to bind the same epitope residues than C40M126. Therefore, all conclusions related to the epitope and the mechanism of action hold for C40M9.

Cyno CD40 is 95% identical to human CD40 in the ECD and differs from human CD40 in only one position within the epitope. Marmoset CD40 has more amino acid differences from human CD40, 4 of which are within the epitope. All the differences are at the periphery of the epitope and likely to be tolerated by the antibody, i.e. it is expected that C40M9 is cross-reactive towards both cyno and marmoset CD40.

Superposition of the antibody-antigen structure on the receptor-ligand complex available from the Protein Data Bank (entry 3QD6) shows that the epitopes of C40M126 and CD40L are non-overlapping. However, C40M126 and CD40L would compete for the same molecule of CD40 due to steric effect, e.g. C40M126 would block the CD40L-CD40 interaction.

Example 10. Pharmacokinetic Study of Anti-CD40 Antibodies in Cynomolgus Monkey Materials and Methods Naïve cynomolgus monkeys fasted overnight (or at least 8 hours) received a single bolus intravenous injection of anti-CD40 antibodies C40M9, C40M126 or a control antibody CP-870,893 at 0.1 mg/kg, 10 mg/kg or 10 mg/kg. Animal welfare for the study was compliance with the U.S. Department of Agriculture's (USDA) Animal Welfare Act (9 Code of Federal Regulations (CFR) Parts 1, 2 and 3).

For bioanalytical studies, approximately 1 mL/sample was collected from femoral artery ore-dose and at 0.5, 1, 2, 4, 8, 12, 24, 48, 72, 96 hours and Days 7, 14, 21 and 28 post-dose. The samples were allowed to clot at ambient temperature for at least 15 minutes and the samples were then centrifuged under ambient conditions within 30 minutes following completion of sample collection at each interval. The resulting serum was split into three approximately equal aliquots, where available, and placed into 96-well plates. Samples were stored frozen at −60 to −90° C.

Results

Male cynomolgus monkeys were administered a single intravenous bolus of C40M9, C40M126 or a control antibody CP-870,893 at a dose of 0.1, 1.0, or 10 mg/kg. In general, effects tended to occur or were most pronounced with administration of CP-870,893. The following findings were observed:

Moderate decreases in red cell mass at 10 mg/kg C40M9 and 1.0 and 10 mg/kg CP-870,893 with evidence of an appropriate regenerative response, as indicated by increases in reticulocyte counts, red blood cell distribution width (RDW), polychromasia, and/or nucleated red blood cells on microscopic blood smear review; decreases in red cell mass trended toward resolution by Days 21 and/or 28 while the regenerative response generally persisted.

Transient, mild to moderate decreases in platelet counts at 0.1, 1.0, and 10 mg/kg CP-870,893.

Transient, moderate decreases in albumin, moderate increases in globulin, and/or neutrophil cytoplasmic change at 10 mg/kg CP-870,893 that were suggestive of a minor inflammatory stimulus.

Mild decreases in fibrinogen at 10 mg/kg CP-870,893 at Days 14 through 28.

Evidence of transiently altered coagulation at 10 mg/kg CP-870,893 indicated by minimal prolongations in APTT and prothrombin time, which were not likely biologically meaningful due to the small magnitude of change.

Hematology

At 72 hours post dose, Day 7, and/or Day 14 collections in males at 10 mg/kg C40M9 and 1.0 and 10 mg/kg CP-870,893 there were moderate decreases in red cell mass (up to −29%; percent change expressed as group mean relative to pretest mean) that were of greater magnitude than decreases in red cell mass (up to −20%) in the other treatment groups. Decreases in red cell mass in the other treatment groups were generally of similar magnitude across groups; they were considered most likely largely procedure-related and due to repeated pharmacokinetic blood collection, although a definitive comparison could not be made due to the lack of controls for comparison. The greater decreases in red cell mass at 10 mg/kg C40M9 and 1.0 and 10 mg/kg CP-870,893 were most likely related to the test articles with concurrent procedure-related contributions. Decreases in red cell mass trended toward resolution by Days 21 and/or 28.

At Day 7 through 28 collections in all groups there were mild to marked increases in reticulocyte counts (up to +883%) relative to pretest that were indicative of an appropriate regenerative response to the decreases in red cell mass. There were also concomitant increases in red blood cell distribution width (RDW; up to +44%, indicative of increased variation in erythrocyte size) and increases in polychromasia and/or nucleated red blood cells on microscopic blood smear review at 1.0 and 10 mg/kg CP-870,893 that were also indicative of a regenerative response. The regenerative response was most pronounced at 10 mg/kg CP-870,893, coinciding with the greatest decrease in red cell mass observed.

Figure 8:
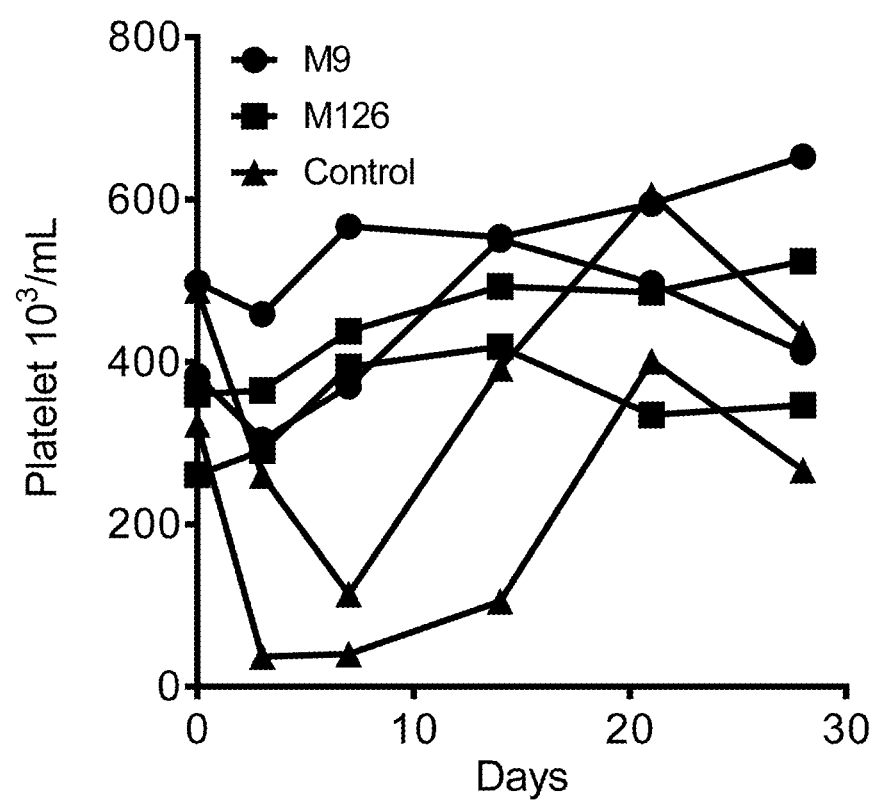
FIG. 8 shows a transient decrease in platelet counts in animals dosed with 10 mg/ml control antibody CP-870,893 while dosing with C40M9 or C40M126 did not result in reduction in platelet counts. Results from two individual animals per group are shown.
Figure 9:
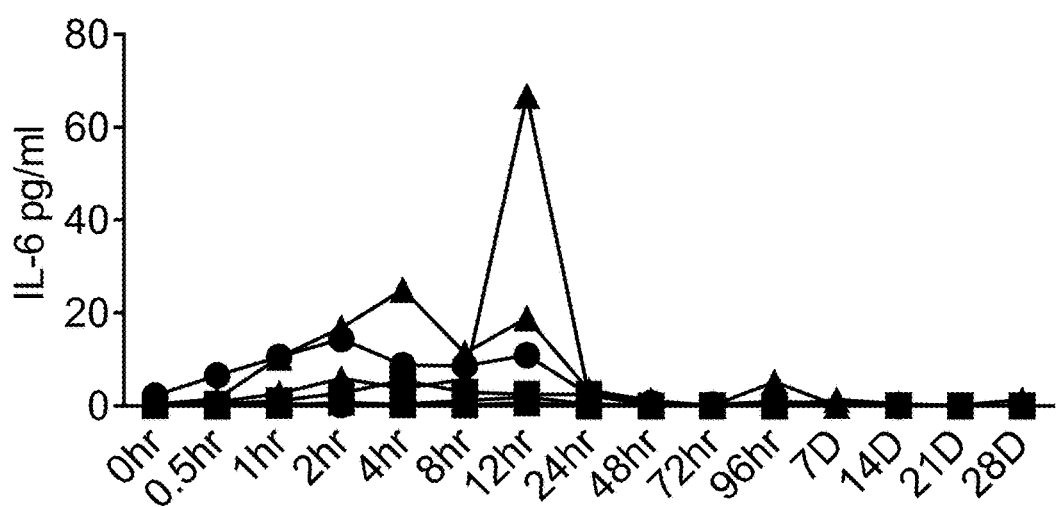
FIG. 9 shows increased IL-6 production (pg/ml) in animals treated with 10 mg/ml control antibody CP-870,893 when compared to animals dosed with C40M9 or C40M126. Results from two individual animals per group are shown.

At 72 hours post dose collections at >0.1 mg/kg CP-870,893 as well as at Day 7 and 14 collections at 10 mg/kg CP-870,893 there were mild to moderate, transient decreases in platelet counts (up to −81%) relative to pretest that were considered CP-870,893-related. These decreases were followed by transient increases in platelet counts at subsequent collections that were indicative of an appropriate regenerative response and had generally resolved at Day 28 collections. FIG. 8 shows the platelet counts over time in animals dosed with 10 mg/kg of C40M9, C40M126 or the control antibody CP-870,893. The transient decrease in platelet counts was not observed in animals dosed with C40M9 or C40M126.

At Day 14 collections in one male at 10 mg/kg CP-870,893 there was neutrophil cytoplasmic change observed on microscopic blood smear review. This change was most indicative of an inflammatory stimulus, as related to decreases in albumin and increases in globulin.

At 72 hours post dose and/or Day 7 collections in males at >0.1 mg/kg CP-870,893 and at 10 mg/kg C40M126 there were transient, mild to moderate decreases in lymphocyte counts (up to −46%) relative to pretest, which had generally resolved at subsequent collections. These changes were of uncertain relation to the test articles due to their generally similar magnitude across treatment groups and the relation of mean and individual values to expected values for biological and procedure-related variation.

All other fluctuations in hematology endpoints were considered not meaningful due to their small magnitude, sporadic nature, proximity to dosing, and/or relation to expected values for biological and procedure-related variation.

Coagulation

At Day 7 and 14 collections in males at 10 mg/kg CP-870,893 there were minimal prolongations in APTT (up to +32%) and prothrombin time (up to +22%) relative to pretest. These changes were CP-870,893-related and indicative of altered coagulation, although not likely biologically meaningful due to the small magnitude of these changes. They had resolved at subsequent collections.

At Day 14, 21, and 28 collections in males at 10 mg/kg CP-870,893 there were mild decreases in fibrinogen (up to −66%) relative to pretest. These changes were CP-870,893-related and may have related to altered coagulation. Other fluctuations in coagulation times (i.e. APTT and prothrombin time) and fibrinogen were considered not meaningful due to their small magnitude, direction of change, and/or relation to expected values.

Clinical Chemistry

At Day 7, 14, and 21 collections in males at 10 mg/kg CP-870,893 there were moderate decreases in albumin (up to −30%) and increases in globulin (up to +33%) relative to pretest. These changes were considered test article-related and were suggestive of a minor inflammatory stimulus, as related to neutrophil cytoplasmic change seen in one of two animals (see Hematology section). These changes trended toward resolution at Day 28 collections. Minimal to mild decreases in albumin (up to −16%) were generally also observed across other treatment groups at all collections, although these decreases typically trended back toward pretest values at Day 21 and/or 28 collections. These decreases were considered most likely procedure-related, as related to decreases in red cell mass (see Hematology section). Decreases in albumin generally had concomitant decreases in calcium because albumin is the major blood carrier of calcium, as well as concomitant decreases in total protein and/or albumin to globulin ratios. These changes lacked correlative findings among other study endpoints.

At 72 hours post dose and/or Day 7 collections in males in all treatment groups except at 1.0 mg/kg C40M126 there were mild to moderate increases in aspartate aminotransferase (AST; up to +529%) and/or alanine aminotransferase (ALT; up to +374%) relative to pretest that had generally resolved at subsequent collections and were most suggestive of minor muscle injury. These changes were considered most likely procedure related, possibly associated with repeated venipuncture, due to their lack of a dose-responsive pattern, transient nature, and lack of correlative findings among other study endpoints.

All other fluctuations in clinical chemistry endpoints were considered not meaningful due to their small magnitude, sporadic nature, proximity to dosing, and/or relation to expected values.

Toxicity data generated in this cyno tolerability study suggests that C40M9 and C40M126 induce less platelets depletion and lower levels of cytokine storm when compared to the control antibody, presumably from APC activation driven by agonistic activity of CD40 antibody. Taken together, C40M9 and C40M126 may induce less toxicity related to CD40 activity while maintaining robust APC activation as shown in in vitro DC activation.

We claim:

1. An isolated agonistic antibody or antigen-binding fragment thereof specifically binding human CD40 of SEQ ID NO: 75, comprising a heavy chain variable region (HCDR) 1 of SEQ ID NO: 5, a HCDR2 of SEQ ID NO: 10, a HCDR3 of SEQ ID NO: 18, a light chain variable region (LCDR) 1 of SEQ ID NO: 32, a LCDR2 of SEQ ID NO: 34 and a LCDR3 of SEQ ID NO: 47.

2. The antibody of claim 1, wherein the antibody binds human CD40 of SEQ ID NO: 75 within human CD40 residues 46-64 and 75-76 of SEQ ID NO: 75.

3. The antibody of claim 2, wherein the antibody has at least one of the following properties:
   a) binds to human CD40 of SEQ ID NO: 75 with a dissociation constant ($K_D$) of about $5 \times 10^{-9}$ M or less, when the $K_D$ is measured using ProteOn XPR36 system at 25° C. in Dulbecco's phosphate buffered saline containing 0.01% poly sorbate 20 (PS-20) and 100 µg/ml bovine serum albumin; or
   b) requires cross-linking for its agonistic activity on B cells and on dendritic cells (DC), wherein agonistic activity on B cells is measured by B cell CD23 surface expression and agonistic activity on DCs is measured by DC CD83 surface expression in the presence of cross-linker anti-human F(ab')$_2$ at 20 µg/ml, when CD23 and CD83 surface expression is measured using flow cytometry.

4. The antibody of claim 1, comprising a heavy chain variable region (VH) of SEQ ID NOs: 62 or 61 and a light chain variable region (VL) of SEQ ID NO: 69.

5. The antibody of claim 1, comprising the VH and the VL of SEQ ID NOs: 62 and 69, respectively.

6. The antibody of claim 1, comprising the VH and the VL of SEQ ID NOs: 61 and 69, respectively.

7. The antibody of claim 1, wherein the antibody comprises a heavy chain framework derived from human IGHV4-39*01 (SEQ ID NO: 73) and a light chain framework derived from human IGLV2-8*01 (SEQ ID NO: 87).

8. The antibody of claim 1, wherein the antibody is an IgG1, IgG2, IgG3 or IgG4 isotype.

9. The antibody of claim 5, comprising the heavy chain and the light chain of SEQ ID NOs: 129 and 136, respectively.

10. The antibody of claim 5, comprising the heavy chain and the light chain of SEQ ID NOs: 128 and 136, respectively.

11. The antibody of claim 6, comprising the heavy chain and the light chain of SEQ ID NOs: 127 and 136, respectively.

12. The antibody of claim 8, further comprising at least one mutation in an Fc region, wherein the at least one mutation in the Fc region is a S267E mutation, a S267E/I332E mutation, a S267E/L328F mutation, a G236D/S267E mutation or an E233D/G237D/H268D/P271G/A330R/P238D mutation, residue numbering according to the EU Index.

13. The antibody of claim 12, wherein the at least one mutation in the Fc region is the S267E mutation.

14. The antibody of claim 1, wherein the antibody is a multispecific antibody.

15. The antibody of claim 14, wherein the antibody is a bispecific antibody.

16. An immunoconjugate comprising the antibody of claim 1 linked to a cytotoxic agent or an imaging agent.

17. A pharmaceutical composition comprising the antibody of claim 1 and a pharmaceutically acceptable carrier.

18. A pharmaceutical composition comprising the immunoconjugate of claim 16 and a pharmaceutically acceptable carrier.

19. A kit comprising the antibody of claim 1.

20. The kit of claim 19, further comprising reagents for detecting the antibody and instructions of use.

21. An isolated agonistic antibody or antigen-binding fragment thereof specifically binding human CD40 of SEQ ID NO: 75, comprising
  a) the HCDR1, the HCDR2, the HCDR3, the LCDR1, the LCDR2 and the LCDR3 of SEQ ID NOs: 1, 8, 22, 28, 38 and 42, respectively, the VH and the VL of SEQ ID NOs: 48 and 63, respectively, and/or the heavy chain (HC) and the light chain (LC) of SEQ ID NOs: 114 and 130, respectively;
  b) the HCDR1, the HCDR2, the HCDR3, the LCDR1, the LCDR2 and the LCDR3 of SEQ ID NOs: 2, 7, 25, 26, 39 and 44, respectively, the VH and the VL of SEQ ID NOs: 49 and 64, respectively, and/or the heavy chain (HC) and the light chain (LC) of SEQ ID NOs: 115 and 131, respectively;
  c) the HCDR1, the HCDR2, the HCDR3, the LCDR1, the LCDR2 and the LCDR3 of SEQ ID NOs: 2, 7, 24, 26, 39 and 44, respectively, the VH and the VL of SEQ ID NOs: 50 and 64, respectively, and/or the heavy chain (HC) and the light chain (LC) of SEQ ID NOs: 116 and 131, respectively;
  d) the HCDR1, the HCDR2, the HCDR3, the LCDR1, the LCDR2 and the LCDR3 of SEQ ID NOs: 2, 7, 23, 26, 39 and 44, respectively, the VH and the VL of SEQ ID NOs: 51 and 64, respectively; or the heavy chain (HC) and the light chain (LC) of SEQ ID NOs: 117 and 131, respectively;
  e) the HCDR1, the HCDR2, the HCDR3, the LCDR1, the LCDR2 and the LCDR3 of SEQ ID NOs: 3, 13, 17, 27, 33 and 43, respectively; the VH and the VL of SEQ ID NOs: 52 and 65, respectively; or the heavy chain (HC) and the light chain (LC) of SEQ ID NOs: 118 and 132, respectively;
  f) the HCDR1, the HCDR2, the HCDR3, the LCDR1, the LCDR2 and the LCDR3 of SEQ ID NOs: 4, 6, 19, 27, 33 and 43, respectively; the VH and the VL of SEQ ID NOs: 53 and 65, respectively; or the heavy chain (HC) and the light chain (LC) of SEQ ID NOs: 119 and 132, respectively;
  g) the HCDR1, the HCDR2, the HCDR3, the LCDR1, the LCDR2 and the LCDR3 of SEQ ID NOs: 4, 6, 20, 27, 33 and 43, respectively; the VH and the VL of SEQ ID NOs: 54 and 65, respectively; or the heavy chain (HC) and the light chain (LC) of SEQ ID NOs: 120 and 132, respectively;
  h) the HCDR1, the HCDR2, the HCDR3, the LCDR1, the LCDR2 and the LCDR3 of SEQ ID NOs: 2, 7, 14, 27, 33 and 43, respectively; the VH and the VL of SEQ ID NOs: 55 and 65, respectively; or the heavy chain (HC) and the light chain (LC) of SEQ ID NOs: 121 and 132, respectively;
  i) the HCDR1, the HCDR2, the HCDR3, the LCDR1, the LCDR2 and the LCDR3 of SEQ ID NOs: 4, 6, 21, 27, 33 and 43, respectively; the VH and the VL of SEQ ID NOs: 56 and 65, respectively; or the heavy chain (HC) and the light chain (LC) of SEQ ID NOs: 122 and 132, respectively;
  j) the HCDR1, the HCDR2, the HCDR3, the LCDR1, the LCDR2 and the LCDR3 of SEQ ID NOs: 4, 9, 15, 30, 36 and 41, respectively, the VH and the VL of SEQ ID NOs: 57 and 66, respectively; or the heavy chain (HC) and the light chain (LC) of SEQ ID NOs: 123 and 133, respectively;
  k) the HCDR1, the HCDR2, the HCDR3, the LCDR1, the LCDR2 and the LCDR3 of SEQ ID NOs: 4, 11, 16, 29, 37 and 40, respectively, the VH and the VL of SEQ ID NOs: 58 and 67, respectively; or the heavy chain (HC) and the light chain (LC) of SEQ ID NOs: 124 and 134, respectively;
  l) the HCDR1, the HCDR2, the HCDR3, the LCDR1, the LCDR2 and the LCDR3 of SEQ ID NOs: 4, 12, 15, 30, 35 and 46, respectively, the VH and the VL of SEQ ID NOs: 59 and 68, respectively, and/or the heavy chain (HC) and the light chain (LC) of SEQ ID NOs: 125 and 135, respectively;
  m) the HCDR1, the HCDR2, the HCDR3, the LCDR1, the LCDR2 and the LCDR3 of SEQ ID NOs: 4, 9, 15, 30, 36 and 41, respectively, the VH and the VL of SEQ ID NOs: 57 and 70, respectively, and/or the heavy chain (HC) and the light chain (LC) of SEQ ID NOs: 123 and 137, respectively;
  n) the HCDR1, the HCDR2, the HCDR3, the LCDR1, the LCDR2 and the LCDR3 of SEQ ID NOs: 4, 9, 15, 31, 36 and 41, respectively, the VH and the VL of SEQ ID NOs: 57 and 71, respectively, and/or the heavy chain (HC) and the light chain (LC) of SEQ ID NOs: 123 and 138, respectively;
  o) the HCDR1, the HCDR2, the HCDR3, the LCDR1, the LCDR2 and the LCDR3 of SEQ ID NOs: 4, 9, 15, 31, 36 and 41, respectively, the VH and the VL of SEQ ID NOs: 57 and 72, respectively, and/or the heavy chain (HC) and the light chain (LC) of SEQ ID NOs: 123 and 139, respectively.

22. The antibody of claim 21, wherein the antibody is an IgG1, IgG2, IgG3 or IgG4 isotype.

23. The antibody of claim 22, further comprising at least one mutation in an Fc region, wherein the at least one mutation in the Fc region is a S267E mutation, a S267E/I332E mutation, a S267E/L328F mutation, a G236D/S267E mutation or a E233D/G237D/H268D/P271G/A330R/P238D mutation, residue numbering according to the EU Index.

24. The antibody of claim 23, wherein the at least one mutation in the Fc region is the S267E mutation, a S267E/I332E mutation, a S267E/L328F mutation, a G236D/S267E mutation or a E233D/G237D/H268D/P271G/A330R/P238D mutation, residue numbering according to the EU Index.

25. The antibody of claim 21, wherein the antibody is a multispecific antibody.

26. The antibody of claim 25, wherein the antibody is a bispecific antibody.

27. An immunoconjugate comprising the antibody of claim 21 linked to a cytotoxic agent or an imaging agent.

28. A pharmaceutical composition comprising the antibody of claim 21 and a pharmaceutically acceptable carrier.

29. A pharmaceutical composition comprising the immunoconjugate of claim 27 and a pharmaceutically acceptable carrier.

30. A kit comprising the antibody of claim 21.

31. The kit of claim 30, further comprising reagents for detecting the antibody and instructions of use.

32. A method of activating antigen presenting cells (APC) and B cells in a subject in need thereof, comprising administering to the subject an isolated antibody of claim 1.

33. The method of claim 32, wherein the subject has a cancer.

34. The method of claim 33, wherein the cancer is a solid tumor or a hematological malignancy.

35. The method of claim 34, wherein the solid tumor is a bladder cancer, a renal cancer, a lung cancer, a non-small cell lung cancer, a pancreatic cancer, an ovarian cancer, a breast cancer or a head and neck cancer.

36. The method of claim 33, wherein the antibody is administered in combination with a second therapeutic agent.

37. The method of claim 36, wherein the second therapeutic agent is a chemotherapeutic agent, a standard of care drug for treatment of a solid tumor or a hematological malignancy, or an immune checkpoint modulator.

38. The method of claim 36, wherein the second therapeutic agent is administered simultaneously, sequentially or separately.

39. A method of activating antigen presenting cells (APC) and B cells in a subject in need thereof, comprising administering to the subject an isolated antibody of claim 21.

40. The method of claim 39, wherein the subject has a cancer.

41. The method of claim 40, wherein the cancer is a solid tumor or a hematological malignancy.

42. The method of claim 41, wherein the solid tumor is a bladder cancer, a renal cancer, a lung cancer, a non-small cell lung cancer, a pancreatic cancer, an ovarian cancer, a breast cancer or a head and neck cancer.

43. The method of claim 40, wherein the antibody is administered in combination with a second therapeutic agent.

44. The method of claim 43, wherein the second therapeutic agent is a chemotherapeutic agent, a standard of care drug for treatment of a solid tumor or a hematological malignancy, or an immune checkpoint modulator.

45. The method of claim 43, wherein the second therapeutic agent is administered simultaneously, sequentially or separately.

* * * * *

SEQUENCE LISTING

<160> NUMBER OF SEQ ID NOS: 175

<210> SEQ ID NO 1
<211> LENGTH: 5

```
<212> TYPE: PRT
<213> ORGANISM: Artificial Sequence
<220> FEATURE:
<223> OTHER INFORMATION: HCDR1 sequence

<400> SEQUENCE: 1

Asp Tyr Ala Met Asn
1               5

<210> SEQ ID NO 2
<211> LENGTH: 5
<212> TYPE: PRT
<213> ORGANISM: Artificial Sequence
<220> FEATURE:
<223> OTHER INFORMATION: HCDR1 sequence

<400> SEQUENCE: 2

Ser Tyr Ala Ile Ser
1               5

<210> SEQ ID NO 3
<211> LENGTH: 5
<212> TYPE: PRT
<213> ORGANISM: Artificial Sequence
<220> FEATURE:
<223> OTHER INFORMATION: HCDR1 sequence

<400> SEQUENCE: 3

Ser Tyr Trp Ile Ser
1               5

<210> SEQ ID NO 4
<211> LENGTH: 5
<212> TYPE: PRT
<213> ORGANISM: Artificial Sequence
<220> FEATURE:
<223> OTHER INFORMATION: HCDR1 sequence

<400> SEQUENCE: 4

Ser Tyr Ala Met Ser
1               5

<210> SEQ ID NO 5
<211> LENGTH: 7
<212> TYPE: PRT
<213> ORGANISM: Artificial Sequence
<220> FEATURE:
<223> OTHER INFORMATION: HCDR1 sequence

<400> SEQUENCE: 5

Ser Ser Ser Tyr Tyr Trp Gly
1               5

<210> SEQ ID NO 6
<211> LENGTH: 17
<212> TYPE: PRT
<213> ORGANISM: Artificial Sequence
<220> FEATURE:
<223> OTHER INFORMATION: HCDR2 sequence

<400> SEQUENCE: 6

Ala Ile Ser Gly Ser Gly Gly Ser Thr Tyr Tyr Ala Asp Ser Val Lys
1               5                   10                  15

Gly

<210> SEQ ID NO 7
```

<211> LENGTH: 17
<212> TYPE: PRT
<213> ORGANISM: Artificial Sequence
<220> FEATURE:
<223> OTHER INFORMATION: HCDR2 sequence

<400> SEQUENCE: 7

Gly Ile Ile Pro Ile Phe Gly Thr Ala Asn Tyr Ala Gln Lys Phe Gln
1               5                   10                  15
Gly

<210> SEQ ID NO 8
<211> LENGTH: 17
<212> TYPE: PRT
<213> ORGANISM: Artificial Sequence
<220> FEATURE:
<223> OTHER INFORMATION: HCDR2 sequence

<400> SEQUENCE: 8

Gly Ile Lys Ser Gly Gly Ser Ser Lys Tyr Tyr Ala Asp Ser Val Lys
1               5                   10                  15
Gly

<210> SEQ ID NO 9
<211> LENGTH: 17
<212> TYPE: PRT
<213> ORGANISM: Artificial Sequence
<220> FEATURE:
<223> OTHER INFORMATION: HCDR2 sequence

<400> SEQUENCE: 9

Ile Ile Asn Asn Asn Val Gly Arg Thr Tyr Tyr Ala Asp Ser Val Lys
1               5                   10                  15
Gly

<210> SEQ ID NO 10
<211> LENGTH: 16
<212> TYPE: PRT
<213> ORGANISM: Artificial Sequence
<220> FEATURE:
<223> OTHER INFORMATION: HCDR2 sequence

<400> SEQUENCE: 10

Asn Ile Tyr Tyr Arg Gly Asp Thr Tyr Tyr Ser Pro Ser Leu Lys Ser
1               5                   10                  15

<210> SEQ ID NO 11
<211> LENGTH: 17
<212> TYPE: PRT
<213> ORGANISM: Artificial Sequence
<220> FEATURE:
<223> OTHER INFORMATION: HCDR2 sequence

<400> SEQUENCE: 11

Thr Ile Asn Asn Ser Gly Gly Gly Thr Tyr Tyr Ala Asp Ser Val Lys
1               5                   10                  15
Gly

<210> SEQ ID NO 12
<211> LENGTH: 17
<212> TYPE: PRT
<213> ORGANISM: Artificial Sequence
<220> FEATURE:
<223> OTHER INFORMATION: HCDR2 sequence

```
<400> SEQUENCE: 12

Val Ile Ser Asp Ser Gly Gly Arg Thr Tyr Tyr Ala Asp Ser Val Lys
1               5                   10                  15

Gly

<210> SEQ ID NO 13
<211> LENGTH: 17
<212> TYPE: PRT
<213> ORGANISM: Artificial Sequence
<220> FEATURE:
<223> OTHER INFORMATION: HCDR2 sequence

<400> SEQUENCE: 13

Tyr Ile Ile Pro Ile Ser Gly Thr Ala Arg Tyr Ala Gln Lys Phe Gln
1               5                   10                  15

Gly

<210> SEQ ID NO 14
<211> LENGTH: 15
<212> TYPE: PRT
<213> ORGANISM: Artificial Sequence
<220> FEATURE:
<223> OTHER INFORMATION: HCDR3 sequence

<400> SEQUENCE: 14

Asp Gly Tyr Arg Arg Tyr Gly Ile Gly Arg Tyr Gly Phe Asp Tyr
1               5                   10                  15

<210> SEQ ID NO 15
<211> LENGTH: 12
<212> TYPE: PRT
<213> ORGANISM: Artificial Sequence
<220> FEATURE:
<223> OTHER INFORMATION: HCDR3 sequence

<400> SEQUENCE: 15

Glu Gly Gly Asp Tyr Tyr Tyr Tyr Gly Met Asp Val
1               5                   10

<210> SEQ ID NO 16
<211> LENGTH: 12
<212> TYPE: PRT
<213> ORGANISM: Artificial Sequence
<220> FEATURE:
<223> OTHER INFORMATION: HCDR3 sequence

<400> SEQUENCE: 16

Glu Gly Gly Lys Tyr Tyr Tyr Tyr Ala Met Asp Val
1               5                   10

<210> SEQ ID NO 17
<211> LENGTH: 15
<212> TYPE: PRT
<213> ORGANISM: Artificial Sequence
<220> FEATURE:
<223> OTHER INFORMATION: HCDR3 sequence

<400> SEQUENCE: 17

Glu Pro Gly Tyr Ser Ser Gly Leu Ser Val Asp Tyr Phe Asp Tyr
1               5                   10                  15

<210> SEQ ID NO 18
<211> LENGTH: 6
<212> TYPE: PRT
<213> ORGANISM: Artificial Sequence
```

```
<220> FEATURE:
<223> OTHER INFORMATION: HCDR3 sequence

<400> SEQUENCE: 18

Gly Phe Arg Phe Asp Tyr
1               5

<210> SEQ ID NO 19
<211> LENGTH: 10
<212> TYPE: PRT
<213> ORGANISM: Artificial Sequence
<220> FEATURE:
<223> OTHER INFORMATION: HCDR3 sequence

<400> SEQUENCE: 19

Gly Pro Ala Tyr Thr Ile Val Phe Asp Tyr
1               5                   10

<210> SEQ ID NO 20
<211> LENGTH: 10
<212> TYPE: PRT
<213> ORGANISM: Artificial Sequence
<220> FEATURE:
<223> OTHER INFORMATION: HCDR3 sequence

<400> SEQUENCE: 20

Gly Pro Val Tyr Ser Leu Val Phe Asp Tyr
1               5                   10

<210> SEQ ID NO 21
<211> LENGTH: 10
<212> TYPE: PRT
<213> ORGANISM: Artificial Sequence
<220> FEATURE:
<223> OTHER INFORMATION: HCDR3 sequence

<400> SEQUENCE: 21

Gly Pro Val Tyr Ser Ser Val Phe Asp Tyr
1               5                   10

<210> SEQ ID NO 22
<211> LENGTH: 10
<212> TYPE: PRT
<213> ORGANISM: Artificial Sequence
<220> FEATURE:
<223> OTHER INFORMATION: HCDR3 sequence

<400> SEQUENCE: 22

His Val Asp Phe Tyr Arg Ala Leu Asp Tyr
1               5                   10

<210> SEQ ID NO 23
<211> LENGTH: 13
<212> TYPE: PRT
<213> ORGANISM: Artificial Sequence
<220> FEATURE:
<223> OTHER INFORMATION: HCDR3 sequence

<400> SEQUENCE: 23

Val Ala Asn Ala Ala Tyr Phe Arg Ser Gly Leu Asp Tyr
1               5                   10

<210> SEQ ID NO 24
<211> LENGTH: 13
<212> TYPE: PRT
<213> ORGANISM: Artificial Sequence
<220> FEATURE:
```

```
<223> OTHER INFORMATION: HCDR3 sequence

<400> SEQUENCE: 24

Val Gly His Pro Ala Trp Trp Arg Asp Ser Leu Asp Tyr
1               5                   10

<210> SEQ ID NO 25
<211> LENGTH: 13
<212> TYPE: PRT
<213> ORGANISM: Artificial Sequence
<220> FEATURE:
<223> OTHER INFORMATION: HCDR3 sequence

<400> SEQUENCE: 25

Val Arg Tyr Ser Ala Trp Tyr Arg Asp Ser Leu Asp Tyr
1               5                   10

<210> SEQ ID NO 26
<211> LENGTH: 17
<212> TYPE: PRT
<213> ORGANISM: Artificial Sequence
<220> FEATURE:
<223> OTHER INFORMATION: LCDR1 sequence

<400> SEQUENCE: 26

Lys Ser Ser Gln Ser Val Leu Tyr Ser Ser Asn Asn Lys Asn Tyr Leu
1               5                   10                  15

Ala

<210> SEQ ID NO 27
<211> LENGTH: 11
<212> TYPE: PRT
<213> ORGANISM: Artificial Sequence
<220> FEATURE:
<223> OTHER INFORMATION: LCDR1 sequence

<400> SEQUENCE: 27

Arg Ala Ser Gln Ser Ile Ser Ser Tyr Leu Asn
1               5                   10

<210> SEQ ID NO 28
<211> LENGTH: 12
<212> TYPE: PRT
<213> ORGANISM: Artificial Sequence
<220> FEATURE:
<223> OTHER INFORMATION: LCDR1 sequence

<400> SEQUENCE: 28

Arg Ala Ser Gln Ser Val Lys Asn Ser Ser Leu Ala
1               5                   10

<210> SEQ ID NO 29
<211> LENGTH: 11
<212> TYPE: PRT
<213> ORGANISM: Artificial Sequence
<220> FEATURE:
<223> OTHER INFORMATION: LCDR1 sequence

<400> SEQUENCE: 29

Ser Gly Asp Lys Leu Gly Asp Lys Tyr Ala Cys
1               5                   10

<210> SEQ ID NO 30
<211> LENGTH: 11
<212> TYPE: PRT
<213> ORGANISM: Artificial Sequence
```

```
<220> FEATURE:
<223> OTHER INFORMATION: LCDR1 sequence

<400> SEQUENCE: 30

Ser Gly Asp Lys Leu Gly Asp Lys Tyr Val Cys
1               5                   10

<210> SEQ ID NO 31
<211> LENGTH: 11
<212> TYPE: PRT
<213> ORGANISM: Artificial Sequence
<220> FEATURE:
<223> OTHER INFORMATION: LCDR1 sequence

<400> SEQUENCE: 31

Ser Gly Asp Lys Leu Gly Asp Lys Tyr Val Ser
1               5                   10

<210> SEQ ID NO 32
<211> LENGTH: 14
<212> TYPE: PRT
<213> ORGANISM: Artificial Sequence
<220> FEATURE:
<223> OTHER INFORMATION: LCDR1 sequence

<400> SEQUENCE: 32

Thr Gly Thr Ser Ser Asp Val Gly Gly Tyr Asn Tyr Val Ser
1               5                   10

<210> SEQ ID NO 33
<211> LENGTH: 7
<212> TYPE: PRT
<213> ORGANISM: Artificial Sequence
<220> FEATURE:
<223> OTHER INFORMATION: LCDR2 sequence

<400> SEQUENCE: 33

Ala Ala Ser Ser Leu Gln Ser
1               5

<210> SEQ ID NO 34
<211> LENGTH: 7
<212> TYPE: PRT
<213> ORGANISM: Artificial Sequence
<220> FEATURE:
<223> OTHER INFORMATION: LCDR2 sequence

<400> SEQUENCE: 34

Glu Val Ser Lys Arg Pro Ser
1               5

<210> SEQ ID NO 35
<211> LENGTH: 7
<212> TYPE: PRT
<213> ORGANISM: Artificial Sequence
<220> FEATURE:
<223> OTHER INFORMATION: LCDR2 sequence

<400> SEQUENCE: 35

His Asp Asn Lys Arg Pro Ser
1               5

<210> SEQ ID NO 36
<211> LENGTH: 7
<212> TYPE: PRT
<213> ORGANISM: Artificial Sequence
<220> FEATURE:
```

```
<223> OTHER INFORMATION: LCDR2 sequence

<400> SEQUENCE: 36

Gln Asp Ser Lys Arg Pro Ser
1               5

<210> SEQ ID NO 37
<211> LENGTH: 7
<212> TYPE: PRT
<213> ORGANISM: Artificial Sequence
<220> FEATURE:
<223> OTHER INFORMATION: LCDR2 sequence

<400> SEQUENCE: 37

Gln Asp Ser Arg Arg Pro Ser
1               5

<210> SEQ ID NO 38
<211> LENGTH: 7
<212> TYPE: PRT
<213> ORGANISM: Artificial Sequence
<220> FEATURE:
<223> OTHER INFORMATION: LCDR2 sequence

<400> SEQUENCE: 38

Thr Ala Ser Ser Arg Ala Thr
1               5

<210> SEQ ID NO 39
<211> LENGTH: 7
<212> TYPE: PRT
<213> ORGANISM: Artificial Sequence
<220> FEATURE:
<223> OTHER INFORMATION: LCDR2 sequence

<400> SEQUENCE: 39

Trp Ala Ser Thr Arg Glu Ser
1               5

<210> SEQ ID NO 40
<211> LENGTH: 9
<212> TYPE: PRT
<213> ORGANISM: Artificial Sequence
<220> FEATURE:
<223> OTHER INFORMATION: LCDR3 sequence

<400> SEQUENCE: 40

Gln Ala Trp Ala Ser Ser Thr Val Val
1               5

<210> SEQ ID NO 41
<211> LENGTH: 9
<212> TYPE: PRT
<213> ORGANISM: Artificial Sequence
<220> FEATURE:
<223> OTHER INFORMATION: LCDR3 sequence

<400> SEQUENCE: 41

Gln Ala Trp Val Ser Ser Thr Val Val
1               5

<210> SEQ ID NO 42
<211> LENGTH: 9
<212> TYPE: PRT
<213> ORGANISM: Artificial Sequence
<220> FEATURE:
<223> OTHER INFORMATION: LCDR3 sequence
```

<400> SEQUENCE: 42

Gln Gln Ser Ser Ala Pro Pro Trp Thr
1               5

<210> SEQ ID NO 43
<211> LENGTH: 9
<212> TYPE: PRT
<213> ORGANISM: Artificial Sequence
<220> FEATURE:
<223> OTHER INFORMATION: LCDR3 sequence

<400> SEQUENCE: 43

Gln Gln Ser Tyr Ser Thr Pro Leu Thr
1               5

<210> SEQ ID NO 44
<211> LENGTH: 9
<212> TYPE: PRT
<213> ORGANISM: Artificial Sequence
<220> FEATURE:
<223> OTHER INFORMATION: LCDR3 sequence

<400> SEQUENCE: 44

Gln Gln Tyr Tyr Ser Thr Pro Leu Thr
1               5

<210> SEQ ID NO 45
<211> LENGTH: 149
<212> TYPE: PRT
<213> ORGANISM: Macaca fascicularis

<400> SEQUENCE: 45

Met Gln Lys Gly Asp Gln Asn Pro Gln Ile Ala Ala His Val Ile Ser
1               5                   10                  15

Glu Ala Ser Ser Lys Thr Thr Ser Val Leu Gln Trp Ala Glu Lys Gly
                20                  25                  30

Tyr Tyr Thr Met Ser Asn Asn Leu Val Thr Leu Glu Asn Gly Lys Gln
            35                  40                  45

Leu Thr Val Lys Arg Gln Gly Leu Tyr Tyr Ile Tyr Ala Gln Val Thr
        50                  55                  60

Phe Cys Ser Asn Arg Glu Ala Ser Ser Gln Ala Pro Phe Ile Ala Ser
65                  70                  75                  80

Leu Cys Leu Lys Ser Pro Gly Arg Phe Glu Arg Ile Leu Leu Arg Ala
                85                  90                  95

Ala Asn Thr His Ser Ser Ala Lys Pro Cys Gly Gln Gln Ser Ile His
            100                 105                 110

Leu Gly Gly Val Phe Glu Leu Gln Pro Gly Ala Ser Val Phe Val Asn
        115                 120                 125

Val Thr Asp Pro Ser Gln Val Ser His Gly Thr Gly Phe Thr Ser Phe
    130                 135                 140

Gly Leu Leu Lys Leu
145

<210> SEQ ID NO 46
<211> LENGTH: 9
<212> TYPE: PRT
<213> ORGANISM: Artificial Sequence
<220> FEATURE:
<223> OTHER INFORMATION: LCDR3 sequence

<400> SEQUENCE: 46

```
Gln Val Trp Asp Ser Ser Thr Val Val
1               5

<210> SEQ ID NO 47
<211> LENGTH: 10
<212> TYPE: PRT
<213> ORGANISM: Artificial Sequence
<220> FEATURE:
<223> OTHER INFORMATION: LCDR3 sequence

<400> SEQUENCE: 47

Ser Ser Tyr Ala Gly Ser Asn Asn Leu Val
1               5                   10

<210> SEQ ID NO 48
<211> LENGTH: 119
<212> TYPE: PRT
<213> ORGANISM: Artificial Sequence
<220> FEATURE:
<223> OTHER INFORMATION: C40H20

<400> SEQUENCE: 48

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
                20                  25                  30

Ala Met Asn Trp Val Arg Gln Ala Pro Gly Lys Gly Leu Glu Trp Val
            35                  40                  45

Ser Gly Ile Lys Ser Gly Gly Ser Ser Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Val Asp Phe Tyr Arg Ala Leu Asp Tyr Trp Gly Gln Gly
            100                 105                 110

Thr Leu Val Thr Val Ser Ser
        115

<210> SEQ ID NO 49
<211> LENGTH: 122
<212> TYPE: PRT
<213> ORGANISM: Artificial Sequence
<220> FEATURE:
<223> OTHER INFORMATION: C40H21

<400> SEQUENCE: 49

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

Ala Arg Val Arg Tyr Ser Ala Trp Tyr Arg Asp Ser Leu Asp Tyr Trp
            100                 105                 110

Gly Gln Gly Thr Leu Val Thr Val Ser Ser
        115                 120

<210> SEQ ID NO 50
<211> LENGTH: 122
<212> TYPE: PRT
<213> ORGANISM: Artificial Sequence
<220> FEATURE:
<223> OTHER INFORMATION: C40H25

<400> SEQUENCE: 50

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Gly His Pro Ala Trp Trp Arg Asp Ser Leu Asp Tyr Trp
            100                 105                 110

Gly Gln Gly Thr Leu Val Thr Val Ser Ser
        115                 120

<210> SEQ ID NO 51
<211> LENGTH: 122
<212> TYPE: PRT
<213> ORGANISM: Artificial Sequence
<220> FEATURE:
<223> OTHER INFORMATION: C40H26

<400> SEQUENCE: 51

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Ala Asn Ala Ala Tyr Phe Arg Ser Gly Leu Asp Tyr Trp
            100                 105                 110

Gly Gln Gly Thr Leu Val Thr Val Ser Ser
        115                 120

<210> SEQ ID NO 52
<211> LENGTH: 124
<212> TYPE: PRT
<213> ORGANISM: Artificial Sequence

```
<220> FEATURE:
<223> OTHER INFORMATION: C40H29

<400> SEQUENCE: 52

Gln Val Gln Leu Val Gln Ser Gly Ala Glu Val Lys Pro Gly Ser
1               5                   10                  15

Ser Val Lys Val Ser Cys Lys Ala Ser Gly Gly Thr Phe Ser Ser Tyr
            20                  25                  30

Trp Ile Ser Trp Val Arg Gln Ala Pro Gly Gln Gly Leu Glu Trp Met
        35                  40                  45

Gly Tyr Ile Ile Pro Ile Ser Gly Thr Ala Arg Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Pro Gly Tyr Ser Ser Gly Leu Ser Val Asp Tyr Phe Asp
            100                 105                 110

Tyr Trp Gly Gln Gly Thr Leu Val Thr Val Ser Ser
        115                 120

<210> SEQ ID NO 53
<211> LENGTH: 119
<212> TYPE: PRT
<213> ORGANISM: Artificial Sequence
<220> FEATURE:
<223> OTHER INFORMATION: C40H30

<400> SEQUENCE: 53

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Pro Ala Tyr Thr Ile Val Phe Asp Tyr Trp Gly Gln Gly
            100                 105                 110

Thr Leu Val Thr Val Ser Ser
        115

<210> SEQ ID NO 54
<211> LENGTH: 119
<212> TYPE: PRT
<213> ORGANISM: Artificial Sequence
<220> FEATURE:
<223> OTHER INFORMATION: C40H32

<400> SEQUENCE: 54

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

```
Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Pro Val Tyr Ser Leu Val Phe Asp Tyr Trp Gly Gln Gly
                100                 105                 110

Thr Leu Val Thr Val Ser Ser
        115

<210> SEQ ID NO 55
<211> LENGTH: 124
<212> TYPE: PRT
<213> ORGANISM: Artificial Sequence
<220> FEATURE:
<223> OTHER INFORMATION: C40H33

<400> SEQUENCE: 55

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
 50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Arg Arg Tyr Gly Ile Gly Arg Tyr Gly Phe Asp
                100                 105                 110

Tyr Trp Gly Gln Gly Thr Leu Val Thr Val Ser Ser
        115                 120

<210> SEQ ID NO 56
<211> LENGTH: 119
<212> TYPE: PRT
<213> ORGANISM: Artificial Sequence
<220> FEATURE:
<223> OTHER INFORMATION: C40H38

<400> SEQUENCE: 56

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Arg Gly Pro Val Tyr Ser Ser Val Phe Asp Tyr Trp Gly Gln Gly
            100                 105                 110

Thr Leu Val Thr Val Ser Ser
        115
```

<210> SEQ ID NO 57
<211> LENGTH: 121
<212> TYPE: PRT
<213> ORGANISM: Artificial Sequence
<220> FEATURE:
<223> OTHER INFORMATION: C40H48

<400> SEQUENCE: 57

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ile Ile Asn Asn Asn Val Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Gly Gly Asp Tyr Tyr Tyr Gly Met Asp Val Trp Gly
            100                 105                 110

Gln Gly Thr Thr Val Thr Val Ser Ser
        115                 120
```

<210> SEQ ID NO 58
<211> LENGTH: 121
<212> TYPE: PRT
<213> ORGANISM: Artificial Sequence
<220> FEATURE:
<223> OTHER INFORMATION: C40H46

<400> SEQUENCE: 58

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Arg Gly Leu Glu Trp Val
        35                  40                  45

Ser Thr Ile Asn Asn Ser Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu His Met Asn Ser Leu Arg Ala Glu Asp Thr Ala Val Tyr Tyr Cys
                85                  90                  95

Ala Lys Glu Gly Gly Lys Tyr Tyr Tyr Ala Met Asp Val Trp Gly
            100                 105                 110

Gln Gly Thr Thr Val Thr Val Ser Ser
        115                 120
```

<210> SEQ ID NO 59
<211> LENGTH: 121
<212> TYPE: PRT

<213> ORGANISM: Artificial Sequence
<220> FEATURE:
<223> OTHER INFORMATION: C40H45

<400> SEQUENCE: 59

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Ala Met Ser Trp Val Arg Gln Ala Pro Gly Lys Gly Leu Glu Trp Val
        35                  40                  45

Ser Val Ile Ser Asp Ser Gly Gly Arg Thr Tyr Tyr Ala Asp Ser Val
    50                  55                  60

Lys Gly Arg Phe Thr Ile Ser Arg Asp Tyr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Gly Gly Asp Tyr Tyr Tyr Tyr Gly Met Asp Val Trp Gly
            100                 105                 110

Gln Gly Thr Thr Val Thr Val Ser Ser
        115                 120

<210> SEQ ID NO 60
<211> LENGTH: 116
<212> TYPE: PRT
<213> ORGANISM: Artificial Sequence
<220> FEATURE:
<223> OTHER INFORMATION: C40H43

<400> SEQUENCE: 60

Gln Leu Gln Leu Gln Glu Ser Gly Pro Gly Leu Val Lys Pro Ser Glu
1               5                   10                  15

Ile Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Asn Ile Tyr Tyr Arg Gly Asp Thr Tyr Tyr Ser Pro Ser
    50                  55                  60

Leu Lys Ser Arg Val Thr Ile Ser Val Asp Thr Ser Lys Asn Gln Phe
65                  70                  75                  80

Ser Leu Lys Leu Asn Ser Val Thr Ala Ala Asp Thr Ala Val Tyr Tyr
                85                  90                  95

Cys Ala Lys Gly Phe Arg Phe Asp Tyr Trp Gly Gln Gly Thr Leu Val
            100                 105                 110

Thr Val Ser Ser
        115

<210> SEQ ID NO 61
<211> LENGTH: 116
<212> TYPE: PRT
<213> ORGANISM: Artificial Sequence
<220> FEATURE:
<223> OTHER INFORMATION: C40H52

<400> SEQUENCE: 61

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

```
Ser Tyr Tyr Trp Gly Trp Ile Arg Gln Pro Pro Gly Lys Gly Leu Glu
        35                  40                  45

Trp Ile Gly Asn Ile Tyr Tyr Arg Gly Asp Thr Tyr Tyr Ser Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Gly Phe Arg Phe Asp Tyr Trp Gly Gln Gly Thr Leu Val
                100                 105                 110

Thr Val Ser Ser
        115

<210> SEQ ID NO 62
<211> LENGTH: 116
<212> TYPE: PRT
<213> ORGANISM: Artificial Sequence
<220> FEATURE:
<223> OTHER INFORMATION: C40H53

<400> SEQUENCE: 62

Gln Leu Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Ser
                 20                  25                  30

Ser Tyr Tyr Trp Gly Trp Ile Arg Gln Pro Pro Gly Lys Gly Leu Glu
        35                  40                  45

Trp Ile Gly Asn Ile Tyr Tyr Arg Gly Asp Thr Tyr Tyr Ser Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Lys Gly Phe Arg Phe Asp Tyr Trp Gly Gln Gly Thr Leu Val
                100                 105                 110

Thr Val Ser Ser
        115

<210> SEQ ID NO 63
<211> LENGTH: 108
<212> TYPE: PRT
<213> ORGANISM: Artificial Sequence
<220> FEATURE:
<223> OTHER INFORMATION: C40L10

<400> SEQUENCE: 63

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Lys Asn Ser
                 20                  25                  30

Ser Leu Ala Trp Tyr Gln Gln Lys Pro Gly Gln Ala Pro Arg Leu Leu
        35                  40                  45

Ile Tyr Thr Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Ser Ser Ala Pro Pro
```

```
                        85                  90                  95

Trp Thr Phe Gly Gln Gly Thr Lys Val Glu Ile Lys
                100                 105

<210> SEQ ID NO 64
<211> LENGTH: 113
<212> TYPE: PRT
<213> ORGANISM: Artificial Sequence
<220> FEATURE:
<223> OTHER INFORMATION: PH9L2

<400> SEQUENCE: 64

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
                20                  25                  30

Ser Asn Asn Lys Asn Tyr Leu Ala Trp Tyr Gln Gln Lys Pro Gly Gln
                35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Leu Thr Phe Gly Gln Gly Thr Lys Val Glu Ile
                100                 105                 110

Lys

<210> SEQ ID NO 65
<211> LENGTH: 107
<212> TYPE: PRT
<213> ORGANISM: Artificial Sequence
<220> FEATURE:
<223> OTHER INFORMATION: PH9L4

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
                35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys
                100                 105

<210> SEQ ID NO 66
<211> LENGTH: 106
<212> TYPE: PRT
<213> ORGANISM: Artificial Sequence
<220> FEATURE:
<223> OTHER INFORMATION: C40L64

<400> SEQUENCE: 66
```

```
Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Val
            20                  25                  30

Cys Trp Tyr Gln Gln Lys Pro Gly Gln Ser Pro Val Val Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Tyr Tyr Cys Gln Ala Trp Val Ser Ser Thr Val Val
                85                  90                  95

Phe Gly Gly Gly Thr Lys Leu Thr Val Leu
            100                 105

<210> SEQ ID NO 67
<211> LENGTH: 106
<212> TYPE: PRT
<213> ORGANISM: Artificial Sequence
<220> FEATURE:
<223> OTHER INFORMATION: C40L63

<400> SEQUENCE: 67

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Arg Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Cys Gln Ala Trp Ala Ser Ser Thr Val Val
                85                  90                  95

Phe Gly Gly Gly Thr Lys Leu Thr Val Leu
            100                 105

<210> SEQ ID NO 68
<211> LENGTH: 106
<212> TYPE: PRT
<213> ORGANISM: Artificial Sequence
<220> FEATURE:
<223> OTHER INFORMATION: C40L62

<400> SEQUENCE: 68

Ser Tyr Glu Leu Thr Gln Pro Pro Ser Val Ser Val Ser Pro Gly Gln
1               5                   10                  15

Thr Ala Ser Ile Ile Cys Ser Gly Asp Lys Leu Gly Asp Lys Tyr Val
            20                  25                  30

Cys Trp Tyr Gln Gln Lys Pro Gly Gln Ser Pro Val Val Val Ile Tyr
        35                  40                  45

His Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Cys Gln Val Trp Asp Ser Ser Thr Val Val
                85                  90                  95
```

Phe Gly Gly Gly Thr Lys Leu Thr Val Leu
            100                 105

<210> SEQ ID NO 69
<211> LENGTH: 110
<212> TYPE: PRT
<213> ORGANISM: Artificial Sequence
<220> FEATURE:
<223> OTHER INFORMATION: BCML12

<400> SEQUENCE: 69

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asn Asn Leu Val Phe Gly Gly Gly Thr Lys Leu Thr Val Leu
            100                 105                 110

<210> SEQ ID NO 70
<211> LENGTH: 106
<212> TYPE: PRT
<213> ORGANISM: Artificial Sequence
<220> FEATURE:
<223> OTHER INFORMATION: C40L70

<400> SEQUENCE: 70

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Val
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Val Ser Ser Thr Val Val
                85                  90                  95

Phe Gly Gly Gly Thr Lys Leu Thr Val Leu
            100                 105

<210> SEQ ID NO 71
<211> LENGTH: 106
<212> TYPE: PRT
<213> ORGANISM: Artificial Sequence
<220> FEATURE:
<223> OTHER INFORMATION: C40L69

<400> SEQUENCE: 71

Ser Tyr Glu Leu Thr Gln Pro Pro Ser Val Ser Val Ser Pro Gly Gln
1               5                   10                  15

```
Thr Ala Ser Ile Thr Cys Ser Gly Asp Lys Leu Gly Asp Lys Tyr Val
            20                  25                  30

Ser Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Val Ser Thr Val Val
                85                  90                  95

Phe Gly Gly Gly Thr Lys Leu Thr Val Leu
            100                 105

<210> SEQ ID NO 72
<211> LENGTH: 106
<212> TYPE: PRT
<213> ORGANISM: Artificial Sequence
<220> FEATURE:
<223> OTHER INFORMATION: C40L68

<400> SEQUENCE: 72

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Val
            20                  25                  30

Ser Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Met
65                  70                  75                  80

Asp Glu Ala Tyr Tyr Tyr Cys Gln Ala Trp Val Ser Thr Val Val
                85                  90                  95

Phe Gly Gly Gly Thr Lys Leu Thr Val Leu
            100                 105

<210> SEQ ID NO 73
<211> LENGTH: 99
<212> TYPE: PRT
<213> ORGANISM: Homo sapiens

<400> SEQUENCE: 73

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 74
```

<211> LENGTH: 96
<212> TYPE: PRT
<213> ORGANISM: Homo sapiens

<400> SEQUENCE: 74

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95
```

<210> SEQ ID NO 75
<211> LENGTH: 277
<212> TYPE: PRT
<213> ORGANISM: Homo sapiens

<400> SEQUENCE: 75

```
Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
        195                 200                 205

Leu Leu Val Leu Val Phe Ile Lys Lys Val Ala Lys Lys Pro Thr Asn
210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255
```

```
Gly Cys Gln Pro Val Thr Gln Glu Asp Gly Lys Glu Ser Arg Ile Ser
            260                 265                 270

Val Gln Glu Arg Gln
        275

<210> SEQ ID NO 76
<211> LENGTH: 173
<212> TYPE: PRT
<213> ORGANISM: Homo sapiens

<400> SEQUENCE: 76

Glu Pro Pro Thr Ala Cys Arg Glu Lys Gln Tyr Leu Ile Asn Ser Gln
1               5                   10                  15

Cys Cys Ser Leu Cys Gln Pro Gly Gln Lys Leu Val Ser Asp Cys Thr
            20                  25                  30

Glu Phe Thr Glu Thr Glu Cys Leu Pro Cys Gly Glu Ser Glu Phe Leu
        35                  40                  45

Asp Thr Trp Asn Arg Glu Thr His Cys His Gln His Lys Tyr Cys Asp
    50                  55                  60

Pro Asn Leu Gly Leu Arg Val Gln Gln Lys Gly Thr Ser Glu Thr Asp
65                  70                  75                  80

Thr Ile Cys Thr Cys Glu Glu Gly Trp His Cys Thr Ser Glu Ala Cys
                85                  90                  95

Glu Ser Cys Val Leu His Arg Ser Cys Ser Pro Gly Phe Gly Val Lys
            100                 105                 110

Gln Ile Ala Thr Gly Val Ser Asp Thr Ile Cys Glu Pro Cys Pro Val
        115                 120                 125

Gly Phe Phe Ser Asn Val Ser Ser Ala Phe Glu Lys Cys His Pro Trp
    130                 135                 140

Thr Ser Cys Glu Thr Lys Asp Leu Val Val Gln Gln Ala Gly Thr Asn
145                 150                 155                 160

Lys Thr Asp Val Val Cys Gly Pro Gln Asp Arg Leu Arg
                165                 170

<210> SEQ ID NO 77
<211> LENGTH: 278
<212> TYPE: PRT
<213> ORGANISM: Macaca fascicularis

<400> SEQUENCE: 77

Met Val Arg Leu Pro Leu Gln Cys Val Leu Trp Gly Cys Leu Leu Thr
1               5                   10                  15

Ala Val Tyr Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Ser Glu
    50                  55                  60

Ser Glu Phe Leu Asp Thr Trp Asn Arg Glu Thr Arg Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Leu His Cys Met
            100                 105                 110

Ser Glu Ser Cys Glu Ser Cys Val Pro His Arg Ser Cys Leu Pro Gly
        115                 120                 125
```

```
Phe Gly Val Lys Gln Ile Ala Thr Gly Val Ser Asp Thr Ile Cys Glu
    130                 135                 140

Pro Cys Pro Val Gly Phe Ser Asn Val Ser Ser Ala Phe Glu Lys
145                 150                 155                 160

Cys Arg Pro Trp Thr Ser Cys Glu Thr Lys Asp Leu Val Gln Gln
                165                 170                 175

Ala Gly Thr Asn Lys Thr Asp Val Val Cys Gly Pro Gln Asp Arg Gln
            180                 185                 190

Arg Ala Leu Val Val Ile Pro Ile Cys Leu Gly Ile Leu Phe Val Ile
            195                 200                 205

Leu Leu Leu Val Leu Val Phe Ile Lys Lys Val Ala Lys Lys Pro Asn
            210                 215                 220

Asp Lys Ala Pro His Pro Lys Gln Glu Pro Gln Glu Ile Asn Phe Leu
225                 230                 235                 240

Asp Asp Leu Pro Gly Ser Asn Pro Ala Ala Pro Val Gln Glu Thr Leu
                245                 250                 255

His Gly Cys Gln Pro Val Thr Gln Glu Asp Gly Lys Glu Ser Arg Ile
            260                 265                 270

Ser Val Gln Glu Arg Gln
            275

<210> SEQ ID NO 78
<211> LENGTH: 173
<212> TYPE: PRT
<213> ORGANISM: Macaca fascicularis

<400> SEQUENCE: 78

Glu Pro Pro Thr Ala Cys Arg Glu Lys Gln Tyr Leu Ile Asn Ser Gln
1               5                   10                  15

Cys Cys Ser Leu Cys Gln Pro Gly Gln Lys Leu Val Ser Asp Cys Thr
            20                  25                  30

Glu Phe Thr Glu Thr Glu Cys Leu Pro Cys Ser Glu Ser Glu Phe Leu
        35                  40                  45

Asp Thr Trp Asn Arg Glu Thr Arg Cys His Gln His Lys Tyr Cys Asp
50                  55                  60

Pro Asn Leu Gly Leu Arg Val Gln Gln Lys Gly Thr Ser Glu Thr Asp
65                  70                  75                  80

Thr Ile Cys Thr Cys Glu Glu Gly Leu His Cys Met Ser Glu Ser Cys
                85                  90                  95

Glu Ser Cys Val Pro His Arg Ser Cys Leu Pro Gly Phe Gly Val Lys
            100                 105                 110

Gln Ile Ala Thr Gly Val Ser Asp Thr Ile Cys Glu Pro Cys Pro Val
        115                 120                 125

Gly Phe Phe Ser Asn Val Ser Ser Ala Phe Glu Lys Cys Arg Pro Trp
130                 135                 140

Thr Ser Cys Glu Thr Lys Asp Leu Val Gln Gln Ala Gly Thr Asn
145                 150                 155                 160

Lys Thr Asp Val Val Cys Gly Pro Gln Asp Arg Gln Arg
                165                 170

<210> SEQ ID NO 79
<211> LENGTH: 98
<212> TYPE: PRT
<213> ORGANISM: Homo sapiens

<400> SEQUENCE: 79
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Tyr Ser Gly Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 80
<211> LENGTH: 98
<212> TYPE: PRT
<213> ORGANISM: Homo sapiens

<400> SEQUENCE: 80

Gln Val Gln Leu Val Gln Ser Gly Ala Glu Val Lys Lys Pro Gly Ser
1               5                   10                  15

Ser Val Lys Val Ser Cys Lys Ala Ser Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 81
<211> LENGTH: 98
<212> TYPE: PRT
<213> ORGANISM: Homo sapiens

<400> SEQUENCE: 81

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 82

```
<211> LENGTH: 98
<212> TYPE: PRT
<213> ORGANISM: Homo sapiens

<400> SEQUENCE: 82

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 83
<211> LENGTH: 259
<212> TYPE: PRT
<213> ORGANISM: Homo sapiens

<400> SEQUENCE: 83

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
                100                 105                 110

Met Gln Lys Gly Asp Gln Asn Pro Gln Ile Ala Ala His Val Ile Ser
            115                 120                 125

Glu Ala Ser Ser Lys Thr Thr Ser Val Leu Gln Trp Ala Glu Lys Gly
130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240
```

```
Val Thr Asp Pro Ser Gln Val Ser His Gly Thr Gly Phe Thr Ser Phe
                245                 250                 255

Gly Leu Leu

<210> SEQ ID NO 84
<211> LENGTH: 101
<212> TYPE: PRT
<213> ORGANISM: Homo sapiens

<400> SEQUENCE: 84

Asp Ile Val Met Thr Gln Ser Pro Asp Ser Leu Ala Val Ser Leu Gly
  1               5                  10                  15

Glu Arg Ala Thr Ile Asn Cys Lys Ser Ser Gln Ser Val Leu Tyr Ser
             20                  25                  30

Ser Asn Asn Lys Asn Tyr Leu Ala Trp Tyr Gln Gln Lys Pro Gly Gln
         35                  40                  45

Pro Pro Lys Leu Leu Ile Tyr Trp Ala Ser Thr Arg Glu Ser Gly Val
     50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Ser Thr Pro
            100

<210> SEQ ID NO 85
<211> LENGTH: 95
<212> TYPE: PRT
<213> ORGANISM: Homo sapiens

<400> SEQUENCE: 85

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Ser Tyr
             20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro
                 85                  90                  95

<210> SEQ ID NO 86
<211> LENGTH: 94
<212> TYPE: PRT
<213> ORGANISM: Homo sapiens

<400> SEQUENCE: 86

Ser Tyr Glu Leu Thr Gln Pro Pro Ser Val Ser Val Ser Pro Gly Gln
  1               5                  10                  15

Thr Ala Ser Ile Thr Cys Ser Gly Asp Lys Leu Gly Asp Lys Tyr Ala
             20                  25                  30

Cys Trp Tyr Gln Gln Lys Pro Gly Gln Ser Pro Val Leu Val Ile Tyr
         35                  40                  45

Gln Asp Ser Lys Arg Pro Ser Gly Ile Pro Glu Arg Phe Ser Gly Ser
     50                  55                  60
```

```
Asn Ser Gly Asn Thr Ala Thr Leu Thr Ile Ser Gly Thr Gln Ala Met
 65                  70                  75                  80

Asp Glu Ala Asp Tyr Tyr Cys Gln Ala Trp Asp Ser Ser Thr
                 85                  90
```

<210> SEQ ID NO 87
<211> LENGTH: 99
<212> TYPE: PRT
<213> ORGANISM: Homo sapiens

<400> SEQUENCE: 87

```
Gln Ser Ala Leu Thr Gln Pro Pro Ser Ala Ser Gly Ser Pro Gly Gln
  1               5                  10                  15

Ser Val Thr Ile Ser Cys Thr Gly Thr Ser Ser Asp Val Gly Gly Tyr
                 20                  25                  30

Asn Tyr Val Ser Trp Tyr Gln Gln His Pro Gly Lys Ala Pro Lys Leu
                 35                  40                  45

Met Ile Tyr Glu Val Ser Lys Arg Pro Ser Gly Val Pro Asp Arg Phe
 50                  55                  60

Ser Gly Ser Lys Ser Gly Asn Thr Ala Ser Leu Thr Val Ser Gly Leu
 65                  70                  75                  80

Gln Ala Glu Asp Glu Ala Asp Tyr Tyr Cys Ser Ser Tyr Ala Gly Ser
                 85                  90                  95

Asn Asn Phe
```

<210> SEQ ID NO 88
<211> LENGTH: 149
<212> TYPE: PRT
<213> ORGANISM: Homo sapiens

<400> SEQUENCE: 88

```
Met Gln Lys Gly Asp Gln Asn Pro Gln Ile Ala Ala His Val Ile Ser
  1               5                  10                  15

Glu Ala Ser Ser Lys Thr Thr Ser Val Leu Gln Trp Ala Glu Lys Gly
                 20                  25                  30

Tyr Tyr Thr Met Ser Asn Asn Leu Val Thr Leu Glu Asn Gly Lys Gln
                 35                  40                  45

Leu Thr Val Lys Arg Gln Gly Leu Tyr Tyr Ile Tyr Ala Gln Val Thr
 50                  55                  60

Phe Cys Ser Asn Arg Glu Ala Ser Ser Gln Ala Pro Phe Ile Ala Ser
 65                  70                  75                  80

Leu Cys Leu Lys Ser Pro Gly Arg Phe Glu Arg Ile Leu Leu Arg Ala
                 85                  90                  95

Ala Asn Thr His Ser Ser Ala Lys Pro Cys Gly Gln Gln Ser Ile His
                100                 105                 110

Leu Gly Gly Val Phe Glu Leu Gln Pro Gly Ala Ser Val Phe Val Asn
                115                 120                 125

Val Thr Asp Pro Ser Gln Val Ser His Gly Thr Gly Phe Thr Ser Phe
130                 135                 140

Gly Leu Leu Lys Leu
145
```

<210> SEQ ID NO 89
<211> LENGTH: 357
<212> TYPE: DNA
<213> ORGANISM: Artificial Sequence
<220> FEATURE:

<223> OTHER INFORMATION: C40M67 VH DNA

<400> SEQUENCE: 89

```
gaagtgcagc tgctggaaag cggcggcggc ctggtgcagc cgggcggcag cctgcgcctg      60
agctgcgcgg cgagcggctt tacctttagc gactatgcga tgaactgggt gcgccaggcg     120
ccgggcaaag gcctggaatg ggtgagcggg atcaagagcg gcggtagctc caaatattat     180
gcggatagcg tgaaaggccg ctttaccatt agccgcgata cagcaaaaa cacactgtat      240
ctgcagatga cagcctgcg cgcggaagat accgcggtgt attattgcgc gaaacacgtt      300
gactttata gggccttgga ctattggggc cagggcaccc tggtgaccgt gagcagc         357
```

<210> SEQ ID NO 90
<211> LENGTH: 366
<212> TYPE: DNA
<213> ORGANISM: Artificial Sequence
<220> FEATURE:
<223> OTHER INFORMATION: C40M66 VH DNA

<400> SEQUENCE: 90

```
caggtgcagc tggtgcagag cggcgcggaa gtgaaaaaac cgggcagcag cgtgaaagtg      60
agctgcaaag cgagcggcgg cacctttagc agctatgcga ttagctgggt gcgccaggcg     120
ccgggccagg gcctggaatg gatgggcggc attattccga tttttggcac cgcgaactat     180
gcgcagaaat tcagggccg cgtgaccatt accgcgatg aaagcaccag caccgcgtat       240
atggaactga gcagcctgcg cagcgaagat accgcggtgt attattgcgc gcgcgttcgg     300
tattcggcgt ggtataggga ctctttggac tattggggcc agggcaccct ggtgacagtc     360
tcgagt                                                                366
```

<210> SEQ ID NO 91
<211> LENGTH: 366
<212> TYPE: DNA
<213> ORGANISM: Artificial Sequence
<220> FEATURE:
<223> OTHER INFORMATION: C40M63 VH DNA

<400> SEQUENCE: 91

```
caggtgcagc tggtgcagag cggcgcggaa gtgaaaaaac cgggcagcag cgtgaaagtg      60
agctgcaaag cgagcggcgg cacctttagc agctatgcga ttagctgggt gcgccaggcg     120
ccgggccagg gcctggaatg gatgggcggc attattccga tttttggcac cgcgaactat     180
gcgcagaaat tcagggccg cgtgaccatt accgcgatg aaagcaccag caccgcgtat       240
atggaactga gcagcctgcg cagcgaagat accgcggtgt attattgcgc gcgcgtaggc     300
catccggctt ggtggcgtga ttcgttggac tattggggcc agggcaccct ggtgaccgtg     360
agcagc                                                                366
```

<210> SEQ ID NO 92
<211> LENGTH: 366
<212> TYPE: DNA
<213> ORGANISM: Artificial Sequence
<220> FEATURE:
<223> OTHER INFORMATION: C40M62 VH DNA

<400> SEQUENCE: 92

```
caggtgcagc tggtgcagag cggcgcggaa gtgaaaaaac cgggcagcag cgtgaaagtg      60
agctgcaaag cgagcggcgg cacctttagc agctatgcga ttagctgggt gcgccaggcg     120
ccgggccagg gcctggaatg gatgggcggc attattccga tttttggcac cgcgaactat     180
```

```
gcgcagaaat tcagggccg cgtgaccatt accgcggatg aaagcaccag caccgcgtat      240
atggaactga gcagcctgcg cagcgaagat accgcggtgt attattgcgc gcgcgttgcc      300
aacgctgcgt atttaggtc tggcttggac tattggggcc agggcaccct ggtgaccgtg      360
agcagc                                                                366

<210> SEQ ID NO 93
<211> LENGTH: 372
<212> TYPE: DNA
<213> ORGANISM: Artificial Sequence
<220> FEATURE:
<223> OTHER INFORMATION: C40M59 VH DNA

<400> SEQUENCE: 93
caggtgcagc tggtgcagag cggcgcggaa gtgaaaaaac cgggcagcag cgtgaaagtg       60
agctgcaaag cgagcggcgg caccttcagc tcctactgga ttagctgggt cgccaggcg      120 ccgggccagg gcctggaatg gatgggctac attattccga tcagtggcac tgcccgctac      180
gcgcagaaat tcagggccg cgtgaccatt accgctgatg aaagcaccag caccgcgtat      240
atggaactga gcagcctgcg cagcgaagat accgcggtgt attattgcgc gcgcgaacca      300
ggctacagta gtggcctgag cgttgactac tttgattact ggggccaggg caccctggtg      360
acagtctcga gt                                                         372

<210> SEQ ID NO 94
<211> LENGTH: 357
<212> TYPE: DNA
<213> ORGANISM: Artificial Sequence
<220> FEATURE:
<223> OTHER INFORMATION: C40M58 VH DNA

<400> SEQUENCE: 94
gaagtgcagc tgctggaaag cggcggcggc ctggtgcagc cgggcggcag cctgcgcctg       60
agctgcgcgg cgagcggctt tacctttagc agctatgcga tgagctgggt cgccaggcg      120 ccgggcaaag gcctggaatg ggtgagcgcg atcagcggct ccgtggctc cacatattat      180 gcggatagcg tgaaaggccg ctttaccatt tcacgagata cagcaaaaa caccctgtat      240 ctgcagatga acagcctgcg cgcggaagat accgcggtgt attattgcgc gcgcggtcca      300
gcatacacta tcgttttga ttattggggc cagggcaccc tggtgacagt ctcgagt         357

<210> SEQ ID NO 95
<211> LENGTH: 357
<212> TYPE: DNA
<213> ORGANISM: Artificial Sequence
<220> FEATURE:
<223> OTHER INFORMATION: C40M56 VH DNA

<400> SEQUENCE: 95
gaagtgcagc tgctggaaag cggcggcggc ctggtgcagc cgggcggcag cctgcgcctg       60
agctgcgcgg cgagcggctt tacctttagc agctatgcga tgagctgggt cgccaggcg      120 ccgggcaaag gcctggaatg ggtgagcgcg atcagcggct ccgtggctc cacatattat      180 gcggatagcg tgaaaggccg ctttaccatt tcacgagata cagcaaaaa caccctgtat      240 ctgcagatga acagcctgcg cgcggaagat accgcggtgt attattgcgc gcgcggtcct      300
gtttattctc tggtttttga ctactggggc cagggcaccc tggtgacagt ctcgagt         357

<210> SEQ ID NO 96
```

<210> SEQ ID NO 96
<211> LENGTH: 372
<212> TYPE: DNA
<213> ORGANISM: Artificial Sequence
<220> FEATURE:
<223> OTHER INFORMATION: C40M55 VH DNA

<400> SEQUENCE: 96

```
caggtgcagc tggtgcagag cggcgcggaa gtgaaaaaac cgggcagcag cgtgaaagtg      60
agctgcaaag cgagcggcgg caccttcagc agctatgcga ttagctgggt gcgccaggcg     120
ccgggccagg gcctggaatg gatgggcggc attattccga tttttggcac cgctaactac     180
gcgcagaaat ttcagggccg cgtgaccatt accgctgatg aaagcaccag caccgcgtat     240
atggaactga gcagcctgcg cagcgaagat accgcggtgt attattgcgc gcgcgatggt     300
tatcggcggt atggcatcgg tcgttacggt ttcgattatt ggggccaggg caccctggtg     360
acagtctcga gt                                                         372
```

<210> SEQ ID NO 97
<211> LENGTH: 357
<212> TYPE: DNA
<213> ORGANISM: Artificial Sequence
<220> FEATURE:
<223> OTHER INFORMATION: C40M51 VH DNA

<400> SEQUENCE: 97

```
gaagtgcagc tgctggaaag cggcggcggc ctggtgcagc cgggcggcag cctgcgcctg      60
agctgcgcgg cgagcggctt taccttagc agctatgcga tgagctgggt gcgccaggcg     120
ccgggcaaag gcctggaatg ggtgagcgcg atcagcggct ccgtggctc cacatattat     180
gcggatagcg tgaaaggccg ctttaccatt tcacgagata acagcaaaaa caccctgtat     240
ctgcagatga acagcctgcg cgcggaagat accgcggtgt attgcgc gcgcggccca     300
gtttattcta gcgttttcga ctattgggc cagggcaccc tggtgacagt ctcgagt         357
```

<210> SEQ ID NO 98
<211> LENGTH: 363
<212> TYPE: DNA
<213> ORGANISM: Artificial Sequence
<220> FEATURE:
<223> OTHER INFORMATION: C40M18 VH DNA

<400> SEQUENCE: 98

```
gaggtgcagc tggtggaatc tggcggagga ctggtgcagc ctggcggcag cctgagactg      60
tcttgtgccg ccagcggctt caccttcagc agctacgcta tgagctgggt ccgacaggcc     120
cctggcaagg gactggaatg ggtgtccatc atcaacaaca cgtgggccg gacctactac     180
gccgacagcg tgaagggcag attcaccatc agcggaca acagcaagaa caccctgtac     240
ctgcagatga acagcctgcg ggccgaggac accgccgtgt actattgtgc caaagagggc     300
ggcgattact actactacgg catggacgtg tggggccagg gcaccaccgt gacagtgtca     360
tct                                                                  363
```

<210> SEQ ID NO 99
<211> LENGTH: 363
<212> TYPE: DNA
<213> ORGANISM: Artificial Sequence
<220> FEATURE:
<223> OTHER INFORMATION: C40M17 VH DNA

<400> SEQUENCE: 99

```
gaggtgcagc tggtggaatc tggcggagga ctggtgcagc ctggcggcag cctgagactg      60
```

| | |
|---|---|
| tcttgtgccg ccagcggctt caccttcagc agctacgcta tgagctgggt ccgacaggcc | 120 |
| cctggcagag gactcgagtg ggtgtccacc atcaacaaca gcggcggagg cacctactac | 180 |
| gccgacagcg tgaagggcag attcaccatc agccgggaca acagcaagaa caccctgtac | 240 |
| ctgcacatga acagcctgcg ggccgaggac accgccgtgt actattgtgc aaagagggc | 300 |
| ggcaagtact actactatgc catggacgtg tggggccagg gcaccaccgt gacagtgtca | 360 |
| tct | 363 |

<210> SEQ ID NO 100
<211> LENGTH: 363
<212> TYPE: DNA
<213> ORGANISM: Artificial Sequence
<220> FEATURE:
<223> OTHER INFORMATION: C40M12 VH DNA

<400> SEQUENCE: 100

| | |
|---|---|
| gaggtgcagc tggtggaatc tggcggagga ctggtgcagc ctggcggcag cctgagactg | 60 |
| tcttgtgccg ccagcggctt caccttcggc agctacgcta tgagctgggt ccgacaggcc | 120 |
| cctggcaagg gactggaatg ggtgtccgtg atcagcgaca gcggcggcag aacctactac | 180 |
| gccgacagcg tgaagggccg gttcaccatc agccgggact acagcaagaa caccctgtac | 240 |
| ctgcagatga acagcctgcg ggccgaggac accgccgtgt actattgtgc aaagagggc | 300 |
| ggcgattact actactacgg catggacgtg tggggccagg gcaccaccgt gacagtgtca | 360 |
| tct | 363 |

<210> SEQ ID NO 101
<211> LENGTH: 348
<212> TYPE: DNA
<213> ORGANISM: Artificial Sequence
<220> FEATURE:
<223> OTHER INFORMATION: C40M9 VH DNA

<400> SEQUENCE: 101

| | |
|---|---|
| cagctccagc tgcaggaatc tggccctggc ctggtcaagc ccagcgagat cctgagcctg | 60 |
| acctgtaccg tgtccggcgg cagcatcagc agcagctctt actactgggg ctggatccgg | 120 |
| cagcctcccg gcaagggact ggaatggatc ggcaacatct actaccgggg cgacacctac | 180 |
| tacagcccca gcctgaagtc cagagtgacc atcagcgtgg acaccagcaa gaaccagttc | 240 |
| tccctgaagc tgaacagcgt gacagccgcc gacaccgccg tgtactactg cgccaagggc | 300 |
| ttcagattcg attactgggg ccagggcacc ctggtcaccg tgtcatct | 348 |

<210> SEQ ID NO 102
<211> LENGTH: 348
<212> TYPE: DNA
<213> ORGANISM: Artificial Sequence
<220> FEATURE:
<223> OTHER INFORMATION: C40M105 VH DNA

<400> SEQUENCE: 102

| | |
|---|---|
| cagctgcagc tgcaggagag cggccccggc ctggtgaagc ccagcgagac cctgagcctg | 60 |
| acctgcaccg tgacggcgg cagcatcagc agcagcagct actactgggg ctggatccgg | 120 |
| cagcccccg gcaagggcct ggagtggatc ggcaacatct actaccgggg cgacacctac | 180 |
| tacagcccca gcctgaagag ccgggtgacc atcagcgtgg acaccagcaa gaaccagttc | 240 |
| agcctgaagc tgagcagcgt gaccgccgcc gacaccgccg tgtactactg cgcccggggc | 300 |

```
ttccggttcg actactgggg ccagggcacc ctggtgaccg tgagcagc                   348
```

<210> SEQ ID NO 103
<211> LENGTH: 348
<212> TYPE: DNA
<213> ORGANISM: Artificial Sequence
<220> FEATURE:
<223> OTHER INFORMATION: C40M121 VH DNA

<400> SEQUENCE: 103

```
cagctgcagc tgcaggagag cggccccggc ctggtgaagc ccagcgagac cctgagcctg        60
acctgcaccg tgagcggcgg cagcatcagc agcagcagct actactgggg ctggatccgg       120
cagccccccg gcaagggcct ggagtggatc ggcaacatct actaccgggg cgacacctac       180
tacagcccca gcctgaagag ccgggtgacc atcagcgtgg acaccagcaa gaaccagttc       240
agcctgaagc tgagcagcgt gaccgccgcc gacaccgccg tgtactactg cgccaagggc       300
ttccggttcg actactgggg ccagggcacc ctggtgaccg tgagcagc                   348
```

<210> SEQ ID NO 104
<211> LENGTH: 324
<212> TYPE: DNA
<213> ORGANISM: Artificial Sequence
<220> FEATURE:
<223> OTHER INFORMATION: C40M67 VL DNA

<400> SEQUENCE: 104

```
gaaattgtgc tgacccagag cccgggcacc ctgagcctga gcccgggcga acgcgcgacc        60
ctgagctgcc gcgcgagcca gagcgttaaa aatagcagtc tggcgtggta tcagcagaaa       120
ccgggccagg cgccgcgcct gctgatttat actgcgagca gccgcgcgac cggcattccg       180
gatcgcttta gcggcagcgg cagcggcacc gatttttaccc tgaccattag ccgcctggaa       240
ccggaagatt ttgcggtgta ttattgccag cagtcctccg cacctccgtg gacttttggc       300
cagggcacca aagtggaaat taaa                                              324
```

<210> SEQ ID NO 105
<211> LENGTH: 339
<212> TYPE: DNA
<213> ORGANISM: Artificial Sequence
<220> FEATURE:
<223> OTHER INFORMATION: C40M66 VL DNA

<400> SEQUENCE: 105

```
gacatcgtga tgacccagag ccccgacagc ctggccgtga gcctgggcga gcgggccacc        60
atcaactgca agagcagcca gagcgtgctg tacagcagca acaacaagaa ctacctggcc       120
tggtaccagc agaagcccgg ccagccccccc aagctgctga tctactgggc cagcacccgg       180
gagagcggcg tgcccgaccg gttcagcggc agcggcagcg gcaccgactt caccctgacc       240
atcagcagcc tgcaggccga ggacgtggcc gtgtactact gccagcagta ctacagcacc       300
cccctgacct tcggcaggg caccaaggtg gagatcaag                              339
```

<210> SEQ ID NO 106
<211> LENGTH: 321
<212> TYPE: DNA
<213> ORGANISM: Artificial Sequence
<220> FEATURE:
<223> OTHER INFORMATION: C40M59 VL DNA

<400> SEQUENCE: 106

```
gacatccaga tgacccagag ccccagcagc ctgagcgcca gcgtgggcga ccgggtgacc        60
```

```
atcacctgcc gggccagcca gagcatcagc agctacctga actggtacca gcagaagccc    120
ggcaaggccc ccaagctgct gatctacgcc gccagcagca tgcagagcgg cgtgcccagc    180
cggttcagcg gcagcggcag cggcaccgac ttcaccctga ccatcagcag cctgcagccc    240
gaggacttcg ccacctacta ctgccagcag agctacagca ccccccctgac cttcggccag   300 ggcaccaagg tggagatcaa g                                              321
```

```
<210> SEQ ID NO 107
<211> LENGTH: 318
<212> TYPE: DNA
<213> ORGANISM: Artificial Sequence
<220> FEATURE:
<223> OTHER INFORMATION: C40M18 VL DNA

<400> SEQUENCE: 107
```

```
tcctacgagc tgacccagcc tccctccgtg tctgtgtctc ctggccagac cgccagcatc     60
acctgtagcg gcgacaagct gggcgacaaa tacgtgtgct ggtatcagca gaagcccggc   120
cagagccccg tggtggtcat ctaccaggac agcaagaggc ccagcggcat ccccgagaga   180
ttcagcggca gcaacagcgg caataccgcc accctgacca tcagcggcac ccaggccatg   240
gacgaggcct actactactg ccaggcttgg gtgtccagca ccgtggtgtt tggcggaggc   300
accaagctga ccgtgctg                                                  318
```

```
<210> SEQ ID NO 108
<211> LENGTH: 318
<212> TYPE: DNA
<213> ORGANISM: Artificial Sequence
<220> FEATURE:
<223> OTHER INFORMATION: C40M17 VL DNA

<400> SEQUENCE: 108
```

```
tcctacgagc tgacccagcc tccctccgtg tctgtgtctc ctggccagac cgccagcatc     60
acctgtagcg gcgacaagct gggcgataag tacgcctgct ggtatcagca gaagcccggc   120
cagagccccg tgctggtcat ctaccaggac agcagaaggc ccagcggcat ccccgagaga   180
ttcagcggca gcaacagcgg caataccgcc accctgacca tcagcggcac ccaggccatg   240
gacgaggccg attactattg tcaggcctgg gccagcagca ccgtggtgtt tggcggcgga   300
acaaagctga ccgtgctg                                                  318
```

```
<210> SEQ ID NO 109
<211> LENGTH: 318
<212> TYPE: DNA
<213> ORGANISM: Artificial Sequence
<220> FEATURE:
<223> OTHER INFORMATION: C40M12 VL DNA

<400> SEQUENCE: 109
```

```
tcctacgagc tgacccagcc tccctccgtg tctgtgtctc ctggccagac cgccagcatc     60
atctgcagcg gcgacaagct gggcgacaaa tacgtgtgct ggtatcagca gaagcccggc   120
cagagccccg tggtggtcat ctaccacgac aacaagaggc ccagcggcat ccccgagaga   180
ttcagcggca gcaacagcgg caataccgcc accctgacca tcagcggcac ccaggccatg   240
gacgaggccg actactactg ccaggtctgg gacagcagca ccgtggtgtt tggcggaggc   300
accaagctga ccgtgctg                                                  318
```

```
<210> SEQ ID NO 110
```

```
<211> LENGTH: 330
<212> TYPE: DNA
<213> ORGANISM: Artificial Sequence
<220> FEATURE:
<223> OTHER INFORMATION: C40M9 VL DNA

<400> SEQUENCE: 110
cagtctgccc tgacacagcc tcctagcgcc tctggctctc ctggccagag cgtgaccatc      60
agctgtaccg gcaccagctc cgacgtgggc ggctacaact acgtgtcctg gtatcagcag     120
caccccggca aggcccctaa gctgatgatc tacgaggtgt ccaagcggcc cagcggcgtg     180
ccagatagat tcagcggcag caagagcggc aacaccgcca gcctgacagt gtctggactg     240
caggccgagg acgaggccga ctactactgt agcagctacg ccggcagcaa caacctggtg     300
ttcggcggag gcaccaagct gaccgtgctg                                      330

<210> SEQ ID NO 111
<211> LENGTH: 318
<212> TYPE: DNA
<213> ORGANISM: Artificial Sequence
<220> FEATURE:
<223> OTHER INFORMATION: C40M102 VL DNA

<400> SEQUENCE: 111
agctacgagc tgacccagcc ccccagcgtg agcgtgagcc ccggccagac cgccagcatc      60
acctgcagcg gcgacaagct gggcgacaag tacgtgtgct ggtaccagca gaagcccggc     120
cagagccccg tgctggtgat ctaccaggac agcaagcggc ccagcggcat ccccgagcgg     180
ttcagcggca gcaacagcgg caacaccgcc accctgacca tcagcggcac ccaggccatg     240
gacgaggccg actactactg ccaggcctgg gtgagcagca ccgtggtgtt cggcggcggc     300
accaagctga ccgtgctg                                                   318

<210> SEQ ID NO 112
<211> LENGTH: 318
<212> TYPE: DNA
<213> ORGANISM: Artificial Sequence
<220> FEATURE:
<223> OTHER INFORMATION: C40M103 VL DNA

<400> SEQUENCE: 112
agctacgagc tgacccagcc ccccagcgtg agcgtgagcc ccggccagac cgccagcatc      60
acctgcagcg gcgacaagct gggcgacaag tacgtgagct ggtaccagca gaagcccggc     120
cagagccccg tgctggtgat ctaccaggac agcaagcggc ccagcggcat ccccgagcgg     180
ttcagcggca gcaacagcgg caacaccgcc accctgacca tcagcggcac ccaggccatg     240
gacgaggccg actactactg ccaggcctgg gtgagcagca ccgtggtgtt cggcggcggc     300
accaagctga ccgtgctg                                                   318

<210> SEQ ID NO 113
<211> LENGTH: 318
<212> TYPE: DNA
<213> ORGANISM: Artificial Sequence
<220> FEATURE:
<223> OTHER INFORMATION: C40M104 VL DNA

<400> SEQUENCE: 113
agctacgagc tgacccagcc ccccagcgtg agcgtgagcc ccggccagac cgccagcatc      60
acctgcagcg gcgacaagct gggcgacaag tacgtgagct ggtaccagca gaagcccggc     120
cagagccccg tggtggtgat ctaccaggac agcaagcggc ccagcggcat ccccgagcgg     180
```

```
ttcagcggca gcaacagcgg caacaccgcc accctgacca tcagcggcac ccaggccatg    240
gacgaggcct actactactg ccaggcctgg gtgagcagca ccgtggtgtt cggcggcggc    300
accaagctga ccgtgctg                                                   318
```

<210> SEQ ID NO 114
<211> LENGTH: 449
<212> TYPE: PRT
<213> ORGANISM: Artificial Sequence
<220> FEATURE:
<223> OTHER INFORMATION: C40M67 heavy chain

<400> SEQUENCE: 114

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Asn Trp Val Arg Gln Ala Pro Gly Lys Gly Leu Glu Trp Val
        35                  40                  45

Ser Gly Ile Lys Ser Gly Gly Ser Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Val Asp Phe Tyr Arg Ala Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335
```

```
Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 115
<211> LENGTH: 452
<212> TYPE: PRT
<213> ORGANISM: Artificial Sequence
<220> FEATURE:
<223> OTHER INFORMATION: C40M66 heavy chain

<400> SEQUENCE: 115

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Arg Tyr Ser Ala Trp Tyr Arg Asp Ser Leu Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Val Glu Pro Lys Ser
    210                 215                 220

Cys Asp Lys Thr His Thr Cys Pro Pro Cys Pro Ala Pro Glu Leu Leu
225                 230                 235                 240
```

-continued

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 116
<211> LENGTH: 452
<212> TYPE: PRT
<213> ORGANISM: Artificial Sequence
<220> FEATURE:
<223> OTHER INFORMATION: C40M63 heavy chain

<400> SEQUENCE: 116

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Gly His Pro Ala Trp Trp Arg Asp Ser Leu Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

-continued

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
        180                 185                 190

Val Pro Ser Ser Ser Leu Gly Thr Gln Thr Tyr Ile Cys Asn Val Asn
    195                 200                 205

His Lys Pro Ser Asn Thr Lys Val Asp Lys Lys Val Glu Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 117
<211> LENGTH: 452
<212> TYPE: PRT
<213> ORGANISM: Artificial Sequence
<220> FEATURE:
<223> OTHER INFORMATION: C40M62 heavy chain

<400> SEQUENCE: 117

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

```
Gly Gly Ile Ile Pro Ile Phe Gly Thr Ala Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Val Ala Asn Ala Ala Tyr Phe Arg Ser Gly Leu Asp Tyr Trp
                100                 105                 110

Gly Gln Gly Thr Leu Val Thr Val Ser Ser Ala Ser Thr Lys Gly Pro
                115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
                195                 200                 205

His Lys Pro Ser Asn Thr Lys Val Asp Lys Lys Val Glu Pro Lys Ser
                210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
                275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Glu Glu Met Thr Lys Asn Gln Val
                355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
                435                 440                 445

Ser Pro Gly Lys
450
```

-continued

```
<210> SEQ ID NO 118
<211> LENGTH: 454
<212> TYPE: PRT
<213> ORGANISM: Artificial Sequence
<220> FEATURE:
<223> OTHER INFORMATION: C40M59 heavy chain

<400> SEQUENCE: 118
```

| | | | | | | | | | | | | | | | |
|---|---|---|---|---|---|---|---|---|---|---|---|---|---|---|---|
| Gln | Val | Gln | Leu | Val | Gln | Ser | Gly | Ala | Glu | Val | Lys | Pro | Gly | Ser | |
| 1 | | | | 5 | | | | | 10 | | | | | 15 | |
| Ser | Val | Lys | Val | Ser | Cys | Lys | Ala | Ser | Gly | Gly | Thr | Phe | Ser | Ser | Tyr |
| | | | 20 | | | | | 25 | | | | | 30 | | |
| Trp | Ile | Ser | Trp | Val | Arg | Gln | Ala | Pro | Gly | Gln | Gly | Leu | Glu | Trp | Met |
| | | 35 | | | | | 40 | | | | | 45 | | | |
| Gly | Tyr | Ile | Ile | Pro | Ile | Ser | Gly | Thr | Ala | Arg | Tyr | Ala | Gln | Lys | Phe |
| | 50 | | | | | 55 | | | | | 60 | | | | |
| Gln | Gly | Arg | Val | Thr | Ile | Thr | Ala | Asp | Glu | Ser | Thr | Ser | Thr | Ala | Tyr |
| 65 | | | | | 70 | | | | | 75 | | | | | 80 |
| Met | Glu | Leu | Ser | Ser | Leu | Arg | Ser | Glu | Asp | Thr | Ala | Val | Tyr | Tyr | Cys |
| | | | | 85 | | | | | 90 | | | | | 95 | |
| Ala | Arg | Glu | Pro | Gly | Tyr | Ser | Ser | Gly | Leu | Ser | Val | Asp | Tyr | Phe | Asp |
| | | | 100 | | | | | 105 | | | | | 110 | | |
| Tyr | Trp | Gly | Gln | Gly | Thr | Leu | Val | Thr | Val | Ser | Ser | Ala | Ser | Thr | Lys |
| | | 115 | | | | | 120 | | | | | 125 | | | |
| Gly | Pro | Ser | Val | Phe | Pro | Leu | Ala | Pro | Ser | Ser | Lys | Ser | Thr | Ser | Gly |
| | 130 | | | | | 135 | | | | | 140 | | | | |
| Gly | Thr | Ala | Ala | Leu | Gly | Cys | Leu | Val | Lys | Asp | Tyr | Phe | Pro | Glu | Pro |
| 145 | | | | | 150 | | | | | 155 | | | | | 160 |
| Val | Thr | Val | Ser | Trp | Asn | Ser | Gly | Ala | Leu | Thr | Ser | Gly | Val | His | Thr |
| | | | | 165 | | | | | 170 | | | | | 175 | |
| Phe | Pro | Ala | Val | Leu | Gln | Ser | Ser | Gly | Leu | Tyr | Ser | Leu | Ser | Ser | Val |
| | | | 180 | | | | | 185 | | | | | 190 | | |
| Val | Thr | Val | Pro | Ser | Ser | Ser | Leu | Gly | Thr | Gln | Thr | Tyr | Ile | Cys | Asn |
| | | 195 | | | | | 200 | | | | | 205 | | | |
| Val | Asn | His | Lys | Pro | Ser | Asn | Thr | Lys | Val | Asp | Lys | Lys | Val | Glu | Pro |
| | 210 | | | | | 215 | | | | | 220 | | | | |
| Lys | Ser | Cys | Asp | Lys | Thr | His | Thr | Cys | Pro | Pro | Cys | Pro | Ala | Pro | Glu |
| 225 | | | | | 230 | | | | | 235 | | | | | 240 |
| Leu | Leu | Gly | Gly | Pro | Ser | Val | Phe | Leu | Phe | Pro | Pro | Lys | Pro | Lys | Asp |
| | | | | 245 | | | | | 250 | | | | | 255 | |
| Thr | Leu | Met | Ile | Ser | Arg | Thr | Pro | Glu | Val | Thr | Cys | Val | Val | Val | Asp |
| | | | 260 | | | | | 265 | | | | | 270 | | |
| Val | Ser | His | Glu | Asp | Pro | Glu | Val | Lys | Phe | Asn | Trp | Tyr | Val | Asp | Gly |
| | | 275 | | | | | 280 | | | | | 285 | | | |
| Val | Glu | Val | His | Asn | Ala | Lys | Thr | Lys | Pro | Arg | Glu | Glu | Gln | Tyr | Asn |
| | 290 | | | | | 295 | | | | | 300 | | | | |
| Ser | Thr | Tyr | Arg | Val | Val | Ser | Val | Leu | Thr | Val | Leu | His | Gln | Asp | Trp |
| 305 | | | | | 310 | | | | | 315 | | | | | 320 |
| Leu | Asn | Gly | Lys | Glu | Tyr | Lys | Cys | Lys | Val | Ser | Asn | Lys | Ala | Leu | Pro |
| | | | | 325 | | | | | 330 | | | | | 335 | |
| Ala | Pro | Ile | Glu | Lys | Thr | Ile | Ser | Lys | Ala | Lys | Gly | Gln | Pro | Arg | Glu |
| | | | 340 | | | | | 345 | | | | | 350 | | |
| Pro | Gln | Val | Tyr | Thr | Leu | Pro | Pro | Ser | Arg | Glu | Glu | Met | Thr | Lys | Asn |
| | | 355 | | | | | 360 | | | | | 365 | | | |
| Gln | Val | Ser | Leu | Thr | Cys | Leu | Val | Lys | Gly | Phe | Tyr | Pro | Ser | Asp | Ile |

```
            370                 375                 380
Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
                435                 440                 445

Ser Leu Ser Pro Gly Lys
                450

<210> SEQ ID NO 119
<211> LENGTH: 449
<212> TYPE: PRT
<213> ORGANISM: Artificial Sequence
<220> FEATURE:
<223> OTHER INFORMATION: C40M58 heavy chain

<400> SEQUENCE: 119

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
                35                  40                  45

Ser Ala Ile Ser Gly Ser Gly Gly Ser Thr Tyr Tyr Ala Asp Ser Val
                50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Pro Ala Tyr Thr Ile Val Phe Asp Tyr Trp Gly Gln Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
                130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
                210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
```

```
                275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Glu Glu Met Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
Lys

<210> SEQ ID NO 120
<211> LENGTH: 449
<212> TYPE: PRT
<213> ORGANISM: Artificial Sequence
<220> FEATURE:
<223> OTHER INFORMATION: C40M56 heavy chain

<400> SEQUENCE: 120

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ala Ile Ser Gly Ser Gly Gly Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Gly Pro Val Tyr Ser Leu Val Phe Asp Tyr Trp Gly Gln Gly
            100                 105                 110
Thr Leu Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
```

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 121
<211> LENGTH: 454
<212> TYPE: PRT
<213> ORGANISM: Artificial Sequence
<220> FEATURE:
<223> OTHER INFORMATION: C40M55 heavy chain

<400> SEQUENCE: 121

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

```
Ala Arg Asp Gly Tyr Arg Arg Tyr Gly Ile Gly Arg Tyr Gly Phe Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 122
<211> LENGTH: 449
<212> TYPE: PRT
<213> ORGANISM: Artificial Sequence
<220> FEATURE:
<223> OTHER INFORMATION: C40M51 heavy chain

<400> SEQUENCE: 122
```

-continued

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Pro Val Tyr Ser Ser Val Phe Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
```

```
                420              425              430
Ala Leu His Asn His Tyr Thr Gln Lys Ser Leu Ser Leu Ser Pro Gly
        435              440              445
Lys

<210> SEQ ID NO 123
<211> LENGTH: 451
<212> TYPE: PRT
<213> ORGANISM: Artificial Sequence
<220> FEATURE:
<223> OTHER INFORMATION: C40M18 heavy chain

<400> SEQUENCE: 123

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ile Ile Asn Asn Asn Val Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Gly Gly Asp Tyr Tyr Tyr Gly Met Asp Val Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335
```

```
Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
        450

<210> SEQ ID NO 124
<211> LENGTH: 451
<212> TYPE: PRT
<213> ORGANISM: Artificial Sequence
<220> FEATURE:
<223> OTHER INFORMATION: C40M17 heavy chain

<400> SEQUENCE: 124

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Arg Gly Leu Glu Trp Val
            35                  40                  45

Ser Thr Ile Asn Asn Ser Gly Gly Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu His Met Asn Ser Leu Arg Ala Glu Asp Thr Ala Val Tyr Tyr Cys
                85                  90                  95

Ala Lys Glu Gly Gly Lys Tyr Tyr Tyr Ala Met Asp Val Trp Gly
            100                 105                 110

Gln Gly Thr Thr Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Val Glu Pro Lys Ser Cys
        210                 215                 220

Asp Lys Thr His Thr Cys Pro Pro Cys Pro Ala Pro Glu Leu Leu Gly
225                 230                 235                 240
```

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 125
<211> LENGTH: 451
<212> TYPE: PRT
<213> ORGANISM: Artificial Sequence
<220> FEATURE:
<223> OTHER INFORMATION: C40M12 heavy chain

<400> SEQUENCE: 125

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Ala Met Ser Trp Val Arg Gln Ala Pro Gly Lys Gly Leu Glu Trp Val
        35                  40                  45

Ser Val Ile Ser Asp Ser Gly Gly Arg Thr Tyr Tyr Ala Asp Ser Val
    50                  55                  60

Lys Gly Arg Phe Thr Ile Ser Arg Asp Tyr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Gly Gly Asp Tyr Tyr Tyr Tyr Gly Met Asp Val Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

```
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Leu Gly Thr Gln Thr Tyr Ile Cys Asn Val Asn His
    195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
        340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
        420                 425                 430

His Glu Ala Leu His Asn His Tyr Thr Gln Lys Ser Leu Ser Leu Ser
        435                 440                 445

Pro Gly Lys
    450

<210> SEQ ID NO 126
<211> LENGTH: 446
<212> TYPE: PRT
<213> ORGANISM: Artificial Sequence
<220> FEATURE:
<223> OTHER INFORMATION: C40M9 heavy chain

<400> SEQUENCE: 126

Gln Leu Gln Leu Gln Glu Ser Gly Pro Gly Leu Val Lys Pro Ser Glu
1               5                   10                  15

Ile Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45
```

-continued

```
Trp Ile Gly Asn Ile Tyr Tyr Arg Gly Asp Thr Tyr Tyr Ser Pro Ser
 50                  55                  60

Leu Lys Ser Arg Val Thr Ile Ser Val Asp Thr Ser Lys Asn Gln Phe
 65                  70                  75                  80

Ser Leu Lys Leu Asn Ser Val Thr Ala Ala Asp Thr Ala Val Tyr Tyr
                 85                  90                  95

Cys Ala Lys Gly Phe Arg Phe Asp Tyr Trp Gly Gln Gly Thr Leu Val
                100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
    355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
    435                 440                 445

<210> SEQ ID NO 127
<211> LENGTH: 446
```

```
<212> TYPE: PRT
<213> ORGANISM: Artificial Sequence
<220> FEATURE:
<223> OTHER INFORMATION: C40M105 heavy chain

<400> SEQUENCE: 127
```

| | | | | | | | | | | | | | | |
|---|---|---|---|---|---|---|---|---|---|---|---|---|---|---|
| Gln | Leu | Gln | Leu | Gln | Glu | Ser | Gly | Pro | Gly | Leu | Val | Lys | Pro | Ser | Glu |
| 1 | | | | 5 | | | | | 10 | | | | | 15 |

| Thr | Leu | Ser | Leu | Thr | Cys | Thr | Val | Ser | Gly | Gly | Ser | Ile | Ser | Ser | Ser |
| 20 | | | | | 25 | | | | | 30 |

| Ser | Tyr | Tyr | Trp | Gly | Trp | Ile | Arg | Gln | Pro | Pro | Gly | Lys | Gly | Leu | Glu |
| | | 35 | | | | | 40 | | | | | 45 |

| Trp | Ile | Gly | Asn | Ile | Tyr | Tyr | Arg | Gly | Asp | Thr | Tyr | Tyr | Ser | Pro | Ser |
| 50 | | | | | 55 | | | | | 60 |

| Leu | Lys | Ser | Arg | Val | Thr | Ile | Ser | Val | Asp | Thr | Ser | Lys | Asn | Gln | Phe |
| 65 | | | | 70 | | | | | 75 | | | | | 80 |

| Ser | Leu | Lys | Leu | Ser | Ser | Val | Thr | Ala | Ala | Asp | Thr | Ala | Val | Tyr | Tyr |
| | | | | 85 | | | | | 90 | | | | | 95 |

| Cys | Ala | Arg | Gly | Phe | Arg | Phe | Asp | Tyr | Trp | Gly | Gln | Gly | Thr | Leu | Val |
| | | | 100 | | | | | 105 | | | | | 110 |

| Thr | Val | Ser | Ser | Ala | Ser | Thr | Lys | Gly | Pro | Ser | Val | Phe | Pro | Leu | Ala |
| | | | 115 | | | | | 120 | | | | | 125 |

| Pro | Ser | Ser | Lys | Ser | Thr | Ser | Gly | Gly | Thr | Ala | Ala | Leu | Gly | Cys | Leu |
| 130 | | | | | 135 | | | | | 140 |

| Val | Lys | Asp | Tyr | Phe | Pro | Glu | Pro | Val | Thr | Val | Ser | Trp | Asn | Ser | Gly |
| 145 | | | | 150 | | | | | 155 | | | | | 160 |

| Ala | Leu | Thr | Ser | Gly | Val | His | Thr | Phe | Pro | Ala | Val | Leu | Gln | Ser | Ser |
| | | | | 165 | | | | | 170 | | | | | 175 |

| Gly | Leu | Tyr | Ser | Leu | Ser | Ser | Val | Val | Thr | Val | Pro | Ser | Ser | Ser | Leu |
| | | | 180 | | | | | 185 | | | | | 190 |

| Gly | Thr | Gln | Thr | Tyr | Ile | Cys | Asn | Val | Asn | His | Lys | Pro | Ser | Asn | Thr |
| | | | 195 | | | | | 200 | | | | | 205 |

| Lys | Val | Asp | Lys | Lys | Val | Glu | Pro | Lys | Ser | Cys | Asp | Lys | Thr | His | Thr |
| 210 | | | | | 215 | | | | | 220 |

| Cys | Pro | Pro | Cys | Pro | Ala | Pro | Glu | Leu | Leu | Gly | Gly | Pro | Ser | Val | Phe |
| 225 | | | | 230 | | | | | 235 | | | | | 240 |

| Leu | Phe | Pro | Pro | Lys | Pro | Lys | Asp | Thr | Leu | Met | Ile | Ser | Arg | Thr | Pro |
| | | | | 245 | | | | | 250 | | | | | 255 |

| Glu | Val | Thr | Cys | Val | Val | Val | Asp | Val | Ser | His | Glu | Asp | Pro | Glu | Val |
| | | | 260 | | | | | 265 | | | | | 270 |

| Lys | Phe | Asn | Trp | Tyr | Val | Asp | Gly | Val | Glu | Val | His | Asn | Ala | Lys | Thr |
| | | 275 | | | | | 280 | | | | | 285 |

| Lys | Pro | Arg | Glu | Glu | Gln | Tyr | Asn | Ser | Thr | Tyr | Arg | Val | Val | Ser | Val |
| 290 | | | | | 295 | | | | | 300 |

| Leu | Thr | Val | Leu | His | Gln | Asp | Trp | Leu | Asn | Gly | Lys | Glu | Tyr | Lys | Cys |
| 305 | | | | | 310 | | | | | 315 | | | | | 320 |

| Lys | Val | Ser | Asn | Lys | Ala | Leu | Pro | Ala | Pro | Ile | Glu | Lys | Thr | Ile | Ser |
| | | | | 325 | | | | | 330 | | | | | 335 |

| Lys | Ala | Lys | Gly | Gln | Pro | Arg | Glu | Pro | Gln | Val | Tyr | Thr | Leu | Pro | Pro |
| | | | 340 | | | | | 345 | | | | | 350 |

| Ser | Arg | Glu | Glu | Met | Thr | Lys | Asn | Gln | Val | Ser | Leu | Thr | Cys | Leu | Val |
| | | | 355 | | | | | 360 | | | | | 365 |

| Lys | Gly | Phe | Tyr | Pro | Ser | Asp | Ile | Ala | Val | Glu | Trp | Glu | Ser | Asn | Gly |
| | | 370 | | | | | 375 | | | | | 380 |

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
        420                 425                 430

Asn His Tyr Thr Gln Lys Ser Leu Ser Leu Ser Pro Gly Lys
    435                 440                 445

<210> SEQ ID NO 128
<211> LENGTH: 446
<212> TYPE: PRT
<213> ORGANISM: Artificial Sequence
<220> FEATURE:
<223> OTHER INFORMATION: C40M121 heavy chain

<400> SEQUENCE: 128

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Asn Ile Tyr Tyr Arg Gly Asp Thr Tyr Tyr Ser Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Lys Gly Phe Arg Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

```
Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
        340                 345                 350

Ser Arg Glu Glu Met Thr Lys Asn Gln Val Ser Leu Thr Cys Leu Val
    355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
        420                 425                 430

Asn His Tyr Thr Gln Lys Ser Leu Ser Leu Ser Pro Gly Lys
    435                 440                 445

<210> SEQ ID NO 129
<211> LENGTH: 446
<212> TYPE: PRT
<213> ORGANISM: Artificial Sequence
<220> FEATURE:
<223> OTHER INFORMATION: C40M126 heavy chain

<400> SEQUENCE: 129

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Asn Ile Tyr Tyr Arg Gly Asp Thr Tyr Tyr Ser Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Lys Gly Phe Arg Phe Asp Tyr Trp Gly Gln Gly Thr Leu Val
        100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
        180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220
```

```
Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Glu His Glu Asp Pro Glu Val
        260                 265                 270

Lys Phe Asn Trp Tyr Val Asp Gly Val Glu Val His Asn Ala Lys Thr
    275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 130
<211> LENGTH: 215
<212> TYPE: PRT
<213> ORGANISM: Artificial Sequence
<220> FEATURE:
<223> OTHER INFORMATION: C40M67 light chain

<400> SEQUENCE: 130

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Lys Asn Ser
            20                  25                  30

Ser Leu Ala Trp Tyr Gln Gln Lys Pro Gly Gln Ala Pro Arg Leu Leu
        35                  40                  45

Ile Tyr Thr Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ser Ser Ala Pro Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140
```

```
Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 131
<211> LENGTH: 220
<212> TYPE: PRT
<213> ORGANISM: Artificial Sequence
<220> FEATURE:
<223> OTHER INFORMATION: C40M66 light chain

<400> SEQUENCE: 131

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Leu Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 132
<211> LENGTH: 214
<212> TYPE: PRT
<213> ORGANISM: Artificial Sequence
<220> FEATURE:
<223> OTHER INFORMATION: C40M59 light chain

<400> SEQUENCE: 132

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 133
<211> LENGTH: 212
<212> TYPE: PRT
<213> ORGANISM: Artificial Sequence
<220> FEATURE:
<223> OTHER INFORMATION: C40M18 light chain

<400> SEQUENCE: 133

Ser Tyr Glu Leu Thr Gln Pro Pro Ser Val Ser Val Ser Pro Gly Gln
 1               5                  10                  15

Thr Ala Ser Ile Thr Cys Ser Gly Asp Lys Leu Gly Asp Lys Tyr Val
            20                  25                  30

Cys Trp Tyr Gln Gln Lys Pro Gly Gln Ser Pro Val Val Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
 65                  70                  75                  80

Asp Glu Ala Tyr Tyr Cys Gln Ala Trp Val Ser Ser Thr Val Val
                85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
130                 135                 140

Thr Val Ala Trp Lys Ala Asp Ser Ser Pro Val Lys Ala Gly Val Glu
145                 150                 155                 160
```

```
Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys Ser
    210

<210> SEQ ID NO 134
<211> LENGTH: 212
<212> TYPE: PRT
<213> ORGANISM: Artificial Sequence
<220> FEATURE:
<223> OTHER INFORMATION: C40M17 light chain

<400> SEQUENCE: 134

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Arg Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Ala Ser Ser Thr Val Val
                85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys Ser
    210

<210> SEQ ID NO 135
<211> LENGTH: 212
<212> TYPE: PRT
<213> ORGANISM: Artificial Sequence
<220> FEATURE:
<223> OTHER INFORMATION: C40M12 light chain

<400> SEQUENCE: 135

Ser Tyr Glu Leu Thr Gln Pro Pro Ser Val Ser Val Ser Pro Gly Gln
1               5                   10                  15

Thr Ala Ser Ile Ile Cys Ser Gly Asp Lys Leu Gly Asp Lys Tyr Val
```

```
                    20                  25                  30
Cys Trp Tyr Gln Gln Lys Pro Gly Gln Ser Pro Val Val Ile Tyr
                35                  40                  45

His Asp Asn Lys Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gln Val Trp Asp Ser Ser Thr Val Val
                 85                  90                  95

Phe Gly Gly Gly Thr Lys Leu Thr Val Leu Gly Gln Pro Lys Ala Ala
                100                 105                 110

Pro Ser Val Thr Leu Phe Pro Pro Ser Ser Glu Glu Leu Gln Ala Asn
                115                 120                 125

Lys Ala Thr Leu Val Cys Leu Ile Ser Asp Phe Tyr Pro Gly Ala Val
                130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
                180                 185                 190

Cys Gln Val Thr His Glu Gly Ser Thr Val Glu Lys Thr Val Ala Pro
                195                 200                 205

Thr Glu Cys Ser
    210

<210> SEQ ID NO 136
<211> LENGTH: 216
<212> TYPE: PRT
<213> ORGANISM: Artificial Sequence
<220> FEATURE:
<223> OTHER INFORMATION: C40M9 light chain

<400> SEQUENCE: 136

Gln Ser Ala Leu Thr Gln Pro Pro Ser Ala Ser Gly Ser Pro Gly Gln
 1               5                  10                  15

Ser Val Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
                35                  40                  45

Met Ile Tyr Glu Val Ser Lys Arg Pro Ser Gly Val Pro Asp Arg Phe
 50                  55                  60

Ser Gly Ser Lys Ser Gly Asn Thr Ala Ser Leu Thr Val Ser Gly Leu
 65                  70                  75                  80

Gln Ala Glu Asp Glu Ala Asp Tyr Tyr Cys Ser Ser Tyr Ala Gly Ser
                 85                  90                  95

Asn Asn Leu Val Phe Gly Gly Gly Thr Lys Leu Thr Val Leu Gly Gln
                100                 105                 110

Pro Lys Ala Ala Pro Ser Val Thr Leu Phe Pro Pro Ser Ser Glu Glu
                115                 120                 125

Leu Gln Ala Asn Lys Ala Thr Leu Val Cys Leu Ile Ser Asp Phe Tyr
                130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
```

165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 137
<211> LENGTH: 212
<212> TYPE: PRT
<213> ORGANISM: Artificial Sequence
<220> FEATURE:
<223> OTHER INFORMATION: C40M102 light chain

<400> SEQUENCE: 137

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Val
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Val Ser Ser Thr Val Val
                85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys Ser
    210

<210> SEQ ID NO 138
<211> LENGTH: 212
<212> TYPE: PRT
<213> ORGANISM: Artificial Sequence
<220> FEATURE:
<223> OTHER INFORMATION: C40M103 light chain

<400> SEQUENCE: 138

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Val
            20                  25                  30

Ser Trp Tyr Gln Gln Lys Pro Gly Gln Ser Pro Val Leu Val Ile Tyr
            35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Val Ser Ser Thr Val Val
                85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys Ser
    210

<210> SEQ ID NO 139
<211> LENGTH: 212
<212> TYPE: PRT
<213> ORGANISM: Artificial Sequence
<220> FEATURE:
<223> OTHER INFORMATION: C40M104 light chain

<400> SEQUENCE: 139

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Val
            20                  25                  30

Ser Trp Tyr Gln Gln Lys Pro Gly Gln Ser Pro Val Val Ile Tyr
            35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Tyr Tyr Tyr Cys Gln Ala Trp Val Ser Ser Thr Val Val
                85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys Ser
    210

<210> SEQ ID NO 140
<211> LENGTH: 1347
<212> TYPE: DNA
<213> ORGANISM: Artificial Sequence
<220> FEATURE:
<223> OTHER INFORMATION: C40M67 HC DNA

<400> SEQUENCE: 140

| | | | | | | |
|---|---|---|---|---|---|---|
| gaagtgcagc | tgctggaaag | cggcggcggc | ctggtgcagc | cgggcggcag | cctgcgcctg | 60 |
| agctgcgcgg | cgagcggctt | tacctttagc | gactatgcga | tgaactgggt | gcgccaggcg | 120 |
| ccgggcaaag | gcctggaatg | ggtgagcggg | atcaagagcg | gcggtagctc | caaatattat | 180 |
| gcggatagcg | tgaaaggccg | ctttaccatt | agccgcgata | acagcaaaaa | caccctgtat | 240 |
| ctgcagatga | acagcctgcg | cgcggaagat | accgcggtgt | attattgcgc | gaaacacgtt | 300 |
| gactttttata | gggccttgga | ctattgggggc | cagggcaccc | tggtgaccgt | gagcagcgcc | 360 |
| tccaccaagg | gcccatcggt | cttccccctg | gcaccctcct | ccaagagcac | ctctgggggc | 420 |
| acagcggccc | tgggctgcct | ggtcaaggac | tacttccccg | aaccggtgac | ggtgtcgtgg | 480 |
| aactcaggcg | ccctgaccag | cggcgtgcac | accttcccgg | ctgtcctaca | gtcctcagga | 540 |
| ctctactccc | tcagcagcgt | ggtgaccgtg | ccctccagca | gcttgggcac | ccagacctac | 600 |
| atctgcaacg | tgaatcacaa | gcccagcaac | accaaggtgg | acaagaaagt | tgagcccaaa | 660 |
| tcttgtgaca | aaactcacac | atgcccaccg | tgcccagcac | ctgaactcct | ggggggaccg | 720 |
| tcagtcttcc | tcttcccccc | aaaacccaag | gacaccctca | tgatctcccg | gacccctgag | 780 |
| gtcacatgcg | tggtggtgga | cgtgagccac | gaagaccctg | aggtcaagtt | caactggtac | 840 |
| gtggacggcg | tggaggtgca | taatgccaag | acaaagccgc | gggaggagca | gtacaacagc | 900 |
| acgtaccgtg | tggtcagcgt | cctcaccgtc | ctgcaccagg | actggctgaa | tggcaaggag | 960 |
| tacaagtgca | aggtctccaa | caaagccctc | ccagccccca | tcgagaaaac | catctccaaa | 1020 |
| gccaaagggc | agccccgaga | accacaggtg | tacaccctgc | ccccatcccg | ggaggagatg | 1080 |
| accaagaacc | aggtcagcct | gacctgcctg | gtcaaaggct | tctatcccag | cgacatcgcc | 1140 |
| gtggagtggg | agagcaatgg | gcagccggag | aacaactaca | agaccacgcc | tcccgtgctg | 1200 |
| gactccgacg | gctccttctt | cctctacagc | aagctcaccg | tggacaagag | caggtggcag | 1260 |
| caggggaacg | tcttctcatg | ctccgtgatg | catgaggctc | tgcacaacca | ctacacgcag | 1320 |
| aagagcctct | ccctgtctcc | gggtaaa | | | | 1347 |

<210> SEQ ID NO 141
<211> LENGTH: 1356
<212> TYPE: DNA
<213> ORGANISM: Artificial Sequence
<220> FEATURE:
<223> OTHER INFORMATION: C40M66 HC DNA

<400> SEQUENCE: 141

| | | | | | | |
|---|---|---|---|---|---|---|
| caggtgcagc | tggtgcagag | cggcgcggaa | gtgaaaaaac | cgggcagcag | cgtgaaagtg | 60 |
| agctgcaaag | cgagcggcgg | cacctttagc | agctatgcga | ttagctgggt | gcgccaggcg | 120 |

```
ccgggccagg gcctggaatg gatgggcggc attattccga tttttggcac cgcgaactat      180
gcgcagaaat ttcagggccg cgtgaccatt accgcggatg aaagcaccag caccgcgtat      240
atggaactga gcagcctgcg cagcgaagat accgcggtgt attattgcgc gcgcgttcgg      300
tattcggcgt ggtataggga ctctttggac tattggggcc agggcaccct ggtgacagtc      360
tcgagtgcct ccaccaaggg cccatcggtc ttccccctgg caccctcctc caagagcacc      420
tctgggggca gcggccct gggctgcctg gtcaaggact acttccccga accggtgacg       480
gtgtcgtgga actcaggcgc cctgaccagc ggcgtgcaca ccttcccggc tgtcctacag      540
tcctcaggac tctactccct cagcagcgtg gtgaccgtgc cctccagcag cttgggcacc      600
cagacctaca tctgcaacgt gaatcacaag cccagcaaca ccaaggtgga caagaaagtt      660
gagcccaaat cttgtgacaa aactcacaca tgcccaccgt gcccagcacc tgaactcctg      720
gggggaccgt cagtcttcct cttccccca aaacccaagg acaccctcat gatctcccgg       780 accccctgagg tcacatgcgt ggtggtggac gtgagccacg aagaccctga ggtcaagttc      840
aactggtacg tggacggcgt ggaggtgcat aatgccaaga caaagccgcg ggaggagcag      900
tacaacagca cgtaccgtgt ggtcagcgtc ctcaccgtcc tgcaccagga ctggctgaat      960
ggcaaggagt acaagtgcaa ggtctccaac aaagccctcc cagcccccat cgagaaaacc     1020
atctccaaag ccaaagggca gccccgagaa ccacaggtgt acaccctgcc cccatcccgg     1080
gaggagatga ccaagaacca ggtcagcctg acctgcctgg tcaaaggctt ctatcccagc     1140
gacatcgccg tggagtggga gagcaatggg cagccggaga caactacaa gaccacgcct       1200 cccgtgctgg actccgacgg ctccttcttc ctctacagca agctcaccgt ggacaagagc     1260
aggtggcagc aggggaacgt cttctcatgc tccgtgatgc atgaggctct gcacaaccac     1320
tacacgcaga agagcctctc cctgtctccg ggtaaa                                1356

<210> SEQ ID NO 142
<211> LENGTH: 1356
<212> TYPE: DNA
<213> ORGANISM: Artificial Sequence
<220> FEATURE:
<223> OTHER INFORMATION: C40M63 HC DNA

<400> SEQUENCE: 142
caggtgcagc tggtgcagag cggcgcggaa gtgaaaaaac cgggcagcag cgtgaaagtg       60
agctgcaaag cgagcggcgg caccttagc agctatgcga ttagctgggt gcgccaggcg       120
ccgggccagg gcctggaatg gatgggcggc attattccga tttttggcac cgcgaactat      180
gcgcagaaat ttcagggccg cgtgaccatt accgcggatg aaagcaccag caccgcgtat      240
atggaactga gcagcctgcg cagcgaagat accgcggtgt attattgcgc gcgcgtaggc      300
catccggctt ggtggcgtga ttcgttggac tattggggcc agggcaccct ggtgaccgtg      360
agcagcgcct ccaccaaggg cccatcggtc ttccccctgg caccctcctc caagagcacc      420
tctgggggca gcggccct gggctgcctg gtcaaggact acttccccga accggtgacg       480
gtgtcgtgga actcaggcgc cctgaccagc ggcgtgcaca ccttcccggc tgtcctacag      540
tcctcaggac tctactccct cagcagcgtg gtgaccgtgc cctccagcag cttgggcacc      600
cagacctaca tctgcaacgt gaatcacaag cccagcaaca ccaaggtgga caagaaagtt      660
gagcccaaat cttgtgacaa aactcacaca tgcccaccgt gcccagcacc tgaactcctg      720
gggggaccgt cagtcttcct cttccccca aaacccaagg acaccctcat gatctcccgg       780 accccctgagg tcacatgcgt ggtggtggac gtgagccacg aagaccctga ggtcaagttc      840
```

```
aactggtacg tggacggcgt ggaggtgcat aatgccaaga caaagccgcg ggaggagcag    900
tacaacagca cgtaccgtgt ggtcagcgtc ctcaccgtcc tgcaccagga ctggctgaat    960
ggcaaggagt acaagtgcaa ggtctccaac aaagccctcc cagcccccat cgagaaaacc   1020
atctccaaag ccaagggcag ccccgagaa ccacaggtgt acaccctgcc cccatcccgg    1080
gaggagatga ccaagaacca ggtcagcctg acctgcctgg tcaaaggctt ctatcccagc   1140
gacatcgccg tggagtggga gagcaatggg cagccggaga caactacaa gaccacgcct    1200 cccgtgctgg actccgacgg ctccttcttc ctctacagca agctcaccgt ggacaagagc   1260
aggtggcagc aggggaacgt cttctcatgc tccgtgatgc atgaggctct gcacaaccac   1320
tacacgcaga agagcctctc cctgtctccg ggtaaa                             1356
```

<210> SEQ ID NO 143
<211> LENGTH: 1356
<212> TYPE: DNA
<213> ORGANISM: Artificial Sequence
<220> FEATURE:
<223> OTHER INFORMATION: C40M62 HC DNA

<400> SEQUENCE: 143

```
caggtgcagc tggtgcagag cggcgcggaa gtgaaaaaac cgggcagcag cgtgaaagtg     60
agctgcaaag cgagcggcgg caccctttagc agctatgcga ttagctgggt gcgccaggcg    120
ccgggccagg gcctggaatg gatgggcggc attattccga ttttggcac cgcgaactat     180 gcgcagaaat ttcagggccg cgtgaccatt accgcggatg aaagcaccag caccgcgtat    240
atggaactga gcagcctgcg cagcgaagat accgcggtgt attattgcgc gcgcgttgcc    300
aacgctgcgt atttaggtc tggcttggac tattggggcc agggcaccct ggtgaccgtg    360
agcagcgcct ccaccaaggg cccatcggtc ttccccctgg cacctcctc caagagcacc    420 tctgggggca gcggccct gggctgcctg gtcaaggact acttcccga accggtgacg    480 gtgtcgtgga actcaggcgc cctgaccagc ggcgtgcaca ccttcccggc tgtcctacag    540
tcctcaggac tctactccct cagcagcgtg gtgaccgtgc cctccagcag cttgggcacc    600
cagacctaca tctgcaacgt gaatcacaag cccagcaaca ccaaggtgga caagaaagtt    660
gagcccaaat cttgtgacaa aactcacaca tgcccaccgt gcccagcacc tgaactcctg    720
gggggaccgt cagtcttcct cttccccca aaacccaagg acaccctcat gatctcccgg    780
acccctgagg tcacatgcgt ggtggtggac gtgagccacg aagaccctga ggtcaagttc    840
aactggtacg tggacggcgt ggaggtgcat aatgccaaga caaagccgcg ggaggagcag    900
tacaacagca cgtaccgtgt ggtcagcgtc ctcaccgtcc tgcaccagga ctggctgaat    960
ggcaaggagt acaagtgcaa ggtctccaac aaagccctcc cagcccccat cgagaaaacc   1020
atctccaaag ccaagggcag ccccgagaa ccacaggtgt acaccctgcc cccatcccgg    1080
gaggagatga ccaagaacca ggtcagcctg acctgcctgg tcaaaggctt ctatcccagc   1140
gacatcgccg tggagtggga gagcaatggg cagccggaga caactacaa gaccacgcct    1200 cccgtgctgg actccgacgg ctccttcttc ctctacagca agctcaccgt ggacaagagc   1260
aggtggcagc aggggaacgt cttctcatgc tccgtgatgc atgaggctct gcacaaccac   1320
tacacgcaga agagcctctc cctgtctccg ggtaaa                             1356
```

<210> SEQ ID NO 144
<211> LENGTH: 1362
<212> TYPE: DNA

<213> ORGANISM: Artificial Sequence
<220> FEATURE:
<223> OTHER INFORMATION: C40M59 HC DNA

<400> SEQUENCE: 144

```
caggtgcagc tggtgcagag cggcgcggaa gtgaaaaaac cgggcagcag cgtgaaagtg      60
agctgcaaag cgagcggcgg caccttcagc tcctactgga ttagctgggt gcgccaggcg     120
ccgggccagg gcctggaatg gatgggctac attattccga tcagtggcac tgcccgctac     180
gcgcagaaat tcagggccg cgtgaccatt accgctgatg aaagcaccag caccgcgtat     240
atggaactga gcagcctgcg cagcgaagat accgcggtgt attattgcgc gcgcgaacca     300
ggctacagta gtggcctgag cgttgactac tttgattact ggggccaggg caccctggtg     360
acagtctcga gtgcctccac caagggccca tcggtcttcc ccctggcacc ctcctccaag     420
agcacctctg gggcacagc ggccctgggc tgcctggtca aggactactt ccccgaaccg     480
gtgacggtgt cgtggaactc aggcgccctg accagcggcg tgcacacctt cccggctgtc     540
ctacagtcct caggactcta ctccctcagc agcgtggtga ccgtgccctc agcagcttg     600
ggcacccaga cctacatctg caacgtgaat cacaagccca gcaacaccaa ggtggacaag     660
aaagttgagc ccaaatcttg tgacaaaact cacacatgcc caccgtgccc agcacctgaa     720
ctcctggggg gaccgtcagt cttcctcttc ccccaaaac ccaaggacac cctcatgatc     780
tcccggaccc ctgaggtcac atgcgtgtg gtggacgtga gccacgaaga ccctgaggtc     840
aagttcaact ggtacgtgga cggcgtggag gtgcataatg ccaagacaaa gccgcgggag     900
gagcagtaca acagcacgta ccgtgtggtc agcgtcctca ccgtcctgca ccaggactgg     960
ctgaatggca aggagtacaa gtgcaaggtc tccaacaaag ccctcccagc ccccatcgag    1020
aaaaccatct ccaaagccaa agggcagccc cgagaaccac aggtgtacac cctgccccca    1080
tcccgggagg agatgaccaa gaaccaggtc agcctgacct gcctggtcaa aggcttctat    1140
cccagcgaca tcgccgtgga gtgggagagc aatgggcagc cggagaacaa ctacaagacc    1200
acgcctcccg tgctggactc cgacggctcc ttcttcctct acagcaagct caccgtggac    1260
aagagcaggt ggcagcaggg gaacgtcttc tcatgctccg tgatgcatga ggctctgcac    1320
aaccactaca cgcagaagag cctctccctg tctccgggta aa                       1362
```

<210> SEQ ID NO 145
<211> LENGTH: 1347
<212> TYPE: DNA
<213> ORGANISM: Artificial Sequence
<220> FEATURE:
<223> OTHER INFORMATION: C40M58 HC DNA

<400> SEQUENCE: 145

```
gaagtgcagc tgctggaaag cggcggcggc ctggtgcagc cggcggcag cctgcgcctg      60
agctgcgcgg cgagcggctt tacctttagc agctatgcga tgagctgggt gcgccaggcg    120
ccgggcaaag gcctggaatg ggtgagcgcg atcagcggct ccggtggctc cacatattat    180
gcggatagcg tgaaaggccg ctttaccatt tcacgagata acagcaaaaa caccctgtat    240
ctgcagatga acagcctgcg cgcggaagat accgcggtgt attattgcgc gcgcggtcca    300
gcatacacta tcgttttga ttattggggc cagggcaccc tggtgacagt ctcgagtgcc    360
tccaccaagg gcccatcggt cttccccctg gcaccctcct ccaagagcac ctctgggggc    420
acagcggccc tgggctgcct ggtcaaggac tacttccccg aaccggtgac ggtgtcgtgg    480
aactcaggcg ccctgaccag cggcgtgcac accttcccgg ctgtcctaca gtcctcagga    540
```

```
ctctactccc tcagcagcgt ggtgaccgtg ccctccagca gcttgggcac ccagacctac      600
atctgcaacg tgaatcacaa gcccagcaac accaaggtgg acaagaaagt tgagcccaaa      660
tcttgtgaca aaactcacac atgcccaccg tgcccagcac ctgaactcct ggggggaccg      720
tcagtcttcc tcttcccccc aaaacccaag gacaccctca tgatctcccg acccctgag       780 gtcacatgcg tggtggtgga cgtgagccac gaagaccctg aggtcaagtt caactggtac      840
gtggacggcg tggaggtgca taatgccaag acaaagccgc gggaggagca gtacaacagc      900
acgtaccgtg tggtcagcgt cctcaccgtc ctgcaccagg actggctgaa tggcaaggag      960
tacaagtgca aggtctccaa caaagccctc ccagccccca tcgagaaaac catctccaaa     1020
gccaaagggc agccccgaga accacaggtg tacaccctgc cccatcccg ggaggagatg      1080 accaagaacc aggtcagcct gacctgcctg gtcaaaggct tctatcccag cgacatcgcc     1140
gtggagtggg agagcaatgg gcagccggag aacaactaca agaccacgcc tcccgtgctg     1200
gactccgacg gctccttctt cctctacagc aagctcaccg tggacaagag caggtggcag     1260
caggggaacg tcttctcatg ctccgtgatg catgaggctc tgcacaacca ctacacgcag     1320
aagagcctct ccctgtctcc gggtaaa                                          1347
```

<210> SEQ ID NO 146
<211> LENGTH: 1347
<212> TYPE: DNA
<213> ORGANISM: Artificial Sequence
<220> FEATURE:
<223> OTHER INFORMATION: C40M56 HC DNA

<400> SEQUENCE: 146

```
gaagtgcagc tgctggaaag cggcggcggc ctggtgcagc cgggcggcag cctgcgcctg       60
agctgcgcgg cgagcggctt taccttagc agctatgcga tgagctgggt gcgccaggcg      120
ccgggcaaag cctggaatg ggtgagcgcg atcagcggct ccgtggctc cacatattat       180 gcggatagcg tgaaaggccg ctttaccatt tcacgagata acagcaaaaa caccctgtat      240
ctgcagatga acagcctgcg cgcggaagat accgcggtgt attattgcgc gcgcggtcct      300
gtttattctc tggttttga ctactggggc cagggcaccc tggtgacagt ctcgagtgcc       360
tccaccaagg gcccatcggt cttccccctg gcaccctcct ccaagagcac ctctggggc      420 acagcggccc tgggctgcct ggtcaaggac tacttccccg aaccggtgac ggtgtcgtgg      480
aactcaggcg ccctgaccag cggcgtgcac accttcccgg ctgtcctaca gtcctcagga      540
ctctactccc tcagcagcgt ggtgaccgtg ccctccagca gcttgggcac ccagacctac      600
atctgcaacg tgaatcacaa gcccagcaac accaaggtgg acaagaaagt tgagcccaaa      660
tcttgtgaca aaactcacac atgcccaccg tgcccagcac ctgaactcct ggggggaccg      720
tcagtcttcc tcttcccccc aaaacccaag gacaccctca tgatctcccg acccctgag       780 gtcacatgcg tggtggtgga cgtgagccac gaagaccctg aggtcaagtt caactggtac      840
gtggacggcg tggaggtgca taatgccaag acaaagccgc gggaggagca gtacaacagc      900
acgtaccgtg tggtcagcgt cctcaccgtc ctgcaccagg actggctgaa tggcaaggag      960
tacaagtgca aggtctccaa caaagccctc ccagccccca tcgagaaaac catctccaaa     1020
gccaaagggc agccccgaga accacaggtg tacaccctgc cccatcccg ggaggagatg      1080 accaagaacc aggtcagcct gacctgcctg gtcaaaggct tctatcccag cgacatcgcc     1140
gtggagtggg agagcaatgg gcagccggag aacaactaca agaccacgcc tcccgtgctg     1200
```

| | |
|---|---|
| gactccgacg gctccttctt cctctacagc aagctcaccg tggacaagag caggtggcag | 1260 |
| caggggaacg tcttctcatg ctccgtgatg catgaggctc tgcacaacca ctacacgcag | 1320 |
| aagagcctct ccctgtctcc gggtaaa | 1347 |

<210> SEQ ID NO 147
<211> LENGTH: 1362
<212> TYPE: DNA
<213> ORGANISM: Artificial Sequence
<220> FEATURE:
<223> OTHER INFORMATION: C40M55 HC DNA

<400> SEQUENCE: 147

| | |
|---|---|
| caggtgcagc tggtgcagag cggcgcggaa gtgaaaaaac cgggcagcag cgtgaaagtg | 60 |
| agctgcaaag cgagcggcgg caccttcagc agctatgcga ttagctgggt gcgccaggcg | 120 |
| ccgggccagg gcctggaatg gatgggcggc attattccga ttttttggcac cgctaactac | 180 |
| gcgcagaaat ttcagggccg cgtgaccatt accgctgatg aaagcaccag caccgcgtat | 240 |
| atggaactga gcagcctgcg cagcgaagat accgcggtgt attattgcgc gcgcgatggt | 300 |
| tatcggcggt atggcatcgg tcgttacggt ttcgattatt ggggccaggg caccctggtg | 360 |
| acagtctcga gtgcctccac caagggccca tcggtcttcc ccctggcacc ctcctccaag | 420 |
| agcacctctg ggggcacagc ggccctgggc tgcctggtca aggactactt ccccgaaccg | 480 |
| gtgacggtgt cgtggaactc aggcgccctg accagcggcg tgcacacctt cccggctgtc | 540 |
| ctacagtcct caggactcta ctccctcagc agcgtggtga ccgtgccctc agcagcttg | 600 |
| ggcacccaga cctacatctg caacgtgaat cacaagccca gcaacaccaa ggtggacaag | 660 |
| aaagttgagc ccaaatcttg tgacaaaact cacacatgcc caccgtgccc agcacctgaa | 720 |
| ctcctggggg gaccgtcagt cttcctcttc cccccaaaac ccaaggacac cctcatgatc | 780 |
| tcccggaccc ctgaggtcac atgcgtggtg gtggacgtga gccacgaaga ccctgaggtc | 840 |
| aagttcaact ggtacgtgga cggcgtggag gtgcataatg ccaagacaaa gccgcgggag | 900 |
| gagcagtaca acagcacgta ccgtgtggtc agcgtcctca ccgtcctgca ccaggactgg | 960 |
| ctgaatggca aggagtacaa gtgcaaggtc tccaacaaag ccctcccagc ccccatcgag | 1020 |
| aaaaccatct ccaaagccaa agggcagccc cgagaaccac aggtgtacac cctgccccca | 1080 |
| tcccgggagg agatgaccaa gaaccaggtc agcctgacct gcctggtcaa aggcttctat | 1140 |
| cccagcgaca tcgccgtgga gtgggagagc aatgggcagc cggagaacaa ctacaagacc | 1200 |
| acgcctcccg tgctggactc cgacggctcc ttcttcctct acagcaagct caccgtggac | 1260 |
| aagagcaggt ggcagcaggg gaacgtcttc tcatgctccg tgatgcatga ggctctgcac | 1320 |
| aaccactaca cgcagaagag cctctccctg tctccgggta aa | 1362 |

<210> SEQ ID NO 148
<211> LENGTH: 1347
<212> TYPE: DNA
<213> ORGANISM: Artificial Sequence
<220> FEATURE:
<223> OTHER INFORMATION: C40M51 HC DNA

<400> SEQUENCE: 148

| | |
|---|---|
| gaagtgcagc tgctggaaag cggcggcggc ctggtgcagc cgggcggcag cctgcgcctg | 60 |
| agctgcgcgg cgagcggctt tacctttagc agctatgcga tgagctgggt gcgccaggcg | 120 |
| ccgggcaaag gcctggaatg ggtgagcgcg atcagcggct ccgtggctc cacatattat | 180 |
| gcggatagcg tgaaaggccg ctttaccatt tcacgagata acagcaaaaa caccctgtat | 240 |

```
ctgcagatga acagcctgcg cgcggaagat accgcggtgt attattgcgc gcgcggccca    300
gtttattcta gcgttttcga ctattggggc cagggcaccc tggtgacagt ctcgagtgcc    360
tccaccaagg gcccatcggt cttccccctg gcacctcct ccaagagcac ctctggggc     420 acagcggccc tgggctgcct ggtcaaggac tacttcccg aaccggtgac ggtgtcgtgg     480
aactcaggcg ccctgaccag cggcgtgcac accttcccgg ctgtcctaca gtcctcagga    540
ctctactccc tcagcagcgt ggtgaccgtg ccctccagca gcttgggcac ccagacctac    600
atctgcaacg tgaatcacaa gcccagcaac accaaggtgg acaagaaagt tgagcccaaa    660
tcttgtgaca aaactcacac atgcccaccg tgcccagcac ctgaactcct ggggggaccg    720
tcagtcttcc tcttcccccc aaaacccaag gacaccctca tgatctcccg gacccctgag    780
gtcacatgcg tggtggtgga cgtgagccac gaagaccctg aggtcaagtt caactggtac    840
gtggacggcg tggaggtgca taatgccaag acaaagccgc gggaggagca gtacaacagc    900
acgtaccgtg tggtcagcgt cctcaccgtc ctgcaccagg actggctgaa tggcaaggag    960
tacaagtgca aggtctccaa caaagccctc ccagccccca tcgagaaaac catctccaaa   1020
gccaaagggc agccccgaga accacaggtg tacaccctgc ccccatcccg ggaggagatg   1080
accaagaacc aggtcagcct gacctgcctg gtcaaaggct tctatcccag cgacatcgcc   1140
gtggagtggg agagcaatgg gcagccggag aacaactaca agaccacgcc tcccgtgctg   1200
gactccgacg gctccttctt cctctacagc aagctcaccg tggacaagag caggtggcag   1260
caggggaacg tcttctcatg ctccgtgatg catgaggctc tgcacaacca ctacacgcag   1320
aagagcctct ccctgtctcc gggtaaa                                       1347
```

<210> SEQ ID NO 149
<211> LENGTH: 1353
<212> TYPE: DNA
<213> ORGANISM: Artificial Sequence
<220> FEATURE:
<223> OTHER INFORMATION: C40M18 HC DNA

<400> SEQUENCE: 149

```
gaggtgcagc tggtggaatc tggcggagga ctggtgcagc ctggcggcag cctgagactg     60
tcttgtgccg ccagcggctt caccttcagc agctacgcta tgagctgggt ccgacaggcc    120
cctggcaagg gactggaatg ggtgtccatc atcaacaaca cgtgggccg acctactac     180 gccgacagcg tgaagggcag attcaccatc agccgggaca acagcaagaa cacccctgtac   240 ctgcagatga acagcctgcg ggccgaggac accgccgtgt actattgtgc caagagggc    300 ggcgattact actactacgg catggacgtg tggggccagg gcaccaccgt gacagtgtca    360
tctgcctcca ccaagggccc atcggtcttc cccctggcac ctcctccaa gagcacctct    420 gggggcacag cggccctggg ctgcctggtc aaggactact ccccgaacc ggtgacggtg    480 tcgtggaact caggcgccct gaccagcggc gtgcacacct tcccggctgt cctacagtcc    540
tcaggactct actccctcag cagcgtggtg accgtgccct ccagcagctt gggcacccag    600
acctacatct gcaacgtgaa tcacaagccc agcaacacca aggtggacaa gaaagttgag    660
cccaaatctt gtgacaaaac tcacacatgc ccaccgtgcc cagcacctga actcctgggg    720
ggaccgtcag tcttcctctt ccccccaaaa cccaaggaca ccctcatgat ctcccggacc    780
cctgaggtca catgcgtggt ggtggacgtg agccacgaag accctgaggt caagttcaac    840
tggtacgtgg acggcgtgga ggtgcataat gccaagacaa agccgcggga ggagcagtac    900
```

| | |
|---|---|
| aacagcacgt accgtgtggt cagcgtcctc accgtcctgc accaggactg gctgaatggc | 960 |
| aaggagtaca agtgcaaggt ctccaacaaa gccctcccag cccccatcga gaaaaccatc | 1020 |
| tccaaagcca agggcagcc ccgagaacca caggtgtaca ccctgccccc atcccgggag | 1080 |
| gagatgacca agaaccaggt cagcctgacc tgcctggtca aaggcttcta tcccagcgac | 1140 |
| atcgccgtgg agtgggagag caatgggcag ccggagaaca actacaagac cacgcctccc | 1200 |
| gtgctggact ccgacggctc cttcttcctc tacagcaagc tcaccgtgga caagagcagg | 1260 |
| tggcagcagg ggaacgtctt ctcatgctcc gtgatgcatg aggctctgca caaccactac | 1320 |
| acgcagaaga gcctctccct gtctccgggt aaa | 1353 |

<210> SEQ ID NO 150
<211> LENGTH: 1353
<212> TYPE: DNA
<213> ORGANISM: Artificial Sequence
<220> FEATURE:
<223> OTHER INFORMATION: C40M17 HC DNA

<400> SEQUENCE: 150

| | |
|---|---|
| gaggtgcagc tggtggaatc tggcggagga ctggtgcagc ctggcggcag cctgagactg | 60 |
| tcttgtgccg ccagcggctt caccttcagc agctacgcta tgagctgggt ccgacaggcc | 120 |
| cctggcagag gactcgagtg ggtgtccacc atcaacaaca gcggcggagg cacctactac | 180 |
| gccgacagcg tgaagggcag attcaccatc agccgggaca cagcaagaa caccctgtac | 240 |
| ctgcacatga acagcctgcg ggccgaggac accgccgtgt actattgtgc caagagggc | 300 |
| ggcaagtact actactatgc catggacgtg tggggccagg gcaccaccgt gacagtgtca | 360 |
| tctgcctcca ccaagggccc atcggtcttc cccctggcac cctcctccaa gagcacctct | 420 |
| gggggcacag cggccctggg ctgcctggtc aaggactact tccccgaacc ggtgacggtg | 480 |
| tcgtggaact caggcgccct gaccagcggc gtgcacacct tcccggctgt cctacagtcc | 540 |
| tcaggactct actccctcag cagcgtggtg accgtgccct ccagcagctt gggcacccag | 600 |
| acctacatct gcaacgtgaa tcacaagccc agcaacacca aggtggacaa gaaagttgag | 660 |
| cccaaatctt gtgacaaaac tcacacatgc ccaccgtgcc cagcacctga actcctgggg | 720 |
| ggaccgtcag tcttcctctt ccccccaaaa cccaaggaca ccctcatgat ctcccggacc | 780 |
| cctgaggtca catgcgtggt ggtggacgtg agccacgaag accctgaggt caagttcaac | 840 |
| tggtacgtgg acggcgtgga ggtgcataat gccaagacaa agccgcggga ggagcagtac | 900 |
| aacagcacgt accgtgtggt cagcgtcctc accgtcctgc accaggactg gctgaatggc | 960 |
| aaggagtaca agtgcaaggt ctccaacaaa gccctcccag cccccatcga gaaaaccatc | 1020 |
| tccaaagcca agggcagcc ccgagaacca caggtgtaca ccctgccccc atcccgggag | 1080 |
| gagatgacca agaaccaggt cagcctgacc tgcctggtca aaggcttcta tcccagcgac | 1140 |
| atcgccgtgg agtgggagag caatgggcag ccggagaaca actacaagac cacgcctccc | 1200 |
| gtgctggact ccgacggctc cttcttcctc tacagcaagc tcaccgtgga caagagcagg | 1260 |
| tggcagcagg ggaacgtctt ctcatgctcc gtgatgcatg aggctctgca caaccactac | 1320 |
| acgcagaaga gcctctccct gtctccgggt aaa | 1353 |

<210> SEQ ID NO 151
<211> LENGTH: 1353
<212> TYPE: DNA
<213> ORGANISM: Artificial Sequence
<220> FEATURE:
<223> OTHER INFORMATION: C40M12 HC DNA

<400> SEQUENCE: 151

```
gaggtgcagc tggtggaatc tggcggagga ctggtgcagc ctggcggcag cctgagactg      60
tcttgtgccg ccagcggctt caccttcggc agctacgcta tgagctgggt ccgacaggcc     120
cctggcaagg gactggaatg ggtgtccgtg atcagcgaca cggcggcag aacctactac      180
gccgacagcg tgaagggccg gttcaccatc agccgggact acagcaagaa caccctgtac    240
ctgcagatga acagcctgcg ggccgaggac accgccgtgt actattgtgc caaagagggc    300
ggcgattact actactacgg catggacgtg tggggccagg gcaccaccgt gacagtgtca    360
tctgcctcca ccaagggccc atcggtcttc cccctggcac cctcctccaa gagcacctct    420
gggggcacag cggccctggg ctgcctggtc aaggactact tccccgaacc ggtgacggtg    480
tcgtggaact caggcgccct gaccagcggc gtgcacacct tcccggctgt cctacagtcc    540
tcaggactct actccctcag cagcgtggtg accgtgccct ccagcagctt gggcacccag    600
acctacatct gcaacgtgaa tcacaagccc agcaacacca aggtggacaa gaaagttgag    660
cccaaatctt gtgacaaaac tcacacatgc ccaccgtgcc cagcacctga actcctgggg    720
ggaccgtcag tcttcctctt ccccccaaaa cccaaggaca cctcatgat ctcccggacc     780
cctgaggtca catgcgtggt ggtggacgtg agccacgaag accctgaggt caagttcaac    840
tggtacgtgg acggcgtgga ggtgcataat gccaagacaa agccgcggga ggagcagtac    900
aacagcacgt accgtgtggt cagcgtcctc accgtcctgc accaggactg gctgaatggc    960
aaggagtaca agtgcaaggt ctccaacaaa gccctcccag cccccatcga gaaaaccatc   1020
tccaaagcca agggcagcc ccgagaacca caggtgtaca ccctgccccc atcccgggag    1080
gagatgacca gaaccaggt cagcctgacc tgcctggtca aaggcttcta tcccagcgac   1140
atcgccgtgg agtgggagag caatgggcag ccggagaaca actacaagac cacgcctccc   1200
gtgctggact ccgacggctc cttcttcctc tacagcaagc tcaccgtgga caagagcagg   1260
tggcagcagg ggaacgtctt ctcatgctcc gtgatgcatg aggctctgca caaccactac   1320
acgcagaaga gcctctccct gtctccgggt aaa                                1353
```

<210> SEQ ID NO 152
<211> LENGTH: 1338
<212> TYPE: DNA
<213> ORGANISM: Artificial Sequence
<220> FEATURE:
<223> OTHER INFORMATION: C40M9 HC DNA

<400> SEQUENCE: 152

```
cagctccagc tgcaggaatc tggccctggc ctggtcaagc ccagcgagat cctgagcctg      60
acctgtaccg tgtccggcgg cagcatcagc agcagctctt actactgggg ctggatccgg    120
cagcctcccg gcaagggact ggaatggatc ggcaacatct actaccgggg cgacacctac    180
tacagcccca gcctgaagtc cagagtgacc atcagcgtgg acaccagcaa gaaccagttc    240
tccctgaagc tgaacagcgt gacagccgcc gacaccgccg tgtactactg cgccaagggc    300
ttcagattcg attactgggg ccagggcacc ctggtcaccg tgtcatctgc ctccaccaag    360
ggcccatcgg tcttcccct ggcaccctcc tccaagagca cctctggggg cacagcggcc    420
ctgggctgcc tggtcaagga ctacttcccc gaaccggtga cggtgtcgtg gaactcaggc    480
gccctgacca gcggcgtgca caccttcccg gctgtcctac agtcctcagg actctactcc    540
ctcagcagcg tggtgaccgt gccctccagc agcttgggca cccagaccta catctgcaac   600
```

| | |
|---|---|
| gtgaatcaca agcccagcaa caccaaggtg acaagaaag ttgagcccaa atcttgtgac | 660 |
| aaaactcaca catgcccacc gtgcccagca cctgaactcc tggggggacc gtcagtcttc | 720 |
| ctcttccccc caaaacccaa ggacaccctc atgatctccc ggacccctga ggtcacatgc | 780 |
| gtggtggtgg acgtgagcca cgaagaccct gaggtcaagt tcaactggta cgtggacggc | 840 |
| gtggaggtgc ataatgccaa gacaaagccg cgggaggagc agtacaacag cacgtaccgt | 900 |
| gtggtcagcg tcctcaccgt cctgcaccag gactggctga atggcaagga gtacaagtgc | 960 |
| aaggtctcca acaaagccct cccagccccc atcgagaaaa ccatctccaa agccaaaggg | 1020 |
| cagccccgag aaccacaggt gtacaccctg cccccatccc gggaggagat gaccaagaac | 1080 |
| caggtcagcc tgacctgcct ggtcaaaggc ttctatccca gcgacatcgc cgtggagtgg | 1140 |
| gagagcaatg ggcagccgga gaacaactac aagaccacgc ctcccgtgct ggactccgac | 1200 |
| ggctccttct tcctctacag caagctcacc gtggacaaga gcaggtggca gcaggggaac | 1260 |
| gtcttctcat gctccgtgat gcatgaggct ctgcacaacc actacacgca gaagagcctc | 1320 |
| tccctgtctc cgggtaaa | 1338 |

<210> SEQ ID NO 153
<211> LENGTH: 1338
<212> TYPE: DNA
<213> ORGANISM: Artificial Sequence
<220> FEATURE:
<223> OTHER INFORMATION: C40M105 HC DNA

<400> SEQUENCE: 153

| | |
|---|---|
| cagctgcagc tgcaggagag cggccccggc ctggtgaagc ccagcgagac cctgagcctg | 60 |
| acctgcaccg tgagcggcgg cagcatcagc agcagcagct actactgggg ctggatccgg | 120 |
| cagccccccg gcaagggcct ggagtggatc ggcaacatct actaccgggg cgacaccctac | 180 |
| tacagcccca gcctgaagag ccgggtgacc atcagcgtgg acaccagcaa gaaccagttc | 240 |
| agcctgaagc tgagcagcgt gaccgccgcc gacaccgccg tgtactactg cgccaggggc | 300 |
| ttccggttcg actactgggg ccagggcacc ctggtgaccg tgagcagcgc ctccaccaag | 360 |
| ggcccatcgg tcttccccct ggcaccctcc tccaagagca cctctggggg cacagcggcc | 420 |
| ctgggctgcc tggtcaagga ctacttcccc gaaccggtga cggtgtcgtg gaactcaggc | 480 |
| gccctgacca gcggcgtgca caccttcccg gctgtcctac agtcctcagg actctactcc | 540 |
| ctcagcagcg tggtgaccgt gccctccagc agcttgggca cccagaccta catctgcaac | 600 |
| gtgaatcaca agcccagcaa caccaaggtg gacaagaaag ttgagcccaa atcttgtgac | 660 |
| aaaactcaca catgcccacc gtgcccagca cctgaactcc tggggggacc gtcagtcttc | 720 |
| ctcttccccc caaaacccaa ggacaccctc atgatctccc ggacccctga ggtcacatgc | 780 |
| gtggtggtgg acgtgagcca cgaagaccct gaggtcaagt tcaactggta cgtggacggc | 840 |
| gtggaggtgc ataatgccaa gacaaagccg cgggaggagc agtacaacag cacgtaccgt | 900 |
| gtggtcagcg tcctcaccgt cctgcaccag gactggctga atggcaagga gtacaagtgc | 960 |
| aaggtctcca acaaagccct cccagccccc atcgagaaaa ccatctccaa agccaaaggg | 1020 |
| cagccccgag aaccacaggt gtacaccctg cccccatccc gggaggagat gaccaagaac | 1080 |
| caggtcagcc tgacctgcct ggtcaaaggc ttctatccca gcgacatcgc cgtggagtgg | 1140 |
| gagagcaatg ggcagccgga gaacaactac aagaccacgc ctcccgtgct ggactccgac | 1200 |
| ggctccttct tcctctacag caagctcacc gtggacaaga gcaggtggca gcaggggaac | 1260 |
| gtcttctcat gctccgtgat gcatgaggct ctgcacaacc actacacgca gaagagcctc | 1320 |

```
tccctgtctc cgggtaaa                                              1338

<210> SEQ ID NO 154
<211> LENGTH: 1338
<212> TYPE: DNA
<213> ORGANISM: Artificial Sequence
<220> FEATURE:
<223> OTHER INFORMATION: C40M121 HC DNA

<400> SEQUENCE: 154
cagctgcagc tgcaggagag cggccccggc ctggtgaagc ccagcgagac cctgagcctg    60
acctgcaccg tgagcggcgg cagcatcagc agcagcagct actactgggg ctggatccgg   120 cagcccccg gcaagggcct ggagtggatc ggcaacatct actaccgggg cgacacctac    180
tacagcccca gcctgaagag ccgggtgacc atcagcgtgg acaccagcaa gaaccagttc   240
agcctgaagc tgagcagcgt gaccgccgcc gacaccgccg tgtactactg cgccaagggc   300
ttccggttcg actactgggg ccagggcacc ctggtgaccg tgagcagcgc ctccaccaag   360
ggcccatcgg tcttccccct ggcaccctcc tccaagagca cctctggggg cacagcggcc   420
ctgggctgcc tggtcaagga ctacttcccc gaaccggtga cggtgtcgtg gaactcaggc   480
gccctgacca gcggcgtgca caccttcccg gctgtcctac agtcctcagg actctactcc   540
ctcagcagcg tggtgaccgt gccctccagc agcttgggca cccagaccta catctgcaac   600
gtgaatcaca agcccagcaa caccaaggtg gacaagaaag ttgagcccaa atcttgtgac   660
aaaactcaca catgcccacc gtgcccagca cctgaactcc tggggggacc gtcagtcttc   720
ctcttccccc caaaacccaa ggacaccctc atgatctccc ggacccctga ggtcacatgc   780
gtggtggtgg acgtgagcca cgaagaccct gaggtcaagt tcaactggta cgtggacggc   840
gtggaggtgc ataatgccaa gacaaagccg cgggaggagc agtacaacag cacgtaccgt   900
gtggtcagcg tcctcaccgt cctgcaccag gactggctga atggcaagga gtacaagtgc   960
aaggtctcca acaaagccct cccagccccc atcgagaaaa ccatctccaa agccaaaggg  1020
cagccccgag aaccacaggt gtacaccctg cccccatccc gggaggagat gaccaagaac  1080
caggtcagcc tgacctgcct ggtcaaaggc ttctatccca gcgacatcgc cgtggagtgg  1140
gagagcaatg ggcagccgga gaacaactac aagaccacgc ctcccgtgct ggactccgac  1200
ggctccttct cctctacag caagctcacc gtggacaaga gcaggtggca gcaggggaac  1260
gtcttctcat gctccgtgat gcatgaggct ctgcacaacc actacacgca gaagagcctc  1320
tccctgtctc cgggtaaa                                              1338

<210> SEQ ID NO 155
<211> LENGTH: 1338
<212> TYPE: DNA
<213> ORGANISM: Artificial Sequence
<220> FEATURE:
<223> OTHER INFORMATION: C40M126 HC DNA

<400> SEQUENCE: 155
cagctgcagc tgcaggagag cggccccggc ctggtgaagc ccagcgagac cctgagcctg    60
acctgcaccg tgagcggcgg cagcatcagc agcagcagct actactgggg ctggatccgg   120 cagcccccg gcaagggcct ggagtggatc ggcaacatct actaccgggg cgacacctac    180
tacagcccca gcctgaagag ccgggtgacc atcagcgtgg acaccagcaa gaaccagttc   240
agcctgaagc tgagcagcgt gaccgccgcc gacaccgccg tgtactactg cgccaagggc   300
```

```
ttccggttcg actactgggg ccagggcacc ctggtgaccg tgagcagcgc ctccaccaag    360
ggcccatcgg tcttccccct ggcaccctcc tccaagagca cctctggggg cacagcggcc    420
ctgggctgcc tggtcaagga ctacttcccc gaaccggtga cggtgtcgtg gaactcaggc    480
gccctgacca gcggcgtgca caccttcccg gctgtcctac agtcctcagg actctactcc    540
ctcagcagcg tggtgaccgt gccctccagc agcttgggca cccagaccta catctgcaac    600
gtgaatcaca agcccagcaa caccaaggtg gacaagaaag ttgagcccaa atcttgtgac    660
aaaactcaca catgcccacc gtgcccagca cctgaactcc tggggggacc gtcagtcttc    720
ctcttccccc caaaacccaa ggacaccctc atgatctccc ggacccctga ggtcacatgc    780
gtggtggtgg acgtgagcca cgaagaccct gaggtcaagt tcaactggta cgtggacggc    840
gtggaggtgc ataatgccaa gacaaagccg cgggaggagc agtacaacag cacgtaccgt    900
gtggtcagcg tcctcaccgt cctgcaccag gactggctga atggcaagga gtacaagtgc    960
aaggtctcca acaaagccct cccagccccc atcgagaaaa ccatctccaa agccaaaggg   1020
cagccccgag aaccacaggt gtacaccctg cccccatccc gggaggagat gaccaagaac   1080
caggtcagcc tgacctgcct ggtcaaaggc ttctatccca gcgacatcgc cgtggagtgg   1140
gagagcaatg ggcagccgga gaacaactac aagaccacgc tcccgtgctg gactccgac   1200
ggctccttct tcctctacag caagctcacc gtggacaaga gcaggtggca gcagggaac   1260
gtcttctcat gctccgtgat gcatgaggct ctgcacaacc actacacgca gaagagcctc   1320
tccctgtctc cgggtaaa                                                 1338

<210> SEQ ID NO 156
<211> LENGTH: 645
<212> TYPE: DNA
<213> ORGANISM: Artificial Sequence
<220> FEATURE:
<223> OTHER INFORMATION: C40M67 LC DNA

<400> SEQUENCE: 156
gaaattgtgc tgacccagag cccgggcacc ctgagcctga gcccgggcga acgcgcgacc     60
ctgagctgcc gcgcgagcca gagcgttaaa aatagcagtc tggcgtggta tcagcagaaa    120
ccgggccagg cgccgcgcct gctgatttat actgcgagca gccgcgcgac cggcattccg    180
gatcgcttta gcggcagcgg cagcggcacc gatttttaccc tgaccattag ccgcctggaa    240
ccggaagatt ttgcggtgta ttattgccag cagtcctccg cacctccgtg gacttttggc    300
cagggcacca aagtggaaat taaacgtacg gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcccctg    540
acgctgagca agcagacta cgagaaacac aaagtctacg cctgcgaagt cacccatcag    600
ggcctgagct cgcccgtcac aaagagcttc aacagggag agtgt                    645

<210> SEQ ID NO 157
<211> LENGTH: 660
<212> TYPE: DNA
<213> ORGANISM: Artificial Sequence
<220> FEATURE:
<223> OTHER INFORMATION: C40M66 LC DNA

<400> SEQUENCE: 157
gacatcgtga tgacccagag ccccgacagc ctggccgtga gcctgggcga gcgggccacc     60
```

```
atcaactgca agagcagcca gagcgtgctg tacagcagca acaacaagaa ctacctggcc      120
tggtaccagc agaagcccgg ccagcccccc aagctgctga tctactgggc cagcacccgg      180
gagagcggcg tgcccgaccg gttcagcggc agcggcagcg gcaccgactt cacccctgacc    240 atcagcagc tgcaggccga ggacgtggcc gtgtactact gccagcagta ctacagcacc       300
cccctgacct tcggccaggg caccaaggtg gagatcaagc ggaccgtggc cgcccccagc      360
gtgttcatct ccccccccag cgacgagcag ctgaagagcg gaaccgcaag cgtggtgtgc      420
ctgctgaaca acttctaccc cggggaggcc aaggtgcagt ggaaggtgga caacgccctg      480
cagagcggca cagccagga gagcgtgacc gagcaggaca gcaaggacag cacctacagc       540
ctgagcagca ccctgaccct gagcaaggcc gactacgaga agcacaaggt gtacgcttgc     600
gaggtgaccc ccagggcct gagcagcccc gtgaccaaga gcttcaaccg gggcgagtgc      660
```

<210> SEQ ID NO 158
<211> LENGTH: 642
<212> TYPE: DNA
<213> ORGANISM: Artificial Sequence
<220> FEATURE:
<223> OTHER INFORMATION: C40M59 LC DNA

<400> SEQUENCE: 158

```
gacatccaga tgacccagag ccccagcagc ctgagcgcca gcgtgggcga ccgggtgacc      60
atcacctgcc gggccagcca gagcatcagc agctacctga actggtacca gcagaagccc     120
ggcaaggccc ccaagctgct gatctacgcc gccagcagcc tgcagagcgg cgtgcccagc     180
cggttcagcg gcagcggcag cggcaccgac ttcaccctga ccatcagcag cctgcagccc    240
gaggacttcg ccacctacta ctgccagcag agctacagca ccccccctgac cttcggccag    300 ggcaccaagg tggagatcaa gcggaccgtg gccgccccca gcgtgttcat cttcccccc     360 agcgacgagc agctgaagag cggaaccgca agcgtggtgt gcctgctgaa caacttctac    420
ccccgggagg ccaaggtgca gtggaaggtg gacaacgccc tgcagagcgg caacagccag    480
gagagcgtga ccgagcagga cagcaaggac agcacctaca gcctgagcag caccctgacc    540
ctgagcaagg ccgactacga aaagcacaag gtgtacgctt gcgaggtgac ccaccagggc    600
ctgagcagcc ccgtgaccaa gagcttcaac cggggcgagt gc                         642
```

<210> SEQ ID NO 159
<211> LENGTH: 636
<212> TYPE: DNA
<213> ORGANISM: Artificial Sequence
<220> FEATURE:
<223> OTHER INFORMATION: C40M18 LC DNA

<400> SEQUENCE: 159

```
tcctacgagc tgacccagcc tcctccgtg tctgtgtctc ctggccagac cgccagcatc      60
acctgtagcg gcgacaagct gggcgacaaa tacgtgtgct ggtatcagca gaagcccggc     120
cagagccccg tggtggtcat ctaccaggac agcaagaggc ccagcggcat ccccgagaga    180
ttcagcggca gcaacagcgg caataccgcc accctgacca tcagcggcac ccaggccatg    240
gacgaggcct actactactg ccaggcttgg gtgtccagca ccgtggtgtt tggcggaggc    300
accaagctga ccgtgctggg tcagcccaag gctgcaccca gtgtcactct gttcccgccc    360
tcctctgagg agcttcaagc caacaaggcc acactggtgt gtctcataag tgacttctac    420
ccgggagccg tgacagtggc ctggaaggcc gatagcagcc ccgtcaaggc gggagtggag    480
```

```
accaccacac cctccaaaca aagcaacaac aagtacgcgg ccagcagcta tctgagcctg    540
acgcctgagc agtggaagtc ccacagaagc tacagctgcc aggtcacgca tgaagggagc    600
accgtggaga agacagtggc ccctacagaa tgttca                              636

<210> SEQ ID NO 160
<211> LENGTH: 636
<212> TYPE: DNA
<213> ORGANISM: Artificial Sequence
<220> FEATURE:
<223> OTHER INFORMATION: C40M17 LC DNA

<400> SEQUENCE: 160
tcctacgagc tgacccagcc tccctccgtg tctgtgtctc ctggccagac cgccagcatc     60
acctgtagcg gcgacaagct gggcgataag tacgcctgct ggtatcagca gaagcccggc    120
cagagccccg tgctggtcat ctaccaggac agcagaaggc ccagcggcat ccccgagaga    180
ttcagcggca gcaacagcgg caataccgcc accctgacca tcagcggcac ccaggccatg    240
gacgaggccg attactattg tcaggcctgg gccagcagca ccgtggtgtt tggcggcgga    300
acaaagctga ccgtgctggg tcagcccaag gctgcaccca gtgtcactct gttcccgccc    360
tcctctgagg agcttcaagc caacaaggcc acactggtgt gtctcataag tgacttctac    420
ccgggagccg tgacagtggc ctggaaggcc gatagcagcc ccgtcaaggc gggagtggag    480
accaccacac cctccaaaca aagcaacaac aagtacgcgg ccagcagcta tctgagcctg    540
acgcctgagc agtggaagtc ccacagaagc tacagctgcc aggtcacgca tgaagggagc    600
accgtggaga agacagtggc ccctacagaa tgttca                              636

<210> SEQ ID NO 161
<211> LENGTH: 636
<212> TYPE: DNA
<213> ORGANISM: Artificial Sequence
<220> FEATURE:
<223> OTHER INFORMATION: C40M12 LC DNA

<400> SEQUENCE: 161
tcctacgagc tgacccagcc tccctccgtg tctgtgtctc ctggccagac cgccagcatc     60
atctgcagcg gcgacaagct gggcgacaaa tacgtgtgct ggtatcagca gaagcccggc    120
cagagccccg tggtggtcat ctaccacgac aacaagaggc ccagcggcat ccccgagaga    180
ttcagcggca gcaacagcgg caataccgcc accctgacca tcagcggcac ccaggccatg    240
gacgaggccg actactactg ccaggtctgg gacagcagca ccgtggtgtt tggcggaggc    300
accaagctga ccgtgctggg tcagcccaag gctgcaccca gtgtcactct gttcccgccc    360
tcctctgagg agcttcaagc caacaaggcc acactggtgt gtctcataag tgacttctac    420
ccgggagccg tgacagtggc ctggaaggcc gatagcagcc ccgtcaaggc gggagtggag    480
accaccacac cctccaaaca aagcaacaac aagtacgcgg ccagcagcta tctgagcctg    540
acgcctgagc agtggaagtc ccacagaagc tacagctgcc aggtcacgca tgaagggagc    600
accgtggaga agacagtggc ccctacagaa tgttca                              636

<210> SEQ ID NO 162
<211> LENGTH: 648
<212> TYPE: DNA
<213> ORGANISM: Artificial Sequence
<220> FEATURE:
<223> OTHER INFORMATION: C40M9 LC DNA

<400> SEQUENCE: 162
```

-continued

```
cagtctgccc tgacacagcc tcctagcgcc tctggctctc ctggccagag cgtgaccatc    60
agctgtaccg gcaccagctc cgacgtgggc ggctacaact acgtgtcctg gtatcagcag   120
caccccggca aggcccctaa gctgatgatc tacgaggtgt ccaagcggcc agcggcgtg    180 ccagatagat tcagcggcag caagagcggc aacaccgcca gcctgacagt gtctggactg   240
caggccgagg acgaggccga ctactactgt agcagctacg ccggcagcaa caacctggtg   300
ttcggcggag gcaccaagct gaccgtgctg ggtcagccca aggctgcacc cagtgtcact   360
ctgttcccgc cctcctctga ggagcttcaa gccaacaagg ccacactggt gtgtctcata   420
agtgacttct acccgggagc cgtgacagtg gcctggaagg ccgatagcag ccccgtcaag   480
gcgggagtgg agaccaccac accctccaaa caaagcaaca caagtacgc ggccagcagc    540 tatctgagcc tgacgcctga gcagtggaag tcccacagaa gctacagctg ccaggtcacg   600
catgaaggga gcaccgtgga agacagtgt gccccctacag aatgttca                648
```

<210> SEQ ID NO 163
<211> LENGTH: 636
<212> TYPE: DNA
<213> ORGANISM: Artificial Sequence
<220> FEATURE:
<223> OTHER INFORMATION: C40M102 LC DNA

<400> SEQUENCE: 163

```
agctacgagc tgacccagcc ccccagcgtg agcgtgagcc ccggccagac cgccagcatc    60
acctgcagcg gcgacaagct gggcgacaag tacgtgtgct ggtaccagca gaagcccggc   120
cagagccccg tgctggtgat ctaccaggac agcaagcggc cagcggcat ccccgagcgg    180 ttcagcggca gcaacagcgg caacaccgcc accctgacca tcagcggcac ccaggccatg   240
gacgaggccg actactactg ccaggcctgg gtgagcagca ccgtggtgtt cggcggcggc   300
accaagctga ccgtgctggg tcagcccaag gctgcaccca gtgtcactct gttcccgccc   360
tcctctgagg agcttcaagc caacaaggcc acactggtgt gtctcataag tgacttctac   420
ccgggagccg tgacagtggc ctggaaggcc gatagcagcc ccgtcaaggc gggagtggag   480
accaccacac cctccaaaca aagcaacaac aagtacgcgg ccagcagcta tctgagcctg   540
acgcctgagc agtggaagtc ccacagaagc tacagctgcc aggtcacgca tgaagggagc   600
accgtggaga agacagtggc ccctacagaa tgttca                              636
```

<210> SEQ ID NO 164
<211> LENGTH: 636
<212> TYPE: DNA
<213> ORGANISM: Artificial Sequence
<220> FEATURE:
<223> OTHER INFORMATION: C40M103 LC DNA

<400> SEQUENCE: 164

```
agctacgagc tgacccagcc ccccagcgtg agcgtgagcc ccggccagac cgccagcatc    60
acctgcagcg gcgacaagct gggcgacaag tacgtgagct ggtaccagca gaagcccggc   120
cagagccccg tgctggtgat ctaccaggac agcaagcggc cagcggcat ccccgagcgg    180 ttcagcggca gcaacagcgg caacaccgcc accctgacca tcagcggcac ccaggccatg   240
gacgaggccg actactactg ccaggcctgg gtgagcagca ccgtggtgtt cggcggcggc   300
accaagctga ccgtgctggg tcagcccaag gctgcaccca gtgtcactct gttcccgccc   360
tcctctgagg agcttcaagc caacaaggcc acactggtgt gtctcataag tgacttctac   420
```

```
ccgggagccg tgacagtggc ctggaaggcc gatagcagcc ccgtcaaggc gggagtggag    480
accaccacac cctccaaaca aagcaacaac aagtacgcgg ccagcagcta tctgagcctg    540
acgcctgagc agtggaagtc ccacagaagc tacagctgcc aggtcacgca tgaagggagc    600
accgtggaga agacagtggc ccctacagaa tgttca                             636

<210> SEQ ID NO 165
<211> LENGTH: 636
<212> TYPE: DNA
<213> ORGANISM: Artificial Sequence
<220> FEATURE:
<223> OTHER INFORMATION: C40M104 LC DNA

<400> SEQUENCE: 165
agctacgagc tgacccagcc ccccagcgtg agcgtgagcc cggccagac cgccagcatc      60 acctgcagcg gcgacaagct gggcgacaag tacgtgagct ggtaccagca gaagcccggc    120
cagagccccg tggtggtgat ctaccaggac agcaagcggc ccagcggcat ccccgagcgg    180
ttcagcggca gcaacagcgg caacaccgcc accctgacca tcagcggcac ccaggccatg    240
gacgaggcct actactactg ccaggcctgg gtgagcagca ccgtggtgtt cggcggcggc    300
accaagctga ccgtgctggg tcagcccaag gctgcaccca gtgtcactct gttcccgccc    360
tcctctgagg agcttcaagc caacaaggcc acactggtgt gtctcataag tgacttctac    420
ccgggagccg tgacagtggc ctggaaggcc gatagcagcc ccgtcaaggc gggagtggag    480
accaccacac cctccaaaca aagcaacaac aagtacgcgg ccagcagcta tctgagcctg    540
acgcctgagc agtggaagtc ccacagaagc tacagctgcc aggtcacgca tgaagggagc    600
accgtggaga agacagtggc ccctacagaa tgttca                             636

<210> SEQ ID NO 166
<211> LENGTH: 120
<212> TYPE: PRT
<213> ORGANISM: Artificial Sequence
<220> FEATURE:
<223> OTHER INFORMATION: Nivolumab VH

<400> SEQUENCE: 166

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser
        115                 120

<210> SEQ ID NO 167
<211> LENGTH: 111
<212> TYPE: PRT
<213> ORGANISM: Artificial Sequence
```

<220> FEATURE:
<223> OTHER INFORMATION: Nivolumab VL

<400> SEQUENCE: 167

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys
            100                 105                 110

<210> SEQ ID NO 168
<211> LENGTH: 113
<212> TYPE: PRT
<213> ORGANISM: Artificial Sequence
<220> FEATURE:
<223> OTHER INFORMATION: Keytruda VH

<400> SEQUENCE: 168

Gln Val Gln Leu Val Glu Ser Gly Gly Val Trp Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser

<210> SEQ ID NO 169
<211> LENGTH: 107
<212> TYPE: PRT
<213> ORGANISM: Artificial Sequence
<220> FEATURE:
<223> OTHER INFORMATION: keytruda VL

<400> SEQUENCE: 169

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly

```
                  50                  55                  60
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ser Ser Asn Trp Pro Arg
                 85                  90                  95

Thr Phe Gly Gln Gly Thr Lys Val Glu Ile Lys
                100                 105

<210> SEQ ID NO 170
<211> LENGTH: 121
<212> TYPE: PRT
<213> ORGANISM: Artificial Sequence
<220> FEATURE:
<223> OTHER INFORMATION: Durvalumab VH

<400> SEQUENCE: 170

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
                20                  25                  30

Trp Met Ser Trp Val Arg Gln Ala Pro Gly Lys Gly Leu Glu Trp Val
             35                  40                  45

Ala Asn Ile Lys Gln Asp Gly Ser Glu Lys Tyr Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Gly Gly Trp Phe Gly Glu Leu Ala Phe Asp Tyr Trp Gly
                100                 105                 110

Gln Gly Thr Leu Val Thr Val Ser Ser
            115                 120

<210> SEQ ID NO 171
<211> LENGTH: 108
<212> TYPE: PRT
<213> ORGANISM: Artificial Sequence
<220> FEATURE:
<223> OTHER INFORMATION: Durvalumab VL

<400> SEQUENCE: 171

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Arg Val Ser Ser Ser
                20                  25                  30

Tyr Leu Ala Trp Tyr Gln Gln Lys Pro Gly Gln Ala Pro Arg Leu Leu
             35                  40                  45

Ile Tyr Asp Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Leu Pro
                 85                  90                  95

Trp Thr Phe Gly Gln Gly Thr Lys Val Glu Ile Lys
                100                 105

<210> SEQ ID NO 172
<211> LENGTH: 118
```

```
<212> TYPE: PRT
<213> ORGANISM: Artificial Sequence
<220> FEATURE:
<223> OTHER INFORMATION: Atezolizumab VH

<400> SEQUENCE: 172

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser
        115

<210> SEQ ID NO 173
<211> LENGTH: 107
<212> TYPE: PRT
<213> ORGANISM: Artificial Sequence
<220> FEATURE:
<223> OTHER INFORMATION: Atezolizumab VL

<400> SEQUENCE: 173

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys
            100                 105

<210> SEQ ID NO 174
<211> LENGTH: 120
<212> TYPE: PRT
<213> ORGANISM: Artificial Sequence
<220> FEATURE:
<223> OTHER INFORMATION: Avelumab VH

<400> SEQUENCE: 174

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
```

```
                   35                  40                  45
Ser Ser Ile Tyr Pro Ser Gly Gly Ile Thr Phe Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser
            115                 120

<210> SEQ ID NO 175
<211> LENGTH: 110
<212> TYPE: PRT
<213> ORGANISM: Artificial Sequence
<220> FEATURE:
<223> OTHER INFORMATION: Avelumab VL

<400> SEQUENCE: 175

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu
            100                 105                 110
```